(12) United States Patent
Turchetta et al.

(10) Patent No.: US 8,349,900 B2
(45) Date of Patent: Jan. 8, 2013

(54) BUPROPION HYDROBROMIDE POLYMORPHS

(75) Inventors: Stefano Turchetta, Patrica (IT); Maurizio Zenoni, Patrica (IT)

(73) Assignee: Valeant International Bermuda, Hamilton (BM)

( * ) Notice: Subject to any disclaimer, the term of this patent is extended or adjusted under 35 U.S.C. 154(b) by 525 days.

(21) Appl. No.: 12/536,772

(22) Filed: Aug. 6, 2009

(65) Prior Publication Data

US 2010/0068270 A1   Mar. 18, 2010

(30) Foreign Application Priority Data

Aug. 7, 2008 (EP) .................................... 08425545
Sep. 22, 2008 (EP) .................................... 08425617

(51) Int. Cl.
*A61K 31/137* (2006.01)
*C07C 225/10* (2006.01)

(52) U.S. Cl. ....................... 514/649; 564/345
(58) Field of Classification Search .................. None
See application file for complete search history.

(56) References Cited

U.S. PATENT DOCUMENTS

| | | | |
|---|---|---|---|
| 6,110,940 A | 8/2000 | Harding et al. | |
| 7,241,805 B2 | 7/2007 | Oberegger et al. | |
| 7,553,992 B2 | 6/2009 | Oberegger et al. | |
| 7,563,823 B2 | 7/2009 | Oberegger et al. | |
| 7,569,610 B2 | 8/2009 | Oberegger et al. | |
| 7,569,611 B2 | 8/2009 | Oberegger et al. | |
| 7,572,935 B2 | 8/2009 | Oberegger et al. | |
| 7,579,380 B2 | 8/2009 | Oberegger et al. | |
| 7,585,897 B2 | 9/2009 | Oberegger et al. | |
| 2007/0281012 A1 | 12/2007 | Oberegger et al. | |
| 2007/0293584 A1 | 12/2007 | Oberegger et al. | |
| 2008/0033044 A1 | 2/2008 | Oberegger et al. | |
| 2008/0038348 A1 | 2/2008 | Oberegger et al. | |
| 2008/0057120 A1 | 3/2008 | Oberegger et al. | |
| 2008/0075774 A1 | 3/2008 | Williams et al. | |
| 2008/0274181 A1 | 11/2008 | Maes et al. | |
| 2009/0004281 A1 | 1/2009 | Nghiem et al. | |

FOREIGN PATENT DOCUMENTS

EP   0 118 036   9/1984

OTHER PUBLICATIONS

P. Heinrich Stahl, "Preparation of Water-Soluble Compounds through Salt Formation", The Practice of Medicinal Chemistry, Copyright © 2003 Elsevier, pp. 601-615.
U.S. Appl. No. 12/620,720, filed Nov. 18, 2009, Williams, et al.
U.S. Appl. No. 12/672,137, filed Feb. 4, 2010, Williams, et al.
U.S. Appl. No. 12/740,223, filed May 25, 2010, Jackson, et al.
U.S. Appl. No. 60/693,906, filed Jun. 27, 2005, Oberegger, et al.
U.S. Appl. No. 11/993,723, filed Dec. 21, 2007, Oberegger, et al.
Mino R Caira, "Crystalline Polymorphism of Organic Compounds", Topics in Current Chemistry, vol. 198, XP-001156954, Jan. 1, 1998, pp. 163-208.

*Primary Examiner* — Paul A Zucker
(74) *Attorney, Agent, or Firm* — Oblon, Spivak, McClelland, Maier & Neustadt, L.L.P.

(57) ABSTRACT

Polymorphous and amorphous forms of bupropion hydrobromide are described.

7 Claims, 40 Drawing Sheets

PXRD of Bupropion Hydrobromide Polymorphic Form I

DSC of Bupropion Hydrobromide Polymorphic form I

PXRD of Bupropion Hydrobromide Form I after 6 months in ICH Conditions (40°C, 75% R.H.)

PXRD of Bupropion Hydrobromide Polymorphic Form II

DSC of Bupropion Hydrobromide Polymorphic form II

PXRD of Bupropion Hydrobromide Polymorphic Form II after 1 month in ICH Conditions (40°C, 75% R.H.)

PXRD of Bupropion Hydrobromide Polymorphic Form III

DSC of Bupropion Hydrobromide Polymorphic form III

PXRD of Bupropion Hydrobromide Polymorphic Form III after 1 month in ICH Conditions (40°C, 75% R.H.)

BUPROPION HYDROBROMIDE POLYMORPHS

RELATED APPLICATIONS

This application claims priority to EP 08425545.4, filed Aug. 7, 2008, and to EP 08425617.1 filed Sep. 22, 2008.

FIELD OF THE INVENTION

The present invention relates to polymorphs of bupropion hydrobromide and formulations containing polymorphs of bupropion hydrobromide, as well as their use for the treatment of conditions (e.g. major depressive disorder, bipolar depression mood disorder, other mood disorder, anxiety disorders, generalized anxiety disorder, panic disorder, post-traumatic stress disorder, nicotine addiction, obesity, attention-deficit hyperactivity disorder, restless legs syndrome, sexual dysfunction, and seasonal affective disorders).

BACKGROUND

Bupropion hydrobromide or 3'-chloro-2-t-butylamino-1-propiophenone hydrobromide is a known antidepressant. See e.g., U.S. Pat. Nos. 7,241,805; 7,569,611; 7,563,992; 7,563,823; and 7,569,610. Its structural formula is:

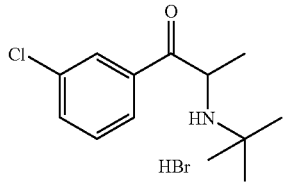 [SMILES: CC(NC(C)(C)C)C(=O)c1cccc(Cl)c1 ; Br]

The neurochemical mechanism of the antidepressant effect of bupropion is not well known. Bupropion affects chemicals within the brain that nerves use to send messages to each other. These chemical messengers are called neurotransmitters. The neurotransmitters that are released by nerves are taken up again by the nerves that release them for reuse (this is referred to as reuptake). Many skilled artisans believe that depression is caused by an imbalance among the amounts of neurotransmitters that are released. Bupropion is a selective catecholamine (dopamine and norepinephrine) reuptake inhibitor, and works by inhibiting the reuptake of the neurotransmitters dopamine and norepinephrine, an action which results in more dopamine and norepinephrine made available to transmit messages to other nerves. It has a small effect, if any, on the serotonin reuptake mechanism. Accordingly, bupropion is unique in that its major effect is on dopamine, an effect which is not shared by selective serotonin re-uptake inhibitors (SSRIs), e.g. paroxetine (PAXIL®), fluoxetine (PROZAC®), sertraline (ZOLOFT®) or the tricyclic antidepressants or TCAs, e.g. amitriptyline (ELAVIL®), imipramine (TOFRANIL®), desipramine (NORPRAMIN®).

Bupropion can also be used to treat other conditions, non-limiting examples of which include nicotine addition (e.g. smoking cessation), weight gain (e.g. obesity), Parkinson's disease, and seasonal affective disorder.

Bupropion hydrochloride is commercially available as an immediate release form (WELLBUTRIN®), a sustained release form (WELLBUTRIN® SR and ZYBAN®), and an extended release form ((WELLBUTRIN® XL). Both WELLBUTRIN® SR and ZYBAN® are chemically and pharmaceutically identical. WELLBUTRIN®, WELLBUTRIN® SR and WELLBUTRIN® XL are used clinically for the management of major depressive disorder, bipolar depression mood disorder, other mood disorder, anxiety disorders, generalized anxiety disorder, panic disorder, post-traumatic stress disorder, and seasonal affective disorders, and have been approved for use in the treatment of major depressive disorder. ZYBAN® has been approved as an aid to patients wanting to quit smoking. WELLBUTRIN®, the immediate release formulation of bupropion, is dosed three times a day, suitably with 6 or more hours in between doses. For patients requiring more than 300 mg bupropion a day, each dose is prescribed not to exceed 150 mg. This requires administration of the tablets at least 4 times a day with at least 4 hours in between doses. The immediate release formulation results in more than a 75% release of the bupropion into the dissolution media in 45 minutes. The sustained release products are dosed twice daily, and the extended release products are dosed once daily.

Certain advantages exist in using bupropion for the treatment of diseases and conditions. For example, bupropion does not inhibit monoamine oxidase, and does not significantly block the reuptake of serotonin, unlike other neuronal monoamine reuptake inhibitors. Administration of bupropion can thus avoid or lessen many adverse effects commonly associated with other antidepressants such as tricyclic agents and monoamine oxidase inhibitors.

It is known that different crystalline forms of one and the same active drug can display different characteristics of solubility and hence bioavailability, and thus permit more appropriate use of the active drug according to whether one requires slow release (in that case using a less-soluble polymorphous form) or quicker availability of the active drug (using a more-soluble polymorphous form), accordingly providing easier modulation of the availability of the drug. Accordingly, it is useful to have different polymorphous forms, with different chemical and physical properties, at one's disposal.

The development of a stable bupropion formulation would be an advance in the art.

DESCRIPTION

While bupropion hydrobromide and three polymorphic forms (I, II, and II) have been previously described (see Background above), the invention here concerns the discovery of new crystalline forms of bupropion hydrobromide designated as Forms IV, V, VI and VII respectively. In addition, certain other embodiments of the present invention relate to the amorphous form of bupropion hydrobromide.

Certain embodiments of the present invention relate to a bupropion composition that comprises a safe and pharmaceutically effective amount of bupropion hydrobromide and/or a polymorph of bupropion hydrobromide; wherein the composition unexpectedly provides for fewer incidences of seizures and/or less severe seizures associated with the administration of bupropion than an otherwise similar or identical composition containing an equivalent molar amount of bupropion hydrochloride.

Certain embodiments of the present invention relate to a bupropion composition that comprises a safe and pharmaceutically effective amount of bupropion hydrobromide and/or a polymorph of bupropion hydrobromide; wherein said composition is more stable, than an otherwise similar or identical composition containing an equivalent molar amount of bupropion hydrochloride and/or a polymorph of bupropion hydrobromide. In particular, such a bupropion hydrobromide composition is more stable than an otherwise similar or identical composition containing an equivalent molar amount of bupropion hydrochloride under certain storage conditions, (for example when stored for 3 months or 6 months at 40 degrees C. and 75% relative humidity) as evidenced by a reduced amount of at least one moiety (e.g. degradation product) that is characteristic of bupropion degradation and/or a reduced fluctuation or reduction in potency after being stored under accelerated storage conditions (for example after storage for 3 months or 6 months), and/or by a reduced fluctuation in the in-vitro dissolution profile in at least one dissolution medium over a 24 hour period.

Certain embodiments of the present invention relate to methods of treating a condition comprising administering a safe and effective amount of bupropion hydrobromide and/or a polymorph of bupropion hydrobromide to a subject in need of bupropion administration.

Certain embodiments of the present invention further contemplate a method of preparing a medicament for the treatment of a condition which can benefit from the administration of bupropion, comprising bringing an effective amount of bupropion hydrobromide and/or a polymorph of bupropion hydrobromide into contact with one or more pharmaceutically acceptable excipients.

Certain embodiments relate to compositions comprising a compound of formula I (bupropion hydrobromide):

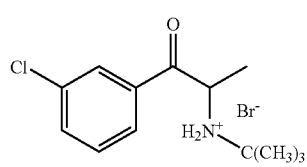

(I)

and/or a polymorph of bupropion hydrobromide, and pharmaceutically acceptable carriers, excipients and/or diluents; said composition having greater stability than a corresponding pharmaceutical composition comprising bupropion hydrochloride and pharmaceutically acceptable carriers, excipients and/or diluents.

In certain embodiments of the present invention, the bupropion salt can be in the form of its anhydrous, hydrated, and solvated forms, in the form of prodrugs, and in the individually optically active enantiomers of the bupropion salt, such as for example (+)-bupropion and (−)-bupropion. Suitable pharmaceutically acceptable salts of bupropion for use in the present invention are more stable than bupropion hydrochloride. In certain embodiments the bupropion hydrobromide salt can also provide for the reduction or avoidance of incidences of seizures associated with the administration of bupropion. Suitable salts of bupropion also include for example, pharmaceutically acceptable acid addition salts. In certain embodiments, the acid addition salt of bupropion can be indirectly obtained by the separate addition of bupropion and an acid to the core formulation.

Certain embodiments of the present invention contemplate the use of bupropion hydrobromide and/or a polymorph of bupropion hydrobromide to prepare a medicament to treat a condition which can benefit from administration of bupropion, wherein said medicament has greater stability than a corresponding medicament comprising bupropion hydrochloride.

As discussed infra and generally known in the art, appropriate dissolution medium and appropriate conditions for assaying the dissolution characteristics of pharmaceutical dosage forms such as tablets are well known in the art and are contained in the United States Pharmacopoeia and its European or Japanese counterparts, and include by way of example dissolution in USP Type 1 apparatus (Rotating Basket Method) in 900 ml water; 0.1 N HCl; 0.1NHCl+0.1% Cetrimide; USP buffer pH 1.5; Acetate buffer pH 4.5; Phosphate Buffer pH 6.5; or Phosphate Buffer pH 7.4 at 75 RPM at 37 degrees C.+/−0.5 degrees C. Additionally, other examples of appropriate dissolution media include USP-3 media and USP-3 dissolution conditions e.g, SGF pH 1.2; Acetate buffer pH 4.5 and Phosphate Buffer pH 6.8.

Certain embodiments of the present invention contemplate the use of bupropion hydrobromide and/or a polymorph of bupropion hydrobromide to produce once-daily administrable tablets or other dosage forms that are bioequivalent to WELLBUTRIN™ or ZYBAN™/WELLBUTRIN™ SR tablets as defined by FDA criteria when administered once daily to a subject in need thereof. In particular at least one of the Tmax, Cmax, or AUC profile of certain embodiments of the present invention is within 80-125% of WELLBUTRIN™ and ZYBAN™/WELLBUTRIN™ when administered once daily to a subject in need thereof. In certain embodiments these formulations are also free of any significant food effect.

Certain embodiments of the present invention provide bupropion hydrobromide dosage forms (e.g. tablets) containing at least one coating (e.g. SMARTCOAT™ coating) which is resistant to dose dumping in high alcohol, (e.g., 40% ethanol).

Certain embodiments of the invention include dosage forms that avoid the so-called dose dumping effect, for example in the presence of ethanol, e.g., 5-40% ethanol. This means that the dosage forms do not deliver the active ingredient significantly more quickly in the presence of, e.g., ethanol as compared to normal stomach contents. Such dosage forms are resistant to dose dumping.

Certain embodiments of the present invention include both oral and non-oral bupropion hydrobromide containing medicaments. For example, the invention embraces compositions suitable for oral, topical, injectable, inhalation and other modes of administration.

Certain embodiments of the present invention include extended release formulations, delayed release formulations, and/or enhanced absorption formulations.

In a more particular implementation of certain embodiments of the invention, a bupropion medicament composition comprises (i) a core that includes bupropion hydrobromide and/or a polymorph of bupropion hydrobromide, a binder and a lubricant; and (ii) a controlled release coat substantially surrounding said core; wherein said composition provides controlled release of said bupropion hydrobromide. Such compositions optionally can comprise one or more additional coatings surrounding the core and/or the controlled release coat such as a moisture barrier coat, enteric coat or a coating that affects the physical integrity and/or appearance of the composition. The binder can be selected from known pharmaceutical binders such as polyvinyl alcohol. The lubricant also can be selected from known pharmaceutical lubricants such as glyceryl behenate. The controlled release coat can include a water-insoluble polymer, a water-soluble polymer, and optionally a plasticizer. The water-insoluble polymer can be selected from a range of water insoluble polymers useful in extended release pharmaceutical compositions such as ethylcellulose. The water-soluble polymer can be selected from a variety of water-soluble polymers useful in extended release pharmaceutical compositions such as polyvinylpyrrolidone. The plasticizer if present can be selected from a range of known plasticizers such as mixtures of polyethylene glycol 4000 and dibutyl sebacate. Certain embodiments of these compositions include once-daily administrable compositions that are bioequivalent to WELLBUTRIN™ or ZYBAN™/WELLBUTRIN™ SR tablets when administered once-daily to a subject in need thereof. These compositions may or may not exhibit a food effect. Further, certain embodiments of these compositions can be resistant to dose dumping in the presence of high alcohol concentrations (e.g., 40% by weight of ethanol).

In another particular implementation of certain embodiments of the present invention, the bupropion composition comprises (i) a core that includes bupropion hydrobromide and/or a polymorph of bupropion hydrobromide, a binder and a lubricant; and (ii) a controlled release coat substantially surrounding said core; wherein said controlled release coat includes an aqueous dispersion of a neutral ester copolymer without any functional groups, a polyglycol having a melting point greater than 55° C., and one or more pharmaceutically acceptable excipients, wherein said coat is coated onto said core and cured at a temperature at least equal to or greater than the melting point of the polyglycol. The composition provides controlled release of said bupropion hydrobromide. Optionally, this medicament can comprise one or more additional coatings surrounding the core and/or controlled release coating such as a moisture barrier coat, enteric coat, coat that precludes dose dumping in specific media such as alcohol, and/or a coating that affects the physical stability or integrity of the medicament and/or its physical appearance.

In a particular implementation of certain embodiments of the present invention, the bupropion composition comprises multiparticulates.

Certain embodiments of the present invention include controlled release matrix tablet formulations.

Certain embodiments of the present invention include a bupropion composition that comprises a second drug. The second drug (e.g. other anti-depressants, SSRI's, anti-anxiety agents, atypical antipsychotic drugs, medications that interact with serotonin neurotransmission, medications that interact with norepinephrine neurotransmission, medications that interact with dopamine neurotransmission) can be administered in combination with the subject bupropion hydrobromide salt. The second drug can elicit a synergistic benefit on bupropion efficacy as well as non-synergistic drug combinations. Non-limiting examples of the second drug include citalopram, escitalopram, venlafaxine, quetiapene, buspirone and mixtures thereof.

In accordance with one aspect of certain embodiments of the present invention, there is provided a controlled release composition comprising (i) a core comprising an effective amount of a bupropion hydrobromide and/or a polymorph of bupropion hydrobromide, a binder, a lubricant; and (ii) a controlled release coat surrounding said core; and optionally (iii) a moisture barrier surrounding said controlled release coat or the core; and; wherein the composition exhibits a dissolution profile such that after 2 hours from about more than 0% to about 20%, including all values and subranges therebetween; preferably from about 2% to about 18%, more preferably from about 4% to about 8%, or about 5%, of the bupropion hydrobromide content is released; after 4 hours from about 15% to about 45%, including all values and subranges therebetween; preferably from about 21% to about 37%, more preferably from about 28% to about 34%, or about 32%, of the bupropion hydrobromide content is released; after 8 hours from about 40% to about 90%, including all values and subranges therebetween, preferably from about 60% to about 85%; more preferably from about 68% to about 74%; or about 74%, of the bupropion hydrobromide content is released, and after 16 hours from about 80% to about 100% including all values and subranges therebetween, preferably not less than about 93%; more preferably not less than about 96%, still more preferably not less than about 99%, of the bupropion hydrobromide content is released, when using a USP apparatus design with a dissolution medium as found in the USP (e.g. USP Apparatus Type 1 at 75 rpm, 900 ml, 0.1N HCl, at 37° C.±0.5° C.); and wherein the bupropion hydrobromide composition is more stable than an otherwise similar or identical composition comprising the equivalent molar amount of bupropion hydrochloride when each are stored under accelerated storage conditions (e.g. stored for 3 months or 6 months at about 40 degrees C. and at about 75% relative humidity).

In certain embodiments the composition exhibits a dissolution profile such that after 2 hours not more than about 0% to about 40%, including all values and subranges therebetween, of the bupropion hydrobromide is released, after 4 hours from about 40% to about 75%, including all values and subranges therebetween, of the bupropion hydrobromide is released, after 8 hours not less than about 75% to about 99%, including all values and subranges therebetween, of the bupropion hydrobromide is released, and after 16 hours not less than about 85% to about 100%, including all values and subranges therebetween of the bupropion hydrobromide is released, when using a USP apparatus design with a dissolution medium as found in the USP (e.g. USP Apparatus Type 1 at 75 rpm, 900 ml, 0.1N HCl, at 37° C.±0.5° C.).

Certain embodiments of the present invention include a bupropion composition that comprises from about 50 mg to about 1000 mg of bupropion hydrobromide or a polymorph of bupropion hydrobromide, including 75 mg, 100 mg, 125 mg, 150 mg, 174 mg, 175 mg, 200 mg, 225 mg, 250 mg, 275 mg, 300 mg, 325 mg, 348 mg, 350 mg, 375 mg, 400 mg, 425 mg, 450 mg, 475 mg, 500 mg, 510 mg, 520 mg, 522 mg, 525 mg, 530 mg, 540 mg, 550 mg, 560 mg, 570 mg, 575 mg, 580 mg, 590 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, and all values and ranges therebetween. For example, certain embodiments include a composition which comprises 174 mg, 348 mg or 522 mg of bupropion hydrobromide per unit dose.

In accordance with one aspect of certain embodiments of the present invention, there is provided an enhanced-absorption tablet comprising (i) a core comprising an effective amount of bupropion hydrobromide and/or a polymorph of bupropion hydrobromide, a binder, a lubricant; and (ii) a controlled release coat surrounding said core; and wherein the enhanced absorption tablet exhibits a dissolution profile such that after 2 hours, from about 0% to about 25%, preferably from about 10% to about 20%, including all values and subranges therebetween of the bupropion hydrobromide content is released; after 4 hours from about 25% to about 55%, preferably from about 30% to about 50%, including all values and subranges therebetween of the bupropion hydrobromide content is released; after 8 hours from about 60% to about 99%, preferably from about 70% to about 90%, including all values and subranges therebetween of the bupropion hydrobromide content is released, and after 16 hours from about 70% to about 100%, preferably more than about 80%, including all values and subranges therebetween, of the bupropion hydrobromide content is released, when using a USP apparatus design with a dissolution medium as found in the USP (e.g. USP Apparatus Type 1 at 75 rpm, 900 ml, 0.1N HCl, at 37° C.±0.5° C.); and wherein the bupropion hydrobromide enhanced-absorption tablet is more stable than an otherwise similar or identical composition comprising the equivalent molar amount of bupropion hydrochloride when each are stored under accelerated storage conditions (e.g. stored for 3 months or 6 months at about 40 degrees C. and at about 75% relative humidity.

In certain embodiments the bupropion hydrobromide composition can comprise a dissolution profile such that after 2 hours from more than about 0% to about 40%, including all values and subranges therebetween, of bupropion hydrobromide is released therefrom; after 4 hours from about 40% to about 75%, including all values and subranges therebetween, of bupropion hydrobromide is released therefrom; after 8 hours from about 75% to about 99%, including all values and subranges therebetween, of bupropion hydrobromide is released therefrom, and after 16 hours from about 85% to about 100%, including all values and subranges therebetween, of bupropion hydrobromide is released therefrom, when using a USP apparatus design with a dissolution medium as found in the USP (e.g. USP Apparatus Type 1 at 75 rpm, 900 ml, 0.1N HCl, at 37° C.±0.5° C.).

As discussed infra, in-vitro dissolution of bupropion from controlled or extended release formulations according to certain embodiments of the invention can be determined by methods well known to those skilled in the pharmaceutical art. Suitable methods are contained in the United States Pharmacopoeia (USP) as well as European and Japanese counterparts of the USP and are exemplified infra. This includes by way of example effecting dissolution in a USP 1 apparatus (Rotating Type Basket Method) in 900 ml water, 0.1N HCl, 0.1NHCl+0.1% Cetrimide, USP Buffer pH 1.5, Acetate Buffer pH 6.5 or Phosphate Buffer pH 7.4 at 75 RPM at 37 degrees C.+/−0.5 degrees C. or by effecting dissolution using a USP dissolution medium such as SGF having a pH 1.2; acetate buffer having a pH of 4.5 or phosphate buffer having a pH of 6.8.

Stable compositions of bupropion hydrobromide (e.g compositions of bupropion hydrobromide or a polymorph of bupropion hydrobromide with enhanced stability as compared to otherwise similar compositions containing bupropion hydrochloride) are known for example from U.S. Pat. No. 7,241,805, U.S. patent application Ser. No. 11/834,848 (Pub. No. 2008-0075774), and U.S. patent application Ser. No. 11/930,644 (Pub. No. 2008-0274181), the contents of which are incorporated herein by reference.

DEFINITIONS

Figure 1:
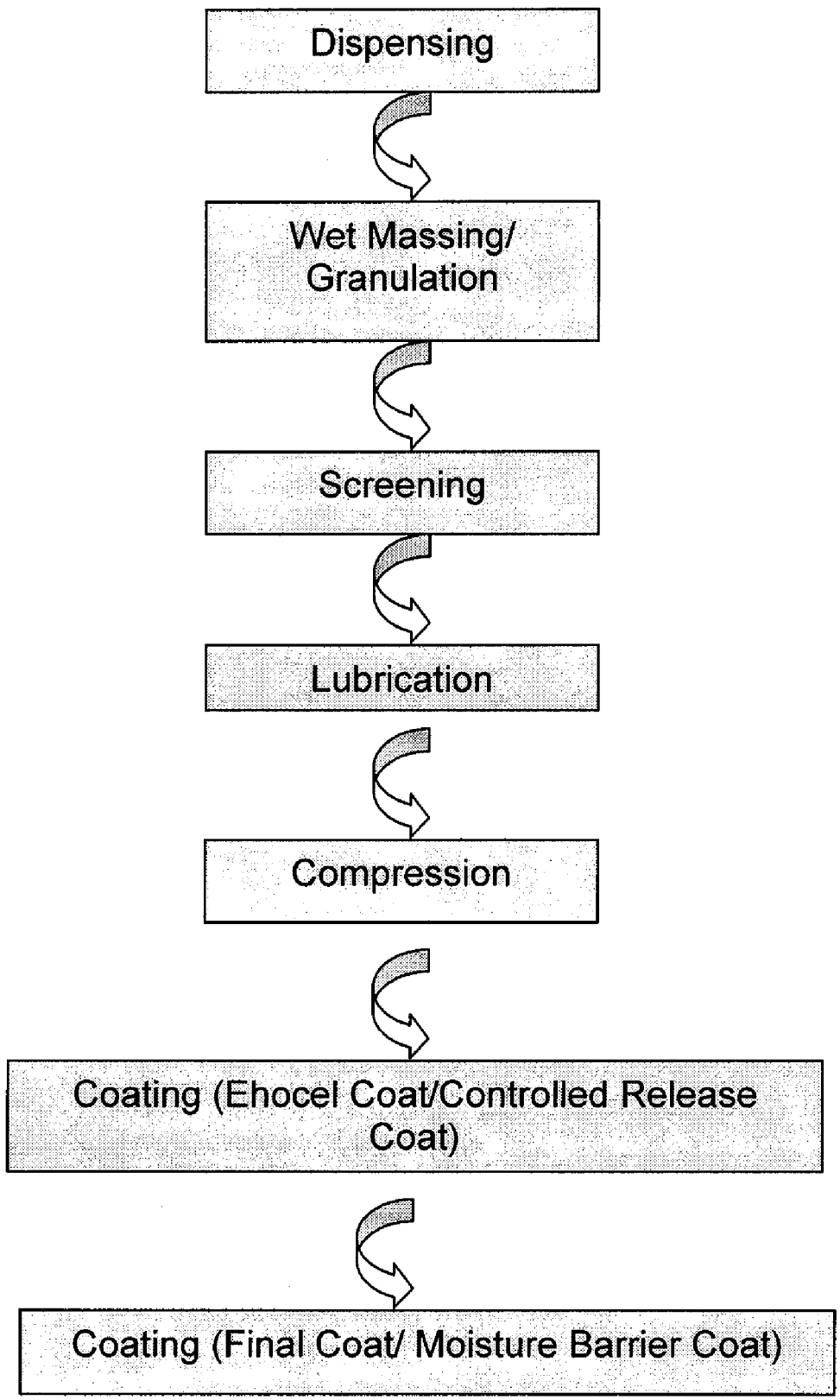
FIG. 1 is a flow chart showing the overall process for the development of bupropion HBr XL tablets.

The following definitions are provided in order to more specifically describe the invention. Otherwise all terms are to be accorded their ordinary meaning as they would be construed by one of ordinary skill in the art, i.e. pharmaceutical drug formulations.

The term "bupropion hydrobromide" as used herein means the bupropion hydrobromide salt, and can also mean the anhydrous, hydrated and solvated forms, prodrugs, polymorphs, and the individually optically active enantiomers of bupropion hydrobromide.

The terms "adverse effects associated with bupropion" or "side effects of bupropion" as used herein are used interchangeably, and mean the adverse drug reactions resulting from the administration of bupropion or a mixture of bupropion with one or more other drugs, non-limiting examples of which include seizures, nausea, vomiting, excitement, agitation, blurred or blurry vision, restlessness, postural tremors, hallucinations/confusional states with the potential for abuse, anxiety, insomnia, headaches and/or migraines, dry mouth, constipation, tremors, sleeping disturbances, dermatologic problems (e.g., rashes), neuropsychiatric signs and symptoms (e.g., delusions and paranoia), weight gain, and combinations thereof.

The term "depression" as used herein refers to any nervous system disorder and/or mental condition. Non-limiting examples of "depression" include major depressive disorder, bipolar depressed mood disorder, adjustment mood disorder, and post-partum mood disorder.

The term "condition" as used herein when referring to the administration of bupropion, means a condition, disease or disorder which can be treated with bupropion. Non-limiting examples of which include depression, seasonal affective disorder, anxiety disorders, generalized anxiety disorder, social anxiety disorder, obsessive compulsive disorder, post traumatic stress disorder (PTSD), panic disorder, disorders requiring a stimulant effect, attention-deficit/hyperactivity disorder (ADHD), narcolepsy, hypersomnia, substance-abuse disorders, stimulant dependence, marijuana dependence, nicotine dependence, obesity, female and male sexual dysfunction (e.g. premature ejaculation), premenstrual syndrome, premenstrual dysphoric disorder, neuropathic pain, fibromyalgia, diabetic neuropathy, viral infection, sleep apnea, sleep disorders, migraines, Parkinson's disease, restless legs syndrome, and combinations thereof.

The terms "treatment", "treating" or "treat" as used herein when referring to a condition, and as understood in the art, are defined to mean an approach for obtaining beneficial or desired results, including clinical results. "Treatment" can also mean prolonging survival of a subject as compared to the expected survival of the subject if not receiving treatment.

The term "palliating" as used herein when referring to a condition means that the extent and/or undesirable clinical manifestations of a condition or disease state are lessened and/or time course of the progression is slowed or lengthened, as compared to not treating the condition.

The term "effective amount" or "pharmaceutically effective amount" as used herein are used interchangeably, and are defined to mean the amount or quantity of the active drug (e.g. bupropion hydrobromide) or polymorph or enantiomer thereof which is sufficient to elicit an appreciable biological response when administered to a patient. It will be appreciated that the precise therapeutic dose will depend on the age and condition of the patient and the nature of the condition to be treated and will be at the ultimate discretion of the attendant physician.

The terms "enhanced stability", "greater stability", "increased stability" or "more stable" as used herein when referring to bupropion hydrobromide, can be used interchangeably in this application, and are defined to mean that the bupropion hydrobromide or composition containing bupropion hydrobromide, shows less degradation as determined by the formation of less of at least one degradation product characteristic of bupropion degradation, than an equivalent molar amount of bupropion hydrochloride or an otherwise similar or identical composition containing an equivalent molar amount of bupropion hydrochloride, when exposed to similar or identical conditions. Non-limiting examples of conditions are those described for example in U.S. Pat. No. 7,241,805.

The term "less degradation" as used herein when referring to bupropion hydrobromide or a composition containing bupropion hydrobromide, is defined to mean any measurable decrease in the amount of at least one bupropion degradation impurity characteristic of bupropion degradation, and/or any measurable difference in the retention of potency, relative to an equivalent molar amount of bupropion hydrochloride or an otherwise similar or identical composition containing an equivalent molar amount of bupropion hydrochloride, when exposed to similar or identical conditions.

The terms "degradation product", "bupropion degradation product", "bupropion degradation impurity" or "impurity" as used herein when referring to the degradation of bupropion, are used interchangeably and are defined to include those listed on page 281 of the 26th edition of the USP and any other degradation product that may appear as peaks on a chromatogram during the assay that are characteristic of bupropion degradation.

The term "dissolution profile" or "release profile" as used herein are used interchangeably in this application, and are defined to mean a quality control test conducted according to instructions found in the United States Pharmacopoeia ("USP"), i.e. using a USP apparatus design with a dissolution medium as found in the USP. Dissolution tests in-vitro measure the rate and extent of dissolution of the active drug in an aqueous dissolution medium. The dissolution rate or in-vitro release rates of drug from the modified release dosage forms of the present invention can be measured using one of many USP apparatus designs and dissolution media; non-limiting examples of which include a USP Type 1 apparatus design or USP Type 2 apparatus design, with a dissolution medium selected from water; 0.1N HCl; 0.1N HCl with added Sodium Chloride (e.g. 15.7 g NaCl/Liter); 0.1N HCl with added 0.1% Cetrimide; USP Buffer pH 1.5; Acetate Buffer pH 4.5; Phosphate Buffer pH 6.5; Phosphate Buffer pH 6.8; and Phosphate Buffer pH 7.4. The terms "% released" and "% dissolved", when referring to a dissolution profile, are used interchangeably in this application and are defined to mean the extent (%) of active drug released in an aqueous dissolution medium (in vitro).

The term "dose dumping" as used herein in respect of "alcohol induced dose dumping" is defined to mean the unintended premature release (in-vitro) of at least one drug from a modified release dosage form. The term "premature release" as used herein is defined to mean a release of at least one drug from a modified release dosage form in 0.1 N HCl containing alcohol (e.g. dissolution medium containing from about 5% to about 40% ethanol, the balance being 0.1 N HCl) wherein the rate of release is faster than the rate of release of the identical drug(s) from the identical modified release dosage form in the otherwise identical 0.1 N HCl not containing alcohol. A non-limiting example of an "alcohol induced dose dumping" is the premature release of bupropion from a modified release tablet over a period of about 2 hours when dissolution is tested in 900 ml of Alcohol USP comprising dissolution media using USP Apparatus Type 1 at 75 rpm at 37° C. In certain embodiments the term "Alcohol USP comprising dissolution media" means any dissolution media comprising from about 5% to about 40% (v/v) of Alcohol USP (e.g. 5% ethanol and 95% 0.1N HCl; 20% ethanol and 80% 0.1N HCl; and 40% ethanol and 60% 0.1N HCl).

The terms "resistant to alcohol", "resistant to ethanol", "resistant to dose dumping", "resistant to alcohol-induced dose dumping" and "resisting dose dumping" as used herein are used interchangeably, and are defined to mean the ability of the dosage form to modify release (in-vitro) of the at least one drug while in the presence of alcohol (e.g. from about 5% to about 40% ethanol), such that there is not a premature release of the at least one drug from the modified release dosage form. For example, in certain embodiments the rate of release of at least one drug from a modified release dosage form in dissolution media containing alcohol (e.g. dissolution medium containing from about 5% to about 40% ethanol) is slower than the rate of release of the identical drug(s) from the identical modified release dosage form in dissolution media not containing alcohol (e.g. dissolution medium containing about 100% 0.1 N HCl).

The term "other drug" or "second drug" as used herein means a drug other than bupropion, including but not limited to anti-depression agents, other neuropsychiatric drugs, atypical antipsychotics, drug that affects central or peripheral serotonin neurotransmission, drugs that affect central norepinephrine neurotransmission, drugs that affect central dopamine neurotransmission, vasodilators, anti-anxiety agents, appetite modulators, sleep modulating drugs, SSRIs, anti-viral agents, anti-pain agents, anti-migraine agents, anti-inflammatories (both steroidal and non-steroidal) serotonin receptor agonists, and more particularly can include citalopram, escitalopram, venlafaxine, clozapine, melperone, amperozide, iloperidone, risperidone, quetiapene, olanzapine, ziprasidone, aripiprazole, reboxetine, Viagra®, sertraline, paroxetine, fluoxetine, gabapentin, valproic acid, amitriptyline, lofepramine, fluvoxamine, imipramine, mirtazapine, nefazodone, nortriptyline, SAM-E, buspirone, combinations thereof, and their pharmaceutically acceptable salts (e.g. the hydrochloride salts, the hydrobromide salts, the hydroiodide salts, and the saccharinate salts), as well as the anhydrous, hydrated, and solvated forms, polymorphs, pro-drugs, and the individually optically active enantiomers of the other drug.

The term "dosage form" as used herein is defined to mean a pharmaceutical preparation or system in which a dose of at least one active drug is included. For example, a dosage form can include at least one modified release dosage form, at least one osmotic dosage form, at least one erosion modified release dosage form, at least one dissolution modified release dosage form, at least one diffusion modified release dosage form, at least one modified release matrix core, at least one modified release matrix core coated with at least one modified release coat, at least one enteric coated dosage form, at least one dosage form surrounded by at least one osmotic subcoat, capsules, minitablets, caplets, uncoated microparticles, microparticles coated with at least one modified release coat, or any combination thereof.

The term "medicament" as used herein refers to oral and non-oral dosage forms, including but not limited to, all modified release dosage forms, osmosis controlled release systems, erosion controlled release systems, dissolution controlled release systems, diffusion controlled release systems, matrix tablets, enteric coated tablets, single and double coated tablets (including the extended release and enhanced absorption tablets as described herein), capsules, minitablets, caplets, coated beads, granules, spheroids, pellets, microparticles, suspensions, topicals such as transdermal and transmucosal compositions and delivery systems (containing or not containing matrices), injectables, and inhalable compositions.

"Modified release dosage forms" as used herein is defined (e.g. as by the United States Pharmacopoeia "USP") as those whose drug release characteristics of time course and/or location are chosen to accomplish therapeutic or convenience objectives not offered by conventional immediate release dosage forms. The rate of release of the active drug from a modified release dosage form is controlled by features of the dosage form and/or in combination with physiologic or environmental conditions rather than by physiologic or environmental conditions alone. The modified release dosage forms of certain embodiments can be contrasted with conventional immediate release dosage forms which typically produce large maximum/minimum plasma drug concentrations (Cmax/Cmin) due to rapid absorption of the drug into the body (i.e., in-vivo, relative to the drug's therapeutic index; i.e., the ratio of the maximum drug concentration needed to produce and maintain a desirable pharmacological response). In conventional immediate release dosage forms, the drug content is released into the gastrointestinal tract within a short period of time, and plasma drug levels peak shortly after dosing. The design of conventional immediate release dosage forms is generally based on getting the fastest possible rate of drug release, and therefore absorbed, often at the risk of creating undesirable dose related side effects. The modified release dosage forms of certain embodiments of the invention, on the other hand, improve the therapeutic value of the active drug by reducing the ratio of the maximum/minimum plasma drug concentration (Cmax/Cmin) while maintaining drug plasma levels within the therapeutic window. The modified release dosage forms of certain embodiments attempt to deliver therapeutically effective amounts of bupropion hydrobromide and mixtures of bupropion hydrobromide with at least one other drug as a once-daily dose so that the ratio Cmax/Cmin in the plasma at steady state is less than the therapeutic index, and to maintain drug levels at constant effective levels to provide a therapeutic benefit over a period of time (e.g. 24-hour period). The modified release dosage forms of certain embodiments of the invention, therefore, avoid large peak-to-trough fluctuations normally seen with conventional or immediate release dosage forms and can provide a substantially flat serum concentration curve throughout the therapeutic period. Modified-release dosage forms can be designed to provide a quick increase in the plasma concentration of the bupropion salt which remains substantially constant within the therapeutic range of bupropion salt for a period of time (e.g. 24-hour period). Alternatively, modified-release dosage forms can be designed to provide a quick increase in the plasma concentration of the drug, which although may not remain constant, declines at a rate such that the plasma concentration remains within the therapeutic range for a period of time (e.g. 24-hour period). The modified release dosage forms of certain embodiments of the invention can be constructed in many forms known to one of ordinary skill in the drug delivery arts and described in the prior art. The USP considers that the terms controlled release, prolonged release and sustained release are interchangeable. Accordingly, the terms "modified-release", controlled-release", "control-releasing", "rate-controlled release", "extended release", "prolonged-release", and "sustained-release" are used interchangeably herein. For the discussion herein, the definition of the term "modified-release" encompasses the scope of the definitions for the terms "extended release", "enhanced-absorption", "controlled release", "sustained release" and "delayed release".

"Controlled release dosage forms", "control-releasing dosage forms", "rate-controlled release dosage forms", or dosage forms which exhibit a "controlled release" of the bupropion hydrobromide or mixtures of bupropion hydrobromide and a second drug, as used herein are used interchangeably in this application and are defined to mean dosage forms which release the bupropion hydrobromide in a controlled manner per unit time in-vivo. For example, controlled release dosage forms can be administered once daily, and release the bupropion hydrobromide at a controlled rate and provide plasma concentrations of the drug that remain controlled with time within the therapeutic range of bupropion over a 24-hour period.

"Sustained-release dosage forms" or dosage forms which exhibit a "sustained-release" of bupropion hydrobromide or mixtures of bupropion hydrobromide and a second drug as used herein is defined to mean dosage forms administered at least once-daily that provide a release of bupropion hydrobromide sufficient to provide a therapeutic dose soon after administration, and then a gradual release over a period of time such that the sustained-release dosage form provides a therapeutic benefit over a period of time (e.g. a 12-hour or 24-hour period).

"Extended-release dosage forms" or dosage forms which exhibit an "extended release" of bupropion hydrobromide or mixtures of bupropion hydrobromide and a second drug as used herein is defined to mean dosage forms administered at least once-daily that release the bupropion hydrobromide slowly, so that plasma concentrations of the bupropion hydrobromide are maintained at a therapeutic level for an extended period of time such that the extended release dosage form provides therapeutic benefit over a period of time (e.g. 24-hour period).

"Delayed-release dosage forms" or dosage forms which exhibit a "delayed release" of bupropion hydrobromide or mixtures of bupropion hydrobromide and a second drug as used herein is defined to mean dosage forms administered at least once-daily that do not effectively release drug immediately following administration but at a later time. Delayed-release dosage forms provide a time delay prior to the commencement of drug-absorption. This time delay is referred to as "lag time" and should not be confused with "onset time" which represents latency, that is, the time required for the drug to reach minimum effective concentration.

"Enhanced absorption dosage forms" or dosage forms which exhibit an "enhanced absorption" of the active drug as used herein is defined to mean dosage forms that when exposed to like conditions, will show higher release and/or more absorption of the bupropion base as compared to other dosage forms with the same or higher amount of bupropion base. The same therapeutic effect can be achieved with less bupropion base in the enhanced absorption dosage form as compared to other dosage forms.

The term "microparticle", as used herein refers to a drug formulation in discrete particulate form, and is interchangeable with the terms "microspheres", "spherical particles", "microcapsules", "particles", "multiparticulates", "granules", "spheroids", beads" and "pellets".

The term "tablet" as used herein refers to a single dosage form, i.e. the single entity containing the active pharmaceutical agent that is administered to the subject. The term "tablet" also includes a tablet that may be the combination of one or more "minitablets".

The term "controlled release matrix" as used herein is defined to mean a dosage form in which the bupropion hydrobromide or mixtures of bupropion hydrobromide and a second drug, is dispersed within a matrix, which matrix can be either insoluble, soluble, or a combination thereof. Controlled release matrix dosage forms of the insoluble type are also referred to as "insoluble polymer matrices", "swellable matrices", or "lipid matrices" depending on the components that make up the matrix. Controlled release matrix dosage forms of the soluble type are also referred to as "hydrophilic colloid matrices", "erodible matrices", or "reservoir systems". Controlled release matrix dosage forms of the invention refer to dosage forms comprising an insoluble matrix, a soluble matrix or a combination of insoluble and soluble matrices in which the rate of release is slower than that of an uncoated non-matrix conventional or immediate release dosage forms or uncoated "normal release matrix" dosage forms. Controlled release matrix dosage forms can be coated with a "control-releasing coat" to further slow the release of the bupropion salt from the controlled release matrix dosage form. Such coated controlled release matrix dosage forms can exhibit "modified-release", controlled-release", "sustained-release", "extended-release", "prolonged-release", "delayed-release" or combinations thereof of the active drug.

The term "normal release matrix" as used herein is defined to mean dosage forms in which the bupropion hydrobromide or mixtures of bupropion hydrobromide and a second drug, is dispersed within a matrix, which matrix can be either insoluble, soluble, or combinations thereof but constructed such that the release of the active drug mimics the release rate of an uncoated non-matrix conventional or immediate release dosage form comprising the drug. The release rate from normal release matrix dosage forms can be slowed down or modified in conjunction with a controlled release coat.

The terms "osmotic dosage form", "osmotic delivery device", "modified release osmotic dosage form" or "controlled release osmotic dosage form" as used herein are used interchangeably in this application, and are defined to mean dosage forms which dispense the bupropion hydrobromide or mixture of bupropion hydrobromide and a second drug, all or in part as a result of the presence of an osmotic agent in the dosage form driving solvent (e.g. water, dissolution media, gastric fluid, intestinal fluid, or mixtures thereof) into the core of the dosage form, which subsequently facilitates the release of drug from the core.

The terms "osmotic agent", "osmagent", "osmotically effective solute", "osmotic enhancer" "osmotically effective compounds", "osmotic solutes", "osmopolymer" and "osmotic fluid imbibing agents" as used herein are used interchangeably, and define any material that is soluble (i.e. can be partially or totally solubilized) or swellable in a solvent (e.g. water) that enters the composition, and which exhibits an osmotic pressure gradient across the selectively-permeable membrane (e.g. controlled release coat), thus increasing the hydrostatic pressure inside the osmotic dosage form.

The terms "controlled release coat", "control releasing coat", "modified release coat" and "rate-controlling coat" as used herein are used interchangeably in this application, and are defined to mean a functional coat which comprises at least one modified release polymer. Non-limiting examples of modified release polymers include pH independent polymers, pH dependent polymers (such as for example enteric or reverse enteric types), soluble polymers, insoluble polymers, lipids, lipidic materials, and mixtures thereof. When applied onto a dosage form, the controlled release coat can modify (e.g. slow) the rate of release of the active drug. For example, the controlled release coat can be designed such that when the coat is applied onto a dosage form, the dosage form in conjunction with the controlled release coat, exhibits a "modified-release", "controlled-release", "sustained-release", "extended-release" and/or "delayed-release" profile. Combinations thereof are permissible. The controlled release coat can optionally comprise additional materials that can alter the functionality of the controlled release coat. The term "modified release" is interchangeable with the terms "controlled release", "control releasing" and "rate controlling". The term "coat" is interchangeable with the term "coating".

The terms "moisture barrier" and "moisture barrier coat" as used herein are used interchangeably and are defined to mean a coating which impedes or retards the absorption of moisture. It is known that bupropion salts are hygroscopic and, as such, are susceptible to decomposition over time under high humidity conditions. Other active drugs can also be susceptible to decomposition over time under high humidity conditions. The proportion of the components of the moisture barrier and the amount of the moisture barrier applied onto the controlled release coat is such that the moisture barrier does not fall within the USP definition and requirement for an enteric coat. Suitably, the moisture barrier is comprised of an enteric and/or acrylic polymer, suitably an acrylic polymer, optionally a plasticizer, and a permeation enhancer. The permeation enhancer is a hydrophilic substance, which allows water to enter without physical disruption of the coating. The moisture barrier can additionally contain other conventional inert excipients, which can improve processing of the extended-release formulation described herein.

The term "enteric coat" as used herein is defined to mean a coating or barrier applied to a dosage form that can control the location in the digestive system where the active drug(s) is absorbed. For example, an enteric coating can be used to: (i) protect the drug from the destructive action of the enzymes or low pH environment of the stomach; (ii) prevent nausea or bleeding associated with the irritation of the gastric mucosa by the drug; and/or (iii) deliver the drug in an undiluted form in the intestine. Based on these criteria, in certain embodiments, the enteric coated dosage form can be regarded as a type of delayed release dosage form. They differ from sustained release dosage forms in that with sustained release dosage forms, the drug release is extended over a period of time to maintain therapeutic blood levels and to decrease the incidence of side effects caused by a rapid release; whereas, with enteric coatings, the primary objective is to confine the release of the drug to a predetermined region of the gastrointestinal tract. Enteric coatings work by presenting a surface that is substantially stable at acidic pH, but breaks down at higher pH to allow release of the drug in the intestine.

The term "enteric polymer" as used herein is defined to mean a polymeric substance that when used in an enteric coat formulation, is substantially insoluble and/or substantially stable under acidic conditions exhibiting a pH of less than about 5 and which are substantially soluble or can decompose under conditions exhibiting a pH of about 5 or more. Non-limiting examples of such enteric polymers include carboxymethylethylcellulose, cellulose acetate phthalate, cellulose acetate succinate, methylcellulose phthalate, hydroxymethylethylcellulose phthalate, hydroxypropylmethylcellulose phthalate, hydroxypropylmethylcellulose acetate succinate, polyvinyl alcohol phthalate, polyvinyl butyrate phthalate, polyvinyl acetal phthalate, a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate and mixtures thereof. Enteric polymers can be used individually or in combination with other hydrophobic or hydrophilic polymers in an enteric coat, a normal release matrix core, a controlled release matrix core, and/or in a controlled release coat. Enteric polymers can be combined with other pharmaceutically acceptable excipients to either facilitate processing of a coat comprising the enteric polymer or to alter the functionality of the coat.

The term "functional coat" as used herein is defined to mean a coating that affects the rate of release in-vitro or in-vivo of the active drug(s).

The term "non-functional coat" as used herein is defined to mean a coating that does not substantially affect the rate of release in-vitro or in-vivo of the active drug, but can enhance the chemical, biological, physical stability characteristics, or the physical appearance of the modified release dosage form.

The term "core" as used herein is defined to mean a solid vehicle in which at least one active drug is uniformly or non-uniformly dispersed. The core can be formed by methods and materials well known in the art, such as for example by compressing, fusing, or extruding the active drug together with at least one pharmaceutically acceptable excipient. The core can be manufactured into, for example, a homogenous or non-homogenous unitary core, a multiparticle, or a plurality of microparticles compressed into a unitary core. Non-limiting examples of cores include microparticle cores, matrix cores, and osmotic cores. The core(s) can be coated with at least one functional coat and/or non-functional coat.

The terms "modified release matrix core", "controlled release matrix core" or "matrix core" when referring to a controlled release matrix dosage form, as used herein are used interchangeably, and are defined to mean a core in which at least one active drug is dispersed within a matrix which controls or delays the release of the active drug over a 24-hour period so as to allow a composition comprising the modified release matrix core to be administered as a once-a-day composition. The release rate of the active drug from the modified release matrix core can be modified by the porosity and tortuosity of the matrix, (i.e. its pore structure). The addition of pore-forming hydrophilic salts, solutes, or wicking agents can influence the release rate, as can the manipulation of processing parameters. For example, the compression force used in the manufacture of the modified release matrix core can alter the porosity of the matrix core and hence the rate of release of the active drug. It will be understood by one of ordinary skill in the art of drug delivery that a more rigid matrix will be less porous and hence release the active drug more slowly compared to a less rigid modified release matrix core. The modified release matrix core can comprise insoluble or inert matrix dosage forms, swellable matrix dosage forms, swellable and erodible matrix dosage form, hydrophobic matrix dosage forms, hydrophilic matrix dosage forms, erodible matrix dosage forms, reservoir dosage forms, or any combination thereof. The modified release matrix core can comprise at least one insoluble matrix, at least one swellable matrix, at least one swellable and erodible matrix, at least one hydrophobic matrix, at least one hydrophilic matrix, at least one erodible matrix, or a combination thereof in which the rate of release is slower than that of uncoated immediate-release dosage forms. Modified release matrix cores can be coated with at least one controlled release coat to further slow the release of the active drug from the modified release matrix core. Such coated modified release matrix cores can exhibit modified-release, controlled-release, sustained-release, extended-release, prolonged-release, bi-phasic release, delayed-release or combinations thereof of the active drug. Modified release matrix cores can also be coated with a non-functional soluble coat.

The term "plasticizer" as used herein includes any compounds capable of plasticizing or softening a polymer or a binder used in the present invention. The use of plasticizers is optional, and can be included in the dosage form to modify the properties and characteristics of the polymers used in the coat(s) or core of the dosage form for convenient processing during manufacture of the coat(s) and/or the core of the dosage form. Once the coat(s) and/or core have been manufactured, certain plasticizers can function to increase the hydrophilicity of the coat(s) and/or the core of the dosage form in the environment of use. During manufacture of the coat(s) and/or core, the plasticizer can lower the melting temperature or glass transition temperature (softening point temperature) of the polymer or binder. Plasticizers can be included with a polymer and lower its glass transition temperature or softening point. Plasticizers also can reduce the viscosity of a polymer. Plasticizers can impart some particularly advantageous physical properties to the dosage forms of the invention.

The terms "pore former", "pore forming agent", and "pore forming additive" as used herein are used interchangeably in this application, and are defined to mean an excipient that can be added to a coating (e.g. the controlled release coat), wherein upon exposure to fluids in the environment of use, the pore former dissolves or leaches from the coating to form pores, channels or paths in the coating, that can fill with the environmental fluid and allow the fluid to enter the core and dissolve the active drug, and modify the release characteristics of the formulation. The pore formers can be inorganic or organic, and include materials that can be dissolved, extracted or leached from the coating in the environment of use.

The term "steady state" as used herein means that the blood plasma concentration curve for a given drug does not substantially fluctuate after repeated doses to dose of the formulation.

"AUC" as used herein means area under the plasma concentration-time curve, as calculated by the trapezoidal rule over a time interval (e.g. complete 24-hour interval); and signifies the extent of the absorption of a drug.

"Cmax" as used herein means the highest plasma concentration of the drug attained within the dosing interval (e.g., 24 hours).

"Cmin" as used herein means the minimum plasma concentration of the drug attained within the dosing interval (e.g. 24 hours).

"Cavg" as used herein means the plasma concentration of the drug within the dosing interval (e.g. 24-hours), and is calculated as AUC/dosing interval.

"Tmax" as used herein means the time period which elapses after administration of the dosage form at which the plasma concentration of the drug attains the highest plasma concentration of drug attained within the dosing interval (e.g. 24 hours).

The term "bioequivalence" as used herein is defined as there being about a 90% or greater probability that the bioavailability (AUC) of the active drug as determined by standard methods is from about 80% to about 125% of the second orally administrable dosage form comprising the same dose of the active drug and that there is about 90% or greater probability that the maximum blood plasma concentration (Cmax) of the active drug as measured by standard methods is from about 80% to about 125% of the second orally administrable dosage form. For example, the reader is referred to the final version of the guidance approved by the US Food and Drug Administration at the time of filing of this patent application i.e., the March 2003 Guidance for Industry Bioavailability and Bioequivalence Studies for Orally Administered Drug Products General Considerations, U.S. Department of Health and Human Services, Food and Drug Administration, Center for Drug Evaluation and Research (CDER), for a detailed discussion on bioequivalence.

The terms "a", "an" or "at least one" as used herein are used interchangeably in this application, and are defined to mean "one" or "one or more".

The numerical parameters set forth in the following specification and attached claims that are modified by the term "about", are approximations that can vary depending upon the technological properties of the particular case. For example, the term "about" can mean within an acceptable error range (e.g. standard deviations) for the particular value as determined by one of ordinary skill in the art, which will depend in part on how the value is measured or determined, e.g., the limitations of the measurement system.

Other terms are defined as they appear in the following description and should be construed in the context with which they appear.

The present invention encompasses the bupropion hydrobromide salt and polymorphs of bupropion hydrobromide, and compositions containing safe and pharmaceutically effective levels of the bupropion hydrobromide salt and/or polymorph of bupropion hydrobromide, that can be used for the treatment of a condition in subjects that can benefit from bupropion administration, wherein the bupropion hydrobromide salt and compositions containing safe and pharmaceutically effective levels of the bupropion hydrobromide salt unexpectedly provide for the reduction of incidences of and/or the reduction in severity of bupropion-induced seizures, and are more stable, as compared with equivalent molar amounts of bupropion hydrochloride or otherwise similar or identical compositions containing equivalent molar amounts of bupropion hydrochloride. Results are described for example in U.S. Pat. No. 7,241,805, and U.S. patent application Ser. No. 11/834,848 (Pub. No. 2008-0075774), the contents of which are incorporated herein by reference.

Also, the present invention encompasses polymorphs thereof and specific purified enantiomeric forms thereof. The present invention also encompasses the use of such bupropion hydrobromide salt and compositions containing the bupropion hydrobromide salt for the treatment of one or more conditions in a subject suitable for treatment by bupropion or pharmaceutically acceptable salts thereof (e.g. depression, obesity, nicotine addiction, and other conditions treatable with bupropion such as are disclosed herein); wherein the incidences of and/or the severity of bupropion-induced seizures is reduced as compared with an equivalent molar amount of bupropion hydrochloride or an otherwise similar or identical composition containing an equivalent molar amount of bupropion hydrochloride.

The present invention encompasses any medicament containing a pharmaceutically effective amount of bupropion hydrobromide and/or a polymorph of bupropion hydrobromide. This includes both oral and non-orally administrable medicaments such as topicals, injectables, aerosols and other inhalable medicaments. Particularly such medicament compositions include orally administrable modified release dosage forms containing bupropion hydrobromide. The dosages can be conveniently presented in unit dosage form and prepared by any of the methods well-known in the art of pharmacy. A "solid dosage form" as used herein, means a dosage form that is neither liquid nor gaseous. Dosage forms include solid dosage forms, such as tablets, powders, microparticles, capsules, suppositories, sachets, troches, patches and lozenges as well as liquid suspensions and elixirs. Capsule dosages contain the solid composition within a capsule that can be made of gelatin or other conventional encapsulating material.

The modified release dosage forms contemplated in the present invention can be multiparticulate or monolithic. For example, those skilled in the pharmaceutical art and the design of medicaments are aware of modified release matrices conventionally used in oral pharmaceutical compositions adopted for modified release and means for their preparation.

A modified release formulation containing bupropion hydrobromide and/or a polymorph of bupropion hydrobromide according to the present invention can be coated with one or more functional or non-functional coatings. Non-limiting examples of functional coatings include controlled release polymeric coatings, moisture barrier coatings, enteric polymeric coatings, and the like. In at least one embodiment of the present invention a bupropion hydrobromide composition comprises a controlled release polymeric coating that includes an acrylic polymer. Suitable acrylic polymers include but are not limited to acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid) (anhydride), polyacrylamide, poly(methacrylic acid anhydride), glycidyl methacrylate copolymers and mixtures thereof.

In at least one embodiment polymerizable quaternary ammonium compounds are employed in the controlled release coat, of which non-limiting examples include quaternized aminoalkyl esters and aminoalkyl amides of acrylic acid and methacrylic acid, for example β-methacryl-oxyethyl-trimethyl-ammonium methosulfate, β-acryloxy-propyl-trimethyl-ammonium chloride, trimethylaminomethyl-methacrylamide methosulfate and mixtures thereof. The quaternary ammonium atom can also be part of a heterocycle, as in methacryloxyethylmethyl-morpholiniom chloride or the corresponding piperidinium salt, or it can be joined to an acrylic acid group or a methacrylic acid group by way of a group containing hetero atoms, such as a polyglycol ether group. Further suitable polymerizable quaternary ammonium compounds include quaternized vinyl-substituted nitrogen heterocycles such as methyl-vinyl pyridinium salts, vinyl esters of quaternized amino carboxylic acids, styryltrialkyl ammonium salts, and mixtures thereof. Other polymerizable quaternary ammonium compounds useful in the present invention include acryl- and methacryl-oxyethyltrimethyl-ammonium chloride and methosulfate, benzyldimethylammoniumethyl-methacrylate chloride, diethylmethylammoniumethyl-acrylate and -methacrylate methosulfate, N-trimethylammoniumpropylmethacrylamide chloride, N-trimethylammonium-2,2-dimethylpropyl-1-methacrylate chloride and mixtures thereof.

In at least one embodiment the acrylic polymer of the controlled release coat is comprised of one or more ammonio methacrylate copolymers. Ammonio methacrylate copolymers (e.g. EUDRAGIT® RS and RL) are described in National Formulary (NF) XVII as fully polymerized copolymers of acrylic and methacrylic acid esters with a low content of quaternary ammonium groups. Two or more ammonio methacrylate copolymers having differing physical properties can be incorporated in the controlled release coat of certain embodiments. For example, it is known that by changing the molar ratio of the quaternary ammonium groups to the neutral (meth)acrylic esters, the permeability properties of the resultant coating can be modified.

In certain other embodiments of the present invention, the controlled release coat further includes a polymer whose permeability is pH dependent, such as anionic polymers synthesized from methacrylic acid and methacrylic acid methyl ester (e.g. EUDRAGIT® L and EUDRAGIT® S). The ratio of free carboxyl groups to the esters is known to be 1:1 in EUDRAGIT® L and 1:2 in EUDRAGIT® S. EUDRAGIT® L is insoluble in acids and pure water, but becomes increasingly permeable above pH 5.0. EUDRAGIT® S is similar, except that it becomes increasingly permeable above pH 7. The hydrophobic acrylic polymer coatings can also include a polymer which is cationic in character based on dimethylaminoethyl methacrylate and neutral methacrylic acid esters (e.g. EUDRAGIT® E). The hydrophobic acrylic polymer coatings of certain embodiments of the present invention can further include a neutral copolymer based on poly(meth)acrylates, such as EUDRAGIT® NE. EUDRAGIT® NE 30D lacquer films are insoluble in water and digestive fluids, but permeable and swellable.

In at least one other embodiment of the invention, the controlled release coat comprises a dispersion of poly(ethylacrylate, methyl methacrylate) 2:1 (KOLLICOAT® EMM 30 D).

In at least one other embodiment of the invention, the controlled release coat comprises a polyvinyl acetate stabilized with polyvinylpyrrolidone and sodium lauryl sulfate such as KOLLICOAT® SR30D. The dissolution profile can be altered by changing the relative amounts of different acrylic resin lacquers included in the coating. Also, by changing the molar ratio of polymerizable permeability-enhancing agent (e.g., the quaternary ammonium compounds) to the neutral (meth)acrylic esters, the permeability properties (and thus the dissolution profile) of the resultant coating can be modified.

In at least one embodiment of the invention the controlled release coat comprises ethylcellulose, which can be used as a dry polymer (e.g. ETHOCEL®) solubilised in organic solvent prior to use, or as an aqueous dispersion. One suitable commercially-available aqueous dispersion of ethylcellulose is AQUACOAT®. AQUACOAT® can be prepared by dissolving the ethylcellulose in a water-immiscible organic solvent and then emulsifying the same in water in the presence of a surfactant and a stabilizer. After homogenization to generate submicron droplets, the organic solvent can be evaporated under vacuum to form a pseudolatex. The plasticizer is not incorporated in the pseudolatex during the manufacturing phase. Thus, prior to using the same as a coating, the AQUACOAT® can be intimately mixed with a suitable plasticizer prior to use. Another suitable aqueous dispersion of ethylcellulose is commercially available as SURELEASE®. This product can be prepared by incorporating plasticizer into the dispersion during the manufacturing process. A hot melt of a polymer, plasticizer (e.g. dibutyl sebacate), and stabilizer (e.g. oleic acid) can be prepared as a homogeneous mixture, which can then be diluted with an alkaline solution to obtain an aqueous dispersion which can be applied directly onto substrates.

Other examples of polymers that can be used in the controlled release coat include cellulose acetate phthalate, cellulose acetate trimaletate, hydroxy propyl methylcellulose phthalate, polyvinyl acetate phthalate, polyvinyl alcohol phthalate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, ethyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, pullulan, collagen, casein, agar, gum arabic, sodium carboxymethyl cellulose, (swellable hydrophilic polymers) poly(hydroxyalkyl methacrylate) (molecular weight from about 5 k to about 5000 k), polyvinylpyrrolidone (molecular weight from about 10 k to about 360 k), anionic and cationic hydrogels, zein, polyamides, polyvinyl alcohol having a low acetate residual, a swellable mixture of agar and carboxymethyl cellulose, copolymers of maleic anhydride and styrene, ethylene, propylene or isobutylene, pectin (molecular weight from about 30 k to about 300 k), polysaccharides such as agar, acacia, karaya, tragacanth, algins and guar, polyacrylamides, POLYOX® polyethylene oxides (molecular weight from about 100 k to about 5000 k), AQUAKEEP® acrylate polymers, diesters of polyglucan, crosslinked polyvinyl alcohol and poly N-vinyl-2-pyrrolidone, hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, methyl ethyl cellulose, ethylhydroxy ethylcellulose, cellulose acetate, cellulose butyrate, cellulose propionate, gelatin, starch, maltodextrin, pullulan, polyvinyl pyrrolidone, polyvinyl alcohol, polyvinyl acetate, glycerol fatty acid esters, polyacrylamide, polyacrylic acid, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures thereof.

In at least one embodiment the dosage forms are coated with polymers in order to facilitate mucoadhesion within the gastrointestinal tract. Non-limiting examples of polymers that can be used for mucoadhesion include carboxymethylcellulose, polyacrylic acid, CARBOPOL™, POLYCARBOPHIL™, gelatin, other natural or synthetic polymers, and mixtures thereof.

In at least one embodiment of the invention, the dosage form is an extended release tablet comprising: (i) a core that includes bupropion hydrobromide or a polymorph of bupropion hydrobromide in an amount of from about 40% to about 99% by weight of tablet dry weight, including all values and ranges therebetween, a binder such as polyvinyl alcohol in an amount of from about 0.5% to about 25% by weight of tablet dry weight, including all values and ranges therebetween, and a lubricant such as glyceryl behenate in an amount of from about 0.1% to about 5% by weight of tablet dry weight, including all values and ranges therebetween; and (ii) a controlled release coat that includes a water-insoluble water-permeable film-forming polymer such as ethylcellulose in an amount of from about 1% to about 12% by weight of tablet dry weight, including all values and ranges therebetween, a water-soluble polymer such as polyvinylpyrrolidone (POVIDONE® USP) in an amount of from about 1.5% to about 10% by weight of tablet dry weight, including all values and ranges therebetween, optionally a plasticizer such as dibutyl sebacate, polyethylene glycol 4000 or a mixture thereof, in an amount of from about 0.5% to about 4% by weight of tablet dry weight, including all values and ranges therebetween, and optionally a wax such as carnauba wax in an amount of from about 0.01% to about 0.05% by weight of tablet dry weight, including all values and ranges therebetween.

In at least one embodiment of the invention, the dosage form is a 174 mg extended release tablet comprising: (i) a core that includes bupropion hydrobromide or a polymorph of bupropion hydrobromide (e.g. about 81% by weight of tablet dry weight), a binder such as polyvinyl alcohol (e.g. about 3% by weight of tablet dry weight), and a lubricant such as glyceryl behenate (e.g. about 3% by weight of tablet dry weight); and (ii) a controlled release coat that includes a water-insoluble water-permeable film-forming polymer such as ethylcellulose (e.g. about 7% by weight of tablet dry weight), a water-soluble polymer such as polyvinylpyrrolidone (POVIDONE® USP), (e.g. about 4% by weight of tablet dry weight), optionally a plasticizer such as dibutyl sebacate, polyethylene glycol 4000 or a mixture thereof (e.g. about 2% by weight of tablet dry weight), and optionally a wax such as carnauba wax (e.g. about 0.03% by weight of tablet dry weight).

In at least one embodiment of the invention, the dosage form is a 348 mg extended release tablet comprising: (i) a core that includes bupropion hydrobromide or a polymorph of bupropion hydrobromide (e.g. about 87% by weight of tablet dry weight), a binder such as polyvinyl alcohol (e.g. about 3% by weight of tablet dry weight), and a lubricant such as glyceryl behenate (e.g. about 3% by weight of tablet dry weight); and (ii) a controlled release coat that includes a water-insoluble water-permeable film-forming polymer such as ethylcellulose (e.g. about 4% by weight of tablet dry weight), a water-soluble polymer such as polyvinylpyrrolidone (POVIDONE® USP), (e.g. about 2% by weight of tablet dry weight), optionally a plasticizer such as dibutyl sebacate, polyethylene glycol 4000 or a mixture thereof (e.g. about 1% by weight of tablet dry weight), and optionally a wax such as carnauba wax (e.g. about 0.01% by weight of tablet dry weight).

In at least one embodiment of the invention, the dosage form is a 522 mg XL tablet comprising: (i) a core that includes bupropion hydrobromide or a polymorph of bupropion hydrobromide (e.g. about 85% by weight of tablet dry weight), a binder such as polyvinyl alcohol (e.g. about 3.5% by weight of tablet dry weight), and a lubricant such as glyceryl behenate (e.g. about 3.5% by weight of tablet dry weight); and (ii) a controlled release coat that includes a water-insoluble water-permeable film-forming polymer such as ethylcellulose (e.g. about 3% by weight of tablet dry weight), a water-soluble polymer such as polyvinylpyrrolidone (POVIDONE® USP), (e.g. about 3.5% by weight of tablet dry weight), optionally a plasticizer such as dibutyl sebacate, polyethylene glycol 4000 or a mixture thereof (e.g. about 1.5% by weight of tablet dry weight), and optionally a wax such as carnauba wax (e.g. about 0.01% by weight of tablet dry weight).

In at least one embodiment a modified release pharmaceutical composition releases bupropion hydrobromide or a polymorph of bupropion hydrobromide in a first dissolution medium consisting of 0.1 N HCl and 5%-40% v/v ethanol at a rate that is less than or equal to about 1.1 times the rate of release of bupropion hydrobromide or a polymorph of bupropion hydrobromide from an identical modified release pharmaceutical composition in a second dissolution medium consisting of 0.1 N HCl measured over the time period of at least from 0 to 2 hours. In certain embodiments the term "less than or equal to about 1.1" includes values below 1.1, such as 1.05, 1.00, 0.95, 0.90, 0.85, 0.80, etc, including all values and subranges between about 1.1 and about 0, but preferably does not equal 0, and more preferably is 0.5-1.1, more preferably 0.75-1.1, even more preferably 0.8-1.0. These measurements are preferably made using a USP Apparatus I at 75 rpm and at 37±0.5° C. In certain embodiments the modified release pharmaceutical composition is placed in 900 ml of dissolution medium for the measurement. In other embodiments the value of "about 1.1" includes values immediately above 1.1, such as 1.30, 1.29, 1.28, 1.27, 1.26, 1.25, 1.24, 1.23, 1.22, 1.21, 1.20, 1.19, 1.18, 1.17, 1.16, 1.15, 1.14, 1.13, 1.12, 1.11, etc, including all values and subranges therebetween. The results is are described in greater detail in U.S. patent application Ser. No. 11/930,644 (Pub. No. 2008-0274181), the contents of which are incorporated herein by reference.

In addition to the modified release dosage forms described herein, other modified release technologies known to those skilled in the art can be used in order to achieve the modified release formulations of certain embodiments of the present invention. Such formulations can be manufactured as a modified release oral formulation, for example, in a suitable tablet or multiparticulate formulation known to those skilled in the art. In either case, the modified release dosage form can optionally include a controlled release carrier which is incorporated into a matrix along with the drug, or which is applied as a controlled release coating.

Polymorphic Forms I, II and III

It is well known that organic molecules can crystallize into solid forms. Moreover the same organic compound may assume different crystalline arrangements in solid form, depending on the conditions under which the crystal product is formed. This phenomenon is commonly known as polymorphism. A number of studies were undertaken to explore the polymorphic forms of bupropion hydrobromide. The crystal forms of the products obtained in the studies were determined by powder X-ray diffraction (PXRD). A RIGAKU miniflex instrument (Radiation Cu K∝c, generator 30 KV, filter Ni) was used to obtain the PXRD data.

Figure 22:
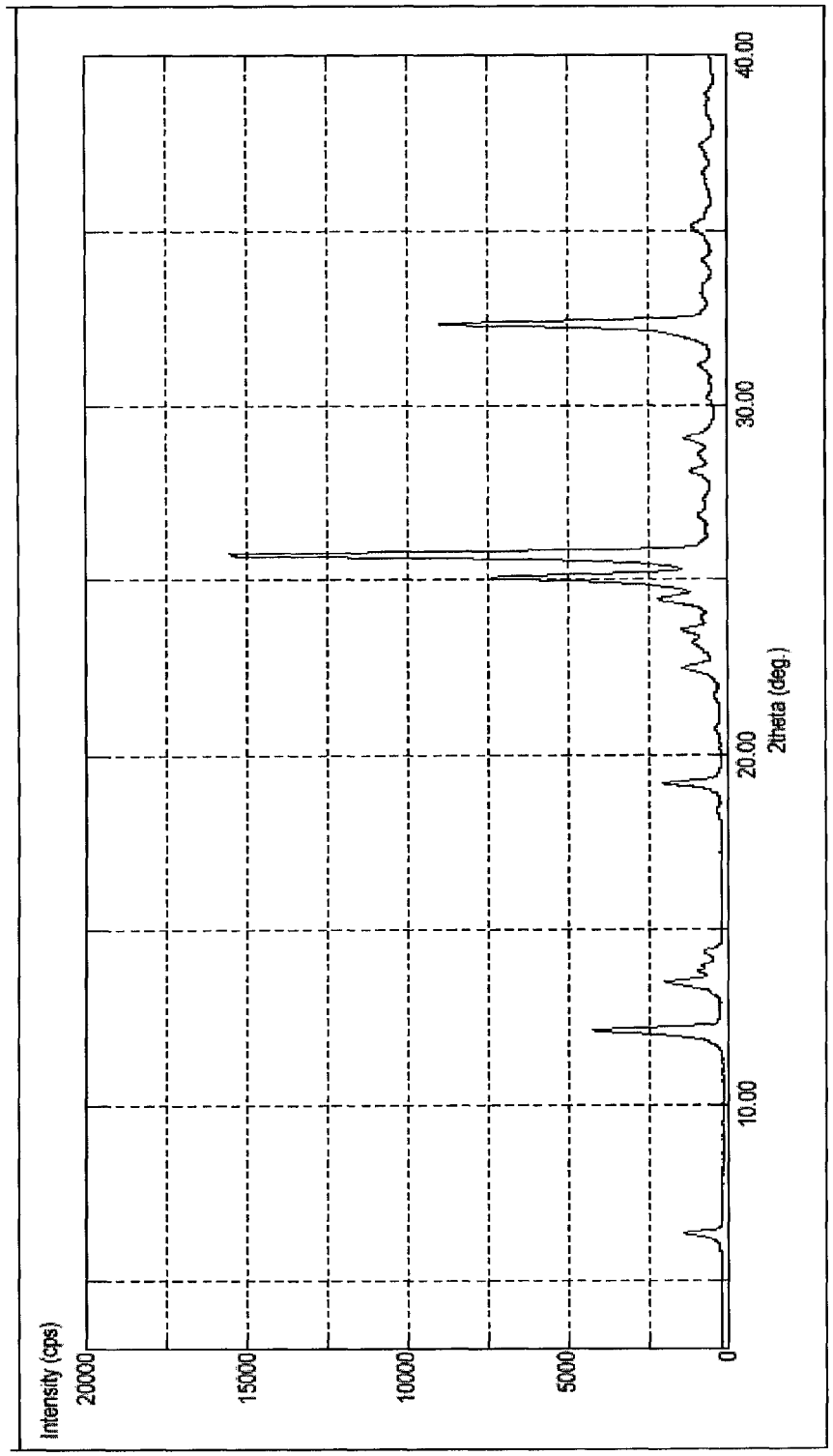
FIG. 22 is a graph showing the relative powder X-ray diffraction (PXRD) for bupropion hydrobromide polymorphic form I.
Figure 23:
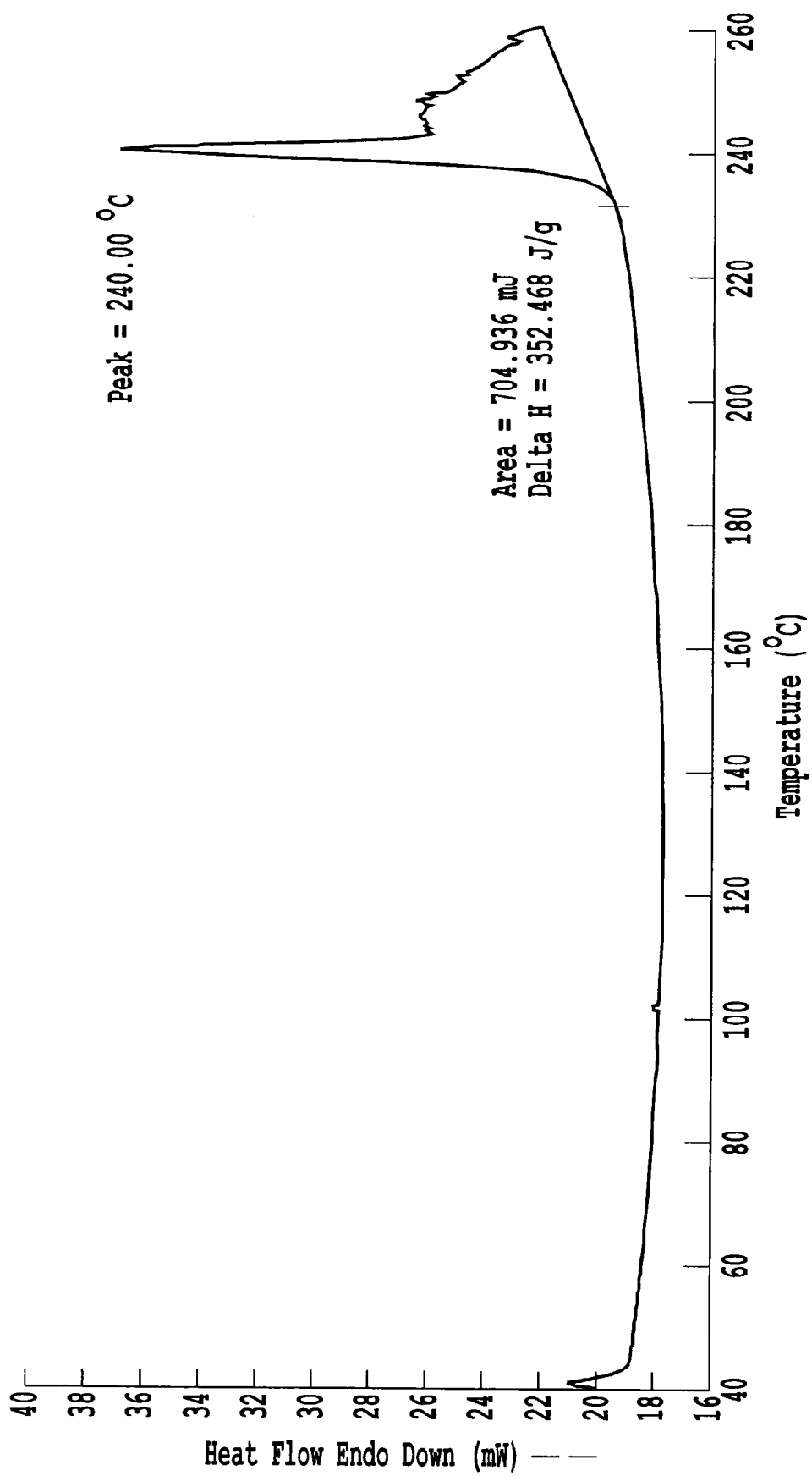
FIG. 23 is a graph showing the differential scanning calorimetry (DSC) profile of bupropion hydrobromide polymorphic form I.
Figure 24:
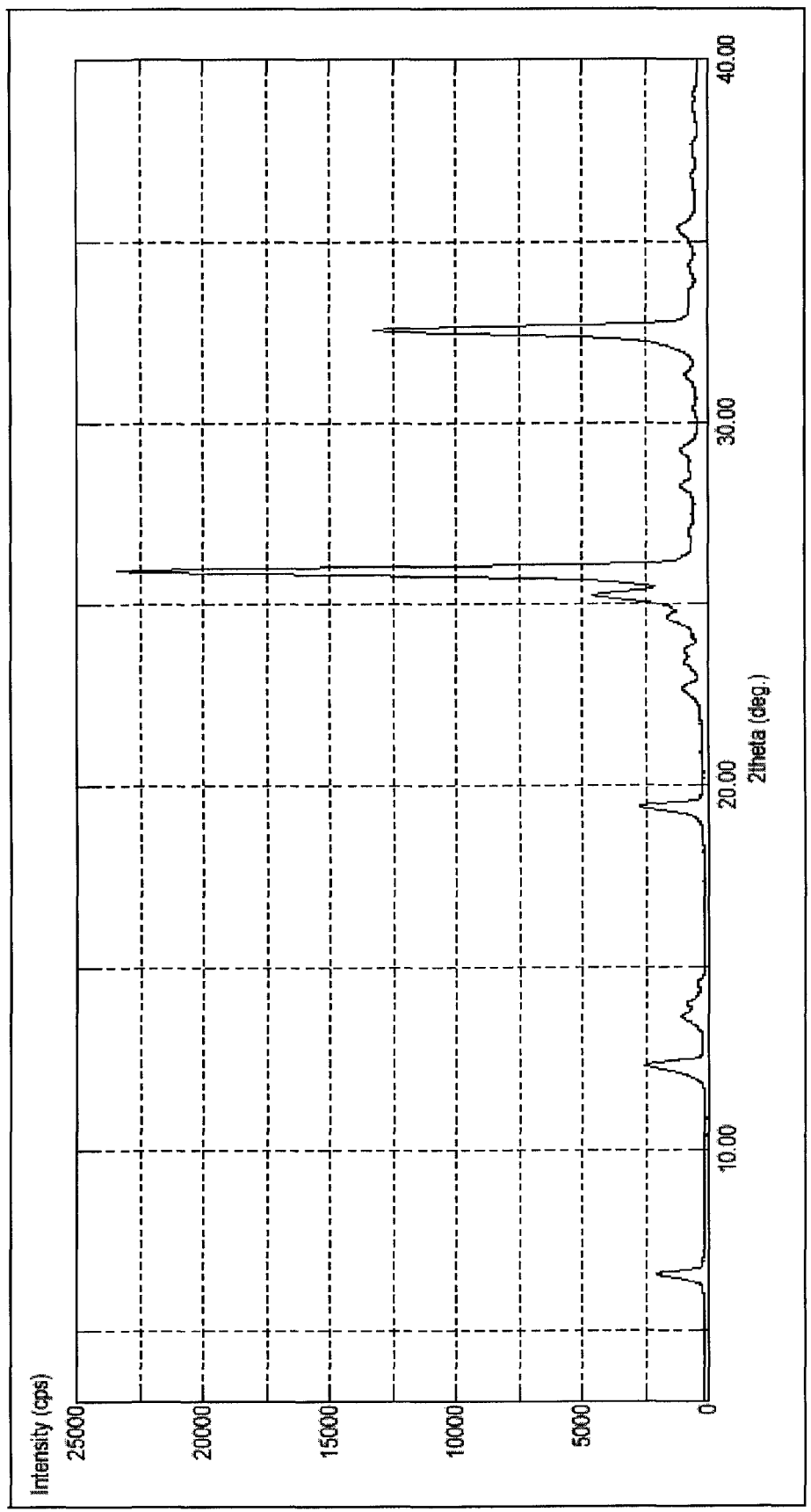
FIG. 24 is a graph of the relative PXRD of a sample of bupropion hydrobromide polymorphic form I after 6 months under the ICH (International Conference on Harmonisation of Technical Requirements for Registration of Pharmaceuticals for Human Use) conditions (40.degree. C., 75% R.H.).

A standard procedure was established to generate bupropion hydrobromide, this standard procedure produces a first polymorphic form which has been termed polymorphic form I. The relative PXRD for Form I is shown in FIG. 22. The differential scanning calorimetry (DSC) profile for Form I is shown in FIG. 23. This procedure was scaled up and generated three industrial batches. The material obtained from the three industrial batches consistently gave the same PXRD profile of crystalline form I. Samples of these batches of form I were tested for accelerated stability at 3 and 6 months under ICH conditions (40° C., 75% R.H.). All the three batches gave exactly the same PXRD after 3 and 6 months of stability testing. The PXRD profile of one of the three batches of form I after 6 months stability testing is shown in FIG. 24. The complete survey of the stability data is reported in Table 39.

Figure 25:
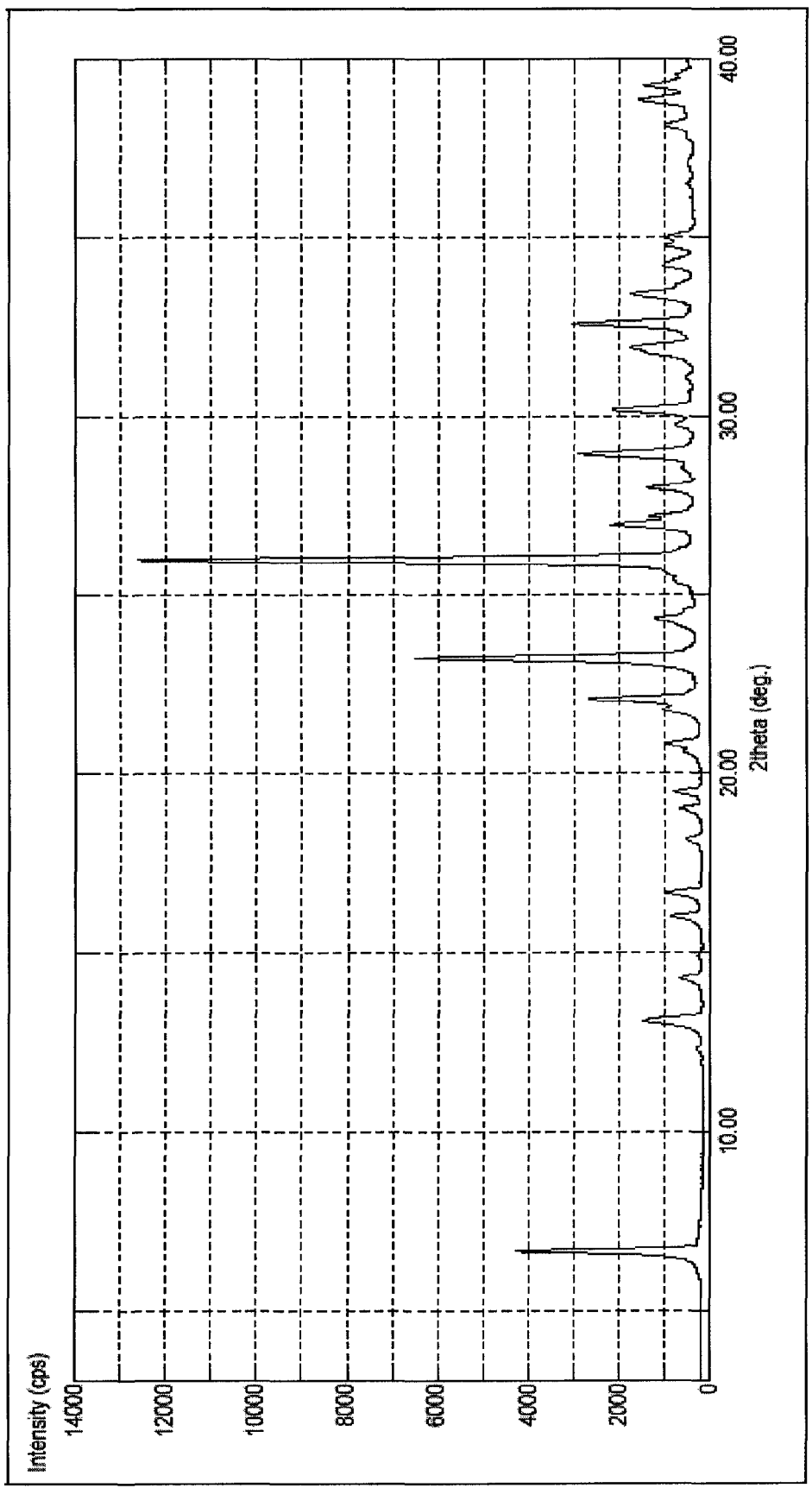
FIG. 25 is a graph showing the relative PXRD for bupropion hydrobromide polymorphic form II.
Figure 26:
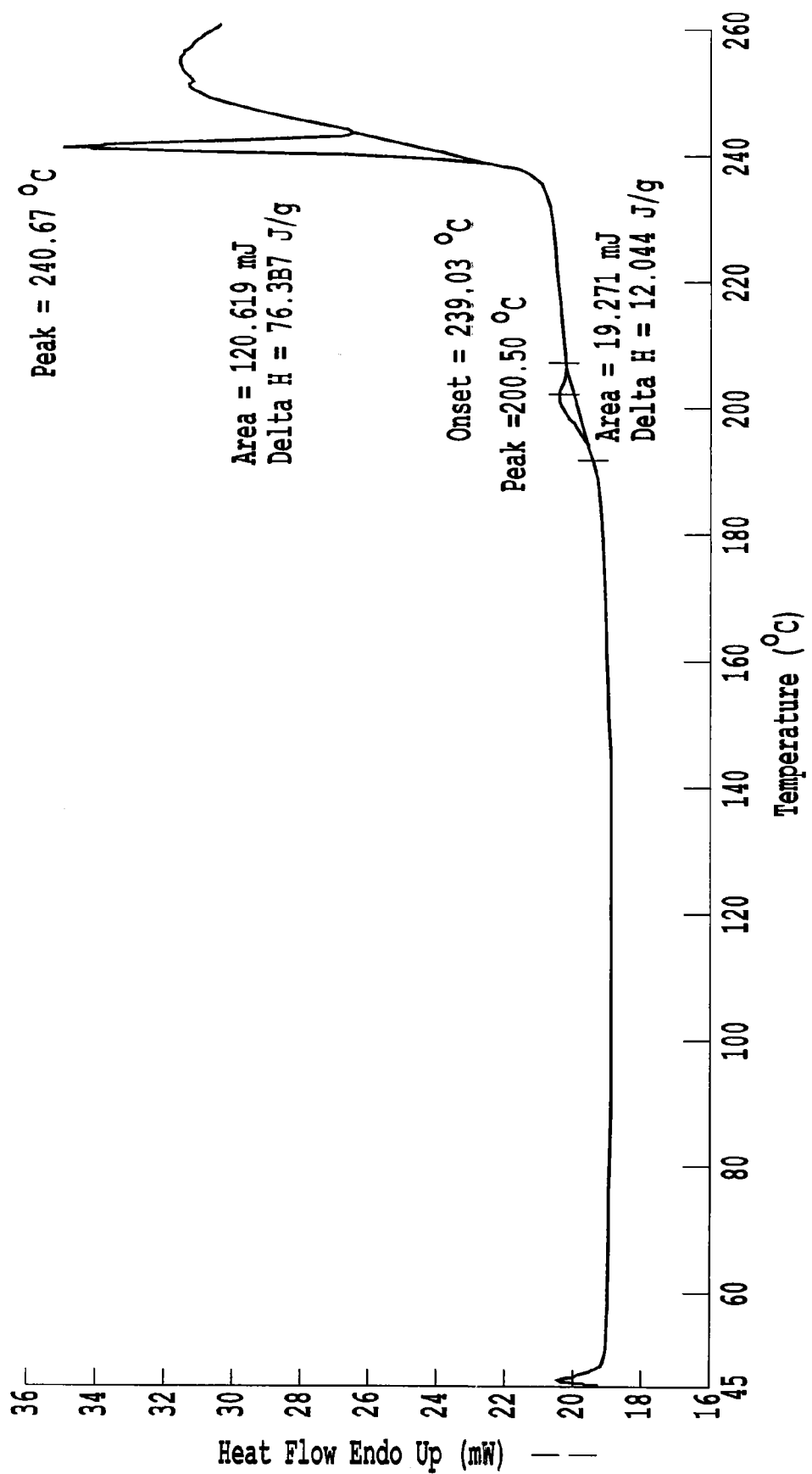
FIG. 26 is a graph showing the DSC profile of bupropion hydrobromide polymorphic form II.
Figure 27:
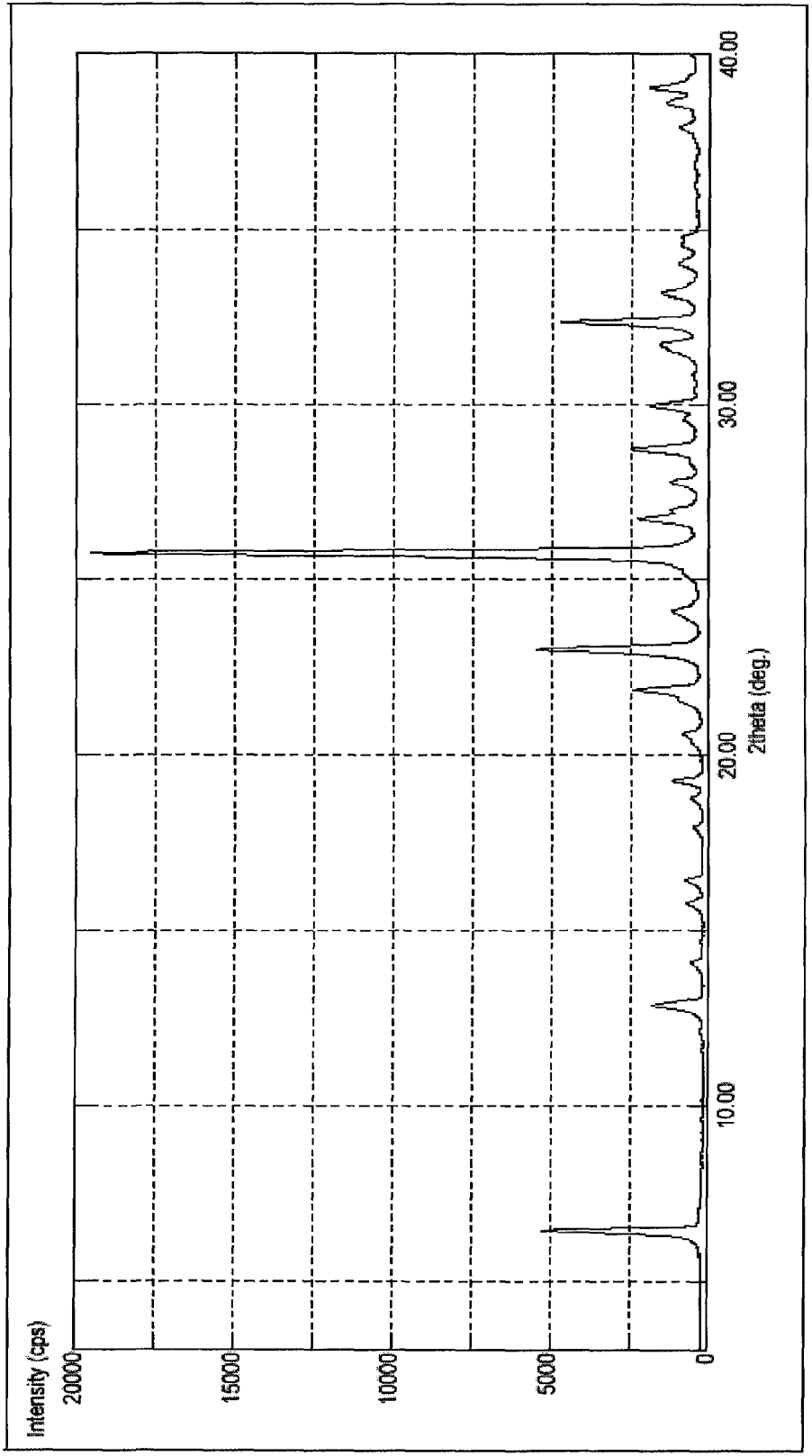
FIG. 27 is a graph of the PXRD of a sample of bupropion hydrobromide polymorphic form II after 1 month under ICH conditions (40.degree. C., 75% R.H.).
Figure 28:
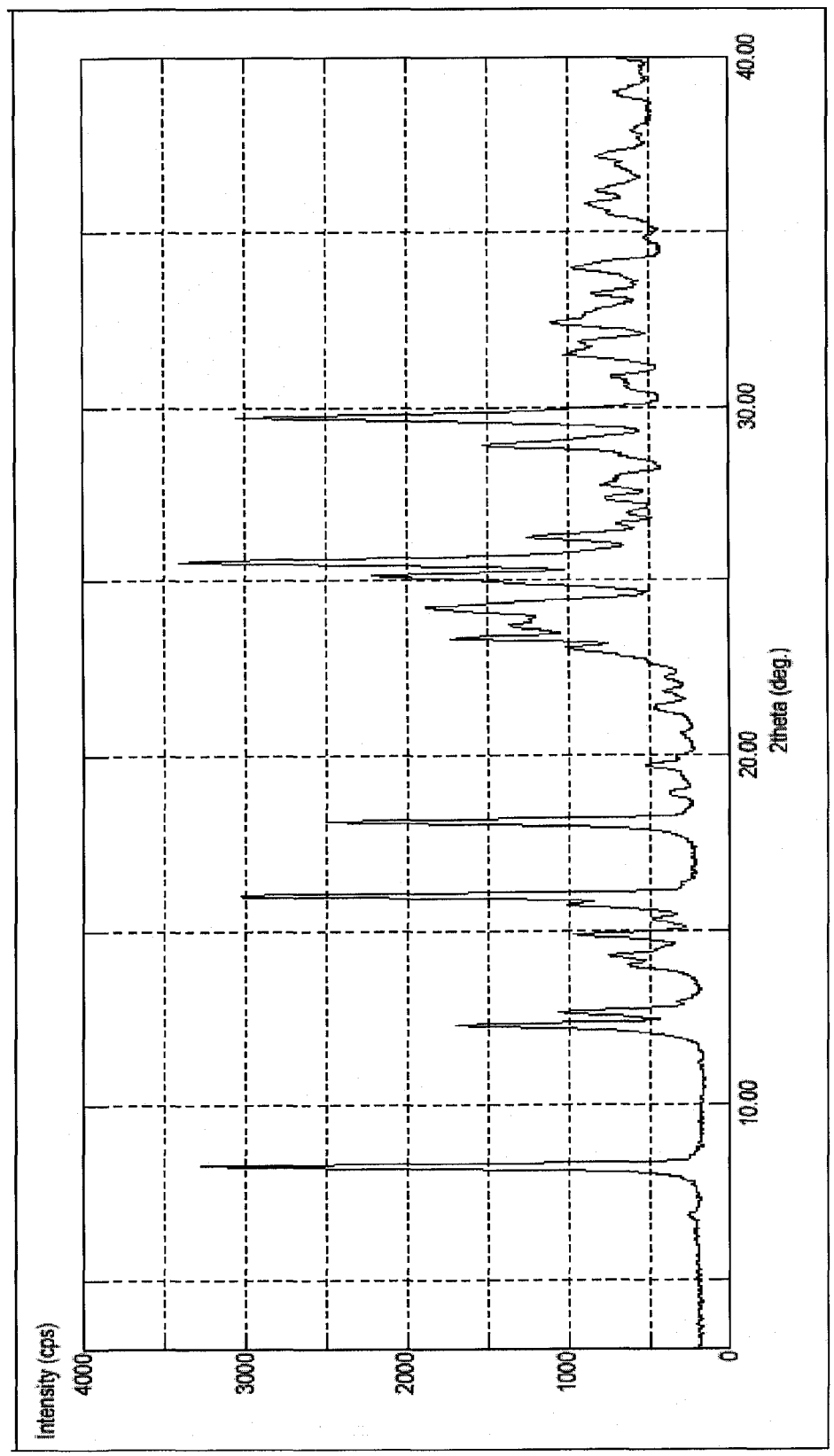
FIG. 28 is a graph showing the relative PXRD for bupropion hydrobromide polymorphic form III.
Figure 29:
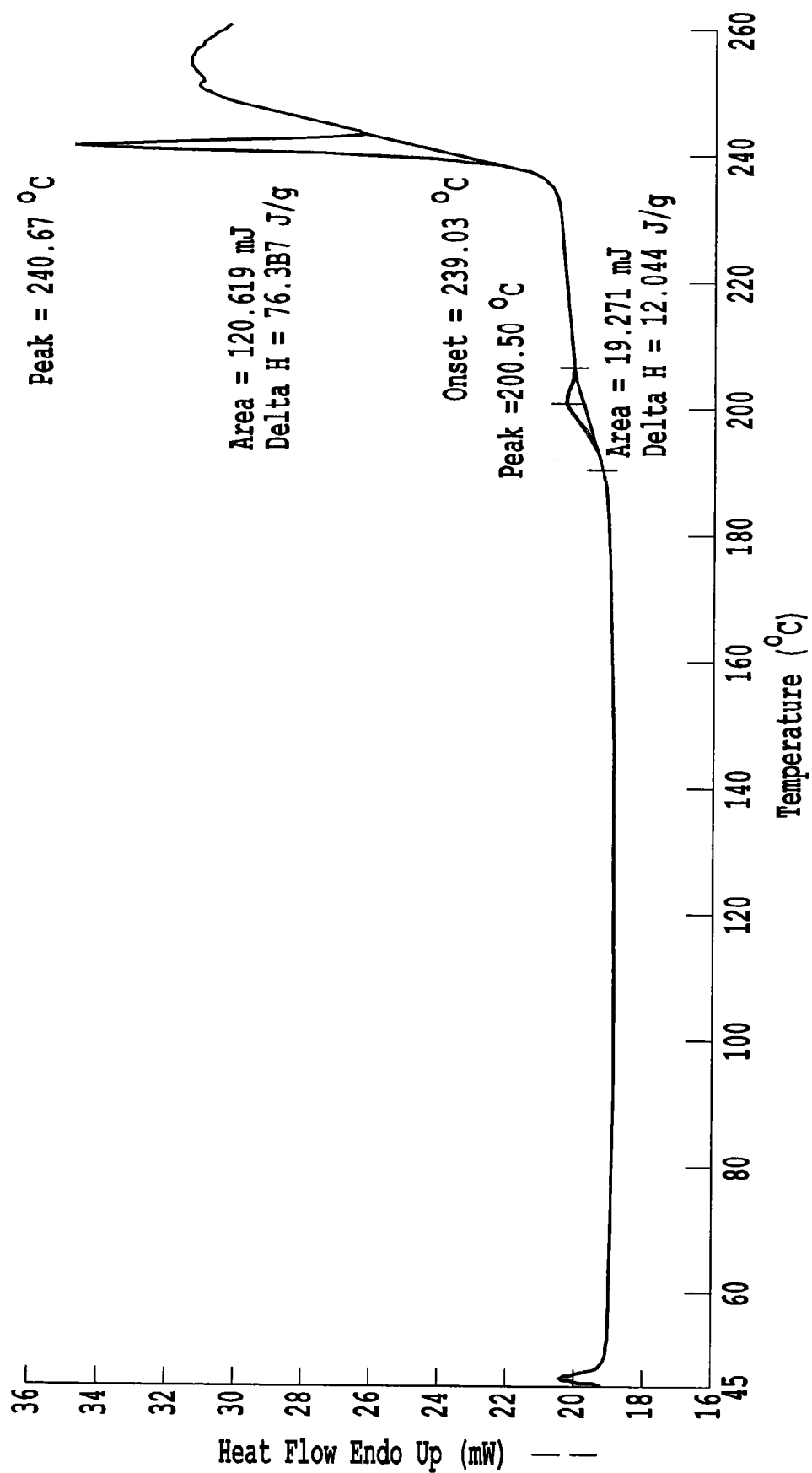
FIG. 29 is a graph showing the DSC profile of bupropion hydrobromide polymorphic form III.
Figure 30:
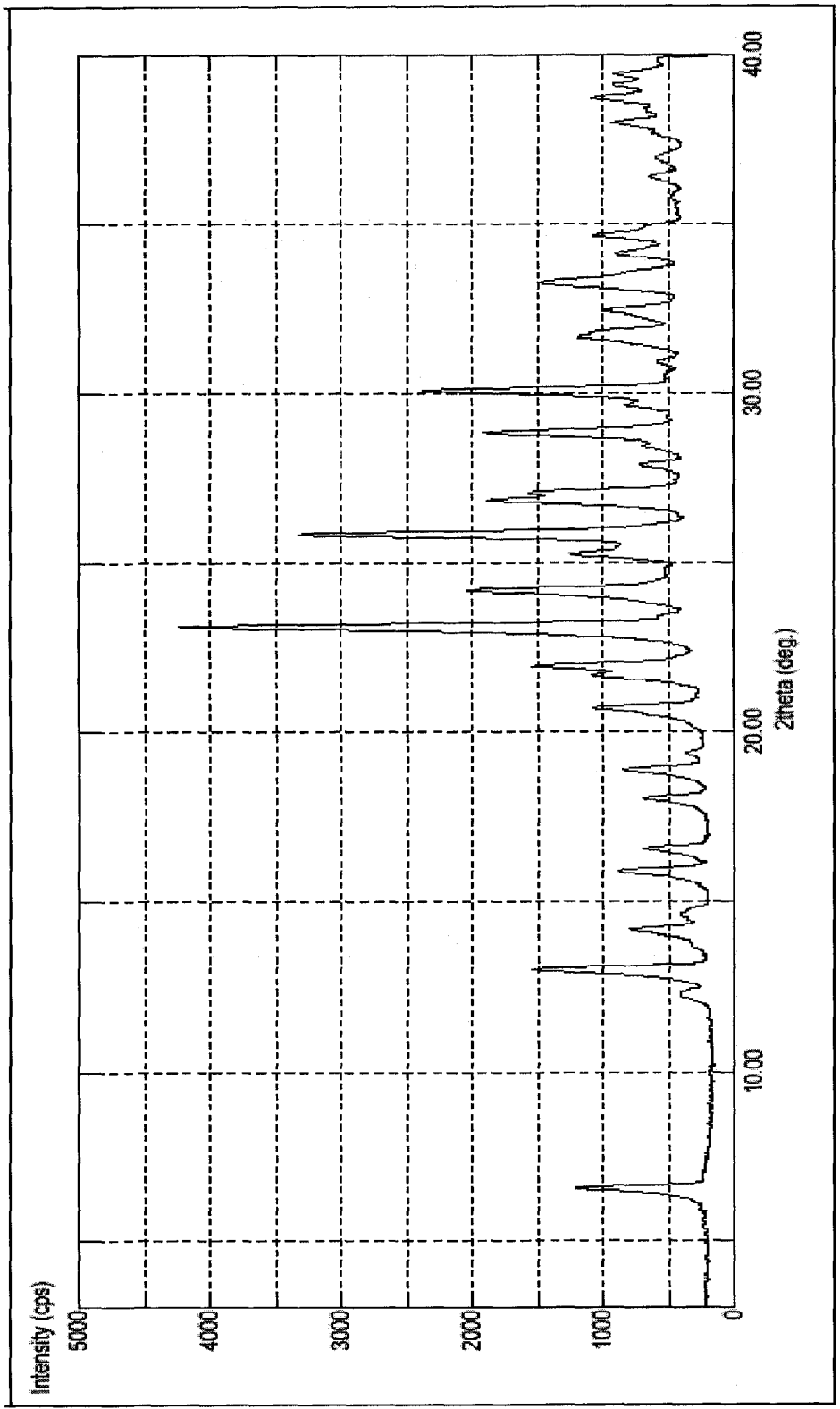
FIG. 30 is a graph of the PXRD of a sample of bupropion hydrobromide polymorphic form III after 1 month under ICH conditions (40.degree. C., 75% R.H.).

Bupropion hydrobromide of form I has been used as the starting material in experiments to identify other polymorphic forms. Two additional polymorphic forms were identified and have been named form II and form III. FIGS. 25 and 26 show the PXRD data and DSC profile respectively of polymorphic form II. FIG. 27 shows the PXRD profile of form II after 1 month stability testing in ICH conditions (40° C., 75% R.H.). FIGS. 28 and 29 show the PXRD data and DSC profile respectively of form III. FIG. 30 shows the PXRD profile of form III after 1 month stability testing in ICH conditions (40° C., 75% R.H.).

Polymorphic form II was obtained by recrystallization of form I from solvents or mixtures of solvents such as acetone-water, methanol, dichloromethane, toluene-methanol and dimethylcarbonate-methanol. Polymorphic form III was obtained by recrystallization of polymorphic form I in methanol. Table 39 provides a list of recrystallization conditions and the polymorphic form obtained under each set of conditions.

Samples of the polymorphic forms II and III were tested after 1 month under the same accelerated stability conditions (ICH conditions of 40° C., 75% R.H.). Polymorphic form II showed no change in the PXRD profile at that time while the PXRD profile of form III showed conversion to form II. This data suggests that polymorphic forms I and II are quite stable while polymorphic form III is not as stable as forms I and II under the test conditions. See Example 3 below.

Polymorphic Forms IV, V, VI and VII, and Amorphous Form

During additional experiments of crystallization of bupropion hydrobromide it was found, unexpectedly, that even though numerous experiments had been conducted previously with the aim of identifying new crystalline forms of bupropion hydrobromide (i.e. forms I, II and III, see Table 39), bupropion hydrobromide can be obtained in additional polymorphous forms not previously known (i.e. forms IV, V, VI and VII).

Moreover, surprisingly, bupropion hydrobromide was isolated in amorphous form in an experiment with lyophilization of an aqueous solution of bupropion hydrobromide and in an experiment with evaporation of a solution of the product in p-xylene. These last two results are particularly unexpected, since test 122 in table 39 (for forms I, II and III) describes how, by treating aqueous solutions of bupropion hydrobromide by the "spray drying" technique, which usually gives products in amorphous form, we obtain instead a product in crystalline form I.

Figure 31:
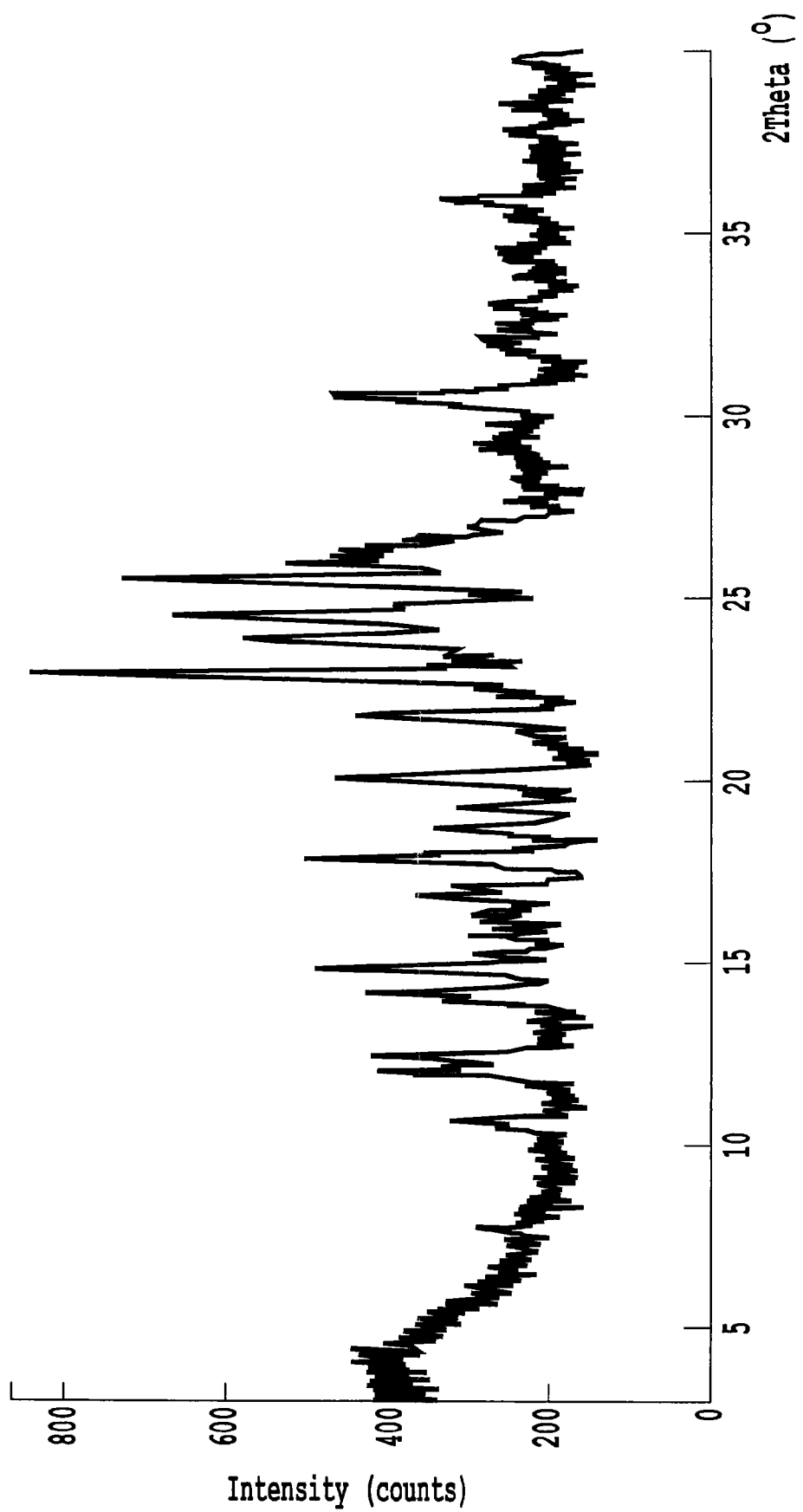
FIG. 31 is a graph showing the relative PXRD for bupropion hydrobromide polymorphic form IV.
Figure 32:
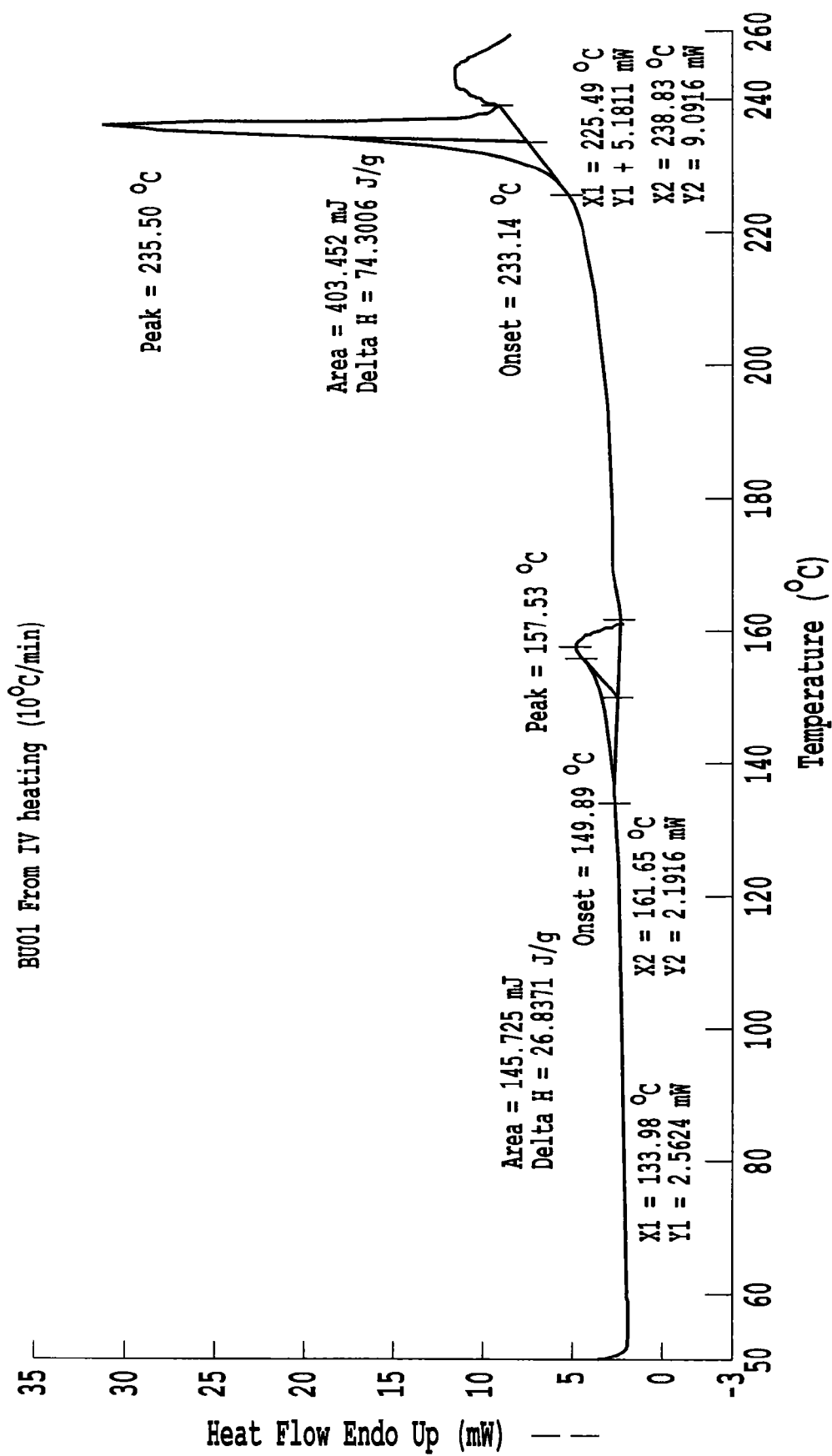
FIG. 32 is a graph showing the DSC profile of bupropion hydrobromide polymorphic form IV.
Figure 33:
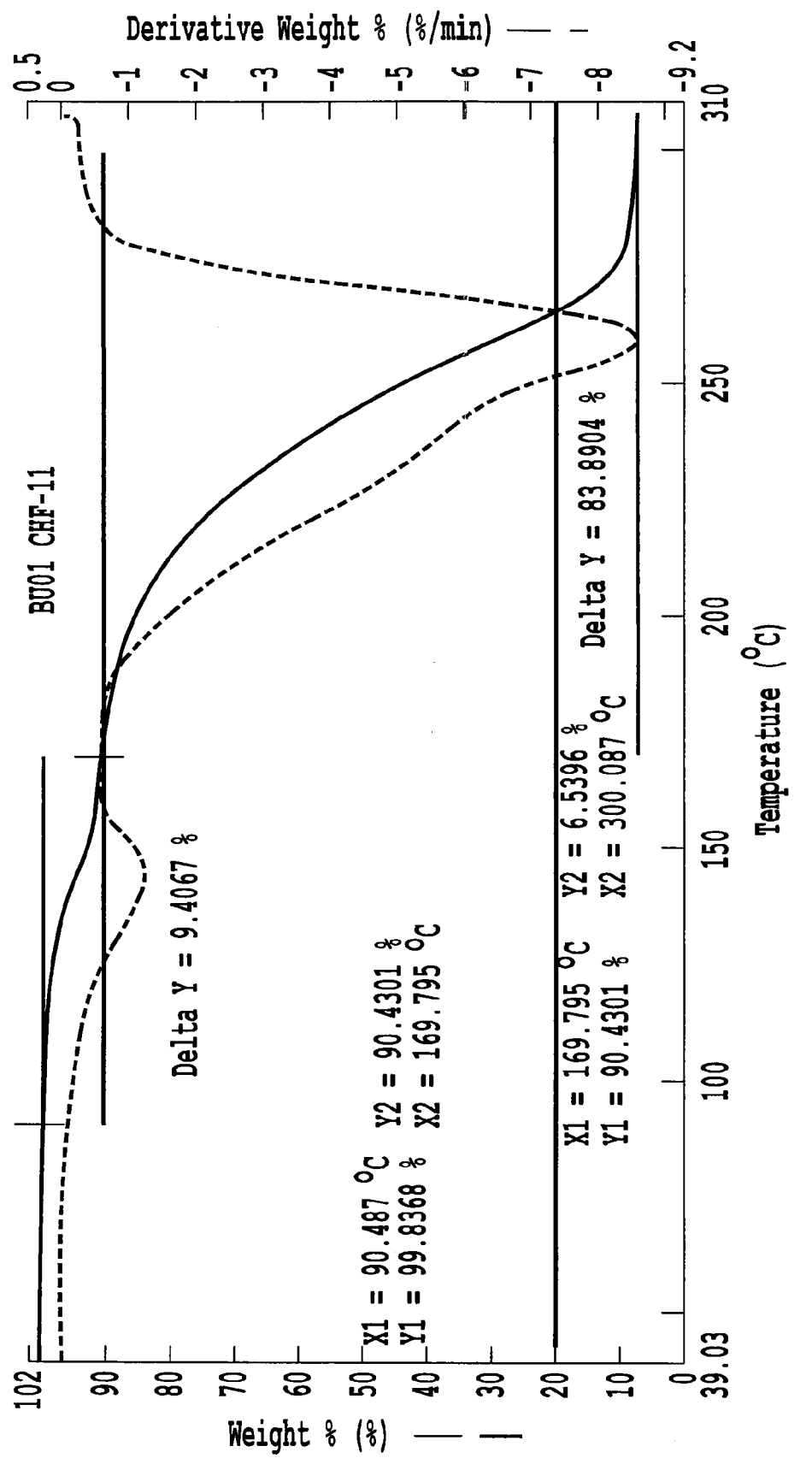
FIG. 33 is a graph showing the TGA profile of bupropion hydrobromide polymorphic form IV.
Figure 34:
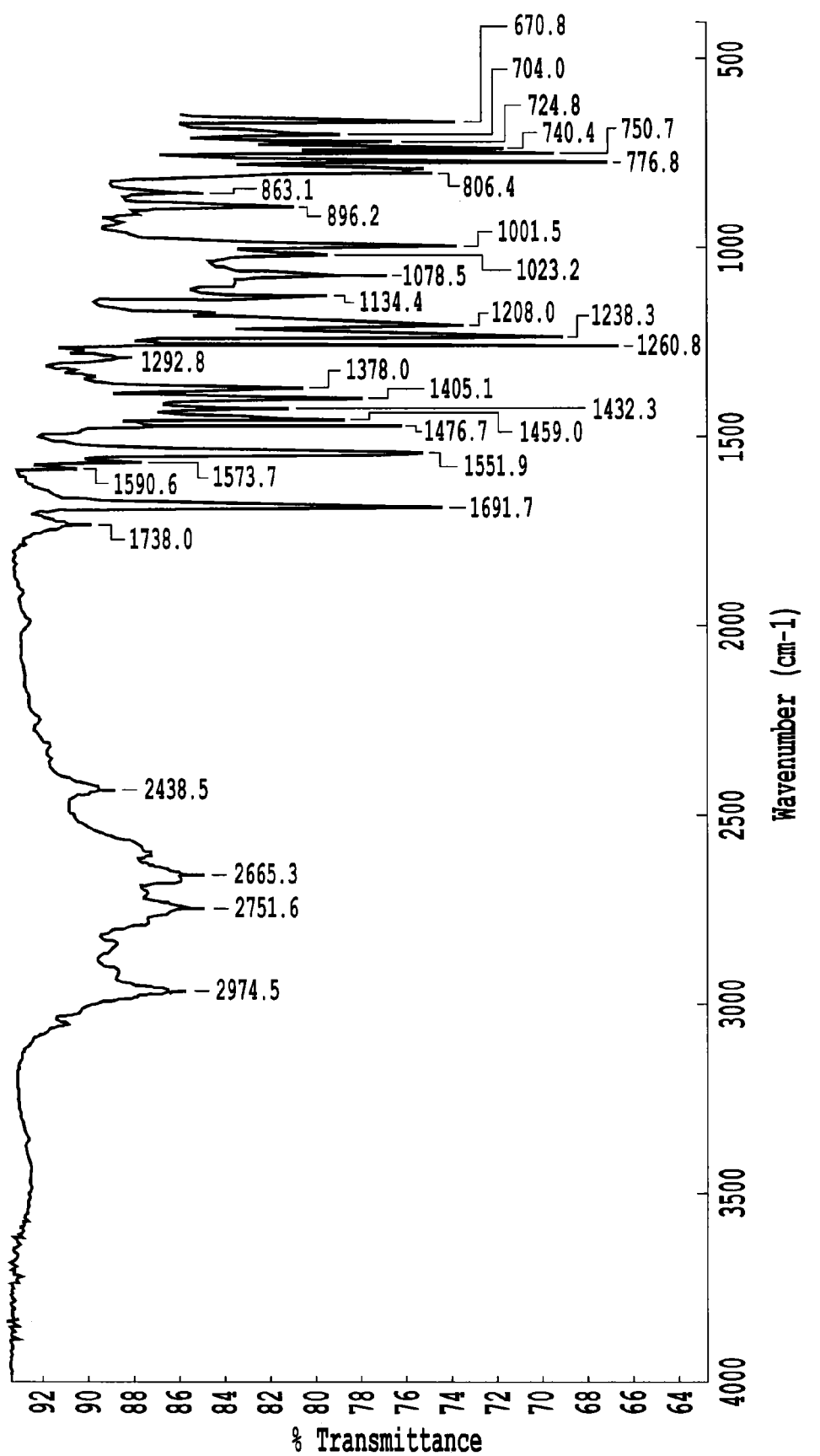
FIG. 34 is a graph showing the IR profile of bupropion hydrobromide polymorphic form IV.

The polymorphous form designated as form IV is characterized by the PXRD profile shown in FIG. 31, by the DSC profile shown in FIG. 32, by the TGA profile shown in FIG. 33 and by the IR profile shown in FIG. 34.

Figure 35:
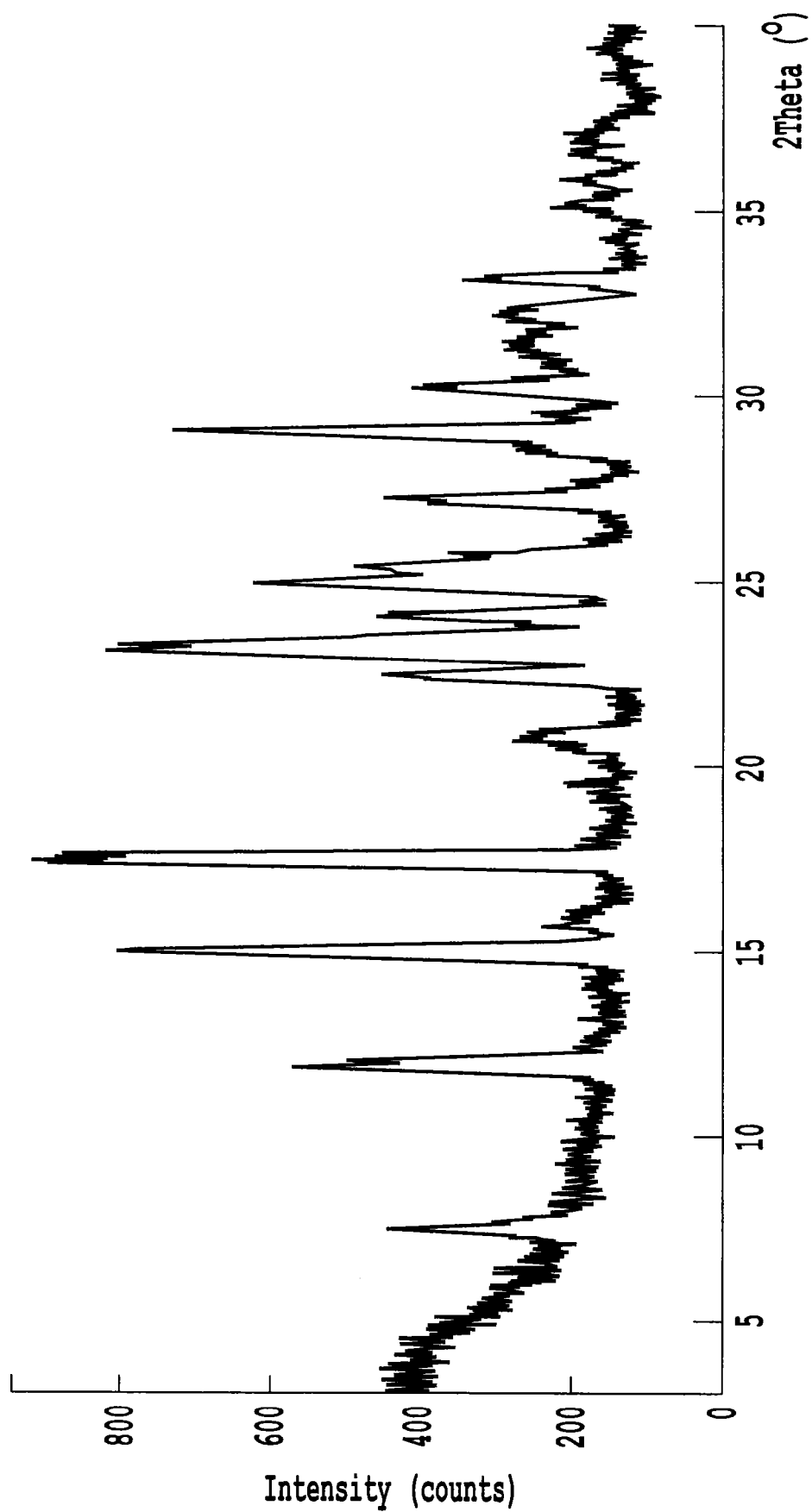
FIG. 35 is a graph showing the relative PXRD for bupropion hydrobromide polymorphic form V.
Figure 36:
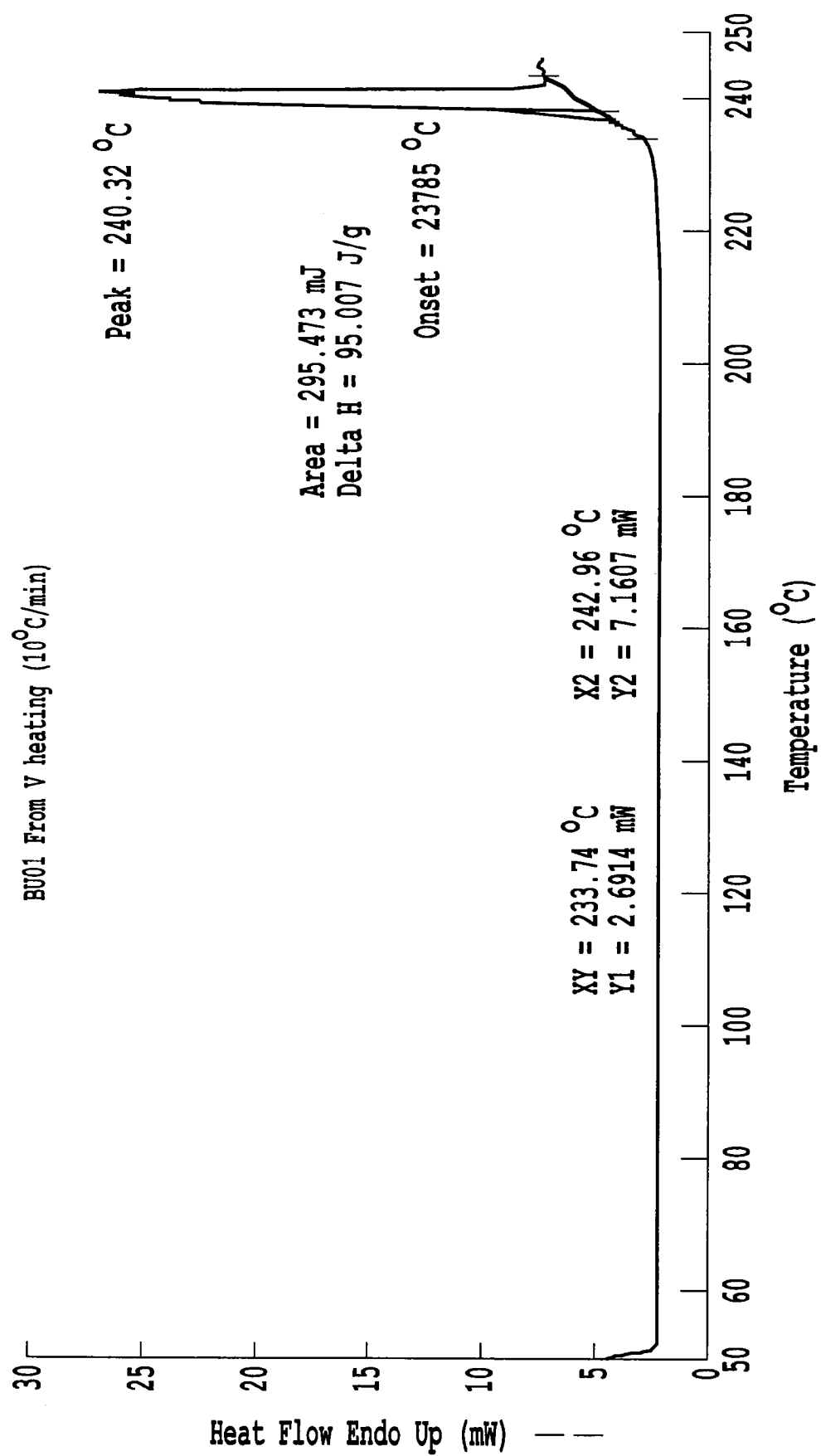
FIG. 36 is a graph showing the DSC profile of bupropion hydrobromide polymorphic form V.
Figure 37:
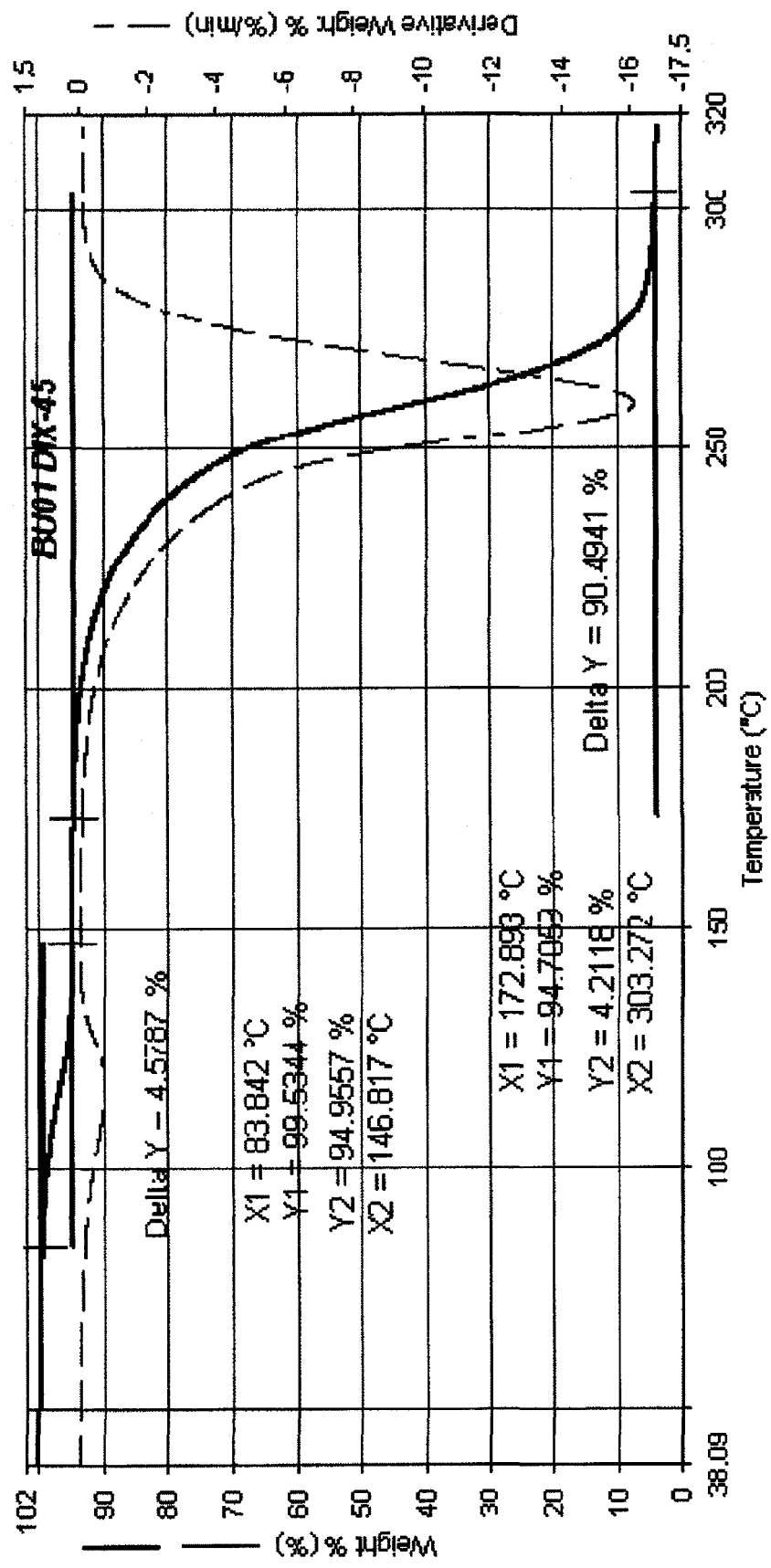
FIG. 37 is a graph showing the TGA profile of bupropion hydrobromide polymorphic form V.
Figure 38:
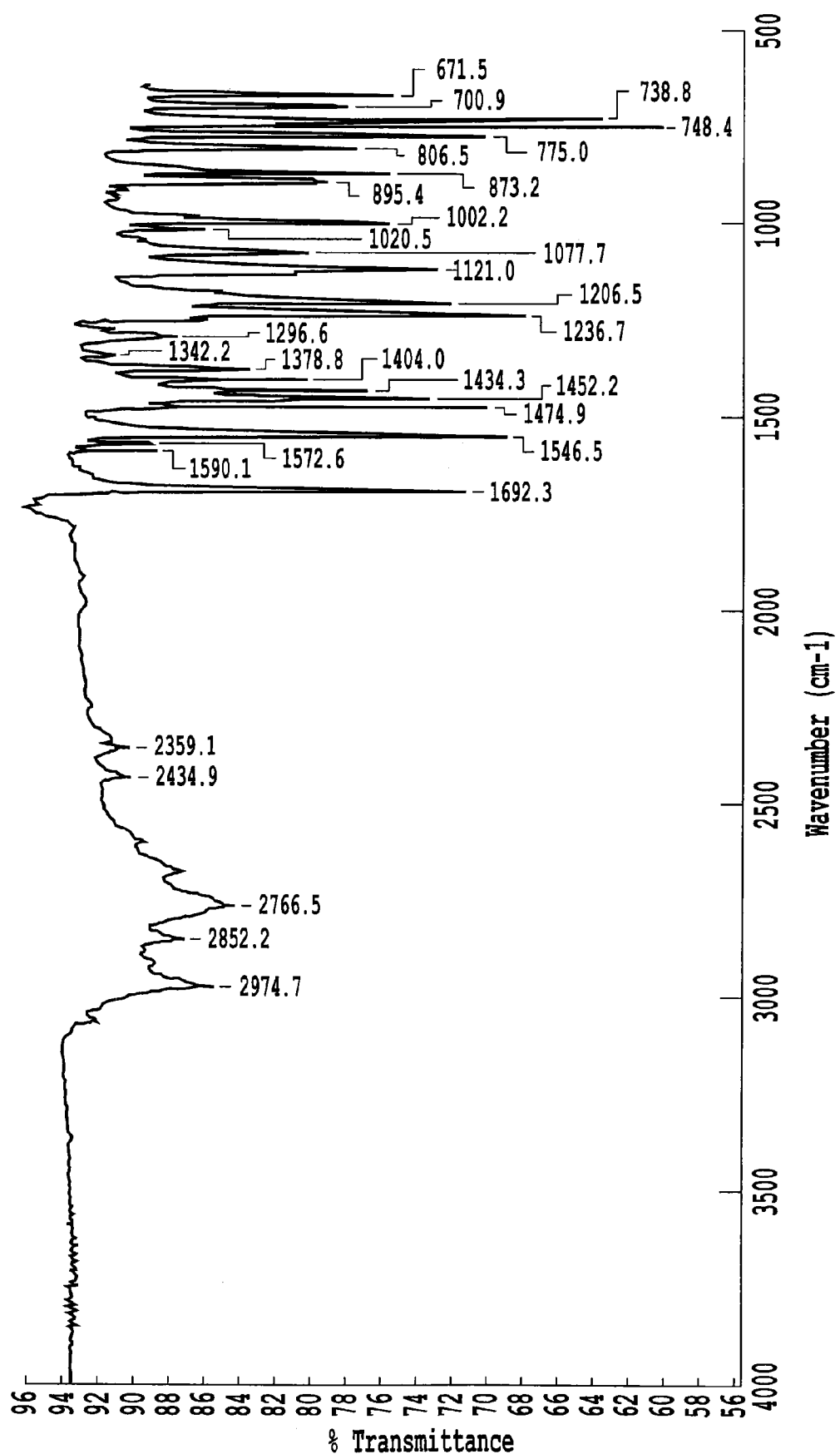
FIG. 38 is a graph showing the IR profile of bupropion hydrobromide polymorphic form V.

The polymorphous form designated as form V is characterized by the PXRD profile shown in FIG. 35, by the DSC profile shown in FIG. 36, by the TGA profile shown in FIG. 37 and by the IR profile shown in FIG. 38.

Figure 39:
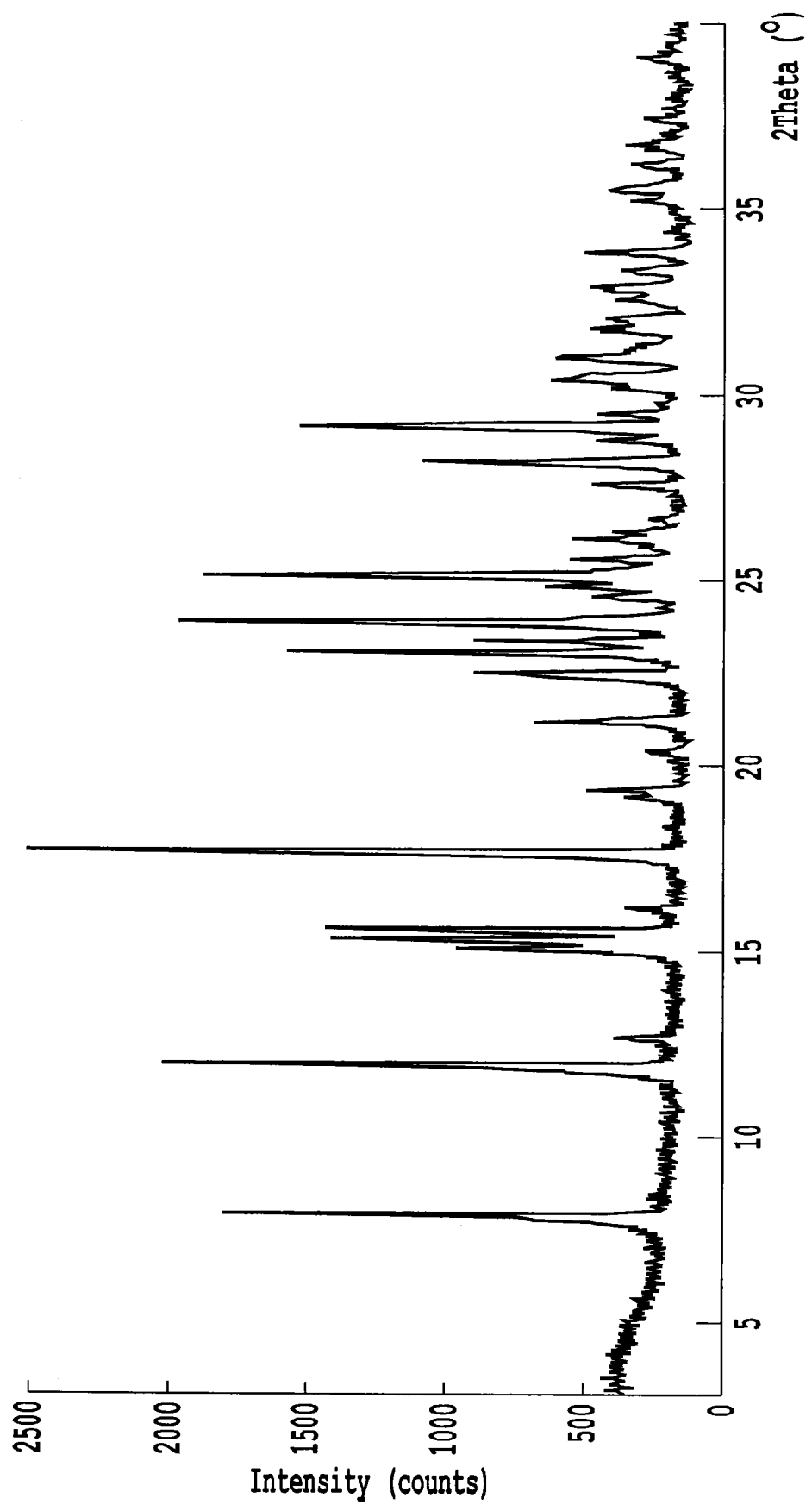
FIG. 39 is a graph showing the relative PXRD for bupropion hydrobromide polymorphic form VI.
Figure 40:
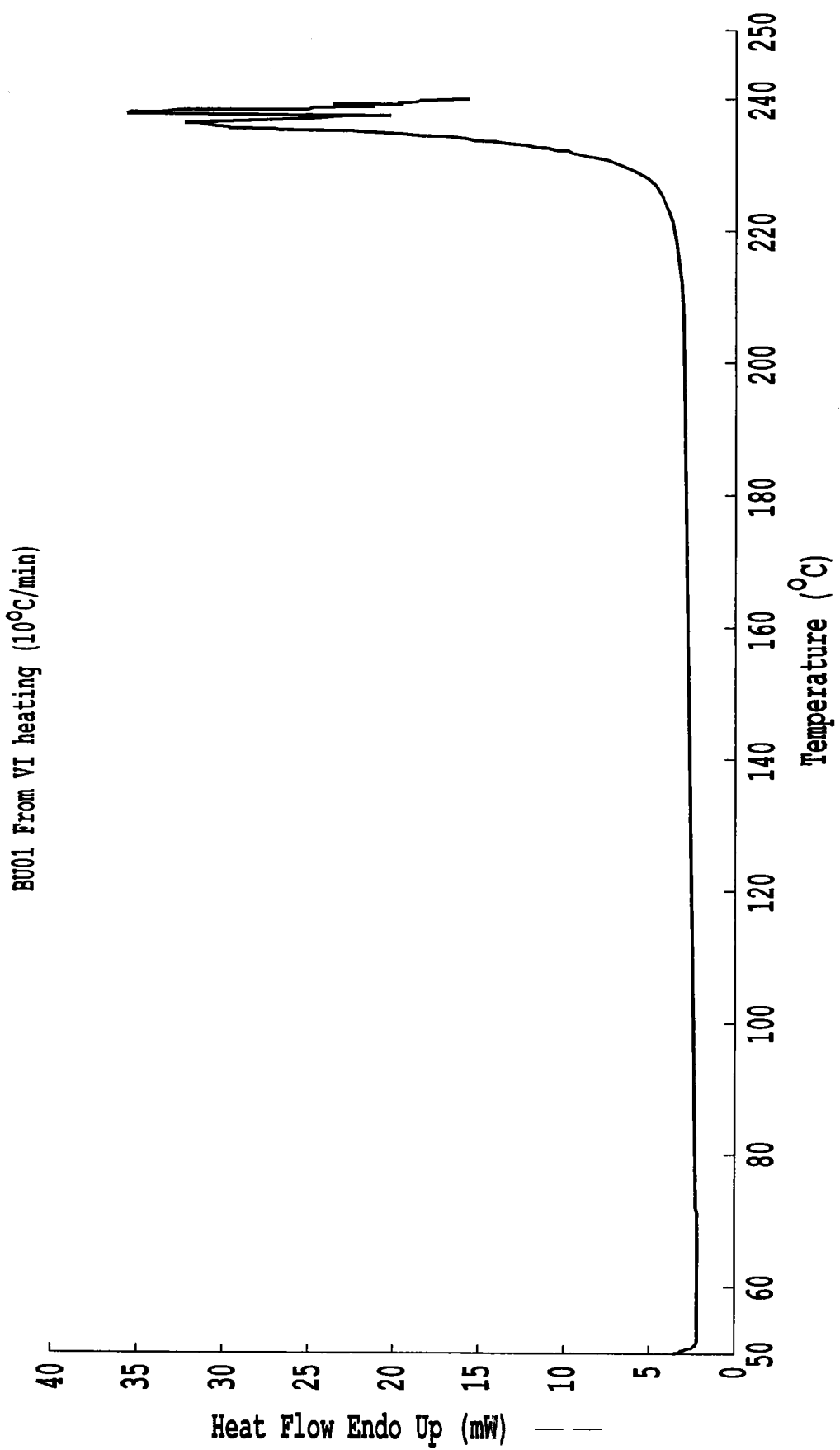
FIG. 40 is a graph showing the DSC profile of bupropion hydrobromide polymorphic form VI.
Figure 41:
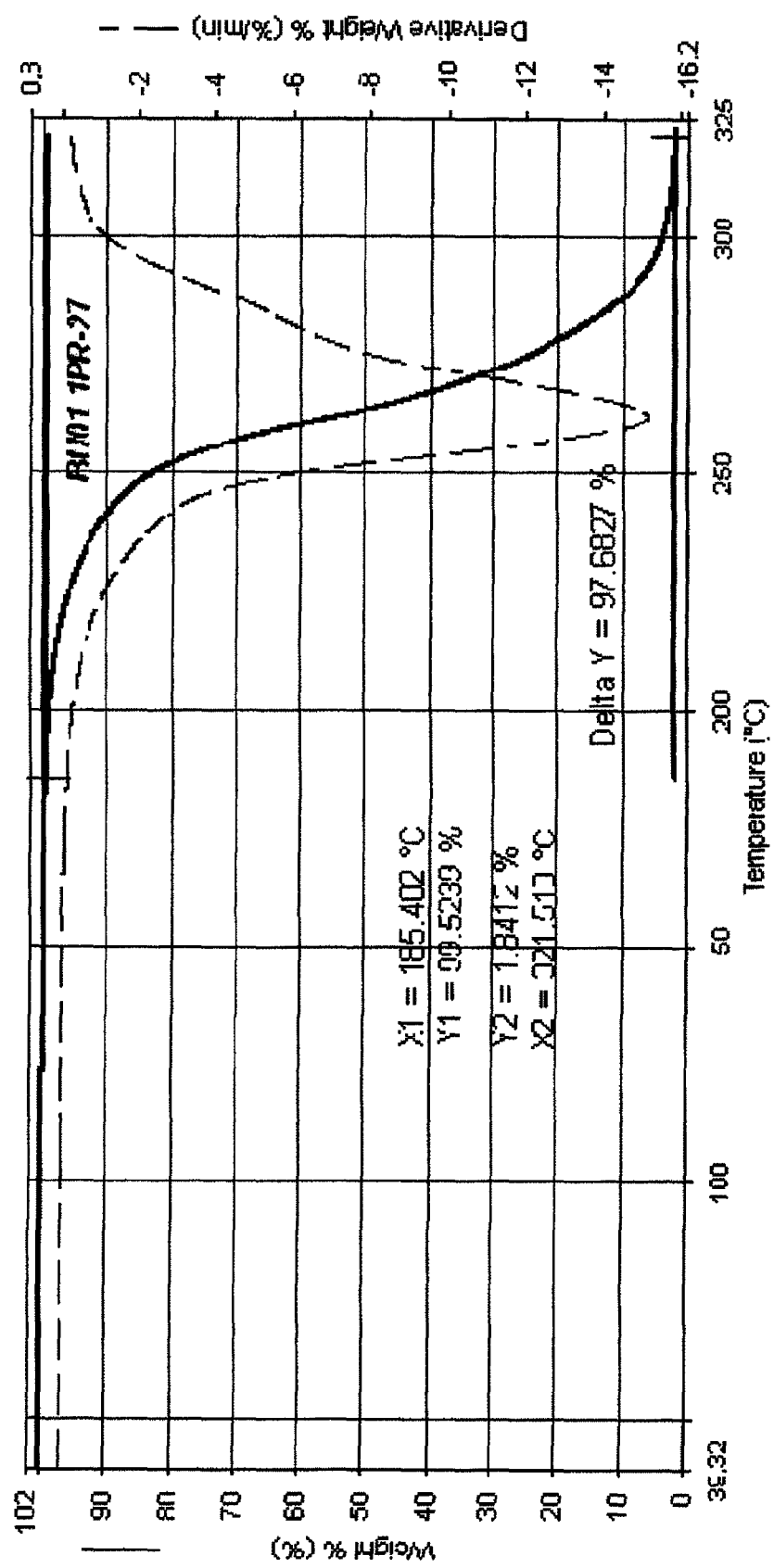
FIG. 41 is a graph showing the TGA profile of bupropion hydrobromide polymorphic form VI.
Figure 42:
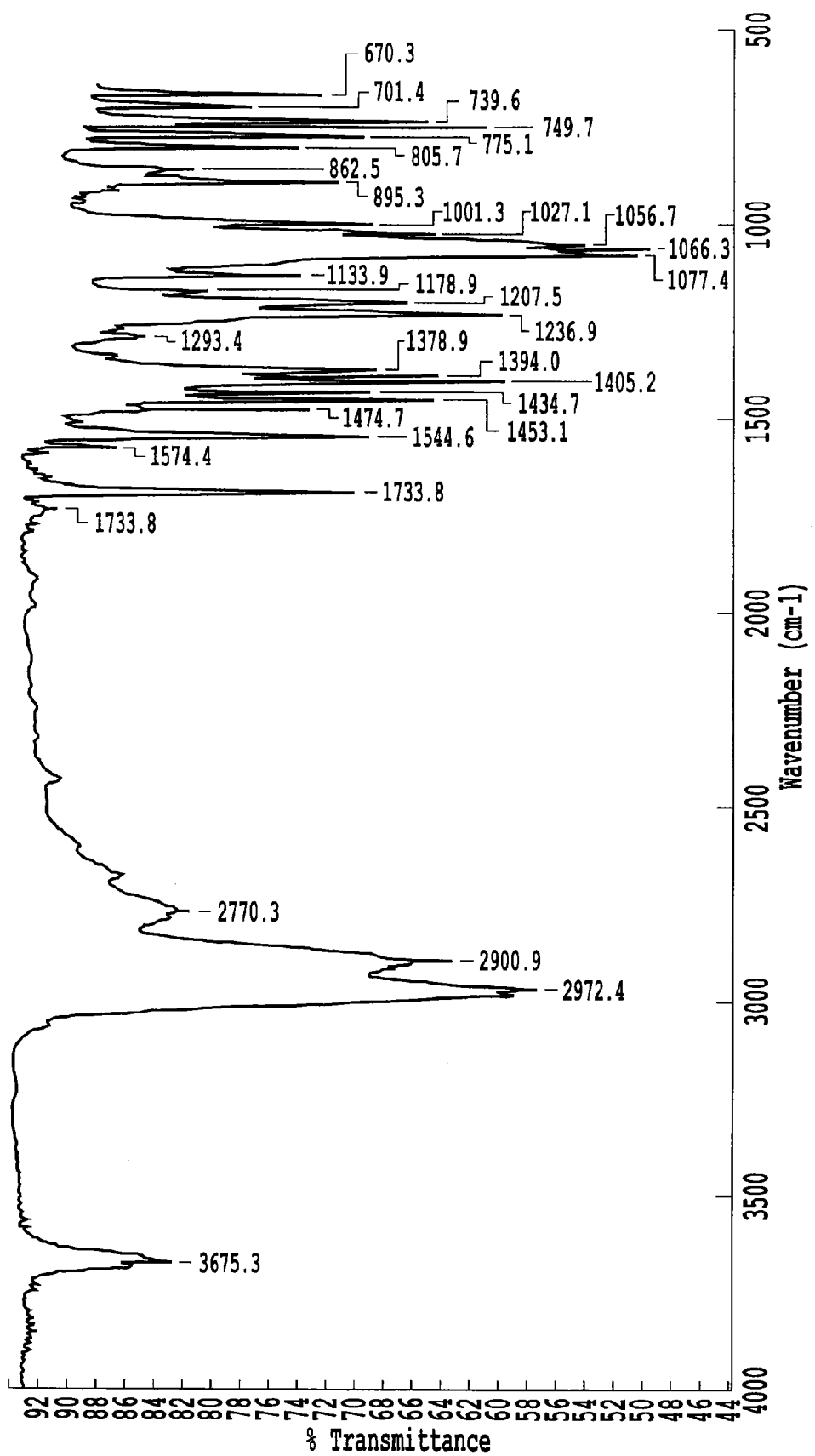
FIG. 42 is a graph showing the IR profile of bupropion hydrobromide polymorphic form VI.

The polymorphous form designated as form VI is characterized by the PXRD profile shown in FIG. 39, by the DSC profile shown in FIG. 40, by the TGA profile shown in FIG. 41 and by the IR profile shown in FIG. 42.

Figure 43:
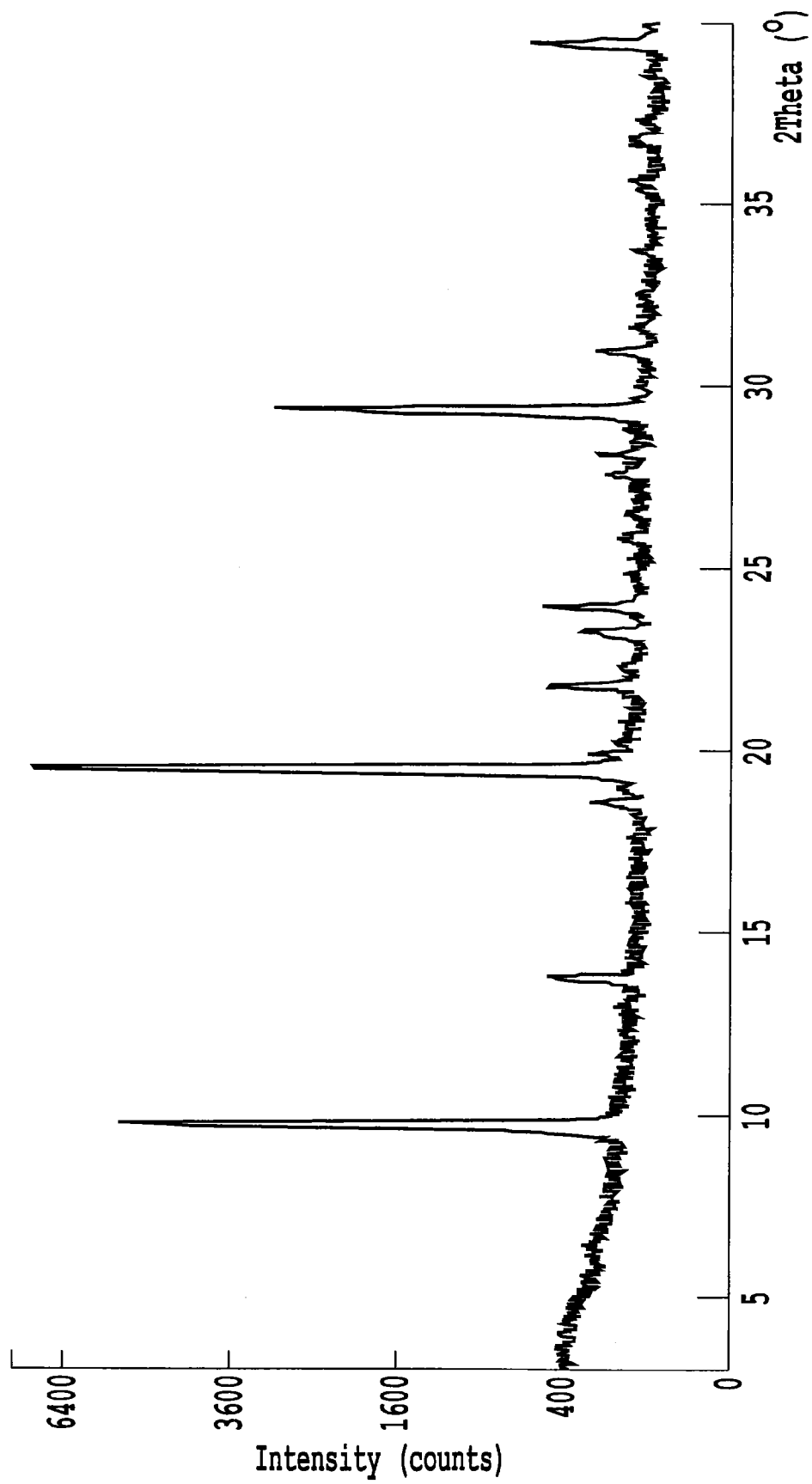
FIG. 43 is a graph showing the relative PXRD for bupropion hydrobromide polymorphic form VII.
Figure 44:
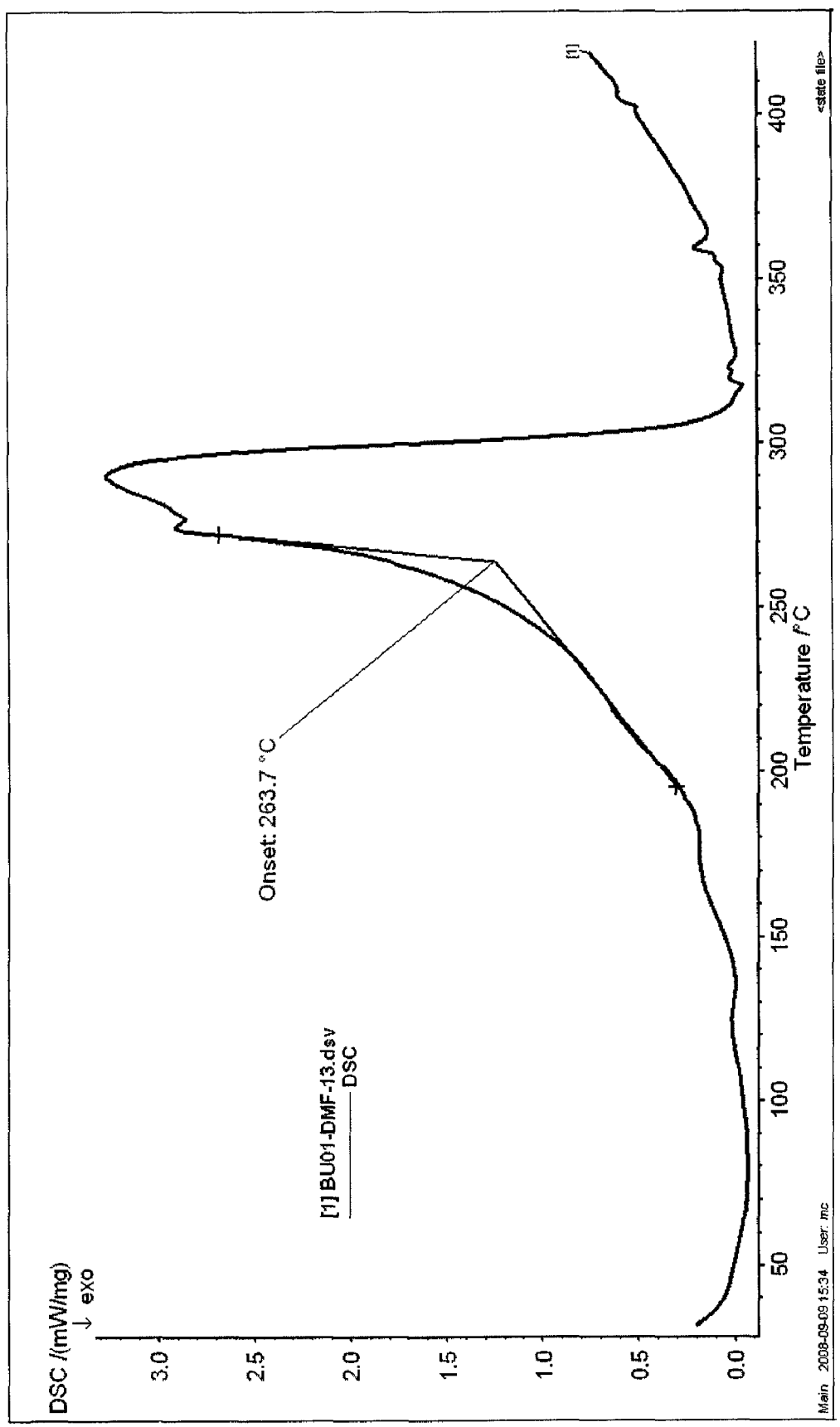
FIG. 44 is a graph showing the DSC profile of bupropion hydrobromide polymorphic form VII.
Figure 45:
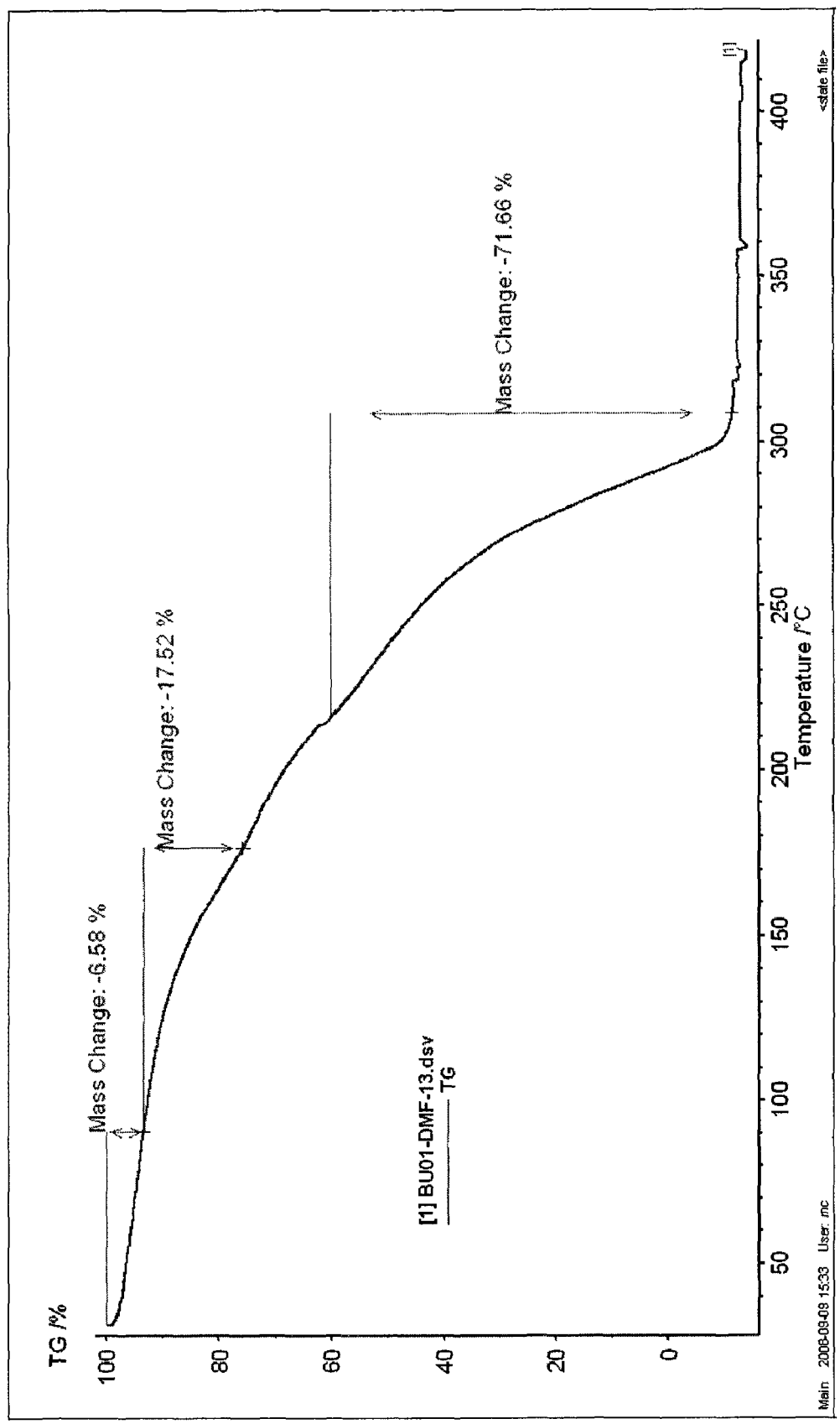
FIG. 45 is a graph showing the TGA profile of bupropion hydrobromide polymorphic form VII.
Figure 46:
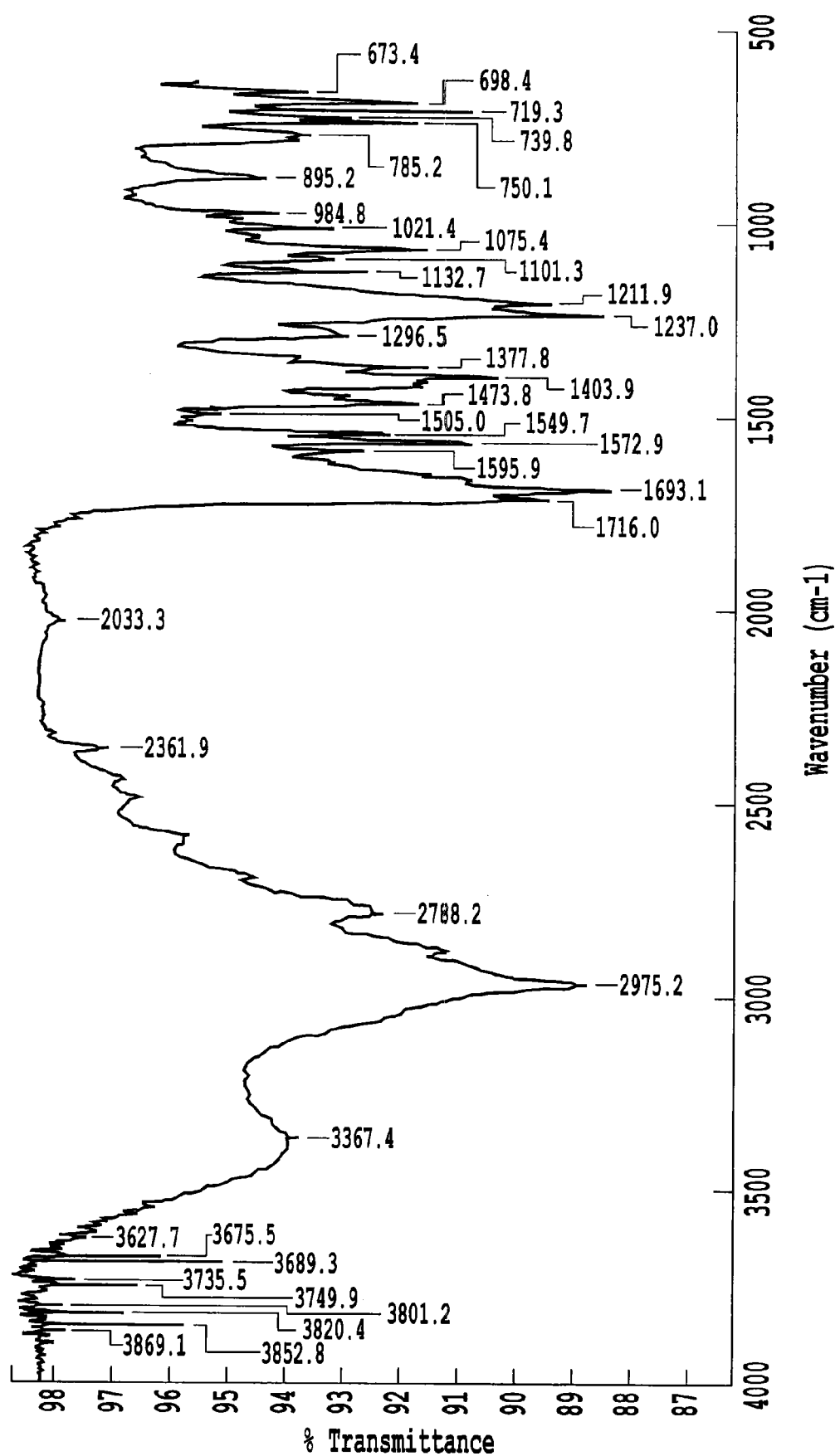
FIG. 46 is a graph showing the IR profile of bupropion hydrobromide polymorphic form VII.

The polymorphous form designated as form VII is characterized by the PXRD profile shown in FIG. 43, by the DSC profile shown in FIG. 44, by the TGA profile shown in FIG. 45 and by the IR profile shown in FIG. 46.

Figure 47:
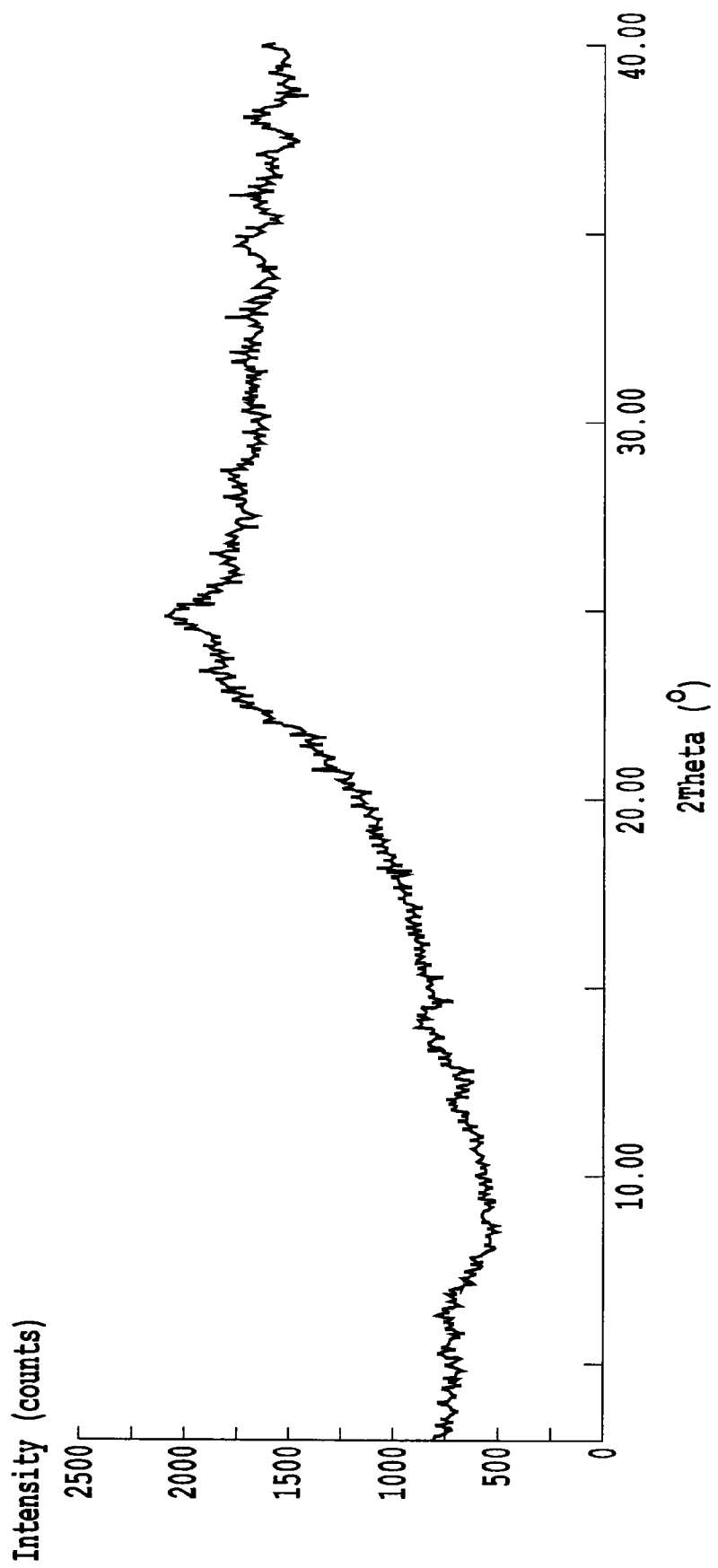
FIG. 47 is a graph showing the relative PXRD for an amorphous form of bupropion hydrobromide.
Figure 48:
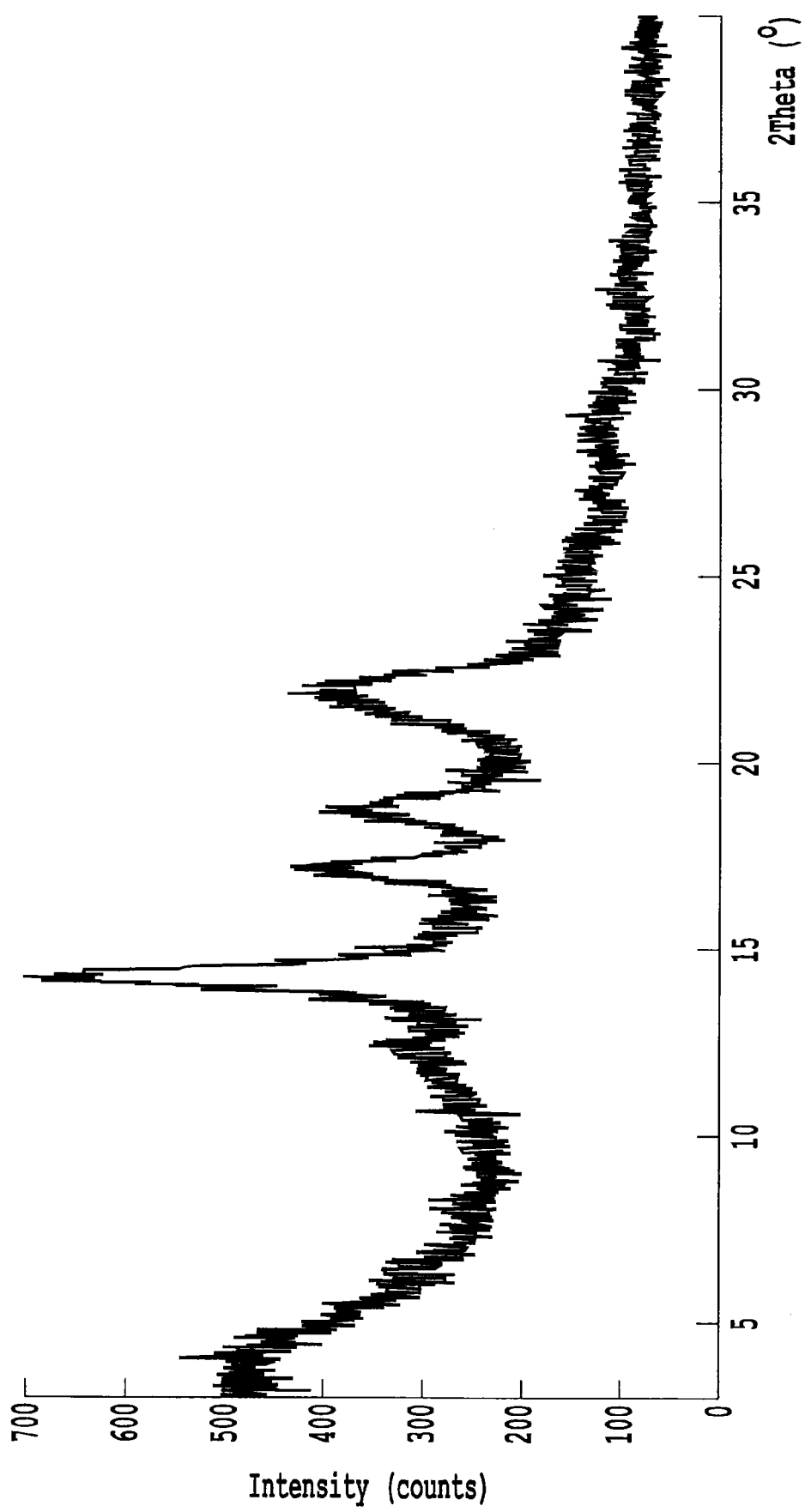
FIG. 48 is a graph showing the relative PXRD for an amorphous form of bupropion hydrobromide.

The amorphous form is characterized by the PXRD profile shown in FIG. 47 and by the PXRD profile shown in FIG. 48.

The PXRD diffraction patterns were obtained on X-ray powder diffraction PANalytical X'pert Pro equipped with X'Celerator, in a measurement range between 3 and 40 2theta. All the DSC experiments were performed with a DSC 7 Perkin Elmer instrument in a temperature range between 25° C. and 250° C. with a heating rate of 10° C./min.

All the TGA experiments were conducted with a TGA 7 Perkin Elmer instrument in a temperature range between 39° C. and 310° C. with a heating rate of 10° C./min.

All the IR spectra were recorded on FT-IR Nicolet from ThermoFischer.

In total, the polymorph screening has identified seven crystalline forms and an amorphous form for Bupropion Hydrobromide. Form II is the thermodynamically stable crystal form as shown by slurry experiments. Form I is a metastable form produced by different experiments but converts into Form II by slurry for 1 week at both room and high temperature. Form I and Form II are the crystalline forms obtained in the majority of experiments. Form VII is also found to be a stable form after 28 days storage. Form IV is only produced by evaporation of a chloroform solution of bupropion hydrobromide. Form V is only produced by interaction of bupropion hydrobromide with dioxane. Form VI is only produced by interaction of bupropion hydrobromide with n-propanol and ethyl acetate. Form VII is only produced by interaction of bupropion hydrobromide with benzonitrile, methyl benzoate, and tetrahydrofuran. Form I, Form II, Form V, Form VI, Form VII and the amorphous form are anhydrous forms. Form III is a solvate of ethanol. Form IV is a solvated crystal form.

Tablets

In certain embodiments of the present invention, there is provided a modified-release tablet having a core comprising bupropion hydrobromide or a polymorph of bupropion hydrobromide and conventional excipients. In certain embodiments the bupropion hydrobromide salt or the polymorph of bupropion hydrobromide or the composition comprising the bupropion hydrobromide or polymorph provides for the reduction of incidences of and/or severity of bupropion-induced seizures, and is more stable as compared with equivalent molar amounts of bupropion hydrochloride or otherwise similar or identical compositions containing equivalent molar amounts of bupropion hydrochloride. The core can be surrounded by a controlled release coat which can control the release of bupropion hydrobromide or mixture of bupropion hydrobromide with a second drug. In other embodiments, a moisture barrier can optionally be added to surround the controlled release coat. This moisture barrier is optional given the enhanced stability of bupropion hydrobromide relative to bupropion hydrochloride and by selection of an appropriate controlled release coating. If present, this moisture barrier can affect in-vitro drug release as well as precluding moisture from coming into contact with the bupropion hydrobromide salt. Optionally, this tablet can further comprise one or more additional functional or non-functional coatings surrounding the core, moisture barrier and/or controlled release coat.

Extended Release (XL) Tablets

In certain embodiments of the present invention, there is provided an extended-release (XL) tablet having a core comprising bupropion hydrobromide and/or a polymorph of bupropion hydrobromide and conventional excipients. In certain embodiments the bupropion hydrobromide salt and/or polymorph of bupropion hydrobromide provides for the reduction of incidences of and/or severity of bupropion-induced seizures, and is more stable, as compared with equivalent molar amounts of bupropion hydrochloride. The core can be surrounded by a controlled release coat, which controls the release of the bupropion hydrobromide salt or polymorph of bupropion hydrobromide. The tablet optionally can comprise one or more additional functional or non-functional coats surrounding the core or controlled release coat. The extended-release tablet of certain embodiments has unexpected enhanced stability.

The XL Core

The core of the extended-release tablet comprises an effective amount of the bupropion hydrobromide salt and/or a polymorph of bupropion hydrobromide, a binder, and a lubricant; and can contain other conventional inert excipients. The amount of the bupropion hydrobromide salt or polymorph of bupropion hydrobromide present in the XL core can vary in an amount from about 40% to about 99% by weight of the tablet dry weight, including all values and ranges therebetween. For example, in certain embodiments bupropion hydrobromide and/or a polymorph of bupropion hydrobromide is present in an amount from about 70% to about 95% by weight of the tablet dry weight, including all values and ranges therebetween. For example, in certain embodiments, the core comprises bupropion hydrobromide and/or a polymorph of bupropion hydrobromide in a proportion of about 40%, about 45%, about 50%, about 55%, about 60%, about 65%, about 70%, about 75%, about 80%, about 85%, about 90%, about 95% or about 99% of the core dry weight.

In at least one embodiment of a 174 mg dose tablet, the bupropion hydrobromide is present in an amount of from about 75% to about 85% by weight of the tablet dry weight, including all values and ranges therebetween. In at least one embodiment of a 348 mg dose tablet, the amount of bupropion hydrobromide can be present in an amount of from about 80% to about 90% by weight of the tablet dry weight, including all values and ranges therebetween. In at least one embodiment of a 522 mg dose tablet, the bupropion hydrobromide is present in an amount of from about 75% to about 90% by weight of the tablet dry weight, including all values and ranges therebetween. In certain embodiments of the 174 mg, 348 mg and 522 mg dose bupropion hydrobromide extended-release tablets of the invention, the amount of bupropion hydrobromide is present in an amount of from about 85% to about 99% by weight of the dry core for each dose, including all values and ranges therebetween.

A binder (also sometimes called adhesive) can be added to a drug-filler mixture to increase the mechanical strength of the granules and tablets during formation. Binders can be added to the formulation in different ways: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction. In this form the binder is referred to as a dry binder. Solution binders are a common way of incorporating a binder into granules. In certain embodiments, the binder used in the XL tablets is in the form of a solution binder. Non-limiting examples of binders useful for the core include hydrogenated vegetable oil, castor oil, paraffin, higher aliphatic alcohols, higher aliphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Specific examples of water-soluble polymer binders include modified starch, gelatin, polyvinylpyrrolidone, cellulose derivatives (such as for example hydroxypropyl methylcellulose (HPMC) and hydroxypropyl cellulose (HPC)), polyvinyl alcohol and mixtures thereof. The amount of binder present can vary from about 0.5% to about 25% by weight of the tablet dry weight, including all values and ranges therebetween. For example, in certain embodiments the binder is present in an amount of from about 0.5% to about 15% by weight of the tablet dry weight, including all values and ranges therebetween For example, in certain embodiments of the 174 mg, 348 mg and 522 mg dose tablets, the binder is present in an amount of from about 1% to about 6% by weight of each dry core weight, including all values and ranges therebetween; and in other embodiments at about 3% by weight of each dry core weight. In at least one embodiment of the 522 mg dose tablet, the binder is present in an amount of about 4% by weight of dry core weight. In at least one embodiment of the invention the binder is polyvinyl alcohol.

Lubricants can be added to pharmaceutical formulations to decrease any friction that occurs between the solid and the die wall during tablet manufacturing. High friction during tabletting can cause a series of problems, including inadequate tablet quality (capping or even fragmentation of tablets during ejection, and vertical scratches on tablet edges) and may even stop production. Accordingly, lubricants are added to tablet formulations of certain embodiments of the XL tablet formulation described herein. Non-limiting examples of lubricants useful for the core include glyceryl behenate, stearic acid, hydrogenated vegetable oils (such as hydrogenated cottonseed oil (STERPTEX®), hydrogenated soybean oil (STEROTEX® HM) and hydrogenated soybean oil & castor wax (STERPTEX® K), stearyl alcohol, leucine, polyethylene glycol (MW 1450, suitably 4000, and higher), magnesium stearate, glyceryl monostearate, stearic acid, polyethylene glycol, ethylene oxide polymers (e.g. CARBOWAX®), sodium lauryl sulfate, magnesium lauryl sulfate, sodium oleate, sodium stearyl fumarate, DL-leucine, colloidal silica, mixtures thereof and others as known in the art. In at least one embodiment of the present invention, the lubricant is glyceryl behenate (e.g. COMPRITOL® 888). The amount of lubricant present can vary from about 0.1% to about 6% by weight of the tablet dry weight, including all values and ranges therebetween. For example, in certain embodiments the amount of lubricant present is from about 2% to about 3% by weight of the tablet dry weight, including all values and ranges therebetween; and in other embodiments the amount of lubricant present is at about 3% by weight of the tablet dry weight. In certain embodiments of the 174 mg, 348 mg and 522 mg dose XL tablets of the invention, the lubricant is present in an amount of about 3% by weight of the tablet dry weight, or from about 1% to about 6% by weight of the dry core weight, including all values and ranges therebetween. For example, in certain embodiments the lubricant is present in an amount of about 3% by weight of the dry core weight for the 174 mg, 348 mg and 522 mg dose XL tablets. In at least one embodiment of the 522 mg dose tablet, the lubricant is present in an amount of about 4% by weight of dry core weight.

At this stage, the XL core formulation of certain embodiments of the present invention is an uncoated immediate release formulation resulting in about 100% dissolution of the bupropion hydrobromide salt or a polymorph of bupropion hydrobromide within about 1 hour. In at least one embodiment the XL core is a normal release matrix formulation. In certain embodiments the core comprises an effective pharmaceutical amount of bupropion hydrobromide and/or a polymorph of bupropion hydrobromide, a binder (e.g. polyvinyl alcohol), and a lubricant (e.g. glyceryl behenate). Additional inert excipients consistent with the objects of the invention can also be added to the core formulation. The additional inert excipients can be added to facilitate the preparation and/or improve patient acceptability of the final extended-release dosage form as described herein. The additional inert excipients are well known to the skilled artisan and can be found in the relevant literature, for example in the Handbook of Pharmaceutical Excipients. Non-limiting examples of such excipients include spray dried lactose, sorbitol, mannitol, and any cellulose derivative.

In certain embodiments the core of the bupropion hydrobromide composition (e.g. core of an XL tablet) can be made according to any one of the methods described in U.S. Pat. No. 7,241,805, U.S. patent application Ser. No. 11/834,848 (Pub. No. 2008-0075774), or U.S. patent application Ser. No. 11/930,644 (Pub. No. 2008-0274181).

In at least one embodiment of the invention, the granules to be compressed to form the core of the bupropion hydrobromide XL tablet of the invention described herein, are manufactured by the wet granulation process. Wet granulation involves agitation of a powder (the active drug) by convention in the presence of a liquid (the solution binder) followed by drying. For forming the granules, which are to be eventually compressed into the tablet cores, the bupropion hydrobromide salt is first granulated, for example, with a solution binder, in a granulator, for example using a fluidized bed granulator (e.g. a fluidized bed granulator manufactured by Glatt (Germany) or Aeromatic (Switzerland)). The binder (e.g. polyvinyl alcohol) is first dissolved or dispersed in a suitable solvent (e.g. water). The solution binder is then top sprayed onto the drug in a granulator (e.g. a fluidized bed granulator). Alternatively, granulation can also be performed in a conventional or high shear mixer. If necessary, the additional inert excipients (e.g. a filler) can be mixed with the bupropion hydrobromide salt prior to the granulation step.

The granules formed are subsequently dried and then sieved prior to blending the granules with the lubricant. In certain embodiments, the dried granules are sieved through a 1.4 mm mesh screen. The sieved granules are then blended with the lubricant, and if necessary, any other additional inert excipients, which can improve processing of the extended-release tablets of the invention. Blending of the granules with the lubricant, and if necessary, any additional inert excipients, such as for example a glidant, can be performed in a V-blender or any other suitable blending apparatus. Glidants can improve the flowability of the powder. This for example, can be helpful during tablet production at high production speeds and during direct compaction. However, because the requirement for adequate flow is high, a glidant is often also added to a granulation before tabletting. The blended granules are subsequently pressed into tablets and are hereinafter referred to as tablet cores. Tablet cores can be obtained by the use of standard techniques and equipment well known to the skilled artisan. For example, the XL tablet cores can be obtained by a rotary press (also referred to as a multi-station press) fitted with suitable punches.

The granules can also be manufactured by using other processes known to the skilled artisan. Examples of other granule manufacturing processes include dry granulation (e.g. slugging, roller compaction), direct compression, extrusion, spheronization, melt granulation, and rotary granulation.

An example of the granulation process for the XL cores (60 kg batch) is as follows: A Fluid Bed Processor is used for granulation in order to agglomerate the particles of the materials to obtain a uniform particle size for the final blend. The granulating solution is prepared by dissolving the binder (e.g. polyvinyl alcohol) in hot purified water while mixing. The percent solids content can be adjusted to obtain a viscosity to control the build up (agglomeration size) of the material. A lower viscosity leads to smaller particles, and a higher viscosity leads to larger particles. In addition, the application rate (e.g. from about 150 gm/min to about 250 gm/min, including all values and ranges therebetween; or about 200 gm/min), position of Spray gun (e.g. center position) and nozzle size (e.g. from about 0.5 mm to about 2 mm, including all values and ranges therebetween; or about 1 mm) and atomization pressure (e.g. from 20 psi to about 40 psi, including all values and ranges therebetween; or about 30 psi) contribute further to control particle size. The active material is fluidized and heated (e.g. from about 35° C. to about 45° C., including all values and ranges therebetween; or about 40° C.) prior to start of solution application. During the spray cycle, the bed temperature (e.g. from about 35° C. to about 45° C.; including all values and ranges therebetween, or about 40° C.) is kept at a constant temperature to avoid over-wetting. Once all the required binder solution is applied, the material is further dried to the targeted LOD value (i.e. loss on drying) (e.g. below about 1%) prior to unloading. The amount of binder (e.g. polyvinyl alcohol) is from about 2% to about 6%, including all values and ranges therebetween, e.g. about 3%; and the solution concentration is from about 3% to about 7%, including all values and ranges therebetween, e.g. about 4.5%. The time of agglomeration process for the 60 kg batch is from about 45 minutes to about 220 minutes including all values and ranges therebetween e.g. about 150 minutes. Once the granulate is dry, material is passed through a 1.4 and 2.00 mm screen to remove any oversized particles. The oversized particles are passed through the mill to reduce oversize particles. Oversized particles are generally not present in an amount to exceed about 5% of total yield. The screened and milled materials are placed into a shell blender (e.g. V-Blender, Bin blender) and the lubricant (e.g. glyceryl behenate) is added. The lubricant is screened and added to the granules and blended at the predetermined number of revolutions or time (e.g. mix time of about 5 min to about 15 min, including all values and ranges therebetween; e.g. including about 10 min). The percent lubricant is from about 0.5% to about 4%, including all values and ranges therebetween (e.g. including about 2%). The level of lubrication is established for sufficient coverage of either larger or smaller particle size distribution. Additional characteristics include bulk density (e.g. from about 0.3 gm/ml to about 0.8 gm/ml, including all values and ranges therebetween, e.g. including about 0.5 gm/ml), and moisture content (e.g. not more than about 1%). Particle size and flow of final blend are factors in obtaining uniform fill of cavities on a rotary press. The flow and top rotation speed of the press are adjusted (dependant on the type/size of press) so as to not jeopardize the weight uniformity of individual tablets. The product blend is passed through a hopper into a feed frame to fill the die cavities passing under the feed frame. Weight adjustments are made to keep the weight within the specified range, and adjustments made to the pressure settings to obtain the required hardness. Some components monitored for the tablets are tablet thickness and friability (e.g. less than about 0.5%). Suitable thickness (related to overall surface area) and lower friability help reduce core damage and loss of active during coating. Tablet samples are removed at predetermined intervals to monitor specifications.

Coatings

The tablet cores can be coated for administration to a subject. In at least one embodiment of the invention, the tablet cores are coated with a controlled release coating ("XL Controlled Release Coat") that can provide an extended release of the bupropion hydrobromide salt or mixture of the bupropion hydrobromide salt and other drug. In at least one other embodiment, the tablet cores are coated with an aqueous controlled release coating that comprises an aqueous dispersion of a neutral ester copolymer without any functional groups ("AQ Controlled Release Coat").

In certain embodiments the tablet dosage form comprises an optional moisture barrier in addition to the controlled release coat. The controlled release coat and the moisture barrier can be applied in two stages. The controlled release coat can be applied directly onto the surface of the tablet cores and functions to control the release of the bupropion hydrobromide salt. The moisture barrier can be applied directly onto the surface of the controlled release coat to impede or retard the absorption of moisture.

Prophetic examples of controlled release coat formulations are provided below. It should be understood that the constituents and/or proportions of the constituents in these coatings as well as the amounts thereof can be varied in order to achieve formulations possessing different release characteristics. In all instances wherein prophetic examples are provided these compositions are intended to be exemplary and it should be understood that the specific procedures, constituents, amounts thereof and the like can be varied in order to obtain a composition possessing desired properties.

In at least one embodiment the controlled release coat is a coating formulation that provides a delayed release of the active drug(s) from the tablet core. In such embodiments the coating formulation to be applied to the core can comprise:

| | |
|---|---|
| EUDRAGIT ® L12.5 | about 50% by weight of coating suspension |
| Triethyl citrate | about 0.63% by weight of coating suspension |
| Talc | about 1.25% by weight of coating suspension |
| Isopropyl alcohol | about 48.12% by weight of coating suspension |
| Solids total = | about 8.1% |
| Polymer content of suspension = | about 6.3% |

In certain embodiments the controlled release coating of the bupropion hydrobromide dosage form (e.g. controlled release coat of an XL tablet) can be made according to any one of the methods described herein.

Preparation of the controlled release coating formulation of such embodiments (e.g. controlled release coat that can provide a delayed release of the active drug) can be as follows: Talc and triethyl citrate are homogenized in the solvent by means of a homogenizer for approximately 10 minutes. The suspension is poured directly into the EUDRAGIT® L12.5 dispersion and stirred gently to avoid sedimentation. The coating is sprayed onto tablets until approximately 5 mg/cm2 of EUDRAGIT® L has been applied to the tablet core.

In at least one embodiment the controlled release coat can provide a sustained release of the active drug from the tablet core. The coating formulation can comprise:

| | |
|---|---|
| EUDRAGIT ® RL 12.5 | about 10% by weight of coating suspension |
| EUDRAGIT ® RS 12.5 | about 30% by weight of coating suspension |
| Dibutyl sebacate | about 0.5% by weight of coating suspension |
| Talc | about 3.5 g by weight of coating suspension |
| Magnesium stearate | about 1% by weight of coating suspension |
| Acetone | about 27.5% by weight of coating suspension |
| Isopropyl alcohol | about 27.5% by weight of coating suspension |
| Solids total = | about 10% |
| Polymer content of suspension = | about 5% |

Preparation of the controlled release coating formulation of such embodiments (i.e. controlled release coat that can provide a sustained release of the active drug) can be as follows: Dibutyl sebacate, talc and magnesium stearate are mixed and finely dispersed together with the diluents acetone and isopropyl alcohol. The suspension is then combined with the EUDRAGIT® polymer dispersions. The coating is sprayed onto the core until approximately 10 mg/cm2 of polymer has been applied to the core.

In at least one embodiment the controlled release coat is a polymer blend coating possessing pH dependent polymer (e.g. EUDRAGIT® L30D55) in combination with a sustained release polymer (e.g. AQUACOAT®). Such a coating formulation can comprise:

| | |
|---|---|
| AQUACOAT® (ethylcellulose 30%) | about 21% by weight of coating suspension |
| EUDRAGIT® L30 D 55 | about 21% by weight of coating suspension |
| Triethyl citrate | about 3% by weight of coating suspension |
| Water | about 55% by weight of coating suspension |
| Solids total = | about 15.6% |
| Polymer content of suspension = | about 12.6% |

Application of the polymer blend coating can be as follows: Coating applied to a 10 mg/cm2 application of polymer to the drug core.

In at least one embodiment the controlled release coat is a drug coating containing at least one other drug (e.g. Citalopram) on top of a core containing bupropion hydrobromide salt. The coating formulation can comprise:

| | |
|---|---|
| KOLLIDON® VA64 (Vinylpyrrolidone-vinyl acetate copolymer) | about 2.5% by weight of drug coating suspension |
| KLUCEL™ EF (Hydroxypropylcellulose) | about 2.5% by weight of drug coating suspension |
| Citalopram | about 2% by weight of drug coating suspension |
| Talc | about 3% by weight of drug coating suspension |
| 2-propanol | about 90% by weight of drug coating suspension |
| Solids total = | about 10% |
| Polymer content of suspension = | about 5% |

Application of the drug coating formulation can be as follows: Drug coating is sprayed onto tablets until the desired amount of other drug (e.g. Citalopram) is applied.

A top-coat can subsequently be applied as a cosmetic coating and also to prevent tablet sticking.

The top-coat formulation applied to the drug coated core can comprise:

| | |
|---|---|
| KOLLIDON® VA64 (Vinylpyrrolidone-vinyl acetate copolymer) | about 2.5% by weight of top-coat suspension |
| KLUCEL™ EF (Hydroxypropylcellulose) | about 2.5% by weight of top-coat suspension |
| Talc | about 2.5% by weight of top-coat suspension |
| Isopropyl alcohol | about 92.5% by weight of top-coat suspension |
| Solids total = | about 7.5% |
| Polymer content of suspension = | about 5% |

Application of the top-coating formulation can be as follows: Coating is applied to about a 2% weight gain (expressed as % of drug coated tablet core)

The Extended Release (XL) Controlled Release Coat

The XL controlled release coat is a semi-permeable coat comprising a water-insoluble, water-permeable film-forming polymer, a water-soluble polymer, and optionally a plasticizer.

Non-limiting examples of water-insoluble, water-permeable film-forming polymers useful for the XL controlled release coat of certain embodiments include cellulose ethers, cellulose esters, polyvinyl alcohol and mixtures thereof. In certain embodiments the water-insoluble, water-permeable film forming polymers can be the ethyl celluloses, and can be selected from the following non-limiting examples: ethyl cellulose grades PR100, PR45, PR20, PR10 and PR7 (ETHOCEL®, Dow), and any combination thereof. In at least one embodiment of the invention, ethyl cellulose grade PR 100 is the water-insoluble, water-permeable film-forming polymer. In certain embodiments the amount of the water-insoluble water-permeable film-forming polymer can vary from about 1% to about 12% by weight of the tablet dry weight, including all values and ranges therebetween. For example, in certain embodiments the amount of the water-insoluble water-permeable film-forming polymer is present in an amount from about 5% to about 10%, and in other embodiments from about 6% to about 8% by weight of the tablet dry weight. In certain embodiments of the 174 mg dose modified-release tablets of the invention, the amount of water-insoluble water permeable film-forming polymer is from about 3% to about 8% by weight of the tablet dry weight, preferably from about 6% to about 7% of the tablet dry weight, including all values and ranges therebetween. With respect to the controlled release coat itself, the amount of water-insoluble water-permeable film-forming polymer in certain embodiments of the 174 mg dose tablet can be from about 35% to about 60% by weight of the controlled release coat dry weight, including all values and ranges therebetween; and in certain embodiments from about 40% to about 50% by weight of the controlled release coat dry weight. In certain embodiments of the 348 mg dose modified-release tablet of the invention, the amount of water-insoluble water-permeable film-forming polymer can be from about 2% to about 5% by weight of the tablet dry weight, including all values and ranges therebetween, and in other embodiments from about 3% to about 4% by weight of the tablet dry weight. With respect to the controlled release coat itself, the water-insoluble water-permeable film-forming polymer in certain embodiments of the 348 mg dose tablet is present in an amount of about 40% by weight of the controlled release coat dry weight. In certain embodiments of the 522 mg dose modified-release tablet of the invention, the amount of water-insoluble water-permeable film-forming polymer can be from about 0.5% to about 10% by weight of the tablet dry weight, including all values and ranges therebetween, and in other embodiments from about 1% to about 6% by weight of the tablet dry weight. With respect to the controlled release coat itself, the water-insoluble water-permeable film-forming polymer in certain embodiments of the 522 mg dose tablet is present in an amount of about 37% by weight of the controlled release coat dry weight.

Non-limiting examples of water-soluble polymers useful for the XL controlled release coat include polyvinylpyrrolidone, hydroxypropyl methylcellulose, hydroxypropyl cellulose and mixtures thereof. In at least one embodiment the water-soluble polymer is polyvinylpyrrolidone (POVIDONE® USP). The amount of water-soluble polymer can vary from about 1.5% to about 10% by weight of the tablet dry weight, including all values and ranges therebetween. For example, in certain embodiments the amount of water-soluble polymer is from about 3% to about 8%, and in other embodiments at about 4% by weight of the tablet dry weight. With respect to the controlled release coat itself, in certain embodiments the amount of water-soluble polymer present is from about 25% to about 55% by weight of the controlled release coat dry weight, including all values and ranges therebetween. For certain embodiments of the 174 mg dose of the extended release tablet of the invention, the amount of water-soluble polymer is from about 3% to about 5% by weight of the tablet dry weight, including all values and ranges therebetween and from about 25% to about 50% by weight of the controlled release coat dry weight, including all values and ranges therebetween. For certain embodiments of the 348 mg dose of the extended release tablet of the invention, the amount of water-soluble polymer present is from about 2% to about 5% of the tablet dry weight including all values and ranges therebetween; and from about 40% to about 50% by weight of the controlled release coat dry weight, including all values and ranges therebetween. For certain embodiments of the 522 mg dose of the extended release tablet of the invention, the amount of water-soluble polymer present is from about 2% to about 5% of the tablet dry weight, including all values and ranges therebetween; and from about 40% to about 50% by weight of the controlled release coat dry weight, including all values and ranges therebetween.

In certain embodiments, the XL controlled release coat further comprises a plasticizer. The use of plasticizers is optional, and they can be added to film coating formulations to modify the physical properties of a polymer to make it more usable during manufacturing. Plasticizers can be high boiling point organic solvents used to impart flexibility to otherwise hard or brittle polymeric materials. Plasticizers generally cause a reduction in the cohesive intermolecular forces along the polymer chains resulting in various changes in polymer properties including a reduction in tensile strength, and increase in elongation and a reduction in the glass transition or softening temperature of the polymer. The amount and choice of the plasticizer can affect the hardness of a tablet and can even affect its dissolution or disintegration characteristics, as well as its physical and chemical stability. Certain plasticizers can increase the elasticity and/or pliability of a coat, thereby decreasing the coat's brittleness. Once the dosage form is manufactured, certain plasticizers can function to increase the hydrophilicity of the coat(s) and/or the core of the dosage form in the environment of use (in-vitro or in-vivo). Non-limiting examples of plasticizers that can be used in the controlled release coat described herein include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropionin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, polyols (e.g. polyethylene glycol) of various molecular weights, and mixtures thereof. It is contemplated and within the scope of the invention, that a combination of plasticizers can be used in the present formulation. In at least one embodiment of the invention, the plasticizer is polyethylene glycol 4000, dibutyl sebacate or a mixture thereof. The amount of plasticizer for the controlled release coat can vary in an amount of from about 0.5% to about 4% by weight of the tablet dry weight, including all values and ranges therebetween. For example, in certain embodiments the plasticizer is present in an amount of from about 2% to about 3% by weight of the tablet dry weight. For certain embodiments of the 174 mg dose extended-release tablet of the invention, the amount of plasticizer present in the controlled release coat is from about 1% to about 4% by weight of the tablet dry weight, including all values and ranges therebetween. For certain embodiments of the 348 mg dose extended release tablet of the invention, the amount of plasticizer present is from about 0.5% to about 4% by weight of the tablet dry weight, including all values and ranges therebetween. For certain embodiments of the 522 mg dose extended release tablet of the invention, the amount of plasticizer present is from about 0.5% to about 4% by weight of the tablet dry weight, including all values and ranges therebetween. In certain embodiments of the 174 mg, 348 mg and 522 mg dosage forms, the plasticizer is present in an amount of from about 6% to about 30% by weight of the controlled release coat dry weight, including all values and ranges therebetween. For example, in certain embodiments the plasticizer is present in an amount of about 12% by weight of the controlled release coat dry weight.

The ratio of water-insoluble water-permeable film forming polymer:plasticizer:water-soluble polymer for the XL controlled release coat of certain embodiments of the invention described herein can vary from about 3:1:4 to about 5:1:2, including all values and ranges therebetween. For example, in certain embodiments the ratio of water-insoluble water-permeable film forming polymer:plasticizer:water-soluble polymer for the XL controlled release coat is about 4:1:3. For certain other embodiments of the XL tablet the ratio of the water-insoluble water-permeable film-forming polymer:plasticizer:water-soluble polymer in the XL controlled release coat is from about 7:2:6 to about 19:5:18, including all values and ranges therebetween. In at least one embodiment the ratio of water-insoluble water-permeable film forming polymer:plasticizer:water-soluble polymer for the XL controlled release coat is about 13:4:12. In at least one embodiment of the 522 mg dosage form, the ratio of water-insoluble water-permeable film forming polymer:plasticizer:water-soluble polymer for the XL controlled release coat is about 13:6:16.

In certain embodiments the XL controlled release coat of the bupropion hydrobromide tablet can be made according to any one of the methods described herein.

Preparation and application of the XL controlled release coat can be as follows. The water-insoluble water-permeable film-forming polymer (e.g. ethylcellulose), and the plasticizer (e.g. polyethylene glycol 4000), are dissolved in an organic solvent (e.g. a mixture of ethyl alcohol). In the manufacture of embodiments that do not require a plasticizer, the water-insoluble water-permeable film-forming polymer can be dissolved in the organic solvent without the plasticizer. The water-soluble polymer (e.g. polyvinyl pyrrolidone) is next added until a homogenous mixture is achieved. The resulting controlled release coat solution is then sprayed onto the tablet cores using a tablet coater, fluidized bed apparatus or any other suitable coating apparatus known in the art until the desired weight gain is achieved. The tablet cores coated with the controlled release coat are subsequently dried. In the manufacture of embodiments that have a moisture barrier, the controlled release coat is dried before the moisture barrier is applied.

An example of the coating process for the XL controlled release coat is as follows: The XL controlled release coat solution is prepared by dissolving the water insoluble polymer (e.g. ethylcellulose) and water soluble polymer (e.g. polyvinylpyrrolidone) and an ethyl alcohol mixture while mixing and is followed with the addition of the plasticizer(s) (e.g. mixture of polyethylene glycol 4000 and dibutyl sebacate). Once completely dissolved, the solution is homogenized to obtain a uniform mixture of appropriate viscosity. This procedure helps obtain a complex mix of a water permeable film to control the release of the active drug. The composition of the solution can be formulated to contain various levels of the water insoluble polymer and water soluble polymer and a mix of the plasticizer(s). The release function is further controlled by the film thickness applied and measured as weight gain of solids in the coating required. Tablets are coated in a perforated coating pan with control of pan speed (e.g. from about 8 rpm to about 14 rpm, including all values and ranges therebetween; and in some cases about 12 rpm), spray rate (e.g. from about 150 gm/min to about 250 gm/min, including all values and ranges therebetween; and in some cases about 200 gm/min), atomization pressure (e.g. from about 15 psi to about 25 psi, including all values and ranges therebetween; and in some cases about 20 psi), supply volume (from about 800 to about 1000 cubic ft/min, including all values and ranges therebetween, and in some cases about 900 cubic ft/min), and air temperature (e.g. from about 50° C. to about 60° C., including all values and ranges therebetween; and in some cases about 55° C.), monitored through a bed temperature and/or outlet temperature of from about 38° C. to about 42° C., including all values and ranges therebetween; and in some cases about 40° C. On completion of the coating cycle, tablets are dried and unloaded into bulk containers. The printing process comprises the transfer of a print image from a print plate covered with edible black ink and transferred via a print roll or print pad onto the surface of the tablets. The printed tablets are transferred through a drying element prior to discharging into bulk containers. Samples for final testing are taken throughout the printing process.

The skilled artisan will appreciate that controlling the permeability can control the release of the bupropion hydrobromide salt and/or the amount of coating applied to the tablet cores. The permeability of the XL controlled release coat can be altered by varying the ratio of the water-insoluble, water-permeable film-forming polymer:plasticizer:water-soluble polymer and/or the quantity of coating applied to the tablet core. A more extended release can be obtained with a higher amount of water-insoluble, water-permeable film forming polymer. The addition of other excipients to the tablet core can also alter the permeability of the controlled release coat. For example, if it is desired that the tablet core further comprise an expanding agent, the amount of plasticizer in the controlled release coat could be increased to make the coat more pliable, as the pressure exerted on a less pliable coat by the expanding agent could rupture the coat. Further, the proportion of the water-insoluble water-permeable film forming polymer and water-soluble polymer can also be altered depending on whether a faster or slower dissolution and/or release profile is desired.

Depending on the dissolution or in-vivo release profile desired, the weight gained after coating the tablet core with the XL controlled release coat typically can vary from about 3% to about 30% of the weight of the dry tablet core, including all values and ranges therebetween. For a 174 mg dose extended release tablet according to certain embodiments, the weight gain can typically vary from about 10% to about 17% of the weight of the dry tablet core, including all values and ranges therebetween. For the 348 mg dose extended release tablet of certain embodiments, the weight gain can vary from about 7% to about 10% of the weight of the dry tablet core, including all values and ranges therebetween For the 522 mg dose extended release tablet of certain embodiments, the weight gain can vary from about 5% to about 15% of the weight of the dry tablet core, including all values and ranges therebetween AQ Controlled Release Coat The AQ controlled release coat is a stable monolithic controlled release coating comprising an aqueous dispersion of a neutral ester copolymer without any functional groups, a poly glycol having a melting point greater than about 55° C., and one or more pharmaceutically acceptable excipients; wherein said coating composition is coated onto the dosage form and cured at a temperature at least equal to or greater than the melting point of the poly glycol. The coating formulation is quite versatile in that it can be used to coat a variety of drug cores and can be easily manipulated to obtain the desired drug release profile.

In certain other embodiments, the AQ controlled release coat comprises an aqueous dispersion of an ethylcellulose, a poly glycol having a melting point greater than about 55° C., and one or more pharmaceutically acceptable excipients; wherein said coating composition is coated onto the dosage form and cured at a temperature at least equal to or greater than the melting point of the poly glycol. Non limiting examples of aqueous dispersions of an ethylcellulose include SURELEASE® (Colorcon, Inc., West Point, Pa., U.S.A.), and AQUACOAT® (FMC Corp., Philadelphia, Pa., U.S.A.). Combinations are operable.

In certain embodiments the AQ controlled release coat is a stable controlled release monolithic coating that is formed by a process that comprises coating the core with a coating composition to form a coated core with an intermediate coating, and curing the coated core to form the AQ controlled release coat. In at least one embodiment the coating composition comprises an aqueous dispersion of a neutral ester copolymer without any functional groups, a poly glycol having a melting point of at least 55° C., and one or more pharmaceutically acceptable excipients. The curing is conducted at a temperature at least equal to or greater than the melting point of the poly glycol. In at least one embodiment the stable AQ controlled release coat comprises a neutral ester copolymer without any functional groups, a poly glycol having a melting point of at least 55° C., and one or more pharmaceutically acceptable excipients.

The aqueous dispersion of a neutral ester copolymer without any functional groups can be an ethyl acrylate and methyl methacrylate copolymer dispersion. Non-limiting examples of ethyl acrylate and methyl methacrylate copolymer dispersions include a 30% aqueous dispersion of a neutral copolymer based on ethyl acrylate and methyl methacrylate (e.g. EUDRAGIT® NE30D), a 40% aqueous dispersion of a neutral copolymer based on ethyl acrylate and methyl methacrylate (e.g. EUDRAGIT® NE40D), EUDRAGIT® NM30D, KOLLICOAT® EMM30D, and combinations thereof. In at least one embodiment the neutral ester copolymer without any functional groups used in the controlled release coating composition is EUDRAGIT® NE30D, EUDRAGIT® NE40D, or a mixture thereof. The neutral ester copolymer without any functional groups can be present in certain embodiments in an amount of from about 1% to about 35% by weight of the coating composition, including all values and subranges therebetween, depending on the therapeutically active agent used and the controlled release profile desired. In certain embodiments the neutral ester copolymer without any functional groups is present in an amount from about 20% to about 99.5% by dry weight of the AQ controlled release coat, including all values and subranges therebetween. In other embodiments the neutral ester copolymer without any functional groups is present in an amount from about 25% to about 60% by dry weight of the AQ controlled release coat, including all values and subranges therebetween. In still other embodiments the neutral ester copolymer without any functional groups is present in an amount from about 37% to about 50% by dry weight of the AQ controlled release coat, including all values and subranges therebetween; for example, including about 38%, about 39%, about 40%, about 41%, about 42%, about 43%, about 44%, about 45%, about 46%, about 47%, about 48%, and about 49% by dry weight of the AQ controlled release coat. In certain embodiments the neutral ester copolymer without any functional groups is present in the coating composition in an amount of from about 0.4% to about 39.8% by dry weight of the tablet including all values and subranges therebetween; in other embodiments in an amount of from about 0.8% to about 24.0% by dry weight of the tablet, including all values and subranges therebetween; and in still other embodiments in an amount of from about 2.0% to about 5.5% by dry weight of the tablet, including all values and subranges therebetween.

Hydrophilic agents can also be included in the AQ controlled release coat to promote wetting of the coat when in contact with gastrointestinal fluids. Non-limiting examples of such hydrophilic agents include hydrophilic water soluble polymers such as hydroxypropyl methylcellulose (HPMC), hydroxypropyl cellulose (HPC) and combinations thereof. In at least one embodiment, HPMC is the hydrophilic water soluble polymer. If hydrophilic agents are to be included in the coat composition, the agents can be present in an amount from about 0.1% to about 10% by weight of the coating composition, including all values and ranges therebetween. For example, in certain embodiments the hydrophilic agents are present in an amount of from about 0.1% to about 5%, and in other embodiments from about 0.1% to about 3% by weight of the controlled release coat composition. In certain embodiments the hydrophilic agent is present in an amount of from greater than about 0% to about 35% by dry weight of the AQ controlled release coat, including all values and subranges therebetween; preferably from about 8% to about 30% by dry weight of the AQ controlled release coat, including all values and subranges therebetween and still further preferably from about 12% to about 26% by dry weight of the AQ controlled release coat, including all values and subranges therebetween. In certain embodiments the hydrophilic agent is present in the coating formulation in an amount of from about 0% to about 14.0% by dry weight of the tablet, including all values and subranges therebetween; preferably from about 0.2% to about 6.0% by dry weight of the tablet, including all values and subranges therebetween; and still further preferably from about 0.8% to about 2.5% by dry weight of the tablet, including all values and subranges therebetween.

The AQ controlled release coat formulation also comprises a poly glycol with a melting point of greater than about 55° C. The poly glycol used in the AQ controlled release coat can be a polyethylene glycol with an average molecular weight ranging from about 4,000 daltons to about 35,000 daltons. Non-limiting examples of a poly glycol with a melting point of greater than 55° C. include polyethylene glycol 4000, polyethylene glycol 4600, polyethylene glycol 6000, polyethylene glycol 8000, polyethylene glycol 10000, polyethylene glycol 12000, polyethylene glycol 20000, polyethylene glycol 35000, and mixtures thereof. In certain embodiments, the poly glycol is selected from the group consisting of polyethylene glycol 6000, polyethylene glycol 8000, polyethylene glycol 10000, polyethylene glycol 12000, and mixtures thereof. In at least one embodiment the poly glycol used in the coating composition of the AQ controlled release coat is polyethylene glycol 8000. The poly glycol can be present in certain embodiments in an amount of from about 0.1% to about 10% by weight of the coating composition, including all values and subranges therebetween. In certain embodiments the poly glycol is present in an amount of from about 0.5% to about 28% by dry weight of the AQ controlled release coat, including all values and subranges therebetween. In other embodiments the poly glycol is present in an amount from about 4% to about 17% by dry weight of the AQ controlled release coat, including all values and subranges therebetween. In still other embodiments the poly glycol is present in an amount from about 7.2% to about 15.2% by dry weight of the AQ controlled release coat, including all values and subranges therebetween; In certain embodiments the poly glycol is present in the coating composition in an amount of from about 0.1% to about 11.2% by dry weight of the tablet, including all values and subranges therebetween; in other embodiments in an amount of from about 0.1% to about 8.0% by dry weight of the tablet, including all values and subranges therebetween; and in still other embodiments in an amount of from about 0.2% to about 2.8% by dry weight of the tablet, including all values and subranges therebetween. Other examples of suitable polyglycol derivatives having a melting point of at least about 55° C. include, but are not limited to, Poloxamer 188, Poloxamer 338, Poloxamer 407, Polyethylene Oxides, Polyoxyethylene Alkyl Ethers, Polyoxyethylene Stearates and mixtures thereof.

In addition to the copolymers and the poly glycol, the AQ controlled release coat formulation comprises at least one pharmaceutically acceptable excipient. The excipients can include but are not limited to anti-tacking agents, emulsifying agents, antifoaming agents, flavourants, colourants, and mixtures thereof. It is known in the art that depending on the intended main function, excipients can affect the properties of the coat in a series of ways, and many substances used in coat formulations can thus be described as multifunctional. A skilled worker will know, based on his technical knowledge, which pharmaceutically acceptable excipients are suitable for the desired AQ controlled release coat composition.

The tackiness of polymeric films is a factor for the coating of solid dosage forms and for the subsequent curing step (post coating thermal treatment). During coating with either cellulosic or acrylic polymers, sometimes an unwanted agglomeration of several granules or beads can occur, for example at higher product processing temperatures. Accordingly, the addition of anti-tacking agents to coating formulations can be desirable in certain embodiments. The anti-tacking agents which can be used in certain embodiments include but are not limited to adipic acid, magnesium stearate, calcium stearate, zinc stearate, hydrogenated vegetable oils, sterotex, glyceryl monostearate, talc (e.g. talc 400), sodium benzoate, sodium lauryl sulfate, magnesium lauryl sulfate, and mixtures thereof. In at least one embodiment, talc is the anti-tacking agent. Talc can also function as a wetting agent. Mixtures of the anti-tacking agents are operable. The amount of anti-tacking agent in the controlled release coat composition can range from about 1% to about 15% by weight of the controlled release coating composition, including all values and ranges therebetween. For example, in certain embodiments the anti-tacking agent is present in an amount of from about 1% to about 7% by weight of the controlled release coating composition. In certain embodiments the anti-tacking agent is present in an amount of from greater than about 0% to about 50% by dry weight of the AQ controlled release coat including all values and subranges therebetween; preferably from about 2% to about 40% by dry weight of the AQ controlled release coat including all values and subranges therebetween and still further preferably from about 10% to about 30% by dry weight of the AQ controlled release coat including all values and subranges therebetween. In certain embodiments the anti-tacking agent is present in the coating formulation in an amount of from about 0% to about 20.0% by dry weight of the tablet, including all values and subranges therebetween; in other embodiments in an amount of from about 0% to about 12.0% by dry weight of the tablet, including all values and subranges therebetween; and in still other embodiments in an amount of from about 0.6% to about 7.0% by dry weight of the tablet, including all values and subranges therebetween.

Certain embodiments can include anti-foaming agents in the AQ controlled release coat composition. Non-limiting examples of useful anti-foaming agents include silicon oil, simethicone, and mixtures thereof. In at least one embodiment, simethicone is the anti-foaming agent used in the AQ controlled release coat composition. The anti-foaming agent can be present in an amount of up to about 0.5% by weight of the AQ controlled release coat composition. For example, in certain embodiment the anti-foaming agent is present in an amount of from about 0.1% to about 0.4% by weight of the AQ controlled release coat composition, including all values and ranges therebetween. In certain embodiments the anti-foaming agent is present in an amount of from greater than about 0% to about 3% by dry weight of the AQ controlled release coat, including all values and subranges therebetween. In other embodiments the anti-foaming agent is present in an amount from about 0.4% to about 2% by dry weight of the AQ controlled release coat, including all values and subranges therebetween. In still other embodiments the anti-foaming agent is present in an amount from about 0.8% to about 1.5% by dry weight of the AQ controlled release coat, including all values and subranges therebetween; for example, including about 0.9%, about 1.0%, about 1.1%, about 1.2%, about 1.3%, and about 1.4% by dry weight of the AQ controlled release coat. In certain embodiments the anti-foaming agent is present in the coating formulation in an amount of from about 0% to about 1.2% by dry weight of the tablet, including all values and subranges therebetween; in other embodiments in an amount of from about 0% to about 0.8% by dry weight of the tablet, including all values and subranges therebetween; and in still other embodiments in an amount of from about 0% to about 0.2% by dry weight of the tablet, including all values and subranges therebetween; for example, including about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, and about 0.19% by dry weight of the tablet.

Certain embodiments can include emulsifying agents (also called emulsifiers or emulgents) in the AQ controlled release coat. Emulsifying agents can facilitate emulsification during manufacture of the AQ controlled release coat, and also provide emulsion stability during the shelf-life of the product. Non-limiting examples of emulsifying agents include naturally occurring materials and their semi synthetic derivatives, such as the polysaccharides, as well as glycerol esters, cellulose ethers, sorbitan esters and polysorbates. Mixtures are operable. In at least one embodiment the emulsifying agent is Polysorbate 80 (polyoxyethylene sorbitan mono-oleate) (e.g. TWEEN® 80). The emulsifying agent can be present in an amount of from about 0% to about 0.5% by weight of the AQ controlled release coat composition, including all values and subranges therebetween. For example, in certain embodiments the emulsifying agent is present in an amount of from about 0.1% to about 0.3% by weight of the AQ controlled release coat composition, including all values and ranges therebetween. In certain embodiments the emulsifying agent is present in an amount of from greater than about 0% to about 2% by dry weight of the AQ controlled release coat, including all values and subranges therebetween. In other embodiments the emulsifying agent is present in an amount from about 0.1% to about 1% by dry weight of the AQ controlled release coat, including all values and subranges therebetween. In still other embodiments the emulsifying agent is present in an amount from about 0.25% to about 0.75% by dry weight of the AQ controlled release coat, including all values and subranges therebetween; for example, including about 0.30%, about 0.35%, about 0.40%, about 0.45%, about 0.50%, about 0.55%, about 0.60%, about 0.65%, and about 0.70% by dry weight of the AQ controlled release coat. In certain embodiments the emulsifying agent is present in the coating formulation in an amount of from greater than about 0% to about 0.8% by dry weight of the tablet, including all values and subranges therebetween; in other embodiments in an amount of from greater than about 0% to about 0.4% by dry weight of the tablet, including all values and subranges therebetween; and in still other embodiments in an amount of from greater than about 0% to about 0.2% by dry weight of the tablet, including all values and subranges therebetween; for example, including about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, and about 0.19% by dry weight of the tablet.

Certain embodiments can include colorants in the film coat formula. Such colorants can be water-insoluble colors (pigments). Pigments have certain advantages over water-soluble colors in that they tend to be more chemically stable towards light, provide better opacity and covering power, and optimize the impermeability of a given film to water vapor. Non-limiting examples of suitable colorants include iron oxide pigments, titanium dioxide, and aluminum Lakes. Mixtures are operable. In at least one embodiment the pigment is titanium dioxide. The pigment or colorant can be present in an amount of from about 0.1% to about 10% by weight of the AQ controlled release coat composition, including all values and ranges therebetween. For example, in certain embodiments the pigment or colorant is present in an amount of from about 0.1% to about 5%, and in other embodiments from about 0.1% to about 2% by weight of the AQ controlled release coat composition. In certain embodiments the colorant is present in an amount of from greater than about 0% to about 20% by dry weight of the AQ controlled release coat, including all values and subranges therebetween. In other embodiments the colorant is present in an amount from greater than about 0% to about 10% by dry weight of the AQ controlled release coat, including all values and subranges therebetween. In still other embodiments the colorant is present in an amount from about 2.2% to about 6.2% by dry weight of the AQ controlled release coat, including all values and subranges therebetween. In certain embodiments the colorant is present in the coating formulation in an amount of from greater than about 0% to about 8.0% by dry weight of the tablet, including all values and subranges therebetween; in other embodiments in an amount of from greater than about 0% to about 5.0% by dry weight of the tablet, including all values and subranges therebetween; and in still other embodiments in an amount of from greater than about 0% to about 1.0% by dry weight of the tablet, including all values and subranges therebetween; for example, including about 0.1%, about 0.2%, about 0.3%, about 0.4%, about 0.5%, about 0.6%, about 0.7%, about 0.8%, and about 0.9% by dry weight of the tablet.

In at least one embodiment, the AQ controlled release coat hydrates when placed into water. In at least one embodiment the dosage form that is coated with the AQ controlled release coat floats in water. In at least one embodiment, the controlled release dosage form, upon oral administration to a patient, provides controlled release of an effective amount of the bupropion hydrobromide to at least one region of the patient's upper gastrointestinal tract (e.g. the stomach).

In certain embodiments the AQ controlled release coat is formed by a process that does not involve the use of an organic solvent. In such embodiments the AQ controlled release coat composition is aqueous based and not solvent based, in contrast to prior art coating compositions that are solvent based (e.g. "PharmaPASS" composition).

In certain embodiments the AQ controlled release coat of the bupropion hydrobromide tablet can be made according to any one of the methods described herein.

The AQ controlled release coat can be applied onto a core comprising an effective amount of the bupropion hydrobromide salt by a process which involves the atomization (spraying) of the coating solution or suspension onto a bed of the tablet cores. Some examples of equipment suitable for film coating include: ACCELA COTA® (Manesty Machines, Liverpool, UK), HI-COATER® (Freund Company, Japan), DRIACOATER™ (Driam Metallprodukt GmbH, Germany), HTF/150 (GS, Italy), and IDA™ (Dumoulin, France). Examples of units that function on a fluidized-bed principle include: AEROMATIC™ (Fielder, Switzerland and UK) and GLATT™ AG (Switzerland). In at least one embodiment, the apparatus used for film coating is the ACCELA COTA®.

The coating fluid can be delivered to the coating apparatus from a peristaltic pump at the desired rate and sprayed onto the rotating or fluidizing tablet cores. The tablet cores are pre-warmed to about 30° C. During the coating process, the product temperature range is maintained at from about 25° C. to about 35° C. by adjusting the flow rate of the inlet and outlet air, temperature of the inlet air and spray rate. A single layer of coat is applied and once spraying is complete, the coated tablet cores are dried from about 30° C. to about 40° C. for a time period of from about 3 to about 5 minutes at a low pan speed and low air flow. The pan is readjusted to jog speed, and drying continues for a time period of from about 12 to about 15 minutes.

The coated tablet cores are placed onto a tray and cured (post coating thermal treatment) in an electrical or steam oven at a temperature above the temperature of the melting point of the polyethylene glycol or derivative thereof. In certain embodiments the curing temperature is greater than the melting point of the polyethylene glycol or derivative thereof. In certain embodiments the curing time is from about 2 to about 7 hours. The cured coated tablets are subsequently cooled to room temperature.

The AQ controlled release coat is quite versatile. The length and time for the delay can be controlled by rate of hydration and the thickness of the coat. The drug release rate subsequent to the delay can be determined by the thickness and permeability of the hydrated coat. Thus, it is possible to regulate the rate of hydration and permeability of the AQ controlled release coat so that the desired controlled-release drug profile can be achieved. There is no preferred coat thickness, as this will depend on the controlled release profile desired. Other parameters in combination with the thickness of the coat include varying the concentrations of some of the ingredients of the stable coat composition of the invention described and/or varying the curing temperature and length of curing the coated tablet cores. The skilled artisan will know which parameters or combination of parameters to change for a desired controlled release profile.

As will be seen from the non-limiting examples described herein, the coatings used in certain embodiments of the present invention are quite versatile. For example, the length and time for the lag time can be controlled by the rate of hydration and the thickness of the controlled release coat. Other parameters in combination with the thickness of the coatings include varying the concentrations of some of the ingredients of the coating compositions of certain embodiments described and/or varying the curing temperature and length of curing the coated tablet cores. The skilled artisan will know which parameters or combination of parameters to change for a desired controlled release profile.

The Moisture Barrier Coat

In certain embodiments, an optional moisture barrier is applied directly onto the controlled release coat. In other embodiments a moisture barrier coat is not included in the dosage form. In certain embodiments the moisture barrier comprises an enteric polymer (e.g. acrylic polymer), a permeation enhancer and optionally a plasticizer.

In certain embodiments, the enteric polymer is an acrylic polymer. For example, the acrylic polymer can be a methacrylic acid copolymer type C [poly(methacrylic acid, methyl methacrylate) 1:1] (e.g. EUDRAGIT® L 30 D-55). The methacrylic acid copolymer can be present in an amount, which can vary from about 1% to about 3% of the tablet dry weight including all values and ranges therebetween and from about 55% to about 70% of the moisture barrier dry weight including all values and ranges therebetween. For the 174 mg dose of the extended release tablet of certain embodiments of the present invention, the methacrylic acid copolymer can vary from about 2% to about 3% of the tablet dry weight including all values and ranges therebetween. For example in the 174 mg tablet of certain embodiments, the amount of methacrylic acid copolymer is present in an amount of about 2.5% of the tablet dry weight. With respect to the moisture barrier itself, the amount of the methacrylic acid copolymer in the 174 mg tablet can be present in an amount of from about 55% to about 70% by weight of the moisture barrier dry weight including all values and ranges therebetween. For example, in the 174 mg tablet of certain embodiments the methacrylic acid copolymer is present in an amount of about 60% of the moisture barrier dry weight. For the 348 mg dose of the extended release tablet of certain embodiments, the amount of the methacrylic acid copolymer can vary from about 1.5% to about 3% of the tablet dry weight including all values and ranges therebetween. For example, in the 348 mg tablet of certain embodiments, the amount of methacrylic acid copolymer is present at an amount of about 2% by weight of the tablet dry weight. With respect to the moisture barrier itself, the methacrylic acid copolymer in the 348 mg tablet typically will be present in an amount of from about 55% to about 70% of the moisture barrier dry weight including all values and ranges therebetween. For example in certain embodiments of the 348 mg tablet the methacrylic acid copolymer is present in an amount of about 60% of the moisture barrier dry weight. For the 522 mg dose of the extended release tablet of certain embodiments, the amount of the methacrylic acid copolymer can vary from about 0.5% to about 5% of the tablet dry weight including all values and ranges therebetween. For example, in the 522 mg tablet of certain embodiments, the amount of methacrylic acid copolymer is present at about 2% by weight of the tablet dry weight. With respect to the moisture barrier itself, the methacrylic acid copolymer in the 522 mg tablet typically will be present in an amount of from about 40% to about 80% of the moisture barrier dry weight. For example, in certain embodiments of the 522 mg tablet the methacrylic acid copolymer is present in an amount of about 65% of the moisture barrier dry weight.

It is known in the art that methacrylic acid copolymers can become brittle, and that coatings that contain methacrylic acid copolymers could be made more elastic and pliable by the addition of a plasticizer. In certain embodiments the moisture barrier coat comprises a plasticizer. Non-limiting examples of plasticizers useful for the moisture barrier coat of certain embodiments include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropionin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof, polyols (e.g. polyethylene glycol) of various molecular weights, and mixtures thereof. In certain embodiments, the plasticizer in the moisture barrier coat comprises a combination of triethyl citrate and polyethylene glycol 4000 (e.g. CARBOWAX® 4000). In certain of these embodiments, the ratio of triethyl citrate to polyethylene glycol 4000 is about 1:2. The plasticizer can be present in the moisture barrier coat of certain embodiments in an amount which can vary from about 0.2% to about 0.5%, including all values and ranges therebetween (e.g. including about 0.3%, and about 0.4% of the tablet dry weight). For example in certain embodiments the plasticizer can be present in an amount of about 0.35% of the tablet dry weight for a 174 mg tablet; in an amount of from about 0.2% to about 0.4% of the tablet dry weight for a 348 mg tablet; and in an amount of from about 0.05% to about 0.5% of the tablet dry weight for a 522 mg tablet, including all values and ranges therebetween. With respect to the moisture barrier itself, the plasticizer if present in certain embodiments can be present in an amount of from about 1% to about 30% by weight of the moisture barrier dry weight, including all values and ranges therebetween. For example, in certain embodiments the plasticizer is present in an amount of from about 10% to about 14% of the moisture barrier dry weight for the 174 mg, 348 mg and 522 mg dose extended release tablet of the present invention. It is well known in the art that depending on the intended main function, excipients to be used in tablets are subcategorized into different groups. However, one excipient can affect the properties of a drug or the tablet as a whole in a series of ways, and many substances used in tablet formulations can therefore be described as multifunctional. For example, the polyethylene glycol used in the plasticizer combination for the moisture barrier can serve not only to increase the hydrophilicity of the moisture barrier, but can also act as a glidant.

In certain embodiments the moisture barrier can further comprise a permeation enhancer that can increase its hydrophilicity, and can also act as a glidant. The permeation enhancer can be a hydrophilic substance and can be selected from the following non-limiting examples: hydrophilic polymers such as hydroxypropylmethylcellulose, cellulose ethers and protein-derived materials of these polymers, the cellulose ethers, such as hydroxyalkylcelluloses, carboxyalkylcelluloses, and mixtures thereof. Also, synthetic water-soluble polymers can be used, such as polyvinylpyrrolidone, cross-linked polyvinyl-pyrrolidone, polyethylene oxide, water-soluble polydextrose, saccharides and polysaccharides, such as pullulan, dextran, sucrose, glucose, lactose, fructose, mannitol, mannose, galactose, sorbitol and mixtures thereof. In at least one embodiment of the present invention, the hydrophilic polymer comprises hydroxypropyl-methylcellulose. Other non-limiting examples of permeation enhancers that can be used in the moisture barrier of certain embodiments include alkali metal salts such as aluminum oxidelithium carbonate, sodium chloride, sodium bromide, potassium chloride, potassium sulfate, potassium phosphate, sodium acetate, sodium citrate, and mixtures thereof. The permeation enhancers or pore-formers, can also be polymers which are soluble in the environment of use, such as CARBOWAX®, CARBOPOL®, and mixtures thereof. Non-limiting examples of pore formers include diols, polyols, polyhydric alcohols, polyalkylene glycols, polyglycols, poly(a-w)alkylenediols, and mixtures thereof. Other permeation enhancers which can be useful in the formulations of the present invention include starch, modified starch, and starch derivatives, gums, including but not limited to xanthan gum, alginic acid, other alginates, benitonite, veegum, agar, guar, locust bean gum, gum arabic, quince psyllium, flax seed, okra gum, arabinoglactin, pectin, tragacanth, scleroglucan, dextran, amylose, amylopectin, dextrin, cross-linked polyvinylpyrrolidone, ion-exchange resins, such as potassium polymethacrylate, carrageenan, kappa-carrageenan, lambda-carrageenan, gum karaya, biosynthetic gum, and mixtures thereof. Other permeation enhancers include materials useful for making microporous lamina in the environment of use, such as polycarbonates comprised of linear polyesters of carbonic acid in which carbonate groups reoccur in the polymer chain, microporous materials such as bisphenol, a microporous poly (vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone), silicon dioxide, colloidal silica, microcrystalline cellulose and any combination thereof. In at least one embodiment of the invention the permeation enhancer is silicon dioxide (e.g. SYLOID® 244FP). The amount of permeation enhancer can vary from about 0.5% to about 1% by weight of the tablet dry weight including all values and ranges therebetween and from about 25% to about 30% by weight of the moisture barrier dry weight including all values and ranges therebetween. For the 174 mg dose extended-release tablet or the 348 mg dose extended-release tablet of certain embodiments of the invention, the permeation enhancer can be present in an amount of about 0.5% to about 2% of the tablet dry weight including all values and ranges therebetween and from about 20% to about 40% by weight of the moisture barrier dry weight including all values and ranges therebetween For example, in certain embodiments of the 174 mg dose tablet, the permeation enhancer is present in an amount of from about 25% to about 30% by weight of the moisture barrier dry weight. For the 348 mg dose extended release tablet of the invention, the permeation enhancer can be present in an amount which can vary from about 0.5% to about 2% by weight of the tablet dry weight, and from about 20% to about 40% by weight of the moisture barrier dry weight. For example, in certain embodiments of the 348 mg dose tablet, the permeation enhancer is present in an amount of from about 25% to about 30% by weight of the moisture barrier dry weight. For the 522 mg dose extended release tablet of the invention, the permeation enhancer can be present in an amount which can vary from about 0.1% to about 2% by weight of the tablet dry weight including all values and ranges therebetween, and from about 20% to about 40% by weight of the moisture barrier dry weight including all values and ranges therebetween. For example, in certain embodiments of the 522 mg dose tablet, the permeation enhancer is present in an amount of from about 25% to about 30% by weight of the moisture barrier dry weight.

In at least one embodiment of the invention, the ratio of the methacrylic acid copolymer:plasticizer:permeation enhancer in the moisture barrier is about 13:2:5.

In certain embodiments the moisture barrier of the bupropion hydrobromide dosage form can be made according to any one of the methods described herein.

The preparation and application of the moisture barrier process can be as follows. The optional plasticizer (e.g. a combination of polyethylene glycol 4000 and triethyl citrate), can be first added to water and the mixture mixed to homogeneity. The methacrylic acid copolymer (e.g. EUDRAGIT® L 30 D-55), is next sieved and added to the plasticizer mixture and mixed to homogeneity. In a separate container the permeation enhancer (e.g. silicon dioxide) is dissolved in water until a homogeneous mixture is achieved. The plasticizer and methacrylic acid copolymer mixture is then combined with the permeation enhancer solution and mixed to homogeneity. The resulting moisture barrier solution is then sprayed onto the tablet cores coated with the controlled release coat using a tablet coater, fluidized bed apparatus or any other suitable coating apparatus known in the art until the desired weight gain is achieved. The tablets coated with the moisture barrier are subsequently dried prior to packaging.

The moisture barrier is applied to the controlled release coated tablet cores such that the weight gain is not more than about 6% of the tablet dry weight for the 174 mg, 348 mg and 522 mg extended release tablets of certain embodiments of the present invention. In certain embodiments the weight gain is not more than about 3.5% of the tablet dry weight for the 174 mg, 348 mg and 522 mg extended release tablets. The amount of the moisture barrier applied typically does not significantly render the extended release tablet described herein more resistant to gastric fluid. However, in certain embodiments the moisture barrier can have an impact on the drug release characteristics.

The moisture barrier as used in certain embodiments, does not function as an enteric coat. Even though the methacrylic acid copolymer, EUDRAGIT® L 30 D-55, is referenced and is used in enteric coating formulations in the art, its functionality is formulation dependent and on the quantity of the material applied. As is known in the art, an enteric coating is applied where a drug may be destroyed or inactivated by gastric juice or where the drug may irritate the gastric mucosa. To meet the requirements for an enteric coat, the test as described in the USP (method A or B) stipulates that after 2 hours in acidic media (e.g. 0.1N HCl), no individual values of at least six experiments exceed about 10% of the active drug dissolved and not less than about 75% dissolved at about 45 minutes in pH about 6.8. The moisture barrier of certain embodiments does not meet this requirement for the following reasons even though the bupropion hydrobromide salt is not negatively affected in acidic media nor is it irritating the gastric mucosa: (1) to obtain enteric integrity with a film containing EUDRAGIT® L 30 D-55, a weight gain of from about 6% to about 8% based on the dry polymer per dosage unit is recommended. The amount of EUDRAGIT® L 30 D-55 solid applied onto the controlled release coated tablet cores is not more than about 6%, and in at least one embodiment, is not more than about 3%, (2) if enteric integrity would be required, the dissolution test for the finished product (i.e., the moisture barrier coated tablet cores) at the 2 hour time point would not stipulate a limit of no more than about 20%, and (3) analytical tests performed on these coatings indicate that the coatings do not meet all the test requirements as an enteric coated product as defined by USP test methods.

The XL tablet of certain embodiments of the invention provides an extended release of the bupropion hydrobromide salt. In at least one embodiment no pore forming agent is present in the XL coating formulation. An extended release bupropion hydrobromide formulation is provided in certain embodiments such that after about 2 hours, not more than about 20% of the bupropion hydrobromide content is released. For example, in certain embodiments, from about 2% to about 18%, preferably from about 4% to about 8%, or about 5% of the bupropion hydrobromide content is released after about 2 hours. After about 4 hours, from about 15% to about 45% of the bupropion hydrobromide content is released. For example, in certain embodiments from about 21% to about 37%, more preferably from about 28% to about 34%, or about 32% of the bupropion hydrobromide content is released after about 4 hours. After about 8 hours, about 40% to about 90% of the bupropion hydrobromide content is released. For example, in certain embodiments from about 60% to about 85%, from about 68% to about 74%, or about 74% of the bupropion hydrobromide content is released after about 8 hours. After about 16 hours not less than about 80% of the bupropion hydrobromide content is released. For example, in certain embodiments of the bupropion hydrobromide content is released after about 16 hours.

Also, extended release tablets are provided in certain embodiments wherein after about 2 hours not more than about 40% (e.g., about 33%) of the bupropion hydrobromide is released; after about 4 hours from about 40 to about 75% of the bupropion hydrobromide is released (e.g., about 59%); after about 8 hours at least about 75% of the bupropion hydrobromide is released (e.g., about 91%); and after about 16 hours at least about 85% of the bupropion hydrobromide is released (e.g., about 97%). In all instances herein when actual or prophetic dissolution profiles are provided this means that the medicament possesses such a profile in at least one dissolution medium under prescribed conditions such as are identified herein and are well known to those skilled in the art. Such dissolution media, dissolution conditions and apparatus for use therein are disclosed in the United States Pharmacopoeia (USP) and European and Japanese counterparts thereof. Additionally, specific examples thereof are provided in this application.

Enhanced Absorption (EA) Tablets

In certain embodiments of the present invention, there is provided an enhanced absorption (EA) tablet having a core comprising a bupropion hydrobromide salt and conventional excipients, wherein the bupropion hydrobromide salt provides for the reduction of incidences of and/or severity of bupropion-induced seizures, and is more stable, as compared with equivalent molar amounts of bupropion hydrochloride. The core is surrounded by an EA coating, which controls the release of the bupropion hydrobromide salt. In certain embodiments, the EA coating consists of one coat. An advantage of the EA tablet includes the lower amount of drug required in the composition to be an effective amount, which in turn can lead to a reduction of side effects. The EA tablet optionally can comprise one or more additional functional or non-functional coats surrounding the core or EA coating.

The EA Core

The core of the EA tablet comprises an effective amount of a bupropion hydrobromide salt, a binder and a lubricant, and can contain other conventional inert excipients. In certain embodiments the core of the EA tablet can comprise the same excipients as, and can be processed in the same manner as the core of the extended release tablet. The amount of the bupropion hydrobromide salt present in the EA core can vary from about 40% to about 99% by weight of the EA tablet dry weight, including all values and ranges therebetween. The EA tablet comprises an effective amount of bupropion hydrobromide salt that can vary from about 50 mg to about 1000 mg, including 100, 150, 200, 250, 300, 350, 400, 450, 500, 510, 520, 530, 540, 550, 560, 570, 580, 590, 600, 650, 700, 750, 800, 85, 900, 950 mg and all values and ranges therebetween. For example, certain embodiments of the EA tablet can comprise about 150 mg, about 300 mg or about 450 mg of bupropion hydrobromide. For a 150 mg dose tablet the bupropion hydrobromide can be present in an amount of from about 76% to about 84% by weight of the tablet dry weight. For a 300 mg dose, the amount of bupropion hydrobromide can be present in an amount of from about 80% to about 83% by weight of the tablet dry weight. For a 450 mg dose, the amount of bupropion hydrobromide can be present in an amount of from about 75% to about 90% by weight of the tablet dry weight. For the 150 mg, 300 mg and 450 mg dose bupropion hydrobromide EA tablets of certain embodiments of the invention, the amount of bupropion hydrobromide can be present at about 94% by weight of the dry core for each dose.

The EA Tablet Coating

The EA tablet cores can be coated in one stage. The EA coating is applied directly onto the surface of the tablet cores and functions to control the release of the bupropion hydrobromide salt. The EA coating is a semi-permeable coat comprising a water-insoluble, water-permeable film-forming polymer, a water-soluble polymer, and optionally a plasticizer. In certain embodiments the EA coating can comprise the same ingredients as, and can be processed in the same manner as the XL controlled release coat.

Non-limiting examples of water-insoluble, water-permeable film-forming polymers useful for the EA coating include those that can be used in the XL controlled release coat. The amount of the water-insoluble water-permeable film-forming polymer can vary from about 1% to about 8% by weight of the tablet dry weight, including all values and ranges therebetween. For example, in certain embodiments the amount of the water-insoluble water-permeable film-forming polymer is from about 2% to about 6% by weight of the tablet dry weight. For certain embodiments of the 150 mg, 300 mg or 450 mg dose EA tablets of certain embodiments of the invention, the amount of water-insoluble water permeable film-forming polymer is from about 1% to about 15% by weight of the tablet dry weight. For example, in certain embodiments of the 150 mg dose EA tablets, the amount of the water-insoluble water-permeable film-forming polymer is present at about 10.5% by weight of the tablet dry weight. With respect to the EA coat itself, the amount of water-insoluble water-permeable film-forming polymer in certain embodiments of the 150 mg dose EA tablets is from about 35% to about 60% by weight of the EA coat dry weight. For example, in certain embodiments of the 150 mg dose EA tablet, the amount of water-insoluble water-permeable polymer is present at about 55% by weight of the EA coat dry weight. For certain embodiments of the 300 mg dose EA tablet of the invention, the amount of water-insoluble water-permeable film-forming polymer is from about 1% to about 8% by weight of the tablet dry weight. For example, in certain embodiments of the 300 mg dose EA tablet, the amount of water-insoluble water-permeable film forming polymer is present at about 6.3% by weight of the tablet dry weight. With respect to the EA coat itself, the water-insoluble water-permeable film-forming polymer in the 300 mg dose EA tablet can be present in an amount of about 55% by weight of the EA coat dry weight. For certain embodiments of the 450 mg dose EA tablet of the invention, the amount of water-insoluble water-permeable film-forming polymer is from about 0.5% to about 10% by weight of the tablet dry weight, and in other embodiments is from about 1% to about 6% by weight of the tablet dry weight. With respect to the EA coat itself, the water-insoluble water-permeable film-forming polymer in the 450 mg dose EA tablet can be present in an amount of about 37% by weight of the EA coat dry weight.

In certain embodiments, the EA coat further comprises a plasticizer. Non-limiting examples of plasticizers that can be used in the EA coat include those that can be used in the XL controlled release coat. The amount of plasticizer that can be used in the EA coat can vary in an amount from about 0.5% to about 4% by weight of the tablet dry weight, including all values and ranges therebetween. In a further embodiment of the invention, when a mixture of two plasticizers is used, the ratio of the two plasticizers can range from about 5:95 to about 95:5, including all values and ranges therebetween. In at least one embodiment of the invention, the plasticizer is polyethylene glycol 4000, dibutyl sebacate, or a mixture thereof. The ratio of polyethylene glycol 4000:dibutyl sebacate can range from about 5:95 to about 95:5. For certain embodiments of the 150 mg dose EA tablet of the invention, the amount of plasticizer present in the EA coat is from about 0.5% to about 4% by weight of the tablet dry weight. For example, in certain embodiments of the 150 mg dose EA tablet, the amount of plasticizer is present at about 3.1% by weight of the tablet dry weight. For certain embodiments of the 300 mg dose EA tablet of the invention, the amount of plasticizer present is from about 0.5% to about 3% by weight of the tablet dry weight. For example, in certain embodiments of the 300 mg dose EA tablet, the amount of plasticizer is present at about 2.0% by weight of the tablet dry weight. For certain embodiments of the 450 mg dose EA tablet of the invention, the amount of plasticizer present is from about 0.5% to about 4% by weight of the tablet dry weight. For certain embodiments of the 150 mg, 300 mg and 450 mg dosage forms, the plasticizer is present in an amount of from about 6% to about 30% by weight of the EA coat dry weight. For example, in certain embodiments the amount of plasticizer is present at about 17% by weight of the EA coat dry weight Non-limiting examples of water-soluble polymers useful for the EA coat include those that can be used in the XL controlled release coat. In at least one embodiment of the invention, the water-soluble polymer is polyvinylpyrrolidone (e.g. Povidone® USP) the amount of which can vary from about 1.5% to about 10% by weight of the tablet dry weight, including all values and ranges therebetween. With respect to the EA coat itself, the amount of water-soluble polymer present can vary from about 20% to about 50% by weight of the EA coat dry weight. For certain embodiments of the 150 mg dose of the EA tablet of the invention, the amount of water-soluble polymer present is from about 1.5% to about 10% by weight of the tablet dry weight or from about 20% to about 50% by weight of the EA coat dry weight. For example, in certain embodiments of the 150 mg dose EA tablet, the water-soluble polymer is present in an amount of about 28% by weight of the EA coat dry weight. For certain embodiments of the 300 mg dose of the EA tablet of the invention, the amount of water-soluble polymer present is from about 1.5% to about 10% of the tablet dry weight and from about 20% to about 50% by weight of the EA coat dry weight. For example, in certain embodiments of the 300 mg dose EA tablet, the water-soluble polymer is present in an amount of about 28% by weight of the EA coat dry weight. For certain embodiments of the 450 mg dose of the EA tablet of the invention, the amount of water-soluble polymer present is from about 2% to about 5% of the tablet dry weight and from about 40% to about 50% by weight of the EA coat dry weight.

The ratio of water-insoluble water-permeable film forming polymer:plasticizer:water-soluble polymer for the EA tablet coating typically will vary from about 3:1:4 to about 5:1:2, including all values and ranges therebetween. For example in certain embodiments the ratio of water-insoluble water-permeable film forming polymer:plasticizer:water-soluble polymer for the EA tablet coating is about 4:1:3. In at least one embodiment of the EA tablet coating, the ratio of the water-insoluble water-impermeable film-forming polymer:plasticizer:water-soluble polymer is from about 7:2:6 to about 19:5:18, and in another embodiment is about 13:4:12. In at least one embodiment of the 450 mg dosage form, the ratio of water-insoluble water-permeable film forming polymer:plasticizer:water-soluble polymer for the EA coating is about 13:6:16.

In certain embodiments the EA coat of the bupropion hydrobromide dosage form can be made according to any one of the methods described for the XL controlled release coat.

Depending on the dissolution or in-vivo release profile desired, the weight gained after coating the tablet core with the EA coat can vary from about 3% to about 30% of the weight of the dry tablet core, including all values and ranges therebetween. For certain embodiments of the 150 mg dose EA tablet of the invention the weight gain is from about 8% to about 20% of the weight of the dry tablet core. For example, in certain embodiments of the 150 mg dose EA tablet, the weight gain is about 14% of the weight of the dry tablet core. For certain embodiments of the 300 mg dose EA tablet of the invention the weight gain is from about 10% to about 15% of the weight of the dry tablet core. For example, in certain embodiments of the 300 mg dose EA tablet, the weight gain is about 13% of the weight of the dry tablet core. For certain embodiments of the 450 mg dose EA tablet of the invention the weight gain is from about 5% to about 15% of the weight of the dry tablet core. For example, in certain embodiments of the 450 mg dose EA tablet, the weight gain is about 8.5% of the weight of the dry tablet core.

The EA tablet provides an enhanced-absorption of the bupropion hydrobromide salt wherein typically no pore forming agent is present in the formulation. An enhanced absorption bupropion hydrobromide formulation is provided such that after about 2 hours, not more than about 25% of the bupropion hydrobromide content is released. For example, in certain embodiments from about 10% to about 20% of the bupropion hydrobromide content is released after about 2 hours. After about 4 hours, from about 25% to about 55% of the bupropion hydrobromide content is released. For example, in certain embodiments from about 30% to about 50% of the bupropion hydrobromide content is released after about 4 hours. After about 8 hours, more than about 60% of the bupropion hydrobromide content is released. For example, in certain embodiments from about 70% to about 90% of the bupropion hydrobromide content is released after about 8 hours. After about 16 hours more than about 70% of the bupropion hydrobromide content is released. For example, in certain embodiments more than about 80% of the bupropion hydrobromide content is released after about 16 hours.

In certain embodiments an enhanced absorption formulation is provided wherein not more than about 40% is released after about 2 hours; after about 4 hours from about 40% to about 75% is released; after about 8 hours at least about 75% is released; and after about 16 hours at least about 85% is released. For example, in at least one embodiment, the bupropion hydrobromide release profile is about 33% after about 2 hours; about 59% after about 4 hours; about 91% after about 8 hours; and about 97% after about 16 hours.

Controlled Release Matrix

In other embodiments of the present invention, a controlled release matrix is provided from which the kinetics of drug release from the matrix core are dependent at least in part upon the diffusion and/or erosion properties of excipients within the composition. In this embodiment controlled release matrices contain an effective amount of a bupropion hydrobromide salt and at least one pharmaceutically acceptable excipient. The amount of the bupropion hydrobromide salt present in the controlled release matrix can vary in an amount of from about 40% to about 90% by weight of the matrix tablet dry weight, including all values and ranges therebetween. For example, in certain embodiments bupropion hydrobromide is present in an amount from about 60% to about 80%, and in other embodiment at about 70% by weight of the matrix tablet dry weight. The controlled release matrix can be multiparticulate or uniparticulate, and can be coated with at least one functional or non-functional coating, or an immediate release coating containing another drug. Functional coatings include by way of example controlled release polymeric coatings, enteric polymeric coatings, and the like. Non-functional coatings are coatings that do not affect drug release but which affect other properties (e.g., they can enhance the chemical, biological, or the physical appearance of the controlled release formulation). Those skilled in the pharmaceutical art and the design of medicaments are well aware of controlled release matrices conventionally used in oral pharmaceutical compositions adopted for controlled release and means for their preparation.

Suitable excipient materials for use in such controlled release matrices are known by those of skill in the art, and include, by way of example, release-resistant or controlled release materials such as hydrophobic polymers, hydrophilic polymers, lipophilic materials and mixtures thereof. Non-limiting examples of hydrophobic, or lipophilic components include glyceryl monostearate, mixtures of glyceryl monostearate and glyceryl monopalmitate (MYVAPLEX™, Eastman Fine Chemical Company), glycerylmonooleate, a mixture of mono, di and tri-glycerides (ATMUL™ 84S), glycerylmonolaurate, paraffin, white wax, long chain carboxylic acids, long chain carboxylic acid esters, long chain carboxylic acid alcohols, and mixtures thereof. The long chain carboxylic acids can contain from about 6 to about 30 carbon atoms; in certain embodiments at least about 12 carbon atoms, and in other embodiments from about 12 to about 22 carbon atoms. In some embodiments this carbon chain is fully saturated and unbranched, while others contain one or more double bonds. In at least one embodiment the long chain carboxylic acids contain about 3-carbon rings or hydroxyl groups. Non-limiting examples of saturated straight chain acids include n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid, melissic acid and mixtures thereof. Also useful are unsaturated monoolefinic straight chain monocarboxylic acids. Non-limiting examples of these include oleic acid, gadoleic acid, erucic acid and mixtures thereof. Also useful are unsaturated (polyolefinic) straight chain monocaboxyic acids. Non-limiting examples of these include linoleic acid, linolenic acid, arachidonic acid, behenolic acid and mixtures thereof. Useful branched acids include, for example, diacetyl tartaric acid. Non-limiting examples of long chain carboxylic acid esters include glyceryl monostearates; glyceryl monopalmitates; mixtures of glyceryl monostearate and glyceryl monopalmitate (MYVAPLEX™ 600, Eastman Fine Chemical Company); glyceryl monolinoleate; glyceryl monooleate; mixtures of glyceryl monopalmitate, glyceryl monostearate glyceryl monooleate and glyceryl monolinoleate (MYVEROL™ 18-92, Eastman Fine Chemical Company); glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate (MYVEROL™ 18-99, Eastman Fine Chemical Company); acetylated glycerides such as distilled acetylated monoglycerides (MYVACET™ 5-07, 7-07 and 9-45, Eastman Fine Chemical Company); mixtures of propylene glycol monoesters, distilled monoglycerides, sodium stearoyl lactylate and silicon dioxide (MYVATEX™ TL, Eastman Fine Chemical Company); mixtures of propylene glycol monoesters, distilled monoglycerides, sodium stearoyl lactylate and silicon dioxide (MYVATEX™ TL, Eastman Fine Chemical Company) d-alpha tocopherol polyethylene glycol 1000 succinate (Vitamin E TPGS, Eastman Chemical Company); mixtures of mono- and diglyceride esters such as ATMUL™ (Humko Chemical Division of Witco Chemical); calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; cetearyl octanoate; C10-C30 cholesterol/lavosterol esters; sucrose long chain carboxylic acid esters; and mixtures thereof. The alcohols useful as excipient materials for controlled release matrices can include the hydroxyl forms of the carboxylic acids exemplified above and also cetearyl alcohol.

In addition, waxes can be useful alone or in combination with the materials listed above, as excipient materials for the controlled release matrix embodiments of the present invention. Non-limiting examples of these include white wax, paraffin, microcrystalline wax, carnauba wax, and mixtures thereof.

The lipophilic agent can be present in an amount of from about 5% to about 90% by weight of the controlled release matrix dosage form, including all values and ranges therebetween. For example, in certain embodiments the lipophilic agent is present in an amount of from about 10% to about 85%, and in other embodiments from about 30% to about 60% by weight of the controlled release matrix dosage form.

Non-limiting examples of hydrophilic polymers that can be used in certain embodiments of the controlled release matrix dosage form include hydroxypropylmethylcellulose (HPMC), hydroxypropylcellulose (HPC), hydroxyethylcellulose (HEC), carboxymethylcellulose (CMC) or other cellulose ethers, polyoxyethylene, alginic acid, acrylic acid derivatives such as polyacrylic acid, CARBOPOL™, polymethacrylate polymer such as EUDRAGIT® RL, RS, R, S, NE and E, acrylic acid polymer, methacrylic acid polymer, hydroyethyl methacrylic acid (HEMA) polymer, hydroxymethyl methacrylic acid (HMMA) polymer, polyvinyl alcohols and mixtures thereof.

The hydrophilic polymer can be present in an amount of from about 10% to about 90% by weight of the controlled release matrix dosage form, including all values and ranges therebetween. For example, in certain embodiments the hydrophilic polymer is present in an amount of from about 20% to about 75%, and in other embodiments from about 30% to about 60% by weight of the controlled release matrix dosage form.

In at least one embodiment, the controlled release matrix dosage form comprises hydroxypropylmethylcellulose (HPMC). Non-limiting examples of hydroxypropyl methylcelluloses that can be used include METHOCEL® E (USP type 2910), METHOCEL® F (USP type 2906), METHOCEL® J (USP type 1828), METHOCEL® K (USP type 2201), and METHOCEL® 310 Series, products of The Dow Chemical Company, Midland, Mich., USA. The average degree of methoxyl substitution in these products can range from about 1.3 to about 1.9 including all values and ranges therebetween (of the three positions on each unit of the cellulose polymer that are available for substitution) while the average degree of hydroxypropyl substitution per unit expressed in molar terms can range from about 0.13 to about 0.82 including all values and ranges therebetween. The dosage form can comprise the different HPMC grades having different viscosities. The size of a HPMC polymer is expressed not as molecular weight but instead in terms of its viscosity as about a 2% solution by weight in water. Different HPMC grades can be combined to achieve the desired viscosity characteristics. For example, the at least one pharmaceutically acceptable polymer can comprise two HPMC polymers such as for example METHOCEL® K3 LV (which has a viscosity of about 3 cps) and METHOCEL® K100M CR (which has a viscosity of about 100,000 cps). In addition, the polymer can comprise two hydroxypropylcellulose forms such as KLUCEL® LF and KLUCEL® EF. In addition, the at least one polymer can comprise a mixture of a KLUCEL® and a METHOCEL®.

In at least one embodiment the controlled release matrix dosage form comprises a polyethylene oxide (PEO). PEO is a linear polymer of unsubstituted ethylene oxide. In certain embodiments poly(ethylene oxide) polymers having viscosity-average molecular weights of about 100,000 Daltons and higher are used. Non-limiting examples of poly(ethylene oxide)s that are commercially available include: POLYOX® NF, grade WSR Coagulant, molecular weight 5 million; POLYOX® grade WSR 301, molecular weight 4 million; POLYOX® grade WSR 303, molecular weight 7 million; POLYOX® grade WSR N-60K, molecular weight 2 million;

and mixtures thereof. These particular polymers are products of Dow Chemical Company, Midland, Mich., USA. Other examples of polyethylene oxides exist and can likewise be used. The required molecular weight for the PEO can be obtained by mixing PEO of differing molecular weights that are available commercially.

In at least one embodiment of the controlled release matrix dosage form, PEO and HPMC are combined within the same controlled release matrix. In certain embodiments, the poly (ethylene oxide)s have molecular weights ranging from about 2,000,000 to about 10,000,000 Da including all values and ranges therebetween. For example, in at least one embodiment the polyethylene oxides have molecular weights ranging from about 4,000,000 to about 7,000,000 Da. In certain embodiments the HPMC polymers have a viscosity within the range of about 4,000 centipoises to about 200,000 centipoises. For example, in at least one embodiment the HPMC polymers have a viscosity of from about 50,000 centipoises to about 200,000 centipoises, and in other embodiments from about 80,000 centipoises to about 120,000 centipoises. The relative amounts of PEO and HPMC within the controlled release matrix can vary within the scope of the invention. In at least one embodiment the PEO:HPMC weight ratio is from about 1:3 to about 3:1 including all values and ranges therebetween. For example, in certain embodiments the PEO:HPMC weight ratio is from about 1:2 to about 2:1. As for the total amount of polymer relative to the entire matrix, this can vary as well and can depend on the desired drug loading. In at least one embodiment the total amount of polymer in the matrix can constitute from about 15% to about 90% by weight of the matrix dosage form including all values and ranges therebetween. For example, in certain embodiments the total amount of polymer in the matrix is from about 20% to about 75%, in other embodiments from about 30% to about 60%, and in still other embodiments from about 10% to about 20% by weight of the matrix dosage form.

In at least one embodiment of the invention the controlled release matrix dosage form comprises a hydrophobic polymer such as ethylcellulose. The viscosity of ethylcellulose can be selected in order to influence of rate the drug release. In certain embodiments the ethylcellulose has a viscosity from about 7 to about 100 cP including all values and ranges therebetween (when measured as a 5% solution at 25° C. in an Ubbelohde viscometer, using a 80:20 toluene:ethanol solvent). In certain embodiments the hydrophobic polymer can constitute from about 10% to about 90% by weight of the matrix dosage form including all values and ranges therebetween. For example, in at least one embodiment the hydrophobic polymer constitutes from about 20% to about 75%, and in other embodiments from about 30% to about 60% by weight of the matrix dosage form.

In at least one embodiment of the invention the controlled release matrix dosage form comprises at least one binder. In certain embodiments the binder is water-insoluble. Examples of binders include hydrogenated vegetable oil, castor oil, paraffin, higher aliphatic alcohols, higher aliphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Non-limiting examples of water-soluble polymer binders include modified starch, gelatin, polyvinylpyrrolidone, cellulose derivatives (such as for example hydroxypropyl methylcellulose (HPMC) and hydroxypropyl cellulose (HPC)), polyvinyl alcohol and mixtures thereof. In at least one embodiment, the binder can be present in an amount of from about 0.1% to about 20% by weight of the matrix dosage form including all values and ranges therebetween. For example, in certain embodiments the binder is present in an amount of from about 0.5% to about 15%, and in other embodiments from about 2% to about 10% by weight of the matrix dosage form.

In at least one embodiment of the invention the controlled release matrix dosage form comprises at least one lubricant. Non-limiting examples of lubricants include stearic acid, hydrogenated vegetable oils (such as hydrogenated cottonseed oil (Sterotex®), hydrogenated soybean oil (STEROTEX® HM) and hydrogenated soybean oil & castor wax (STEROTEX® K)) stearyl alcohol, leucine, polyethylene glycol (MW 1450, suitably 4000, and higher), magnesium stearate, glyceryl monostearate, stearic acid, glycerylbehenate, polyethylene glycol, ethylene oxide polymers (e.g. CARBOWAX®), sodium lauryl sulfate, magnesium lauryl sulfate, sodium oleate, sodium stearyl fumarate, DL-leucine, colloidal silica, and mixtures thereof. The lubricant can be present in an amount of from about 0 to about 4% by weight of the compressed uncoated matrix including all values and ranges therebetween. For example, in certain embodiments the lubricant is present in an amount of from about 0% to about 2.5% by weight of the compressed, uncoated matrix.

In at least one embodiment of the invention the controlled release matrix dosage form comprises a plasticizer. Non-limiting examples of plasticizers include dibutyl sebacate, diethyl phthalate, triethyl citrate, tributyl citrate, triacetin, citric acid esters such as triethyl citrate NF XVI, tributyl citrate, dibutyl phthalate, 1,2-propylene glycol, polyethylene glycols, propylene glycol, diethyl phthalate, castor oil, acetylated monoglycerides, phthalate esters, and mixtures thereof. In at least one embodiment, the plasticizer can be present in an amount of from about 1% to about 70% by weight of the controlled release polymer in the matrix dosage form including all values and ranges therebetween. For example, in certain embodiments the plasticizer is present in an amount of from about 5% to about 50%, and in other embodiments from about 10% to about 40% by weight of the controlled release polymer in the matrix dosage form.

In at least one embodiment of the invention the controlled release matrix dosage form comprises at least one diluent, non-limiting examples of which include dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol, sucralfate, calcium hydroxyl-apatite, calcium phosphates, fatty acid salts such as magnesium stearate, and mixtures thereof. In certain embodiments the diluent can be added in an amount so that the combination of the diluent and the active substance comprises up to about 60%, and in other embodiments up to about 50%, by weight of the composition.

In at least one embodiment of the invention the controlled release matrix dosage form comprises a solubilizer. The solubilizer can act to increase the instantaneous solubility of the bupropion salt. The solubilizer can be selected from hydrophilic surfactants or lipophilic surfactants or mixtures thereof. The surfactants can be anionic, nonionic, cationic, and zwitterionic surfactants. The hydrophilic non-ionic surfactants can be selected from the group comprised of, but not limited to: polyethylene glycol sorbitan fatty acid esters and hydrophilic transesterification products of a polyol with at least one member of the group from triglycerides, vegetable oils, and hydrogenated vegetable oils such as glycerol, ethylene glycol, polyethylene glycol, sorbitol, propylene glycol, pentaerythritol, or a saccharide, d-α-tocopheryl polyethylene glycol 1000 succinate. The ionic surfactants can be selected from the group comprised of, but not limited to: alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof. The lipophilic surfactants can be selected from the group comprised of, but not limited to: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group from glycerides, vegetable oils, hydrogenated vegetable oils, fatty acids and sterols; oil-soluble vitamins/vitamin derivatives; PEG sorbitan fatty acid esters, PEG glycerol fatty acid esters, polyglycerized fatty acid, polyoxyethylene-polyoxypropylene block copolymers, sorbitan fatty acid esters; and mixtures thereof. In at least one embodiment the solubilizer can be selected from: PEG-20-glyceryl stearate (e.g. CAPMUL® by Abitec), PEG-40 hydrogenated castor oil (e.g. CREMOPHOR RH 40® by BASF), PEG 6 corn oil (e.g. LABRAFIL® by Gattefosse), lauryl macrogol-32 glyceride (e.g. GELUCIRE44/14® by Gattefosse) stearoyl macrogol glyceride (e.g. GELUCIRE50/13® by Gattefosse), polyglyceryl-10 mono dioleate (e.g. CAPROL® PEG860 by Abitec), propylene glycol oleate (e.g. LUTROL® by BASF), Propylene glycol dioctanoate (e.g. CAPTEX® by Abitec), Propylene glycol caprylate/caprate (e.g. LABRAFAC® by Gattefosse), Glyceryl monooleate (e.g. PECEOL® by Gattefrosse), Glycerol monolinoleate (e.g. MAISINE® by Gattefrosse), Glycerol monostearate (e.g. CAPMUL® by Abitec), PEG-20 sorbitan monolaurate (e.g. TWEEN20® by ICI), PEG-4 lauryl ether (e.g. BRIJ30® by ICI), Sucrose distearate (e.g. SUCROESTER7® by Gattefosse), Sucrose monopalmitate (e.g. SUCROESTER15® by Gattefosse), polyoxyethylene-polyoxypropylene block copolymer (e.g. LUTROL® series BASF), polyethylene glycol 660 hydroxystearate, (e.g. SOLUTOL® by BASF), Sodium lauryl sulfate, Sodium dodecyl sulphate, Dioctyl suphosuccinate, L-hydroxypropyl cellulose, hydroxylethylcellulose, hydroxylpropylcellulose, Propylene glycol alginate, sodium taurocholate, sodium glycocholate, sodium deoxycholate, betains, polyethylene glycol (e.g. CARBOWAX® by DOW), d-α-tocopheryl polyethylene glycol 1000 succinate, (Vitamin E TPGS® by Eastman), and mixtures thereof. In at least one other embodiment the solubilizer can be selected from PEG-40 hydrogenated castor oil (e.g. CREMOPHOR RH 40® by BASF), lauryl macrogol-32 glyceride (e.g. GELUCIRE44/14® by Gattefosse) stearoyl macrogol glyceride (e.g. GELUCIRE 50/13® by Gattefosse), PEG-20 sorbitan monolaurate (e.g. TWEEN 20® by ICI), PEG-4 lauryl ether (e.g. BRIJ30® by ICI), polyoxyethylene-polyoxypropylene block copolymer (e.g. LUTROL® series BASF), Sodium lauryl sulphate, Sodium dodecyl sulphate, polyethylene glycol (e.g. CARBOWAX® by DOW), and mixtures thereof.

In at least one embodiment of the invention the controlled release matrix dosage form comprises a swelling enhancer. Swelling enhancers are members of a category of excipients that swell rapidly to a large extent resulting in an increase in the size of the tablet. At lower concentrations, these excipients can be used as superdisintegrants; however at concentrations above 5 w/w these agents can function as swelling enhancers and help increase the size of the matrix dosage form. According to certain embodiments of the matrix dosage forms of the invention, examples of swelling enhancers include but are not limited to: low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules, pregelatinised starch, sodium carboxymethyl starch and mixtures thereof. In at least one embodiment of the matrix dosage forms, the swelling enhancer is cross-linked polyvinyl pyrrolidone. The content of the swelling enhancer can be from about 5% to about 90% by weight of the matrix dosage form including all values and ranges therebetween. For example, in certain embodiments the swelling enhancer is present in an amount of from about 10% to about 70%, and in other embodiments from about 15% to about 50% by weight of the matrix dosage form.

In at least one embodiment of the invention the controlled release matrix dosage form comprises additives for allowing water to penetrate into the core of the preparation (hereinafter referred to as "hydrophilic base"). In certain embodiments, the amount of water required to dissolve 1 g of the hydrophilic base is not more than about 5 ml, and in other embodiments is not more than about 4 ml at the temperature of about 20° C.±5° C. The higher the solubility of the hydrophilic base in water, the more effective is the base in allowing water into the core of the preparation. The hydrophilic base includes, inter alia, hydrophilic polymers such as polyethylene glycol (PEG); (e.g. PEG400, PEG1500, PEG4000, PEG6000 and PEG20000, produced by Nippon Oils and Fats Co.) and polyvinylpyrrolidone (PVP); (e.g. PVP K30, of BASF), sugar alcohols such as D-sorbitol, xylitol, or the like, sugars such as sucrose, anhydrous maltose, D-fructose, dextran (e.g. dextran 40), glucose or the like, surfactants such as polyoxyethylene-hydrogenated castor oil (HCO; e.g. CREMOPHOR® RH40 produced by BASF, HCO-40 and HCO-60 produced by Nikko Chemicals Co.), polyoxyethylene-polyoxypropylene glycol (e.g. Pluronic® F68 produced by Asahi Denka Kogyo K.K.), polyoxyethylene-sorbitan high molecular fatty acid ester (TWEEN®; e.g. TWEEN® 80 produced by Kanto Kagaku K.K.), or the like; salts such as sodium chloride, magnesium chloride, or the like; organic acids such as citric acid, tartaric acid, or the like; amino acids such as glycine, .β-alanine, lysine hydrochloride, or the like; and amino sugars such as meglumine. In at least one embodiment the hydrophilic base is PEG6000, PVP, D-sorbitol, or mixtures thereof.

In another embodiment of the invention the controlled release matrix dosage form comprises at least one disintegrant. Non-limiting examples of disintegrants for use in the matrix dosage form include croscarmellose sodium, crospovidone, alginic acid, sodium alginate, methacrylic acid DVB, cross-linked PVP, microcrystalline cellulose, polacrilin potassium, sodium starch glycolate, starch, pregelatinized starch and mixtures thereof. In at least one embodiment the disintegrant is selected from cross-linked polyvinylpyrrolidone (e.g. KOLLIDON® CL), cross-linked sodium carboxymethylcellulose (e.g. AC-DI-SOL™), starch or starch derivatives such as sodium starch glycolate (e.g. EXPLOTAB®), or combinations with starch (e.g. PRIMOJEL™), swellable ion-exchange resins, such as AMBER- LITE™ IRP 88, formaldehyde-casein (e.g. ESMA SPRENG™), and mixtures thereof. In at least one embodiment the disintegrant is sodium starch glycolate. The disintegrant can be present in certain embodiments in an amount of from about 0% to about 20% of the total weight of the matrix including all values and ranges therebetween.

The controlled release matrices of the present invention can further contain one or more pharmaceutically acceptable excipients such as granulating aids or agents, colorants, flavorants, pH adjusters, anti-adherents, glidants and like excipients conventionally used in pharmaceutical compositions.

In at least one embodiment of the invention comprising water swellable polymers formulated into the matrix, the release kinetics of the bupropion hydrobromide salt from the matrix are dependent upon the relative magnitude of the rate of polymer swelling at the moving rubbery/glassy front and the rate of polymer erosion at the swollen polymer/dissolution medium front. The release kinetics for the release of the bupropion hydrobromide salt from the matrix can be approximated by the following equation:

$$Mt/MT = kt^n$$

where t is time,
Mt is the amount of the pharmaceutical agent which has been released at time t,
MT is the total amount of the pharmaceutical agent contained in the matrix,
k is a constant, and
n is the release kinetics exponent This equation is valid so long as n remains nearly constant. When n is equal to one, the release of the pharmaceutical agent from the matrix has zero-order kinetics. The amount of pharmaceutical agent released is then directly proportional to the time.

Where the swelling process of the polymer chosen for the excipient is the primary process controlling the drug release (compared to erosion of the swollen polymer), non-zero order release kinetics can result. Generally, these release kinetics dictate a value of n approaching 0.5, leading to square-root Fickian-type release kinetics.

In at least one embodiment of the invention, polymers are selected for inclusion into the formulation to achieve zero order kinetics. The release kinetics of the matrix can also be dictated by the pharmaceutical agent itself. A drug which is highly soluble (e.g. bupropion) can tend to be released faster than drugs which have low solubility. Where a drug has high solubility, polymer swelling and erosion takes place rapidly to maintain zero order release kinetics. If the swelling and erosion take place too slowly, the swelling process of the polymer is the primary process controlling the drug release (since the drug will diffuse from the swollen polymer before the polymer erodes). In this situation, non-zero order release kinetics can result. As a result, the administration of a highly soluble pharmaceutical agent requires a relatively rapidly swelling and eroding excipient. To use such a material to produce a matrix which will last for 24 hours can require a large matrix. To overcome this difficulty, a doughnut-shaped matrix with a hole though the middle can be used with a less rapidly swelling and eroding polymer. With such a matrix, the surface area of the matrix increases as the matrix erodes. This exposes more polymer, resulting in more polymer swelling and erosion as the matrix shrinks in size. This type of matrix can also be used with very highly soluble pharmaceutical agents to maintain zero order release kinetics.

In at least one other embodiment of the invention, zero order drug release kinetics can be achieved by controlling the surface area of the matrix dosage form that is exposed to erosion. When water is allowed to diffuse into a polymer matrix composition zero order release is obtained when the release rate is governed or controlled by erosion of a constant surface area per time unit. In order to ensure that the erosion of the polymer matrix composition is the predominant release mechanism, it is helpful to provide a polymer matrix composition which has properties that ensures that the diffusion rate of water into the polymer matrix composition substantially corresponds to the dissolution rate of the polymer matrix composition into the aqueous medium. Thus, by adjusting the nature and amount of constituents in the polymer matrix composition a zero order release mechanism can be achieved. The compositions employed are coated in such a manner that at least one surface is exposed to the aqueous medium and this surface has a substantially constant or controlled surface area during erosion. In the present context controlled surface area relates to a predetermined surface area typically predicted from the shape of the coat of the unit dosage system. It may have a simple uniform cylindrical shape or the cylindrical form can have one or more tapered ends in order to decrease (or increase) the initial release period.

Accordingly, these embodiments provide a method for controlling the release of a bupropion salt into an aqueous medium by erosion of at least one surface of a pharmaceutical composition comprising
(i) a matrix composition comprising (a) a polymer or a mixture of polymers, (b) a bupropion hydrobromide salt and, optionally, (c) one or more pharmaceutically acceptable excipients, and
(ii) a coating having at least one opening exposing at the one surface of said matrix, the coating comprising: (a) a first cellulose derivative which has thermoplastic properties and which is substantially insoluble in the aqueous medium in which the composition is to be used, and at least one of (b) a second cellulose derivative which is soluble or dispersible in water, (c) optionally a plasticizer, or (d) a filler, the method comprising adjusting the concentration and/or the nature of the ingredients making up the matrix composition in such a manner that the diffusion rate of the aqueous medium into the matrix composition corresponds to 100%±30% such as, for example 100%±25%, 100%±20%, 100%±15% or 100%±10%, or 100% of the dissolution rate of the matrix composition so as to obtain a zero order release of at least about 60% w/w such as, for example at least about 65% w/w, at least about 70% w/w, at least about 75% w/w, at least about 80% w/w, at least about 85% w/w, at least about 90% w/w, at least about 95% w/w or at least about 97% to about 98% w/w of the bupropion hydrobromide salt from the pharmaceutical composition when subject to an in-vitro dissolution test.

In at least one other embodiment of the invention, zero order drug release is approached through the use of: (a) a deposit-core comprising the bupropion hydrobromide salt and having defined geometric form, (b) a support-platform applied to said deposit-core, and is characterized in that the deposit-core contains, mixed with the bupropion hydrobromide salt, a polymeric material having a high degree of swelling on contact with water or aqueous liquids, a gellable polymeric material, said polymeric materials being replaceable by a single polymeric material having both swelling and gelling properties, and other adjuvants able to provide the mixture with suitable characteristics for its compression and for its intake of water, said support-platform comprising a polymeric material insoluble in aqueous liquids and partially coating said deposit-core.

These and further characteristics and advantages of the system according to certain embodiments of the matrix dosage form will be more apparent from the description of embodiments of the invention given hereinafter by way of non-limiting example. The deposit-core can generally be obtained by compressing the mixture containing the bupropion hydrobromide salt to a pressure of from about 1000 to about 4000 kg/cm2 including all values and ranges therebetween, to thus assume a defined geometric form. Polymeric materials having a high degree of swelling can generally be cross-linked insoluble polymers, whereas gellable polymeric materials are soluble, and can control the intake of water.

The coating platform comprises a polymeric material insoluble in water and optionally insoluble in biodegradable biological liquids, and able to maintain its impermeability characteristics at least until the complete transfer of the bupropion hydrobromide salt contained in the deposit-core. It is applied to a part of the external deposit-core surface chosen such as to suitably direct and quantitatively regulate the release of the bupropion hydrobromide salt. In this respect, as the support-platform is impermeable to water, the polymeric material of the deposit-core in certain embodiments can swell only in that portion of the deposit not coated with the platform.

The support-platform can be obtained by compressing prechosen polymeric materials onto the deposit-core, by immersing the deposit-core in a solution of said polymeric materials in normal organic solvents, or by spraying said solutions. Polymeric materials usable for preparing the support-platform can be chosen from the class comprising acrylates, celluloses and derivatives such as ethylcellulose, cellulose acetate-propionate, polyethylenes and methacrylates and copolymers of acrylic acid, polyvinylalcohols and mixtures thereof. This platform can have a thickness of from about 2 mm (for example, if applied by compression) to about 10 microns (for example, if applied by spraying or immersion) including all values and ranges therebetween, and comprises from about 10% to about 90% of the total surface of the system including all values and ranges therebetween.

A factor in controlling the release of the bupropion hydrobromide salt is the intensity and duration of the swelling force developed by the swellable polymeric materials contained in the deposit-core on contact with aqueous fluids. In this respect, the energy for activating, executing and regulating the release of the bupropion hydrobromide salt can be determined by the swelling force developed in the deposit-core when this comes into contact with water or with biological liquids. Said force has an intensity and duration which can vary in relation to the type and quantity of the polymeric materials used in formulating the deposit, and it lies between limits having a maximum value which occurs in the case of a deposit mainly containing the swellable polymer, and a minimum value which occurs in the case of a deposit mainly containing the gellable polymer. Said swellable polymer can be present in an amount of from about 5% to about 80% by weight including all values and ranges therebetween, and said gellable polymer present in an amount of from about 10% to about 90% by weight including all values and ranges therebetween, with respect to the mixture forming the deposit-core.

A further control factor is the geometry of the support-platform, which limits the swelling of the deposit and directs the emission of material from it. Within the scope of these embodiments it is possible to conceive many systems for the controlled release of bupropion hydrobromide, which base their operation on the swelling force and differ from each other by the type of support-platform used.

In at least one other embodiment of the invention designed to achieve zero order release of the bupropion hydrobromide salt, the kinetics of drug release from a controlled release matrix is governed by a combination of different polymers with different swelling characteristics. More specifically, the bupropion hydrobromide salt is first granulated with or encapsulated in a less swellable polymer, such as a gum, to form a granule. This granule is disposed in a matrix of a more swellable, erodible polymer. The more swellable erodible polymer has a diffusion rate coefficient which is greater than the diffusion rate coefficient of the relatively less swellable polymer. Averaged over the entire period of drug release, the diffusion rate for the more swellable polymer is greater than the diffusion rate for the less swellable polymer. It is this general difference in rates of diffusion between the first and second polymers which controls the rate of drug release and allows the system to approach zero order drug delivery over the drug release period. In at least one embodiment, pectin and HPMC are present as the more swellable polymers in ratios of from about 2:7 to about 4:5 including all values and ranges therebetween, and gelatin is present as the less swellable polymer.

In at least one other embodiment of the invention there is provided a controlled release matrix composition comprising bupropion hydrobromide incorporated within a homogeneous matrix including effective amounts of at least two polymers having opposing wettability characteristics, wherein at least one polymer is selected which demonstrates a stronger tendency towards hydrophobicity and the other polymer(s) is selected which demonstrates a stronger tendency towards hydrophilicity. In at least one embodiment the polymer demonstrating a stronger tendency towards hydrophobicity is ethylcellulose (EC) whereas the polymer demonstrating a stronger tendency towards hydrophilicity is hydroxyethylcellulose (HEC) and/or hydroxypropyl methylcellulose (HPMC). The composition and device of the present invention can be provided as a matrix and can be optionally encased in a coating material which prevents the burst and/or food effect associated with orally ingested medicaments and imparts gastrointestinal "stealth" characteristics. In accordance with at least one embodiment is a method for preparing a device for the controlled release of the bupropion hydrobromide salt, the method comprising blending bupropion hydrobromide with from about 5% to about 25% by weight of hydrophilic polymer including all values and ranges therebetween, and from about 1% to about 25% by weight of hydrophobic polymer including all values and ranges therebetween, adding suitable pharmaceutical excipients, surface active agents and lubricants, granulating the mixture with solvents such as isopropyl alcohol, drying the granular mixture, milling the dried mixture, adding from about 5% to about 70% by weight of ethylcellulose including all values and ranges therebetween, adding a lubricant and optionally a glidant and compressing the granules into matrices. The matrices are optionally encased in a gastrointestinal encasement or a pharmaceutically acceptable film coat.

In another embodiment of the present invention, a swellable matrix dosage form is provided in which the bupropion hydrobromide salt is dispersed in a polymeric matrix that is water-swellable rather than merely hydrophilic, that has an erosion rate that is substantially slower than its swelling rate, and that releases the bupropion hydrobromide salt primarily by diffusion. The rate of diffusion of the bupropion hydrobromide salt out of the swellable matrix can be slowed by increasing the drug particle size, by the choice of polymer used in the matrix, and/or by the choice of molecular weight of the polymer. The swellable matrix is comprised of a relatively high molecular weight polymer that swells upon ingestion. In at least one embodiment the swellable matrix swells upon ingestion to a size that is at least twice its unswelled volume, and that promotes gastric retention during the fed mode. Upon swelling, the swellable matrix can also convert over a prolonged period of time from a glassy polymer to a polymer that is rubbery in consistency, or from a crystalline polymer to a rubbery one. The penetrating fluid then causes release of the bupropion hydrobromide salt in a gradual and prolonged manner by the process of solution diffusion, i.e., dissolution of the bupropion hydrobromide salt in the penetrating fluid and diffusion of the dissolved bupropion hydrobromide salt back out of the swellable matrix. The swellable matrix itself is solid prior to administration and, once administered, remains undissolved in (i.e., is not eroded by) the gastric fluid for a period of time sufficient to permit the majority of the bupropion hydrobromide salt to be released by the solution diffusion process during the fed mode. The rate-limiting factor in the release of the bupropion hydrobromide salt from the swellable matrix is therefore controlled diffusion of the bupropion hydrobromide salt from the swellable matrix rather than erosion, dissolving or chemical decomposition of the swellable matrix.

As such, the swelling of the polymeric matrix can achieve at least the following objectives: (i) renders the matrix sufficiently large to cause retention in the stomach during the fed mode; (ii) localizes the release of the drug to the stomach and small intestine so that the drug will have its full effect without colonic degradation, inactivation, or loss of bioavailability; (iii) retards the rate of diffusion of the drug long enough to provide multi-hour, controlled delivery of the drug into the stomach.

The bupropion hydrobromide salt in the swellable matrix can be present in an effective amount of from about 0.1% to about 99% by weight of the matrix including all values and ranges therebetween. For example, in certain embodiments bupropion hydrobromide is present in the swellable matrix in an amount of from about 0.1% to about 90%, in other embodiments from about 5% to about 90%, in still other embodiments from about 10% to about 80%, and in even still other embodiments from about 25% to about 80% by weight of the swellable matrix.

The water-swellable polymer forming the swellable matrix in accordance with these embodiments of the present invention can be any polymer that is non-toxic, that swells in a dimensionally unrestricted manner upon imbibition of water, and that provides for a modified release of the bupropion hydrobromide salt. Non-limiting examples of polymers suitable for use in the swellable matrix include cellulose polymers and their derivatives, such as for example, hydroxyethylcellulose, hydroxypropylcellulose, carboxymethylcellulose, and microcrystalline cellulose, polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, poly(2-ethyl-2-oxazoline), poly(ethyleneimine), polyurethane hydrogels, and crosslinked polyacrylic acids and their derivatives, and mixtures thereof. Further examples include copolymers of the polymers listed in the preceding sentence, including block copolymers and grafted polymers. Specific examples of copolymers include PLURONIC® and TECTONIC®, which are polyethylene oxide-polypropylene oxide block copolymers.

The terms "cellulose" and "cellulosic", as used within this section regarding the swellable matrix embodiments of the present invention, can denote a linear polymer of anhydroglucose. Non-limiting examples of cellulosic polymers include alkyl-substituted cellulosic polymers that ultimately dissolve in the gastrointestinal (GI) tract in a predictably delayed manner. In certain embodiments the alkyl-substituted cellulose derivatives are those substituted with alkyl groups of 1 to 3 carbon atoms each. Non-limiting examples include methylcellulose, hydroxymethyl-cellulose, hydroxyethylcellulose, hydroxypropylcellulose, hydroxypropylmethylcellulose, carboxymethylcellulose, and mixtures thereof. In terms of their viscosities, one class of alkyl-substituted celluloses includes those whose viscosity is within the range of about 100 to about 110,000 centipoises as a 2% aqueous solution at 20° C. Another class includes those whose viscosity is within the range of about 1,000 to about 4,000 centipoises as a 1% aqueous solution at 20° C. In certain embodiments the alkyl-substituted celluloses are hydroxyethylcellulose and hydroxypropylmethylcellulose. In at least one embodiment the hydroxyethylcellulose is NATRASOL® 250HX NF.

Polyalkylene oxides that can be used in certain embodiments of the swellable matrices include those having the properties described above for alkyl-substituted cellulose polymers. In at least one embodiment the polyalkylene oxide is poly(ethylene oxide), which term is used herein to denote a linear polymer of unsubstituted ethylene oxide. In at least one embodiment the poly(ethylene oxide) polymers have molecular weights of about 4,000,000 and higher. For example, in certain embodiment the poly(ethylene oxide) polymers have molecular weights within the range of about 4,500,000 to about 10,000,000 including all values and ranges therebetween, and in other embodiments have molecular weights within the range of about 5,000,000 to about 8,000,000. In certain embodiments the poly(ethylene oxide)s are those with a weight-average molecular weight within the range of about $1\times10^5$ to about $1\times10^7$, and in other embodiments within the range of about $9\times10^5$ to about $8\times10^6$. Poly(ethylene oxide)s are often characterized by their viscosity in solution. For example, in certain embodiments the poly(ethylene oxide)s have a viscosity range of about 50 to about 2,000,000 centipoises for a 2% aqueous solution at 20° C. In at least one embodiment the poly(ethylene oxide) is one or more of POLYOX® NF, grade WSR Coagulant, molecular weight 5 million, and grade WSR 303, molecular weight 7 million. Mixtures thereof are operable.

Polysaccharide gums, both natural and modified (semi-synthetic) can be used in the swellable matrix embodiments of the present invention. Non-limiting examples include dextran, xanthan gum, gellan gum, welan gum, rhamsan gum, and mixtures thereof. In at least one embodiment the polysaccharide gum is xanthan gum.

Crosslinked polyacrylic acids that can be used in the swellable matrices of the present invention include those whose properties are the same as those described above for alkyl-substituted cellulose and polyalkylene oxide polymers. In certain embodiments the crosslinked polyacrylic acids are those with a viscosity ranging from about 4,000 to about 40,000 centipoises for a 1% aqueous solution at 25° C. Non-limiting examples of suitable crosslinked polyacrylic acids include CARBOPOL® NF grades 971P, 974P and 934P. Further examples of suitable crosslinked polyacrylic acids include polymers known as WATER LOCK®, which are starch/acrylates/acrylamide copolymers.

The hydrophilicity and water swellability of these polymers can cause the drug-containing swellable matrices to swell in size in the gastric cavity due to ingress of water in order to achieve a size that can be retained in the stomach when introduced during the fed mode. These qualities also cause the swellable matrices to become slippery, which provides resistance to peristalsis and further promotes their retention in the stomach. The release rate of drug from the swellable matrix is primarily dependent upon the rate of water imbibition and the rate at which the drug dissolves and diffuses from the swollen polymer, which in turn is related to the drug concentration in the swellable matrix. Also, because these polymers dissolve very slowly in gastric fluid, the swellable matrix maintains its physical integrity over at least a substantial period of time, for example in many cases at least about 90% and in certain embodiments over about 100% of the dosing period. The particles will then slowly dissolve or decompose. Complete dissolution or decomposition may not occur until about 24 hours or more after the intended dosing period ceases, although in most cases, complete dissolution or decomposition will occur within about 10 to about 24 hours after the dosing period.

The amount of polymer relative to the drug can vary, depending on the drug release rate desired and on the polymer, its molecular weight, and excipients that may be present in the formulation. The amount of polymer will typically be sufficient to retain at least about 40% of the drug within the swellable matrix about one hour after ingestion (or immersion in the gastric fluid). In certain embodiments, the amount of polymer is such that at least about 50% of the drug remains in the matrix about one hour after ingestion; in other embodiments at least about 60%, and in still other embodiments at least about 80% of the drug remains in the swellable matrix about one hour after ingestion. In certain embodiments the drug will be substantially all released from the swellable matrix within about 10 hours; and in other embodiments within about 8 hours, after ingestion, and the polymeric matrix will remain substantially intact until all of the drug is released. In other embodiments the amount of polymer will be such that after about 2 hours no more than about 40% is released; after about 4 hours from about 40% to about 75% is released; after about 8 hours at least about 75% is released, and after about 16 hours at least about 85% is released. The term "substantially intact" is used herein to denote a polymeric matrix in which the polymer portion substantially retains its size and shape without deterioration due to becoming solubilized in the gastric fluid or due to breakage into fragments or small particles.

In other exemplary embodiments the swellable matrix after about 2 hours will release no more than about 40% of the bupropion hydrobromide, after about 4 hours from about 40% to about 75%, after about 8 hours at least about 75%, and after about 16 hours at least about 85% of the bupropion hydrobromide.

The water-swellable polymers of the swellable matrices can be used individually or in combination. Certain combinations will often provide a more controlled release of the drug than their components when used individually. Examples include cellulose-based polymers combined with gums, such as hydroxyethyl cellulose or hydroxypropyl cellulose combined with xanthan gum. Another example is poly (ethylene oxide) combined with xanthan gum.

The benefits of certain embodiments of this invention can be achieved over a wide range of drug loadings and polymer levels, with the weight ratio of drug to polymer ranging in general from about 0.01:99.99 to about 80:20, including all values and ranges therebetween. For example, in certain embodiments the drug loadings (expressed in terms of the weight percent of drug relative to total of drug and polymer) are within the range of about 15% to about 80% including all values and ranges therebetween; in other embodiments within the range of about 30% to about 80% including all values and ranges therebetween; and in still other embodiments within the range of about 30% to about 70% including all values and ranges therebetween. In at least one embodiment the drug loading is within the range of about 0.01% to about 80% including all values and ranges therebetween, and in at least one other embodiment from about 15% to about 80% including all values and ranges therebetween. In at least one embodiment the weight ratio of bupropion hydrobromide to polymer in the swellable matrix is from about 15:85 to about 80:20 including all values and ranges therebetween.

The formulations of the swellable matrices of the present invention can assume the form of microparticles, tablets, or microparticles retained in capsules. In at least one embodiment the formulation comprises microparticles consolidated into a packed mass for ingestion, even though the packed mass will separate into individual particles after ingestion. Conventional methods can be used for consolidating the microparticles in this manner. For example, the microparticles can be placed in gelatin capsules known in the art as "hard-filled" capsules and "soft-elastic" capsules. The compositions of these capsules and procedures for filling them are known among those skilled in drug formulations and manufacture. The encapsulating material should be highly soluble so that the particles are freed and rapidly dispersed in the stomach after the capsule is ingested.

In certain embodiments of the swellable matrices of the present invention, the formulation contains an additional amount of bupropion hydrobromide salt or other drug applied as a quickly dissolving coating on the outside of the microparticle or tablet. This coating is referred to as a "loading dose" and it is included for immediate release into the recipient's bloodstream upon ingestion of the formulation without first undergoing the diffusion process that the remainder of the drug in the formulation must pass before it is released. The "loading dose" can be high enough to quickly raise the blood concentration of the drug but not high enough to produce the transient overdosing that is characteristic of immediate release dosage forms that are not formulated in accordance with this invention.

In at least one embodiment of the swellable matrices of the present invention, the dosage form is a size 0 gelatin capsule containing either two or three pellets of drug-impregnated polymer. For two-pellet capsules, the pellets are cylindrically shaped, about 6.6 mm or about 6.7 mm in diameter (or more generally, from about 6.5 mm to about 7 mm in diameter including all values and ranges therebetween) and about 9.5 mm or about 10.25 mm in length (or more generally, from about 9 mm to about 12 mm in length including all values and ranges therebetween). For three-pellet capsules, the pellets are again cylindrically shaped, about 6.6 mm in diameter and about 7 mm in length. For a size 00 gelatin capsule with two pellets, the pellets are cylindrical, about 7.5 mm in diameter and about 11.25 mm in length. For a size 00 gelatin capsule with three pellets, the pellets are cylindrical, about 7.5 mm in diameter and about 7.5 mm in length. In at least one other embodiment, the dosage form is a single, elongated tablet, with dimensions of about 18 mm to about 22 mm in length including all values and ranges therebetween, from about 6.5 mm to about 10 mm in width including all values and ranges therebetween, and from about 5 mm to about 7.5 mm in height including all values and ranges therebetween. In at least one other embodiment, the dosage form is a single, elongated tablet, with dimensions of from about 18 mm to about 22 mm in length including all values and ranges therebetween, from about 6.5 mm to about 7.8 mm in width including all values and ranges therebetween, and from about 6.2 mm to about 7.5 mm in height including all values and ranges therebetween. In at least one embodiment the dimensions are about 20 mm in length, about 6.7 mm in width, and about 6.4 mm in height. These are merely examples; the shapes and sizes can be varied considerably.

In certain embodiments the bupropion hydrobromide-containing matrix can be made according to any one of the methods described herein.

The particulate drug/polymer mixture or drug-impregnated swellable polymer matrix of certain embodiments can be prepared by various conventional mixing, comminution and fabrication techniques readily apparent to those skilled in the chemistry of drug formulations. Examples of such techniques include: (1) Direct compression, using appropriate punches and dies, such as those available from Elizabeth Carbide Die Company, Inc., McKeesport, Pa., USA; the punches and dies are fitted to a suitable rotary tableting press, such as the Elizabeth-Hata single-sided Hata Auto Press machine, with either 15, 18 or 22 stations, and available from Elizabeth-Hata International, Inc., North Huntington, Pa., USA; (2) Injection or compression molding using suitable molds fitted to a compression unit, such as those available from Cincinnati Milacron, Plastics Machinery Division, Batavia, Ohio, USA; (3) Granulation followed by compression; and (4) Extrusion in the form of a paste, into a mold or to an extrudate to be cut into lengths.

In regards to the swellable matrices of certain embodiments of the present invention, when microparticles are made by direct compression, the addition of lubricants can be helpful and, in certain embodiments, helpful to promote powder flow and to prevent capping of the microparticle (breaking off of a portion of the particle) when the pressure is relieved. Non-limiting examples of suitable lubricants include magnesium stearate (in a concentration of from about 0.25% to about 3% by weight including all values and ranges therebetween, and in certain embodiments less than about 1% by weight, in the powder mix), and hydrogenated vegetable oil (in certain embodiments hydrogenated and refined triglycerides of stearic and palmitic acids at from about 1% to about 5% by weight including all values and ranges therebetween, for example in at least one embodiment at about 2% by weight). Additional excipients can be added to enhance powder flowability and reduce adherence.

Certain embodiments of the swellable matrices of the present invention can find utility when administered to a subject who is in the digestive state (also referred to as the postprandial or "fed" mode). The postprandial mode is distinguishable from the interdigestive (or "fasting") mode by their distinct patterns of gastroduodenal motor activity, which determine the gastric retention or gastric transit time of the stomach contents.

The controlled release matrices of certain embodiments of the present invention can be manufactured by methods known in the art. An example of a method of manufacturing controlled release matrices is melt-extrusion of a mixture containing the bupropion salt, hydrophobic polymer(s), hydrophilic polymer(s), and optionally a binder, plasticizer, and other excipient(s) as described above. Other examples of methods of manufacturing controlled release matrices include wet granulation, dry granulation (e.g. slugging, roller compaction), direct compression melt granulation, and rotary granulation.

Additionally, controlled release particles which can be compressed or placed in capsules can be produced by combining the bupropion hydrobromide salt and a hydrophobic fusible component and/or a diluent, optionally with a release modifying agent including a water soluble fusible material or a particulate soluble or insoluble organic or inorganic material. Examples of potential hydrophobic fusible components include hydrophobic materials such as natural or synthetic waxes or oils (e.g., hydrogenated vegetable oil, hydrogenated castor oil, microcrystalline wax, Beeswax, carnauba wax and glyceyl monostearate). In at least one embodiment the hydrophobic fusible component has a melting point from about 35° C. to about 140° C. including all values and ranges therebetween. Examples of release modifying agents include polyethylene glycol and particulate materials such as dicalcium phosphate and lactose.

In certain embodiments, controlled release matrices can be produced by mechanically working a mixture of bupropion hydrobromide salt, a hydrophobic fusible component, and optionally a release component including a water soluble fusible material or a particulate soluble or insoluble organic or inorganic material under mixing conditions that yield aglomerates, breaking down the agglomerates to produce controlled release seeds having desired release properties; and optionally adding more carrier or diluent and repeating the mixing steps until controlled release seeds having desired release properties are obtained. These particles also can be size separated (e.g. by sieving and encapsulated in capsules or compressed into a matrix).

The amount of the hydrophobic fusible material used in the foregoing methods can range from about 10% to about 90% by weight including all values and ranges therebetween.

Mixers useful in such methods are known and include conventional high-speed mixers with stainless steel interiors. For example, a mixture can be processed until a bed temperature of about 40° C. or higher is realized, and the mixture achieves a cohesive granular texture comprising desired particle sizes.

As noted if the mixture contains agglomerates, they can be broken down using conventional methods to produce a mixture of powder and particles of the desired size which, can be size-separated using a sieve, screen or mesh of the appropriate size. This material can be returned to a high-speed mixer and further processed as desired until the hydrophobic fusible materials begin to soften/melt, and optionally additional hydrophobic material can be added and mixing continued until particles having a desired size range are obtained. Still further, particles containing bupropion hydrobromide salt can be produced by melt processing as known in the art and combined into capsules or compressed into matrices.

These particles can be combined with one or more excipients such as diluents, lubricants, binding agents, flow aids, disintegrating agents, surface acting agents, water soluble materials, colorants, and the like.

In addition, the controlled release matrices can optionally be coated with one or more functional or non-functional coatings using well-known coating methods. Examples of coatings can include the XL controlled release coat and the EA matrix coating described herein, which can further control the release of the bupropion hydrobromide salt and/or other drug.

In at least one embodiment, the controlled release matrices can each be coated with at least one taste-masking coating. The taste-masking coating can mask the taste of the bupropion hydrobromide salt in the matrices. In at least one embodiment the taste-masking coating formulations contain polymeric ingredients. It is contemplated that other excipients consistent with the objects of the present invention can also be used in the taste-masking coating.

In at least one embodiment of the matrix dosage form, the taste-masking coating comprises a polymer such as ethylcellulose, which can be used as a dry polymer (such as ETHOCEL) solubilised in organic solvent prior to use, or as an aqueous dispersion. One commercially-available aqueous dispersion of ethylcellulose is AQUACOAT®. AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, the Aquacoat is intimately mixed with a suitable plasticizer prior to use. Another aqueous dispersion of ethylcellulose is commercially available as SURELEASE®. This product can be prepared by incorporating plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

In other embodiments of the matrix dosage form, polymethacrylate acrylic polymers can be employed as taste masking polymers. In at least one embodiment, the taste masking coating is an acrylic resin lacquer used in the form of an aqueous dispersion, such as EUDRAGIT® or KOLLICOAT®. In further embodiments, the acrylic coating comprises a mixture of two acrylic resin lacquers EUDRAGIT® RL and EUDRAGIT® RS, respectively. EUDRAGIT® RL and EUDRAGIT® RS are copolymers of acrylic and methacrylic esters with a low content of quaternary ammonium groups, the molar ratio of ammonium groups to the remaining neutral (meth)acrylic esters being 1:20 in EUDRAGIT® RL and 1:40 in EUDRAGIT® RS. The mean molecular weight is 150,000. The code designations RL (high permeability) and RS (low permeability) refer to the permeability properties of these agents. EUDRAGIT® RL/RS mixtures are insoluble in water and in digestive fluids. However, coatings formed from the same are swellable and permeable in aqueous solutions and digestive fluids. EUDRAGIT® RL/RS dispersions or solutions of the certain embodiments can be mixed together in any desired ratio in order to ultimately obtain a taste masking coating having a desirable drug dissolution profile. Controlled release formulations of certain embodiments can be obtained, for example, from a retardant coating derived from 100% EUDRAGIT® RL; 50% EUDRAGIT® RL with 50% EUDRAGIT® RS; and 10% EUDRAGIT® RL with 90% EUDRAGIT® RS.

In other embodiments of the matrix dosage form, the taste masking polymer can be an acrylic polymer which is cationic in character based on dimethylaminoethyl methacrylate and neutral methacrylic acid esters (such as EUDRAGIT® E). The hydrophobic acrylic polymer coatings of the present invention can further include a neutral copolymer based on poly(meth)acrylates, such as EUDRAGIT® NE. EUDRAGIT® NE 30D lacquer films are insoluble in water and digestive fluids, but permeable and swellable.

In other embodiments of the matrix dosage form, the taste masking polymer is a dispersion of poly(ethylacrylate, methyl methacrylate) 2:1 (KOLLICOAT® EMM 30 D).

In other embodiments of the matrix dosage form, the taste masking polymer can be a polyvinyl acetate stabilized with polyvinylpyrrolidone and sodium lauryl sulfate such as KOLLICOAT® SR30D.

Other taste masking polymers that can be used in the matrix dosage forms include hydroxypropylcellulose (HPC); hydroxypropylmethylcellulose (HPMC); hydroxyethylcellulose; gelatin; gelatin/acacia; gelatin/acacia/vinvylmethylether maleic anhydride; gelatin/acacia/ethylenemaleic anhydride; carboxymethyl cellulose; polyvinvylalcohol; nitrocellulose; polyvinylalcohol-polyethylene glycol graftcopolymers; shellac; wax and mixtures thereof.

The taste-masking coatings can be applied to the matrices from one or more organic or aqueous solvent solutions or suspensions. In at least one embodiment of the matrix dosage forms the organic solvents that can be used to apply the taste-masking coatings include one or more of acetone, lower alcohols such as ethanol, isopropanol and alcohol/water mixtures, chlorinated hydrocarbons, and the like. Devices used to coat the matrices of certain embodiments with a taste-masking coating include those conventionally used in pharmaceutical processing, such as fluidized bed coating devices. The controlled release coatings applied to the matrices can contain ingredients other than the cellulosic polymers. One or more colorants, flavorants, sweeteners, can also be used in the taste-masking coating.

In some embodiments of the matrix dosage forms, a pore former can be included into the taste masking coat in order to influence the rate of release of bupropion hydrobromide from the matrix. In other embodiments, a pore former is not included in the taste masking coat. The pore formers can be inorganic or organic, and may be particulate in nature and include materials that can be dissolved, extracted or leached from the coating in the environment of use. Upon exposure to fluids in the environment of use, the pore-formers can for example be dissolved, and channels and pores are formed that fill with the environmental fluid.

For example, the pore-formers of certain embodiments of the matrix dosage forms can comprise one or more water-soluble hydrophilic polymers in order to modify the release characteristics of the formulation. Examples of suitable hydrophilic polymers that can be used as pore-formers include hydroxypropylmethylcellulose, cellulose ethers and protein-derived materials of these polymers, the cellulose ethers, such as hydroxyalkylcelluloses, carboxyalkylcelluloses and mixtures thereof. Also, synthetic water-soluble polymers can be used, examples of which include polyvinylpyrrolidone, cross-linked polyvinyl-pyrrolidone, polyethylene oxide, water-soluble polydextrose, saccharides and polysaccharides, such as pullulan, dextran, sucrose, glucose, fructose, mannitol, lactose, mannose, galactose, sorbitol and mixtures thereof. In at least one embodiment, the hydrophilic polymer comprises hydroxypropyl-methylcellulose.

Other non-limiting examples of pore-formers that can be used in the taste masking coat include alkali metal salts such as lithium carbonate, sodium chloride, sodium bromide, potassium chloride, potassium sulfate, potassium phosphate, sodium acetate, sodium citrate and mixtures thereof. The pore-forming solids can also be polymers which are soluble in the environment of use, such as CARBOWAX™ and CARBOPOL™. In addition, the pore-formers embrace diols, polyols, polyhydric alcohols, polyalkylene glycols, polyglycols, poly(a-w)alkylenediols and mixtures thereof. Other pore-formers which can be useful in the formulations of certain embodiments of the present invention include starch, modified starch, and starch derivatives, gums, including but not limited to xanthan gum, alginic acid, other alginates, benitonite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambda-carrageenan, gum karaya, biosynthetic gum, and mixtures thereof. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly (urethane), poly(imides), poly(benzimidazoles), collodion, regenerated proteins, semi-solid cross-linked poly(vinylpyrrolidone), and mixtures thereof.

In general, the amount of pore-former included in the taste masking coatings of certain embodiments of the matrix dosage forms can be from about 0.1% to about 80%, by weight including all values and ranges therebetween, relative to the combined weight of polymer and pore-former. The percentage of pore former as it relates to the dry weight of the taste-masking polymer, can have an influence on the drug release properties of the coated matrix. In at least one embodiment that uses water soluble pore formers such as hydroxypropylmethylcellulose, a taste masking polymer:pore former dry weight ratio of from about 10:1 to about 1:1 including all values and ranges therebetween can be present. In certain embodiments the taste masking polymer:pore former dry weight ratio is from about 8:1 to about 1.5:1 including all values and ranges therebetween; and in other embodiments from about 6:1 to about 2:1 including all values and ranges therebetween. In at least one embodiment using EUDRAGIT® NE30D as the taste masking polymer and a hydroxypropylmethylcellulose (approx 5 cps viscosity (in a 2% aqueous solution)) such as METHOCEL® E5, PHARMACOAT® 606G as the water soluble pore former, a taste masking polymer:pore former dry weight ratio of about 2:1 is present.

Colorants that can be used in the taste-masking coating of certain embodiments of the matrix dosage forms include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

Flavorants that can be used in the taste-masking coating of certain embodiments of the matrix dosage forms include natural and synthetic flavoring liquids. An illustrative list of such flavorants includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such as lemon, orange, grape, lime and grapefruit, and fruit essences, including apple, pear, peach, grape, strawberry, raspberry, cherry, plum, pineapple, apricot, or other fruit flavors. Other useful flavorants include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodenal (citrus mandarin); and mixtures thereof.

Sweeteners that can be used in the taste-masking coating of certain embodiments of the matrix dosage forms include glucose (corn syrup), dextrose, invert sugar, fructose, and mixtures thereof (when not used as a carrier); saccharin and its various salts, such as sodium salt; dipeptide sweeteners such as aspartame; dihydrochalcone compounds, glycyrrhizin; Steva Rebaudiana (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-1-2,2-dioxide, particularly the potassium salt (acesulfame-K), and sodium and calcium salts thereof. The sweeteners can be used alone or in any combination thereof.

The matrix taste masking coat can also include one or more pharmaceutically acceptable excipients such as lubricants, emulsifiers, anti-foaming agents, plasticizers, solvents and the like.

Lubricants can be included to help reduce friction of coated matrices during manufacturing. The lubricants that can be used in the taste masking coat of certain embodiments of the present invention include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (e.g. COMPRITOL™), STEAR-O-WET™, MYVATEX™ TL and mixtures thereof. In at least one embodiment, the lubricant is selected from magnesium stearate, talc and a mixture thereof. The lubricant can be present in an amount of from about 1% to about 100% by weight of the polymer dry weight in the taste masking coat including all values and ranges therebetween. For example, in certain embodiments wherein the taste masking polymer is EUDRAGIT® NE30D or EUDRAGIT® NE40D together with a hydrophilic pore former, the lubricant is present in an amount of from about 1% to about 30% by weight of the polymer dry weight including all values and ranges therebetween; in other embodiments from about 2% to about 20% including all values and ranges therebetween; and in still other embodiments at about 10% by weight of the matrix taste masking coat dry weight. In another embodiment where the taste masking polymer is ethylcellulose (ETHOCEL™ PR100, PR45, PR20, PR10 or PR7 polymer, or a mixture thereof), the lubricant can be present in an amount of from about 10% to about 100% by weight of the matrix taste-masking coat dry weight including all values and ranges therebetween; in another embodiment from about 20% to about 80% including all values and ranges therebetween; and in still another embodiments at about 50% by weight of the matrix taste masking coat dry weight. In other embodiments, the taste masking coat does not include a pore former.

Emulsifying agent(s) (also called emulsifiers or emulgents) can be included in the matrix taste masking coat to facilitate actual emulsification during manufacture of the coat, and also to ensure emulsion stability during the shelf-life of the product. Emulsifying agents useful for the matrix taste masking coat composition of certain embodiments include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. In at least one embodiment, the emulsifying agent is TWEEN™ 80. The emulsifying agent(s) can be present in an amount of from about 0.01% to about 5% by weight of the matrix taste masking polymer dry weight including all values and ranges therebetween. For example, in certain embodiments the emulsifying agent is present in an amount of from about 0.05% to about 3% including all values and ranges therebetween; in other embodiments from about 0.08% to about 1.5% including all values and ranges therebetween, and in still other embodiments at about 0.1% by weight of the matrix taste masking polymer dry weight.

Anti-foaming agent(s) can be included in the matrix taste masking coat to reduce frothing or foaming during manufacture of the coat. Anti-foaming agents useful for the coat composition include, but are not limited to simethicone, polyglycol, silicon oil, and mixtures thereof. In at least one embodiment the anti-foaming agent is Simethicone C. The anti-foaming agent can be present in an amount of from about 0.1% to about 10% of the matrix taste masking coat weight including all values and ranges therebetween. For example, in certain embodiments the anti-foaming agent is present in an amount of from about 0.2% to about 5% including all values and ranges therebetween; in other embodiments from about 0.3% to about 1% including all values and ranges therebetween, and in still other embodiments at about 0.6% by weight of the matrix taste masking polymer dry weight.

Plasticizer(s) can be included in the matrix taste masking coat to provide increased flexibility and durability during manufacturing. Plasticizers that can be used in the matrix taste masking coat of certain embodiments include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropionin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. The plasticizer can be present in an amount of from about 1% to about 80% of the taste masking polymer dry weight including all values and ranges therebetween. For example, in certain embodiments the plasticizer is present in an amount of from about 5% to about 50% including all values and ranges therebetween, in other embodiments from about 10% to about 40% including all values and ranges therebetween, and in still other embodiments at about 20% of the taste masking polymer dry weight.

In some embodiments mixtures of plasticizers are provided, e.g., a mixture of PEG 4000 and Dibutyl Sebacate (DBS). For example, in a 174 mg bupropion hydrobromide tablet, PEG4000 is present in an amount of 1.6% by weight of the total formulation and DBS is present in an amount of 0.8% by weight of the total formulation, in a 348 mg bupropion hydrobromide tablet, PEG4000 is present in an amount of 0.9% by weight of the total formulation and DBS is present in an amount of 0.4% by weight of the total formulation, and in a 522 mg bupropion hydrobromide tablet, PEG4000 is present in an amount of 0.9% by weight of the total formulation and DBS is present in an amount of 0.4% by weight of the total formulation, The taste-masking coating can be present in an amount of from about 1% to about 90% by weight of the matrix including all values and ranges therebetween, depending upon the choice of polymer, the ratio of polymer:pore former, and the total surface area of the matrix formulation. Since a certain thickness of taste masking coating has to be achieved in order to achieve effective taste masking, the amount of taste masking polymer coating used during manufacture is related to the total surface area of the batch of uncoated matrices that requires a coating. For example, the taste masking polymer surface area coverage can range from about 0.5 mg/cm2 to about 20 mg/cm2 including all values and ranges therebetween. For example, in certain embodiments the surface area coverage of the taste masking polymer is from about 0.6 mg/cm2 to about 10 mg/cm2 including all values and ranges therebetween, and in other embodiments is from about 1 mg/cm2 to about 5 mg/cm2 including all values and ranges therebetween. In at least one embodiment of the invention, EUDRAGIT® E is employed as the taste masking polymer at a surface area coverage of about 4 mg/cm2.

In the absence of an accurate determination of total surface area of a matrix, the amount of taste masking polymer to be applied can be expressed as a percentage of the uncoated matrix. For example, in certain embodiments the taste-masking coating is present in an amount of from about 5% to about 60% including all values and ranges therebetween; in other embodiments from about 10% to about 40% including all values and ranges therebetween; and in still other embodiments from about 15% to about 35% by weight of the matrix including all values and ranges therebetween. In at least one embodiment the taste-masking coating is present in an amount of about 30% by weight of the matrix.

Prophetic examples of matrix tablet formulations are described below. It should be understood that these examples are intended to be exemplary and that the specific constituents, amounts thereof, and formulation methods may be varied therefrom in order to achieve different release characteristics:

In at least one embodiment, the controlled matrices comprise:

| | |
|---|---|
| Bupropion HBr | about 30.0% by weight of the matrix |
| Hydroxypropylmethylcellulose E50 | about 10.0% by weight of the matrix |
| Hydroxypropylmethylcellulose K15M | about 30.0% by weight of the matrix |
| Calcium phosphate dehydrate | about 9.5% by weight of the matrix |
| ATMUL ™ 84S (mono/di/tri glycerides) | about 20.0% by weight of the matrix |
| Magnesium stearate | about 0.5% by weight of the matrix |

Preparation of the matrix formulation can be as follows: combine the drug, a portion of each HPMC, calcium phosphate and Atmul 84S in a planetary mixer and dry mix for 15 minutes. Add a solution of the remainder of the HPMC in water to the mixer while mixing, until a wet mass is obtained. Pass the wet material through a screen to make the resultant granules of uniform size (to achieve uniform drying) and dry in an oven at about 40° C. for about 24 hours. Mill the dried granules through a Fitzpatrick Mill, knives forward, and collect the material in a mixer. Add the magnesium stearate and mix for about 5 minutes. The resultant mixture is tabletted on a suitable tablet press.

In at least one embodiment, the controlled release matrices comprise a deposit-core and support-platform. Preparation of the deposit-core can be as follows: Deposit-cores can be prepared using the following materials in the stated quantities:

| | |
|---|---|
| Bupropion HBr | about 45.0 g |
| hydroxypropylmethylcellulose (METHOCEL ® K 100M-Colorcon) | about 35.0 g |
| mannitol | about 10.0 g |
| ethylcellulose (high viscosity-BDH) | about 3.75 g |
| 3.75 g magnesium stearate | about 1.0 g |
| 5:1 ethanol-chloroform mixture | about 75.0 ml |

The bupropion hydrobromide is mixed intimately with the mannitol and hydroxypropylmethylcellulose in a suitable mixer. The solution of ethylcellulose in ethanol-chloroform is prepared separately, and is used for wetting the previously obtained powder mixture. The resultant homogeneous mass is forced through an 800 micron screen and then dried to obtain a granulate which is passed through a 420 micron screen. The homogeneous granulate obtained is mixed with the magnesium stearate and then compressed using concave punches of diameter 7 mm (radius of curvature 9 mm) using a pressure of about 3000 kg/cm2 to obtain cylindrical deposit-cores with convex bases.

Application of the support-platform can be as follows: The support-platform can be applied by coating one or both the convex bases of the deposit-core with a solution of about 15 g low-permeability acrylic-methacrylic copolymer (EUDRAGIT® RS) in methylene chloride of a quantity to make up to 100 ml. Thereafter about 0.3 ml of said solution is applied to each base to be covered, taking care to protect the lateral core surface. The system is then dried with tepid air. The quantity of polymeric material deposited is sufficient to keep the structure intact during transfer.

In at least one embodiment, the matrix formulation is a polyethylene oxide (PEO) based tablet matrix formulation comprising:

| | |
|---|---|
| Bupropion Hydrobromide | about 50% |
| PEO WSR Coagulant (polyethylene oxide) | about 15% |
| METHOCEL ® K100M (hydroxypropylmethyl cellulose) | about 15% |
| Avicel PH101 (microcrystalline cellulose) | about 19% |
| Magnesium Stearate | about 1% |

Preparation of the PEO based tablet matrix formulation can be as follows: excipients dry blended in an appropriate mixer and compressed into tablets using conventional apparatus.

Multiparticulates

In certain embodiments of the present invention, a multiparticulate system is provided which contains multiple microparticles each containing an effective amount of bupropion hydrobromide and at least one pharmaceutically acceptable excipient. The multiparticulates can be contained within a capsule, or can be compressed into a matrix or tablet, that upon ingestion dissolves into multiple units (e.g. pellets), wherein the sub-units or pellets possess the desired controlled release properties of the dosage form. The multiparticulates or the multiple unit dosage forms can be surrounded by one or more coatings. Examples of such coatings include polymeric controlled release coatings, delayed release coatings, enteric coatings, immediate release coatings, taste-masking coatings, extended release coatings, and non-functional coatings.

The bupropion hydrobromide salt in the microparticles of certain embodiments can be present in an effective amount of from about 0.1% to about 99% by weight of the microparticles including all values and ranges therebetween. For example, in certain embodiments bupropion hydrobromide is present in the microparticles in an amount of from about 0.1% to about 90% including all values and ranges therebetween, in other embodiments from about 5% to about 90% including all values and ranges therebetween, in still other embodiments from about 10% to about 80% including all values and ranges therebetween, and in even still other embodiments from about 25% to about 80% by weight of the microparticle including all values and ranges therebetween. In certain embodiments wherein the microparticles are manufactured using a spheronization process, the bupropion hydrobromide can be present in the microparticles in an amount of from about 0.1% to about 60% including all values and ranges therebetween; in other such embodiments from about 5% to about 50% including all values and ranges therebetween; and in still other such embodiments from about 10% to about 40% by weight of the microparticle including all values and ranges therebetween. In at least one embodiment wherein the microparticles are manufactured using a spheronization process, the bupropion hydrobromide is present in the microparticle in an amount of about 30% by weight of the microparticle.

In addition to the bupropion hydrobromide salt, the microparticles of the present invention also include at least one pharmaceutically acceptable excipient. Excipients can be added to facilitate in the preparation, patient acceptability and functioning of the dosage form as a drug delivery system. Examples of possible excipients include spheronization aids, solubility enhancers, disintegrating agents, diluents, lubricants, binders, fillers, glidants, suspending agents, emulsifying agents, anti-foaming agents, flavoring agents, coloring agents, chemical stabilizers, pH modifiers, and mixtures thereof. Depending on the intended main function, excipients to be used in formulating compositions are subcategorized into different groups. However, one excipient can affect the properties of a composition in a series of ways, and many excipients used in compositions can thus be described as being multifunctional.

The microparticles of certain embodiments of the present invention can be manufactured using standard techniques known to one of skill in the art. In certain embodiments the microparticles can be made according to any one of the methods described herein. Useful microparticles include drug-layered microparticles and drug-containing microparticles.

Drug-Containing Microparticles

Microparticles containing drug in the core can be prepared by a number of different procedures. For example: In a spray drying process, an aqueous solution of core material and hot solution of polymer is atomized into hot air, the water then evaporates, and the dry solid is separated in the form of pellets, for example by air suspension. A spray-drying process can produce hollow pellets when the liquid evaporates at a rate that is faster than the diffusion of the dissolved substances back into the droplet interior, or if due to capillary action the dissolved substance migrates out with the liquid to the droplet surface, leaving behind a void. Another example is a spray congealing process, where a slurry of drug material that is insoluble in a molten mass is spray congealed to obtain discrete particles of the insoluble materials coated with the congealed substance. A further example is a fluidized bed based granulation/pelletization process, where a dry drug is suspended in a stream of hot air to form a constantly agitated fluidized bed. An amount of binder or granulating liquid is then introduced in a finely dispersed form to cause pelletization.

The drug-containing microparticles of certain embodiments of the present invention can also be made by, for example, a spheronization process. One method of manufacturing the drug-containing microparticles is the applicant's proprietary CEFORM™ (Centrifugally Extruded & Formed Microspheres/Microparticles) technology, which is the simultaneous use of flash heat and centrifugal force, using proprietary designed equipment, to convert dry powder systems into microparticles of uniform size and shape. The production of microparticles containing an active drug using this CEFORM™ technology is known. Certain embodiments of the present invention deal with the use of LIQUIFLASH® processing to spheronize compositions containing one or more active drugs to form LIQUIFLASH® microparticles.

With the CEFORM™ technology, the processing of the drug-containing microparticles of certain embodiments of the present invention is carried out in a continuous fashion, whereby a pre-blend of drug and excipients is fed into a spinning "microsphere head", also termed as a "spheronizing head". The microsphere head, which is a multi-aperture production unit, spins on its axis and is heated by electrical power. The drug and excipient(s) pre-blend is fed into the center of the head with an automated feeder. The material moves, via centrifugal force, to the outer rim where the heaters, located in the rim of the head, heat the material. Microparticles are formed when the molten material exits the head, which are then cooled by convection as they fall to the bottom of the microparticle chamber. The product is then collected and stored in suitable product containers. Careful selection of the types and levels of excipient(s) control microparticle properties such as sphericity, surface morphology, and dissolution rate. One advantage of such a process is that the microparticles are produced and collected from a dry feedstock without the use of any solvents.

There are at least two approaches that can be used to produce drug-containing microparticles using the CEFORM process: (i) the encapsulation approach and (ii) the co-melt approach. In the encapsulation approach, the process is conducted below the melting point of the drug. Therefore, the excipients are designed to melt and entrain the drug particles on passing through the apertures to form microparticles. The resulting microparticles contain the drug, in its native state, essentially enveloped by or as an intimate matrix with the resolidified excipients. In the co-melt approach, the process is conducted above the melting point of the drug. In this case, the drug and the excipients melt or become fluid simultaneously upon exposure to the heat. The molten mixture exits the head and forms microparticles, which cool as they fall to the bottom of the collection bin where they are collected.

In at least one embodiment the microparticles are manufactured using the encapsulation approach. In the encapsulation approach the excipient(s) which are chosen have a lower melting point than the drug (e.g. bupropion hydrobromide) with which they will be combined. Therefore the spheronizing process can be performed at lower temperatures, than the melting point of the drug. As a result, this can reduce the risk of polymeric interconversion, which can occur when using processing temperatures close to the melting point.

In a prophetic example of certain embodiments of the present invention, the manufacturing process for the microparticles can hypothetically be as follows: Spheronization aid is screened through a 425 micron (μm) screen. In at least one embodiment, the spheronization aid is distilled glyceryl monostearate (i.e. DMG-03VF). About 50% of the spheronization aid is added to a bowl in a high shear mixer. In at least one embodiment, the bowl is a 6 liter bowl and the high shear mixer is a Diosna P1-6 high speed mixer granulator. The active drug is then added to the bowl of the mixer, and then the remainder of the spheronization aid is added. The material is then blended in the mixer for a time from about 1 minute to about 30 minutes including all values and ranges therebetween; in certain embodiments from about 3 minutes to about 10 minutes; and in at least one embodiment at about 6 minutes. The mixer motor speed is from about 50 rpm to about 2000 rpm including all values and ranges therebetween; in certain embodiments from about 200 rpm to about 500 rpm; and in at least one embodiment at about 300 rpm. The chopper motor speed is from about 50 rpm to about 2000 rpm including all values and ranges therebetween; in certain embodiments from about 200 rpm to about 500 rpm; and in at least one embodiment at about 400 rpm. The blended material is then spheronized in a CEFORM™ spheronizing head. The spheronizing head speed is from about 5 Hz to about 60 Hz including all values and ranges therebetween; in certain embodiments from about 10 Hz to about 30 Hz; and in at least one embodiment at about 15 Hz. In at least one embodiment the CEFORM™ spheronizing head is a 5 inch head. The spheronizing head temperature is maintained at a temperature from about 70° C. to about 130° C. including all values and ranges therebetween; in certain embodiments from about 90° C. to about 110° C.; and in at least one embodiment at about 100° C. The microparticles obtained from the spinning process are then screened through a screen that is from about 150 μm to about 800 μm including all values and ranges therebetween.

For microparticles manufactured using a spheronization process such as the CEFORM™ process, the microparticles include, in addition to the bupropion hydrobromide salt, at least one spheronization aid. Spheronization aids can assist the drug-containing mix to form robust durable spherical particles. Some examples of materials useful as spheronization aids include, but are not limited to glyceryl monostearate, glyceryl behenate, glyceryl dibehenate, glyceryl palmitostearate, hydrogenated oils such as hydrogenated castor oil marketed under the name CUTINA™ HR, fatty acid salts such as magnesium or calcium stearate, polyols such as mannitol, sorbitol, xylitol, stearic acid, palmitic acid, sodium lauryl sulfate, polyoxyethylene ethers, esterified polyoxyethylenes such as PEG-32 distearate, PEG-150 distearate, cetostearyl alcohol, waxes (e.g. carnauba wax, white wax, paraffin wax) and wax-like materials. Certain thermo-plastic or thermo-softening polymers can also function as spheronization aids. Some non-limiting examples of such thermo-plastic or thermo-softening polymers include Povidone, cellulose ethers and polyvinylalcohols. Combinations of spheronization aids can be used. In at least one embodiment, the spheronization aid includes glyceryl monostearate (i.e. DMG-03VF). The spheronization aid can be present in an amount of from about 0.1% to about 99% by weight of the microparticle including all values and ranges therebetween. For example, in certain embodiments the spheronization aid is present in an amount of from about 5% to about 90% including all values and ranges therebetween; in other embodiments from about 10% to about 80% including all values and ranges therebetween; in still other embodiments from about 20% to about 70% including all values and ranges therebetween; and in even still other embodiments from about 30% to about 60% by weight of the microparticle including all values and ranges therebetween. In at least one embodiment the spheronization aid is present in an amount of about 50% by weight of the microparticle. In at least one other embodiment, the microparticles include about 50% (w/w) of bupropion hydrobromide and about 50% (w/w) of the spheronization aid.

In certain embodiments, each microparticle can also include at least one solubility enhancer. Solubility enhancers can be surfactants. Certain embodiments of the invention include a solubility enhancer that is a hydrophilic surfactant.

Hydrophilic surfactants can be used to provide any of several advantageous characteristics to the compositions, including: increased solubility of the bupropion hydrobromide salt in the microparticle; improved dissolution of the bupropion hydrobromide salt; improved solubilization of the bupropion hydrobromide salt upon dissolution; enhanced absorption and/or bioavailability of the bupropion hydrobromide salt. The hydrophilic surfactant can be a single hydrophilic surfactant or a mixture of hydrophilic surfactants, and can be ionic or non-ionic.

Likewise, various other embodiments of the invention include a lipophilic component, which can be a lipophilic surfactant, including a mixture of lipophilic surfactants, a triglyceride, or a mixture thereof. The lipophilic surfactant can provide any of the advantageous characteristics listed above for hydrophilic surfactants, as well as further enhancing the function of the surfactants. These various embodiments are described in more detail below.

As is well known in the art, the terms "hydrophilic" and "lipophilic" are relative terms. To function as a surfactant, a compound includes polar or charged hydrophilic moieties as well as non-polar hydrophobic (lipophilic) moieties; i.e., a surfactant compound is amphiphilic. An empirical parameter commonly used to characterize the relative hydrophilicity and lipophilicity of non-ionic amphiphilic compounds is the hydrophilic-lipophilic balance (the "HLB" value). Surfactants with lower HLB values are more lipophilic, and have greater solubility in oils, whereas surfactants with higher HLB values are more hydrophilic, and have greater solubility in aqueous solutions.

Using HLB values as a rough guide, hydrophilic surfactants can generally be considered to be those compounds having an HLB value greater than about 10, as well as anionic, cationic, or zwitterionic compounds for which the HLB scale is not generally applicable. Similarly, lipophilic surfactants can be compounds having an HLB value less than about 10.

It should be appreciated that the HLB value of a surfactant is merely a rough guide generally used to enable formulation of industrial, pharmaceutical and cosmetic emulsions. For many surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Likewise, for certain polypropylene oxide containing block copolymers (poloxamers, available commercially as PLURONIC® surfactants), the HLB values may not accurately reflect the true physical chemical nature of the compounds. Finally, commercial surfactant products are generally not pure compounds, but are often complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or lipophilicity for use in the present invention, as described herein.

Solubility enhancers can be any surfactant suitable for use in pharmaceutical compositions as known in the art. Suitable surfactants can be anionic, cationic, zwitterionic or non-ionic. Refined, distilled or fractionated surfactants, purified fractions thereof, or re-esterified fractions, are within the scope of the invention.

Although polyethylene glycol (PEG) itself does not function as a surfactant, a variety of suitable PEG-fatty acid esters have useful surfactant properties, as is known in the art. Polyethylene glycol (PEG) fatty acid diesters are also suitable for use as surfactants in the compositions of the present invention, as is known in the art. In general, mixtures of surfactants are also useful in the present invention, including mixtures of two or more commercial surfactant products as is known in the art (e.g. PEG-fatty acid esters are marketed commercially as mixtures or mono- and diesters).

A large number of suitable surfactants of different degrees of lipophilicity or hydrophilicity can be prepared by reaction of alcohols or polyalcohols with a variety of natural and/or hydrogenated oils, as is known in the art. In certain embodiments, the oils used are castor oil or hydrogenated castor oil or an edible vegetable oil such as corn oil, olive oil, peanut oil, palm kernel oil, apricot kernel oil, or almond oil. Non-limiting examples of alcohols include glycerol, propylene glycol, ethylene glycol, polyethylene glycol, sorbitol, pentaerythritol and mixtures thereof.

Polyglycerol esters of fatty acids as is known in the art, are also suitable surfactants for the present invention. Esters of propylene glycol and fatty acids as is known in the art are also suitable surfactants for use in the present invention. In general, mixtures of surfactants are also suitable for use in the present invention. In particular, mixtures of propylene glycol fatty acid esters and glycerol fatty acid esters, as is known in the art, are suitable and are commercially available. Another class of suitable surfactants is the class of mono- and diglycerides, as are known in the art. These surfactants are generally lipophilic. Sterols and derivatives of sterols are also suitable surfactants for use in the present invention as is known in the art. These surfactants can be hydrophilic or lipophilic. A variety of PEG-sorbitan fatty acid esters are known in the art and are available and suitable for use as surfactants in the present invention. In general, these surfactants are hydrophilic, although several lipophilic surfactants of this class can be used. Suitable ethers of polyethylene glycol and alkyl alcohols are known in the art and are suitable surfactants for use in the present invention. Esters of sugars are known in the art and are suitable surfactants for use in the present invention. Several hydrophilic PEG-alkyl phenol surfactants are known in the art and are available, and are suitable for use in the present invention.

The POE-POP block copolymers are a unique class of polymeric surfactants. The unique structure of the surfactants, with hydrophilic POE and lipophilic POP moieties in well-defined ratios and positions, provides a wide variety of surfactants suitable for use in the present invention. These surfactants are available under various trade names, including SYNPERONIC™ PE series (ICI); PLURONIC® series, EMKALYX™, LUTROL™, SUPRONIC™ MONOLAN™, PLURACARE™, and PLURODAC™. The generic term for these polymers is "poloxamer" (CAS 9003-11-6). These polymers have the formula:

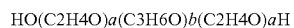

where "a" and "b" denote the number of polyoxyethylene and polyoxypropylene units, respectively. The suitable surfactants of this class are known in the art.

Sorbitan esters of fatty acids are suitable surfactants for use in the present invention and are known in the art. Esters of lower alcohols (C2 to C4) and fatty acids (C8 to C18) are suitable surfactants for use in the present invention and are known in the art. Ionic surfactants, including cationic, anionic and zwitterionic surfactants, are suitable hydrophilic surfactants for use in the present invention and are known in the art.

In certain embodiments, the surfactant is an anionic surfactant such as a fatty acid salt, a bile salt, or a combination thereof. In other embodiments the surfactant is a cationic surfactant such as a carnitine.

Examples of ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine.

Ionizable surfactants, when present in their unionized (neutral, non-salt) form, are lipophilic surfactants suitable for use in the compositions of the present invention, and are known in the art. Particular examples of such surfactants include free fatty acids, particularly C6-C22 fatty acids, and bile acids. More specifically, suitable unionized ionizable surfactants include the free fatty acid and bile acid forms of any of the fatty acid salts and bile salts.

Derivatives of oil-soluble vitamins, such as vitamins A, D, E, K, etc., are also useful surfactants for the compositions of the present invention. An example of such a derivative is tocopheryl PEG-1000 succinate (TPGS).

In certain embodiments, surfactants or mixtures of surfactants that solidify at ambient room temperature are used. In other embodiments, surfactants or mixtures of surfactants that solidify at ambient room temperature in combination with particular lipophilic components, such as triglycerides, or with addition of appropriate additives, such as viscosity modifiers, binders, thickeners, and the like, are used.

Examples of non-ionic hydrophilic surfactants include alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols with fatty acids, glycerides, vegetable oils, hydrogenated vegetable oils, and sterols; sugar esters, sugar ethers; sucroglycerides; polyethoxylated fat-soluble vitamins or derivatives; and mixtures thereof.

In certain embodiments, the non-ionic hydrophilic surfactant is selected from the group comprising polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene vegetable oils; polyoxyethylene hydrogenated vegetable oils, and mixtures thereof. The glyceride can be a monoglyceride, diglyceride, triglyceride, or a mixture thereof.

In certain other embodiments, the surfactants used are non-ionic hydrophilic surfactants that are reaction mixtures of polyols and fatty acids, glycerides, vegetable oils, hydrogenated vegetable oils or sterols. These reaction mixtures are largely composed of the transesterification products of the reaction, along with often complex mixtures of other reaction products. The polyol can be glycerol, ethylene glycol, polyethylene glycol, sorbitol, propylene glycol, pentaerythritol, a saccharide, or a mixture thereof.

The hydrophilic surfactant can also be, or include as a component, an ionic surfactant. Examples of ionic surfactants include alkyl ammonium salts; bile acids and salts, analogues, and derivatives thereof; fusidic acid and derivatives thereof; fatty acid derivatives of amino acids, oligopeptides, and polypeptides; glyceride derivatives of amino acids, oligopeptides, and polypeptides; acyl lactylates; mono-, diacetylated tartaric acid esters of mono-, diglycerides; succinylated monoglycerides; citric acid esters of mono-, diglycerides; alginate salts; propylene glycol alginate; lecithins and hydrogenated lecithins; lysolecithin and hydrogenated lysolecithins; lysophospholipids and derivatives thereof; phospholipids and derivatives thereof salts of alkylsulfates; salts of fatty acids; sodium docusate; carnitines; and mixtures thereof.

In certain embodiments the ionic surfactants include bile acids and salts, analogues, and derivatives thereof; lecithins, lysolecithin, phospholipids, lysophospholipids and derivatives thereof salts of alkylsulfates; salts of fatty acids; sodium docusate; acyl lactylates; mono-, diacetylated tartaric acid esters of mono-, diglycerides; succinylated monoglycerides; citric acid esters of mono-diglycerides; carnitines; and mixtures thereof.

Examples of ionic surfactants include lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

In certain embodiments, ionic surfactants used include lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, glycodeoxycholate, cholylsarcosine, caproate, caprylate, caprate, laurate, oleate, lauryl sulfate, docusate, and salts and mixtures thereof. In at least one embodiment, the ionic surfactant is selected from lecithin, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, taurocholate, caprylate, caprate, oleate, lauryl sulfate, docusate, and salts and mixtures thereof.

Examples of lipophilic surfactants include alcohols; polyoxyethylene alkylethers; fatty acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; and mixtures thereof.

As with the hydrophilic surfactants, lipophilic surfactants can be reaction mixtures of polyols and fatty acids, glycerides, vegetable oils, hydrogenated vegetable oils, and sterols.

In certain embodiments, the lipophilic surfactants include one or more selected from the group comprising fatty acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono/diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; and reaction mixtures of polyols and fatty acids, glycerides, vegetable oils, hydrogenated vegetable oils, sterols, and mixtures thereof.

In certain other embodiments, the lipophilic surfactants include one or more selected from the group comprising lower alcohol fatty acids esters; polypropylene glycol fatty acid esters; propylene glycol fatty acid esters; glycerol fatty acid esters; acetylated glycerol fatty acid esters; lactic acid derivatives of mono/diglycerides; sorbitan fatty acid esters; polyoxyethylene vegetable oils; and mixtures thereof. Among the glycerol fatty acid esters, the esters can be mono- or diglycerides, or mixtures of mono- and diglycerides, where the fatty acid moiety is a C6 to C22 fatty acid.

Other embodiments include lipophilic surfactants which are the reaction mixture of polyols and fatty acids, glycerides, vegetable oils, hydrogenated vegetable oils, and sterols. Examples of polyols are polyethylene glycol, sorbitol, propylene glycol, pentaerythritol, and mixtures thereof.

Combinations of solubility enhancers (i.e. surfactants) can be used. Examples of macrogol fatty acid esters useful as solubility enhancers include GELUCIRE® 50/13 and GELUCIRE® 44/14. In at least one embodiment the solubility enhancer is GELUCIRE® 50/13. The solubility enhancer can be present in an amount of from about 0.1% to about 70% by weight of the microparticle including all values and ranges therebetween. For example, in certain embodiments, the solubility enhancer is present in an amount of from about 1% to about 50% including all values and ranges therebetween; in other embodiments from about 10% to about 30% including all values and ranges therebetween; in still other embodiments from about 15% to about 25% by weight of the microparticle including all values and ranges therebetween. In at least one embodiment the solubility enhancer is present in an amount of about 20% by weight of the microparticle.

It is contemplated that in some embodiments, one or more other pharmaceutically acceptable excipients consistent with the objects of the present invention can be used in the microparticles, such as a lubricant, a binder, a pH modifier, a filler and/or a glidant.

The process for manufacturing the drug-containing microparticles of certain embodiments of the present invention by spheronization are not limited to the CEFORM™ technology, and any other technology resulting in the formation of the microparticles consistent with the objects of the present invention can also be used. For example, microparticles of certain embodiments of the invention can also be manufactured by extrusion/spheronization, granulation or pelletization.

Extrusion/spheronization is a multi-step process used to make uniformly sized spherical particles. The technique offers the ability to incorporate high levels of active ingredients without producing excessively large particles. The main steps in the process are:

Dry-mixing of ingredients to achieve a homogenous powder dispersion;
Wet massing using for example a high-shear wet granulator to form rod shaped particles of uniform diameter;
Extrusion to form rod-shaped particles of uniform diameter;
Spheronization to round off the rods into spherical particles;
Screening to achieve the desired narrow particle size distribution.

The mixing vessel used for dry-mixing can be of any size and shape compatible with the size of the formulation to be produced. For example, commercially available mixing devices such as planetary mixers, high shear mixers, or twin cone blenders can be used. If relatively small quantities of formulation are to be prepared, a simple mortar and pestle can be sufficient to mix the ingredients. The type of mixing vessel would be apparent to one skilled in the pharmaceutical art. The moistened mass formed by wet-massing in conventional granulation equipment is extruded through a perforated mesh in order to produce cylindrical filaments.

The port of the meshes can determine the diameter of the filaments. A port ranging from about 0.2 mm to about 3 mm including all values and ranges therebetween, can be used in this process. In at least one embodiment utilizing this process, the port ranges from about 0.4 mm to about 2 mm including all values and ranges therebetween. The extrusion can be carried out using screw, double screw, "sieve and basket" kind, "roll extruder", "ram extruder" extruders or any other pharmaceutically acceptable means to produce cylindrical filaments. In certain embodiments utilizing this extrusion/spheronization process, a double screw coaxial extruder is used. The spheronization device comprises a hollow cylinder with a horizontal rotating plate. The filaments are broken in short segments which are transformed in spherical or quasi-spherical particles on the upper surface of the rotating plate at a velocity ranging from about 200 rpm to about 2,000 rpm including all values and ranges therebetween. The particles can be dried in any pharmaceutically acceptable way, such as for example by air drying in a static condition. The particles are used as they are or they are coated to obtain granules to use in tablets, capsules, packets or other pharmaceutical formulations.

A prophetic example of an extrusion/spheronization formulation comprising bupropion hydrobromide can be as follows: In this example, the bupropion hydrobromide can be present in an amount of from about 1% to about 80% w/w including all values and ranges therebetween. In certain embodiments within this example, the bupropion hydrobromide is present in an amount of from about 1% to about 50% w/w; in other embodiments from about 10% to about 30%; and in still other embodiments about 10% w/w. In this example, the filler can be present in an amount of from about 0% to about 80% w/w including all values and ranges therebetween. In certain embodiments of this example, the filler is present in an amount of from about 10% to about 60%; and in other embodiments at about 40% w/w. In this example, the microcrystalline cellulose can be present in an amount of from about 10% to about 90% w/w including all values and ranges therebetween. In certain embodiments of this example, the microcrystalline cellulose is present in an amount of from about 10% to about 70%; and in other embodiments from about 20% to about 50% w/w. In this example, the binder can be present in an amount of from about 0% to about 10% w/w including all values and ranges therebetween. In certain embodiments of this example, the binder is present in an amount of from about 1% to about 8%; and in other embodiments from about 2% to about 4% w/w. In this example, water can be present in an amount of from about 10% to about 80% w/w including all values and ranges therebetween. In certain embodiments of this example, water is present in an amount of from about 15% to about 70%; and in other embodiments from about 20% to about 50% w/w. Suitable fillers that can be used in this example include but are not limited to calcium phosphate dibasic, tricalcium phosphate, calcium carbonate, starch (such as corn, maize, potato and rice starches), modified starches (such as carboxymethyl starch, etc.), microcrystalline cellulose, sucrose, dextrose, maltodextrins, lactose, and fructose. Suitable lubricants that can be used in this example include but are not limited to metal stearates (such as calcium, magnesium on zinc stearates), stearic acid, hydrogenated vegetable oils, talc, starch, light mineral oil, sodium benzoate, sodium chloride, sodium lauryl sulfate, magnesium lauryl sulfate, sodium stearyl fumarate, glyceryl behenate and polyethylene glycol (such as CARBOWAX™ 4000 and 6000). Suitable antiadherents in this example include but are not limited to colloidal silicon dioxide. Suitable binders in this example include but are not limited to ethyl cellulose, a polymethacrylate polymer, polyvinylalcohol, polyvinyl pyrrolidone, polyvinylpyrrolidone-vinylacetate copolymer (e.g. KOLLIDON® VA64) hydroxyethylcellulose, low molecular weight hydroxypropylmethylcellulose (e.g. viscosity of about 1-50 cps at about 20° C.; about 2-12 cps at about 20° C.; or about 4-6 cps at about 20° C.), hydroxypropylcellulose polymethacrylates, and mixtures thereof.

The drug-containing microparticles formed by extrusion/spheronization in this prophetic example can be produced using cross-linked amphiphilic polymers by the following steps: (a) the mixing of one or more cross-linked amphiphilic polymers with bupropion hydrobromide and optionally other pharmaceutical excipients in order to obtain a uniform mixture in the form of dry powder to which a suitable amount of liquid is added to obtain a pasty consistency; (b) the extrusion of the mixture obtained from step (a) through a perforated mesh in order to obtain cylindrical filaments having desired length and diameter; (c) the spheronization of the filaments in order to obtain a product in the form of spherical multiparticulates; (d) the drying of the product; and (e) the optional depositing of a drug on the surface of the microparticles. "Cross-linked amphiphilic polymer" refers in this example to polymers showing characteristics of swellability in the whole pH range of aqueous solutions and also in solvents or solvent mixtures having different polarity characteristics. The polymers can be cross-linked either physically through the interpenetration of the macromolecular meshes, or chemically, thus showing points of link among the macromolecular chains. Non-limiting examples of such polymers include cross-linked polyvinyl pyrrolidone, sodium carboxymethylcellulose, sodium glycolate starch and dextrans. Optional excipients include dispersing, emulsifying, wetting agents and coloring agents. The expression "uniform mixture" in this example means that the components of the mixture are uniformly dispersed in the formulation by a mixing process which assures the uniform distribution of each component. A reasonable mixing time can range from about 1 to about 60 minutes including all values and ranges therebetween, using one of the mixing equipments conventionally used for the dry mixing of the powders (e.g. "V", fixed body, rotating body, sigma mixers). The term "liquid" in this example means any liquid substance or mix (solution or emulsion) of liquids of normal pharmaceutical use able to moisten the powder mix, as for example water, aqueous solutions having different pH, organic solvents of normal pharmaceutical use (e.g. alcohols, chlorinated solvents), and oils. Among the oils and surfactants which can be used in this example are: natural oils, either saturated or unsaturated (olive, peanut, soybean, corn, coconut, palm, sesame and similar oils); semisynthetic and synthetic mono-, di- and triglycerides containing saturated and/or unsaturated fatty acids and their polyhydroxyethylated derivatives (caprico-caprilic triglycerides [MYGLIOL™, CAPTEX™, LABRAFAC™, LIPO™], saturated or unsaturated polyhydroxylated triglycerides of various kind [LABRAFIL™, LABRAFAC™ Hydro, GELUCIRE™]); liquid waxes (isopropyl myristate, isopropyl-caprinate, -caprylate, -laurate, -palmitate, -stearate); fatty acids esters (ethyl oleate, oleyl oleate); silicone oils; polyethylene glycols (PEG 200, PEG 400, PEG 600, PEG 1000, and so on); polyglycolic glycerides (for example LABRASOL™); polyglycols (propylene glycol, tetraglycol, and ethoxydiglycol (TRANSCUTOL™), sorbitan-esters of fatty acids (for example SPAN®, ARLACEL®, BRIJ®), polyoxyethylenesorbitan esters of fatty acids (for example TWEEN®, CAPMUL®, LIPOSORB®), polypropylene oxide-polyethylene oxide (Poloxamer) copolymers, polyethylene glycol esters (PEG)-glycerol (LABRASOL®, LABRAFIL®), PEG esters and long chain aliphatic acids or alcohols (for example CREMOPHOR®), polyglycerid esters (PLUROL®), saccharide, fatty acid esters (sucro-esters), and mixtures thereof. Moreover, anionic surfactants (for example sodium lauryl sulfate, sodium stearate, sodium oleate) or cationic surfactants (for example tricetol), can be used as well as lecithins, phospholipids and their semi-synthetic or synthetic derivatives. Also bupropion hydrobromide and/or excipients can be dissolved, dispersed and/or emulsified in such liquids.

In a particular embodiment formed by an extrusion/spheronization process from the prophetic example described above, the moistening liquid comprises an oil/surfactant system wherein the bupropion hydrobromide optionally emulsified with an aqueous phase is dissolved or dispersed. The amount of liquid with respect to the solid used in the preparation of the mixture can range from about 1% to about 80% by weight including all values and ranges therebetween. As a prophetic example of this embodiment, a mixture of bupropion hydrobromide and KOLLIDON™ CL in a ratio equal to about 1:3 by weight is co-milled obtaining the mixture in the form of powder having about 100% of granulometry lower than about 50 microns. The mixture is moistened using a liquid demineralized water containing KOLLIDON™ 25 (polyvinyl pyrrolidone, BASF) in a solution 3% w/w. The extrusion is carried out forcing the moistened mass through a threader having diameter of the holes equal to about 1 mm. The operative parameters in this prophetic example can be as follows: powder flow rate: about 4.5 kg/h; liquid flow rate: about 4.1 kg/h; torsional stress: about 27%; head temperature: about 46° C.; and screw rotation velocity: about 140 rpm. The extrusion filaments are then processed in a spheronizator adjusted at a velocity equal to about 1,000 rpm for about 2 minutes. The obtained microparticles are then dried in a fluid bed for about 2 hours to a maximum temperature equal to about 59° C. At the end of the drying the product is discharged and is mechanically screened separating the fraction ranging from about 0.7 mm to about 1.2 mm.

Another prophetic example of a drug-containing microparticle embodiment of the invention formed by an extrusion/spheronization process, uses a charged resin, the steps of which can comprise: (a) adding the charged resin, bupropion hydrobromide and other excipients, to a mixing vessel; (b) mixing the ingredients to obtain a uniform mixture; (c) adding a granulating solution—a liquid capable of wetting the dry mixture. Liquids resulting in conversion of the dry powder mixture into a wet granulation that supports subsequent extrusion and spheronization (marumerization) are included.

Typically, water or aqueous solutions are employed. Alcohols, typically ethanol or isopropanol, can be included with the granulating water to enhance the workability of the granulation. In another embodiment of this invention, one or more of the components of the formulation is first dissolved in water and this solution is used to produce the wet granulation. An active ingredient or an excipient which is present at very low concentration can initially be dissolved or suspended in the granulating solvent to assure more uniform distribution throughout the formulation. (d) granulating the mixture until a uniform granulation results; (e) extruding the wet granulation through a screen to produce strands of granulation; (f) spheronizing the strands of granulation to produce spherical multiparticulates; and (g) collecting and drying the spherical multiparticulates. By "charged resin" is meant in this example to mean a polymer with ionizable functional groups that becomes useful in the embodiment of this invention. This broadly encompasses any polymer that upon ionization, is capable of producing cationic or anionic polymeric chains and which support spheronization. Typically from about 10% to about 70% by weight of the spherical multiparticulate is charged resin. Non limiting examples of these charged resins include sodium polystyrene sulfonate (e.g. AMBERLITE IR-P69™; the chloride salt of cholestyramine resin USP (e.g. AMBERLITE IR-P276™; the acid form of methacrylic acid-divinyl benzene (e.g. AMBERLITE IRP64™; carboxypolymethylenes (e.g. CARBOPOL™ 974P and CARBOPOL™ 934P, and sodium polyacrylate (e.g. AQUAKEEP™ J-550. In order for the resin to maintain the desired degree of ionization, agents which produce an acidic or basic environment during granulation and spheronization can be included within the formulation. Among the groups of compounds that can exert this effect are acids, bases, and the salts of acids and bases such as adipic acid, citric acid, fumaric acid, tartaric acid, succinic acid, sodium carbonate, sodium bicarbonate, sodium citrate, sodium acetate, sodium phosphates, potassium phosphates, ammonium phosphate, magnesium oxide, magnesium hydroxide, sodium tartrate, and tromethamine. Certain compounds can be added to the granulation to provide the proper degree of hydration of the charged resin, medicament and excipients. These hydrating agents include sugars such as lactose, sucrose, mannitol, sorbitol, pentaerythritol, glucose and dextrose. Polymers such as polyethylene glycol as well as surfactants and other organic and inorganic salts can also be used to modulate polymer hydration.

In another prophetic example, multiparticulates containing bupropion hydrobromide can be obtained as follows:

| Component | Percent w/w |
|---|---|
| Bupropion HBr | about 8.7 |
| Disodium Phosphate | about 7.0 |
| Monosodium phosphate | about 1.7 |
| Sodium dodecyl sulfate | about 21.7 |
| Sodium Chloride | about 17.4 |
| Povidone 29-32K | about 8.7 |
| AMBERLITE IRP-69 | about 34.8 |
| Butylated Hydroxyanisol | about 0.0002 |

In this prophetic example, approximately 5.75 kg of the above formulation is mixed in a planetary mixer for about 15 minutes. The butylated hydroxyanisol is dissolved in about 60 cc of ethanol and water is added to bring the final solution to a volume of about 133 cc. This solution is added to the planetary mixer over about a two (2) minute period. The mixer is then granulated with seven aliquots of about 250 cc of water added over about a fifteen minute period. The granulation thus formed is extruded through a 1.0 mm screen and aliquots spheronized by marumerization at approximately 1200 rpm for approximately 10 minutes each. The spherical multiparticulates formed are then dried at about 50° C. for about 24 hours.

Another embodiment of this invention involves the production of drug containing microparticles in the form of 'pearls'. Pearls can be manufactured by mixing bupropion hydrobromide with one or more pharmaceutical excipients in molten form; the melt is forced to pass through a nozzle which is subjected to a vibration; the pearls formed are allowed to fall in a tower countercurrentwise to a gas; and the solid pearls are collected in the bottom of the tower. In this example, the quantity of bupropion hydrobromide can vary from about 5% to about 95% by weight including all values and ranges therebetween; and in certain embodiments from about 40% to about 60% by weight including all values and ranges therebetween. The additives which enable the crystallization of the supercooled product to be induced in this example can be chosen from the following: fatty alcohols such as: cetyl alcohol, stearyl alcohol, fatty acids such as: stearic acid, palmitic acid, glycerol esters such as: glycerol palmitostearate, glycerol stearate (e.g. PRECIROL™), glycerol behenate (e.g. COMPRITOL™), hydrogenated oils such as: hydrogenated castor oil (e.g. CUTINA™ HR), fatty acid salts such as: magnesium or calcium stearate, polyols such as: mannitol, sorbitol, xylitol, waxes such as: white wax, carnauba wax, paraffin wax, polyoxyethylene glycols of high molecular weight, and esterified polyoxyethylenes such as: PEG-32 distearate, and PEG-150 distearate. To these crystallization additives it can be desirable in this example to add polymers which are soluble or dispersible in the melt, and which provide a controlled and adjustable dissolution of the pearls when they are used, examples of which include: cellulose derivatives (hydroxypropyl cellulose, hydroxypropyl methyl cellulose, hydroxyethyl cellulose, ethyl cellulose, carboxymethyl cellulose), acrylic resins (e.g. EUDRAGIT®), polyvinyl acetates (e.g. RHODOPAS®), polyalkylene (ethylene propylene), polylactic, maleic anhydride, silicone resins, and mixtures thereof. In addition, inorganic additives can be added to accelerate the solidification of the active substances, examples of which include: silicas, inorganic oxides such as titanium or iron oxide, phosphates, carbonates, clays, and talc. In addition, a surface-active agent can be added to improve the dispersion of the active substance in the crystallization additive, examples of which include: sorbitol esters, the polyoxyethylene polysorbates (e.g. TWEEN®), and glycols such as glycerine or propylene glycol. The process for the preparation of pearls comprise preparing a melt of the bupropion hydrobromide with one or more excipients. This melt can be prepared by separately melting the various constituents and then mixing them or by melting the mixture of the constituents, possible insoluble compounds being added at the end of the melting so as to obtain a homogeneous mass. The nature of the constituents of the melt is chosen by the person skilled in the art, which is considered as a function of the compatibility of the constituents, the viscosity of the mixture of constituents, the nozzle diameter, the hydrophilicity of the active substance, the surface tension of the active substance, the particle size of the insoluble additives, the flow rate of the nozzle, the temperature of the tower, its height and, above all, the size of the desired pearls, the proportion of bupropion hydrobromide to be included therein and the desired release time of the active substance.

Alternative procedures other than extrusion or spheronization for manufacturing drug-containing microparticles can include wet granulation, solvent granulation and melt granulation. All of these techniques involve the addition of an inactive binder to aggregate smaller particles into larger granules. For example, wet granulation and solvent granulation involve the addition of a liquid binder which aggregates the active materials and excipients into granules. After granulation, the liquid can be removed by a separate drying step. Melt granulation is similar to wet granulation, but uses a low melting point solid material as a binder. The solid binder in melt granulation is melted and acts as a liquid binder thereby aggregating the powdered active material and excipients into granules. The binder thereby, can be incorporated into the granules when the granules cool.

Certain embodiments of the present invention include microparticles manufactured by a process for producing granules by rotomelt granulation that comprises mixing bupropion hydrobromide and a powdered excipient material that has a higher melting point than bupropion hydrobromide in a zone wherein both powdered materials are maintained in a fluidized state by a rising stream of gas in an apparatus having a rapidly rotating horizontal-disk located within a vertical vessel having a bottom surface; wherein said rapidly rotating disk is located on the bottom surface of the vertical vessel wherein said gas is at a temperature sufficient to cause the bupropion hydrobromide to at least partially melt thereby causing said powdered materials to aggregate and form granules. Other embodiments of the present invention include microparticles manufactured by a process for producing granules by rotomelt granulation comprising mixing powdered binder material and bupropion hydrobromide wherein the bupropion hydrobromide has a higher melting point than the powdered binder material in a zone wherein both powdered materials are maintained in a fluidized state by a rising stream of gas in an apparatus having a rapidly rotating horizontal-disk located within a vertical vessel having a bottom surface; and wherein said rapidly rotating disk is located on the bottom surface of the vertical vessel wherein said gas is at a temperature sufficient to cause the powdered binder material to at least partially melt thereby causing said powdered materials to aggregate and form granules.

In rotomelt granulation, one of the feed powders must have a lower melting point than the other powder in order to serve as a binder. The feed powders are introduced into a vertical vessel with rotatable horizontal-disk located in the bottom of the vessel. The powder is maintained in fluidized state by at least one stream of filtered air being circulated from the bottom of the vertical vessel through one or more inlets. The rotatable horizontal disk is then rotated while the air supplied to fluidize the powder is maintained at a temperature sufficient to soften or melt the lower melting point powder. The temperature to which the binder must be heated to soften can be empirically determined by observing the formation of granules at various temperatures for various binders. It is presently believed that temperatures from about 3° C. to about 5° C. below the melting point or melting range, including all values and ranges therebetween, provides sufficient softening to result in granule formation. The lower melting point powder then acts as a binding agent to promote the aggregation of powder particles into granules. Suitable powders for use in rotomelt granulation have a diameter size in the range of from about 5 microns to about 150 microns including all values and ranges therebetween; and in certain embodiments have a diameter size in the range of about 35 microns to about 80 microns. The temperature which the components will be exposed to depends on the binder employed to aggregate the powders. Generally, the melting point of the binder is above about 30° C.; and in certain embodiments is below about 100° C.

The powders used in these microparticles manufactured by rotomelt granulation can be formed into granules by at least two alternative granulation mechanisms. The first mechanism for granule formation utilizes a larger particulate binder and a smaller particulate powder. The temperature during the rotomelt granulation is then elevated only to the point where the external surface of the binder particles become tacky. As the second powdered material of a smaller size is contacted with the tacky surface it forms a microlayer on the surface of the binder particle. This granulation mechanism results in granules which have size distribution similar to the original binder particles employed. Alternatively, the rotomelt granulation can be conducted at a temperature at which the binder acts as a cement bridging the gaps between the unmelted particles (this is referred to as agglomeration). This mechanism results in the formation of granules where the components are intermingled. For each binder used the mechanism can be controlled primarily by the temperature at which the rotomelt granulation is performed. Those skilled in the art will appreciate that the granules formed can be observed by electron microscopy to determine the type of granulation process occurring. If one particular type of granule is desired, the process conditions or starting materials can be varied to produce the desired granules.

In at least one embodiment of the present invention, bupropion hydrobromide is melted to act as a binding agent in the rotomelt granulation process. Examples of suitable excipients include those selected from the following: fillers, lubricants, glidants and antiadherents. Suitable fillers include but are not limited to calcium phosphate dibasic, tricalcium phosphate, calcium carbonate, starch (such as corn, maize, potato and rice starches), modified starches (such as carboxymethyl starch, etc.), microcrystalline cellulose, sucrose, dextrose, maltodextrins, lactose, and fructose. The amount of binder added to aggregate the particles into granules can be in the range of from about 10% w/w to about 80% w/w including all values and ranges therebetween; and in certain embodiments is in the range of from about 30% w/w to about 70% w/w of the powdered materials in the rotomelt granulation. The remaining weight percentage to provide a total of about 100% w/w can be one or more suitable powdered pharmaceutical actives. Optionally the rotomelt granulation can also contain from about 0% to about 60% w/w including all values and ranges therebetween, of one or more powdered excipients wherein the total weight of all the powdered materials equals about 100% w/w. The binder used in these embodiment of the invention can be a pharmaceutically acceptable dry powder having a particle size in the range of from about 5 μm to about 150 μm including all values and ranges therebetween; and in certain embodiments in the range of from about 35 μm to about 80 μm. Suitable binders for rotomelt granulation are low melting point powdered binders, examples of which include: polyethylene glycol 4000, polyethylene glycol 6000, stearic acid, and low melting point waxes. Suitable low melting point waxes include but are not limited to glyceryl monostearate, hydrogenated tallow, myristyl alcohol, myristic acid, stearyl alcohol, substituted monoglycerides, substituted diglycerides, substituted triglycerides, white beeswax, carnauba wax, castor wax, japan wax, acetylate monoglycerides and combinations thereof. The binders can have a melting point of from about 30° C. to about 100° C. including all values and ranges therebetween; and in certain embodiments from about 40° C. to about 85° C.

As a prophetic example of these embodiments that are manufactured by a rotomelt granulation process, about 320 g of bupropion hydrobromide and about 80 g PEG 8000 is dry blended and poured into a Glatt 1.1 chamber set-up as a rotary granulator with a longitudinal plate. Inlet air temperature is set to about 60° C. and the product chamber heated to approximately 50° C. The blend is fluidized at approximately 120 m3/hr and the frictional plate set to about 900 rpm. The product chamber temperature is raised to about 60° C. and then gradually reduced to about 20° C. over a period of approximately 20 minutes, during which spheronization is achieved.

Other embodiments of the invention involve the formation of a microparticle that has a core which includes bupropion hydrobromide and a compound which is sweet in taste and which has a negative heat of solution. Examples of compounds falling into this category include mannitol and sorbitol. Sugars or artificial sweeteners to which, for example, menthol have been added can also work as well. A binder and/or other excipient can also be disposed within the core. The amount of sweetening compound used can depend on a number of factors including the size of the resulting microparticles, the size or volume of the resulting tablet, the sturdiness of the microparticle-coated microparticulant, the speed at which the tablet will disintegrate in the mouth, the degree of sweetness imparted by the particular sweetener used, either in the microparticle or in the tablet, or both, the amount of drug used, and the like. For example, particularly rugged microparticles can be less likely to break during chewing and/or compression. Therefore, the amount of material provided to protect against the release of objectionably flavored material can be lessened. In other cases a greater relative amount of sweetening compound can be used. Generally, the amount of sweetening material used will range from greater than zero to about 80% of the weight of the resulting microparticles including all values and ranges therebetween. The sweetener and bupropion hydrobromide can be combined in any number of known ways, such as for example by wet granulation, dry granulation, agglomeration, or spray coating. For example, the sweetener can be used as an adsorbent for the active agent. Alternatively, particles of each can also be simply mixed together. One or more binders, or other adjuvants can also be used in the formulation of a tablet as well. Binders in these embodiments include, for example: starch (for example, in an amount of from about 5% to about 10% including all values and ranges therebetween, as an aqueous paste); pregelatinized starch (for example, in an amount of about 5% to about 10% including all values and ranges therebetween, added dry to powder); gelatin (for example, in an amount of from about 2% to about 10% including all values and ranges therebetween, as an aqueous solution, or about 2% in starch paste); polyvinylpyrrolidone (for example, in an amount of from about 2% to about 20% including all values and ranges therebetween, in an aqueous or alcoholic solution); methylcellulose (for example, in an amount of from about 2% to about 10% including all values and ranges therebetween, as an aqueous solution); sodium carboxy methylcellulose (for example, in an amount of from about 2% to about 10% including all values and ranges therebetween, as an aqueous solution); ethylcellulose (for example, in an amount of from about 5% to about 10% including all values and ranges therebetween, as an alcohol or hydroalcoholic solution); polyacrylamides (Polymer JR) (for example, in an amount of from about 2% to about 8% including all values and ranges therebetween, as an aqueous solution); polyvinyloxoazolidone (Devlex) (for example, in an amount of from about 5% to about 10% including all values and ranges therebetween, as an aqueous or hydroalcoholic solution); and polyvinyl alcohols (for example, in an amount of from about 5% to about 20% including all values and ranges therebetween, in aqueous solutions). Other adjuvants can also be used in forming the core of the microparticles of the present embodiments of the invention, non-limiting examples of which include: calcium sulfate NF, Dibasic Calcium phosphate NF, Tribasic calcium sulfate NF, starch, calcium carbonate, microcrystalline cellulose, modified starches, lactose, sucrose and the like, STA-RXT™, AVICEL™, SOLKA-FLOC™ BW40, alginic acid, EXPLOTAB™, AUTOTAB™, guar gum, kaolin VECGUM™, and bentonite. These adjuvants can be used in up to about 20% w/w; and in certain embodiments are present in an amount of from about 3% to about 5% w/w including all values and ranges therebetween.

As a prophetic example of these embodiments that have a core comprising bupropion hydrobromide and a compound which is sweet in taste, bupropion hydrobromide can be granulated using the following procedure: Polyvinylpyrrolidone K-30 USP (about 240.0 gm) is dissolved into distilled water (about 1,890.0 gm) with agitation. Mannitol powder USP (about 11,160 gm) and bupropion hydrobromide (about 600.0 gm) are placed in a Zanchetta 50-liter granulator/processor. After an initial two-minute dry mix of the powders with the chopper on and the propeller adjusted to about 200 rpm, the polyvinylpyrrolidone K-30 solution is slowly sprayed into the mixing powder bed using an air-driven spray system. The total time of granulation including the time of solution addition is approximately eight minutes. The granulation end-point is determined visually and by the consistency of the resulting material. The material is then discharged onto trays and dried at about 80° C. utilizing supplied dry air for a period of about six hours to a moisture content of not more than about 0.08 percent. The dried material is then passed through a hammermill (knives forward) equipped with a U.S. #40 (420 micron) screen.

Other embodiments of this invention involve the combined granulation and coating of bupropion hydrobromide into microparticles in which the drug is at least partly located within the microparticle core but capable of immediate release. To do this, the bupropion hydrobromide and a granular disintegrant are first dry-mixed; the powder obtained is then granulated, in the presence of a mixture of excipients comprising at least one binder capable of binding the particles together to give grains; the grains thus formed are then coated by spraying with a suspension comprising at least one coating agent and a membrane disintegrant; and then the coated granules obtained are dried. The distinction between the actual granulation and coating steps is relatively theoretical, insofar as, even though the primary function of the binder used in the granulation step is to bind together the particles, it nevertheless already partially coats the grains formed. Similarly, even though the primary function of the coating agent used in the actual coating step is to complete the final coating of each of the grains, it may, however, arbitrarily bind other coated grains by a mechanism of granular agglomeration. The binder and the coating agent are chosen from the group comprising cellulose polymers and acrylic polymers. However, even though the binder and the coating agent are chosen from the same group of compounds, they nevertheless differ from each other in their function as previously mentioned. Among the cellulose polymers that can be advantageously chosen are ethylcellulose, hydroxypropylcellulose (HPC), carboxymethylcellulose (CMC) and hydroxypropylmethylcellulose (HPMC), or mixtures thereof. Among the acrylic polymers that can be advantageously chosen are the ammonio-methacrylate copolymer (EUDRAGIT® RL or RS), the polyacrylate (EUDRAGIT® NE) and the methacrylic acid copolymer (EUDRAGIT® L or S). In at least one embodiment, the binder is of the same nature as the coating agent. To further accelerate the release of the bupropion hydrobromide, the coating suspension also comprises a permeabilizer which, on account of its intrinsic solubility properties, causes perforation of the membrane coating, thus allowing the bupropion hydrobromide to be released. Non-limiting examples of permeabilizers include povidone and its derivatives, polyethylene glycol, silica, polyols and low-viscosity cellulose polymers. Polymers of the type such as hypromellose, whose viscosity is equal to about 6 centipoises, are used, for example, as low-viscosity cellulose polymer. In at least one embodiment, the dry-mixing of initial powder and the granulation, coating and drying steps are performed in a fluidized bed. In this case, the initial powder mixture is first fluidized before being granulated by spraying said powder with the excipient mixture comprising at least the binder, the grains obtained then being coated by spraying with the coating suspension, the coated granules formed finally being dried in the fluidized bed. In at least one embodiment, the mixture of excipients used during the granulation step and the coating suspension used during the coating step form a single mixture. In this case, the granulation step can be distinguished from the spraying step by varying different parameters, such as the rate of spraying of the mixture and the atomization pressure of said mixture. Thus, only some of the mixture of excipients is used during the granulation step, while the other portion can be used during the coating step.

Thus, the rate of spraying of the coating suspension is higher during the granulation step than during the coating step, whereas the atomization pressure of the coating suspension is lower during the granulation step than during the coating step. In practice, at the laboratory scale in a fluidized-bed device, for example of the type such as Glatt GPCG1, during the granulation step, the rate of spraying of the coating suspension is from about 10 grams/minute to about 25 grams/minute including all values and ranges therebetween, and the atomization pressure is from about 1 bar to about 1.8 bar including all values and ranges therebetween. During the coating step, the rate of spraying of the coating suspension is from about 5 grams/minute to about 15 grams/minute including all values and ranges therebetween, while the atomization pressure is from about 1.5 bar to about 2.5 bar including all values and ranges therebetween. In at least one embodiment, from about 10% to about 20% including all values and ranges therebetween, of the mixture of excipients is sprayed during the granulation step, the remainder being sprayed during the coating step.

As a prophetic example of these embodiments that involve the combined granulation and coating of bupropion hydrobromide into microparticles in which the drug is at least partly located within the microparticle core but capable of immediate release, the microparticles can be manufactured according to the following process: A granulation solution is first prepared by dissolving about 48 g of ethylcellulose in about 273 g of ethyl alcohol. A coating suspension is then prepared by mixing about 97 g of ethylcellulose, about 28.5 g of polyethylene glycol 6000, about 26 g of sodium croscarmellose, about 10 g of precipitated silica and about 27.5 g of aspartame in about 1900 g of ethyl alcohol, until a homogeneous suspension is obtained. The powder mixture consisting of about 700 grams of bupropion hydrobromide and about 35 grams of Acdisol is then fluidized. The granulation is then started by spraying the granulation solution for about 15 to about 20 minutes at a spraying rate of about 25 grams/minute and a suspension atomization pressure of about 0.8 bar. The actual coating is then performed by spraying the coating suspension for about 1 hour 30 minutes at a spraying rate of about 15 to about 20 grams/minute and a suspension spraying pressure of about 1.5 bar.

Other embodiments of the invention involve coating the bupropion hydrobromide material, thereby forming a drug-containing microparticle. One such process for achieving this involves:

Blending and fluidizing a powder mix of active principle and an adjuvant in order to obtain individual grains,
Separately liquefying under warm conditions a lipid matrix agent comprising either an ester of behenic acid and alcohol or an ester of palmitic/stearic acid and alcohol,
Coating the fluidized powder mix under warm conditions by spraying the lipid matrix agent over the individual grains,
Lowering the temperature of the combined product in order to allow the lipid matrix agent to solidify.

This process does not require an evaporation phase or a drying phase, since it does not require a wet-route or solvent-route granulation step, thus making it possible to be freed from any risk due to the presence of toxic residues in the final product. Furthermore, it is not necessary to carry out the quantitative determination of the traces of solvents, an analysis that can be very expensive. According to the process of this embodiment of the invention, the spraying conditions and thus the coating characteristics can be modified, in order to vary the release profile of bupropion hydrobromide, by varying several parameters, the adjustment characteristics of which remain simple. Thus, the spraying air pressure can be increased in order to promote the formation of a homogeneous film of lipid matrix agent around the grains. Advantageously, the rate of spraying of the lipid matrix agent can simultaneously be decreased. In this case, the bupropion hydrobromide release profile, that is to say a percentage of dissolution as a function of the time, is obtained which can be low, corresponding to a slow release of the drug. Conversely, the spraying air pressure can be decreased in order to promote the agglomeration of the grains with one another. Advantageously, the rate of spraying of the lipid matrix agent can simultaneously be increased. In this case, a release profile of the grains obtained can be obtained which is high, corresponding to a rapid release of bupropion hydrobromide. In practice and according to the mass of powder employed, the value of the rate of spraying of the lipid matrix agent can be from two to four times higher when it is desired to promote the agglomeration of the grains with one another than when it is desired to promote the formation of a homogeneous film around the grains. On the other hand, the value of the spraying air pressure can be from one to two times lower when it is desired to promote the agglomeration of the grains with one another than when it is desired to promote the formation of a homogeneous film around the grains. According to the process for manufacturing these embodiments, it is possible, after having determined a given drug release profile, to vary the values of spraying air pressure and of spraying rate throughout the coating stage, making it possible to promote the formation of a homogeneous film around the grains or to promote the agglomeration of the grains. Once the sequence of the duration of the spraying air pressure and of the spraying rate has been determined, the coating operation can be carried out continuously and automatically. According to another characteristic of the process of manufacturing these embodiments, the temperature of the mixture of liquefied matrix agent and of spraying air is greater by about 35° C. to about 60° C. than the melting temperature of the lipid matrix agent. Likewise, the temperature of the fluidization air and that of the powder is approximately equal to the melting temperature of the lipid matrix agent, plus or minus about 10° C. Furthermore, in order to obtain a mixture of individual grains, an air-operated fluidized bed device or a turbine device can be used. Furthermore, the lipid matrix agent can be sprayed by the air spray technique, that is to say liquid spraying under pressure in the presence of compressed air. According to at least one embodiment, use is made of a powder comprising the drug and the adjuvant. In other words, after mixing and fluidizing the combined constituents of the powder, the lipid matrix agent is sprayed over the individual grains obtained. In order to avoid adhesion of the coated grains obtained, whether in the case where all the grains are treated or whether in the case where only a portion of the grains is treated, a stage of lubrication of the grains is inserted between the coating stage and the stage of putting into a pharmaceutical form. Furthermore, in order to obtain greater stability of the pharmaceutical composition, that is to say in order to minimize modifications relating to the release of the bupropion hydrobromide over time, the granules or tablets obtained in certain embodiments of this example can be subjected to a maturing stage in an oven, for at least about 8 hours, at a temperature of from about 45° C. to about 60° C.; and in certain embodiments at about 55° C.

As a prophetic example of these drug-containing microparticle embodiments that are formed by coating the bupropion hydrobromide material, the drug-containing microparticles can be manufactured according to the following process: A mixture of powder is prepared comprising: bupropion hydrobromide; dicalcium phosphate dehydrate; and polyvinylpyrrolidone. Batches of granules are prepared by a process comprising the following stages: the mixture of powder obtained is sieved; the said powder is mixed, heating while by means of an air-operated fluidized bed, in order to obtain individual grains; the lipid matrix agent (glyceryl behenate, e.g. COMPRITOL® 880 ATO) is liquefied separately at about 120° C.; the lipid matrix agent is sprayed over the heated powder mixture, and, finally, the temperature is lowered in order to allow the lipid matrix agent to solidify. These stages are carried out while varying various parameters, either in order to promote the formation of a homogeneous film around the grains or in order to promote the agglomeration of the grains, in accordance with the following table:

| Parameters | Batch 1 | Batch 2 | Batch 3 | Batch 4 |
|---|---|---|---|---|
| % by weight of lipid matrix | | | | |
| agent (COMPRITOL ® 888 ATO) | 5 | 4 | 4 | 5 |
| Fluidization air flow rate (m3/h) | 80 | 110 | 80 | 80 |
| Agglomeration | | | | |
| Atomization air pressure (bar) | 2 | | 1.5 | 1.5 |
| Temperature of the powder bed (° C.) | 70 | | 70 | 74 |
| Spraying rate for COMPRITOL ® (g/min) | 42 | | 40 | 40 |
| Coating | | | | |
| Atomization air pressure (bar) | 2.5 | 3.5 | 2 | 2 |
| Temperature of the powder bed (° C.) | 70 | 66 | 71 | 70 |
| Spraying rate for COMPRITOL ® (g/min) | 41 | 20 | 40 | 40 |

Another embodiment of the invention for coating the bupropion hydrobromide material, thereby forming a drug-containing microparticle, involves the formation of coated microcrystals that can subsequently be incorporated into a tablet. Through selection of the appropriate polymer the microcrystals can possess diversified features such as gastroresistance and controlled release due to the fact that the said coated or non-coated microcrystals and microgranules preserve, after having been shaped in the form of a multiparticulate tablet, their initial properties amongst which are included masking of taste, gastroresistance and controlled release of the bupropion hydrobromide. In certain embodiments of this example, the following non-limiting list of polymers can be selected for coating of the bupropion hydrobromide in conventional fluidized based coating equipment: ethylcellulose (EC); hydroxypropylcellulose (HPC); hydroxypropylmethylcellulose (HPMC); gelatin; gelatin/acacia; gelatin/acacia/vinvylmethylether maleic anhydride; gelatin/acacia/ethylenemaleic anhydride; carboxymethyl cellulose; polyvinvylalcohol; cellulose acetate phthalate; nitrocellulose; shellac; wax; polymethacrylate polymers such as EUDRAGIT® RS; EUDRAGIT® RL or combinations of both, EUDRAGIT® E and EUDRAGIT® NE30D; KOLLICOAT™ SR30D; and mixtures thereof.

Drug-Layered Microparticles

The drug-layered microparticles of certain embodiments can be made by coating an inert particle or core, such as a non-pareil sphere (e.g. sugar sphere), with the bupropion hydrobromide salt and a polymeric binder. In certain embodiments of the drug-layered microparticles, the inert cores include water-insoluble materials such as cellulose spheres or silicon dioxide. In other embodiments, the inert cores include water-soluble materials such as starch, salt or sugar spheres. The inert cores can have a diameter ranging from about 100 microns to about 2000 microns including all values and ranges therebetween. For example, in certain embodiments the diameter of the inert cores range from about 150 microns to about 1500 microns. In at least one embodiment, the inert cores are sugar spheres NF, containing not less than about 62.5% and not more than about 91.5% of sucrose including all values and ranges therebetween. In at least one embodiment the inert cores have substantially consistent bulk density, low friability, and low dust generation properties. In at least one embodiment, the inert cores are coated with an osmotic sub-coat comprising an osmotic agent and a polymeric binding agent. Further, the inert cores can initially be coated with a seal-coat to provide a more consistent core surface and to minimize any osmotic effects. The seal-coat layer can be applied to the core prior to the application of the drug, polymeric binder, and any polymeric film layers. In at least one embodiment, the seal-coat layer does not substantially modify the release of the bupropion hydrobromide salt. Examples of suitable sealants that can be used in the seal-coat include permeable or soluble agents such as hydroxypropyl methylcellulose, hydroxypropyl cellulose, ethylcellulose, a polymethacrylate polymer, hydroxypropyl ethylcellulose, xanthan gum, and mixtures thereof. In at least one embodiment the sealant used in the seal-coat is hydroxypropyl methylcellulose. Other agents can be added to improve the processability of the sealant. Examples of such agents include talc, colloidal silica, polyvinyl alcohol, titanium dioxide, micronised silica, fumed silica, glycerol monostearate, magnesium trisilicate, magnesium stearate, and mixtures thereof. The seal-coat layer can be applied from solution (e.g. aqueous) or suspension using a fluidised bed coater (e.g. Wurster coating), or in a pan coating system. Examples of such seal-coats coatings are commercially available (e.g. OPADRY® White Y-1-7000 and OPADRY® OY/B/28920 White).

The binding agent of these drug-layered embodiments is used to adhere the bupropion hydrobromide salt layer to the inert core or seal-coat of the core. In certain embodiments, the binding agent is water soluble, possesses sufficiently high adhesivity in order to adhere the bupropion hydrobromide salt layer to the inert core, and possesses an appropriate viscosity to provide substantial adhesion between the inert core and the bupropion hydrobromide salt. In other embodiments the binding agent is water-insoluble. In at least one embodiment the binding agent is ethyl cellulose, a polymethacrylate polymer, polyvinylalcohol, polyvinyl pyrrolidone, polyvinylpyrrolidone-vinylacetate copolymer (such as KOLLIDON® VA64), hydroxyethylcellulose, low molecular weight hydroxypropylmethylcellulose (e.g. viscosity of about 1-50 cps at about 20° C.; about 2-12 cps at about 20° C.; or about 4-6 cps at about 20° C.), hydroxypropylcellulose polymethacrylates, or mixtures thereof. For example, in certain embodiments the composition of the binder for bupropion hydrobromide is from about 1% to about 25% w/w including all values and ranges therebetween; in other embodiments from about 2% to about 10% w/w; and in still other embodiments from about 3% to about 5% w/w, expressed as a percentage of the total weight of the core.

Solvents can be used to apply the bupropion hydrobromide salt to the inert core, examples of which include lower alcohols such as ethanol, isopropanol and alcohol/water mixtures, acetone and chlorinated hydrocarbons.

The drug-layered microparticles can be prepared by forming a suspension or solution of the binder and the bupropion hydrobromide salt and then layering the suspension or solution on to the inert or sub-coated core using any of the layering techniques known in the art, such as fluidized bed coating or pan coating. This can be affected in a single coating or the process can be carried out in multiple layers, optionally with intervening drying/evaporation steps. This process can be conducted so as to produce microparticles containing a desired amount of bupropion hydrobromide salt and achieve the desired dosage and release thereof upon in-vivo administration.

In certain embodiments, the drug-layered microparticles can be manufactured using for example, the procedure in the following hypothetical experiment: Bupropion hydrobromide (about 2.8 kg) and hydroxypropyl methylcellulose (METHOCEL® E5) (about 0.40 kg) is dissolved in a mixture of water and isopropyl alcohol. The active drug solution can then be sprayed onto sugar spheres 30/35 (about 1.06 kg) in a fluidized bed processor with a Wurster insert. The active core microparticles can then be dried in a fluidized bed processor until the loss on drying is below about 1%. The bupropion microparticles can then be passed through a 16 mesh screen and a 30 mesh screen and microparticles can be collected that are smaller than 16 mesh and larger than 30 mesh.

Microparticle Taste-Masking Coatings

The microparticles of the present invention can each be coated with at least one taste-masking coating. The taste-masking coating can mask the taste of the active drug in the microparticles. In at least one embodiment the taste-masking coating formulations contain polymeric ingredients. It is contemplated that other excipients consistent with the objects of the present invention can also be used in the taste-masking coating.

In at least one embodiment, the taste-masking coating comprises a polymer such as ethylcellulose, which can be used as a dry polymer (e.g. ETHOCEL®) solubilised in organic solvent prior to use, or as an aqueous dispersion. One commercially-available aqueous dispersion of ethylcellulose is AQUACOAT®. AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, the AQUACOAT® is intimately mixed with a suitable plasticizer prior to use. Another aqueous dispersion of ethylcellulose is commercially available as SURELEASE®. This product can be prepared by incorporating plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

In other embodiments, polymethacrylate acrylic polymers can be employed as taste masking polymers. In at least one embodiment, the taste masking coating is an acrylic resin lacquer used in the form of an aqueous dispersion (e.g. EUDRAGIT® or KOLLICOAT®). In further embodiments, the acrylic coating comprises a mixture of two acrylic resin lacquers (e.g. EUDRAGIT® RL and EUDRAGIT® RS, respectively).

EUDRAGIT® RL and EUDRAGIT® RS are copolymers of acrylic and methacrylic esters with a low content of quaternary ammonium groups, the molar ratio of ammonium groups to the remaining neutral (meth)acrylic esters being 1:20 in EUDRAGIT® RL and 1:40 in EUDRAGIT® RS. The mean molecular weight is 150,000. The code designations RL (high permeability) and RS (low permeability) refer to the permeability properties of these agents. EUDRAGIT® RL/RS mixtures are insoluble in water and in digestive fluids. However, coatings formed from the same are swellable and permeable in aqueous solutions and digestive fluids. EUDRAGIT® RL/RS dispersions or solutions of certain embodiments can be mixed together in any desired ratio in order to ultimately obtain a taste masking coating having a desirable drug dissolution profile. In certain embodiments formulations can be obtained, for example, from a coating derived from 100% EUDRAGIT® RL; 50% EUDRAGIT® RL with 50% EUDRAGIT® RS; and 10% EUDRAGIT® RL with 90% EUDRAGIT® RS.

In other embodiments, the taste masking polymer can be an acrylic polymer which is cationic in character based on dimethylaminoethyl methacrylate and neutral methacrylic acid esters (e.g. EUDRAGIT® E). The hydrophobic acrylic polymer coatings of the present invention can further include a neutral copolymer based on poly(meth)acrylates, such as EUDRAGIT® NE. EUDRAGIT® NE 30D lacquer films are insoluble in water and digestive fluids, but permeable and swellable.

In other embodiments, the taste masking polymer is a dispersion of poly(ethylacrylate, methyl methacrylate) 2:1 (KOLLICOAT® EMM 30 D, BASF).

In other embodiments, the taste masking polymer can be a polyvinyl acetate stabilized with polyvinylpyrrolidone and sodium lauryl sulfate such as KOLLICOAT® SR30D (BASF).

Other taste masking polymers include hydroxypropylcellulose (HPC); hydroxypropylmethylcellulose (HPMC); hydroxyethylcellulose; gelatin; gelatin/acacia; gelatin/acacia/vinvylmethylether maleic anhydride; gelatin/acacia/ethylenemaleic anhydride; carboxymethyl cellulose; polyvinylalcohol; nitrocellulose; polyvinylalcohol-polyethylene glycol graft-copolymers; shellac; wax and mixtures thereof.

The taste-masking coatings can be applied to the microparticles from one or more organic or aqueous solvent solutions or suspensions. In at least one embodiment the organic solvents that can be used to apply the taste-masking coatings include one or more of acetone, lower alcohols such as ethanol, isopropanol and alcohol/water mixtures, chlorinated hydrocarbons, and the like. Devices used to coat the microparticles of the invention with a taste-masking coating include those conventionally used in pharmaceutical processing, such as fluidized bed coating devices. The coatings applied to the microparticles can contain ingredients other than the functional polymers. One or more colorants, flavorants, sweeteners, can also be used in the taste-masking coating.

In some embodiments a pore former can be included into the taste masking coat in order to influence the rate of release of bupropion hydrobromide from the microparticle. In other embodiments, a pore former is not included in the taste masking coat. The pore formers can be inorganic or organic, and include materials such as particulate materials that can be dissolved, extracted or leached from the coating in the environment of use. Upon exposure to fluids in the environment of use, the pore-formers can for example be dissolved, and channels and pores are formed that fill with the environmental fluid.

For example, the pore-formers of certain embodiments can comprise one or more water-soluble hydrophilic polymers in order to modify the release characteristics of the formulation. Examples of suitable hydrophilic polymers used as poreformers include hydroxypropylmethylcellulose, cellulose ethers and protein-derived materials of these polymers, the cellulose ethers, such as hydroxyalkylcelluloses and carboxyalkylcelluloses. Also, synthetic water-soluble polymers can be used, examples of which include polyvinylpyrrolidone, cross-linked polyvinyl-pyrrolidone, polyethylene oxide, water-soluble polydextrose, saccharides and polysaccharides, such as pullulan, dextran, sucrose, glucose, fructose, mannitol, lactose, mannose, galactose, sorbitol and mixtures thereof. In at least one embodiment, the hydrophilic polymer comprises hydroxypropyl-methylcellulose.

Other non-limiting examples of pore-formers that can be used in certain embodiments containing a taste masking coat include alkali metal salts such as lithium carbonate, sodium chloride, sodium bromide, potassium chloride, potassium sulfate, potassium phosphate, sodium acetate, sodium citrate and mixtures thereof. The pore-forming solids can also be polymers which are soluble in the environment of use, such as CARBOWAX™, and CARBOPOL™. In addition, the poreformers embrace diols, polyols, polyhydric alcohols, polyalkylene glycols, polyglycols, poly(a-w)alkylenediols and mixtures thereof. Other pore-formers which can be useful in the formulations of certain embodiments of the present invention include starch, modified starch, and starch derivatives, gums, including but not limited to xanthan gum, alginic acid, other alginates, benitonite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambdacarrageenan, gum karaya, biosynthetic gum, and mixtures thereof. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly (vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone), and mixtures thereof.

In general, the amount of pore-former included in the taste masking coatings of certain embodiments of the present invention can be from about 0.1% to about 80%, by weight including all values and ranges therebetween, relative to the combined weight of polymer and pore-former. The percentage of pore former as it relates to the dry weight of the taste-masking polymer, can have an influence on the drug release properties of the coated microparticle. In at least one embodiment that uses water soluble pore formers such as hydroxypropylmethylcellulose, a taste masking polymer: pore former dry weight ratio of from about 10:1 to about 1:1 including all values and ranges therebetween, can be present. In certain embodiments the taste masking polymer:pore former dry weight ratio is from about 8:1 to about 1.5:1; and in other embodiments from about 6:1 to about 2:1. In at least one embodiment using EUDRAGIT® NE30D as the taste masking polymer and a hydroxypropylmethylcellulose (approx 5 cps viscosity (in a 2% aqueous solution)) such as METHOCEL® E5, Pharmacoat 606G as the water soluble pore former, a taste masking polymer:pore former dry weight ratio of about 2:1 is present.

Colorants that can be used in the taste-masking coating include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

Flavorants that can be used in the taste-masking coating include natural and synthetic flavoring liquids. An illustrative list of such flavorants includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such as lemon, orange, grape, lime and grapefruit, and fruit essences, including apple, pear, peach, grape, strawberry, raspberry, cherry, plum, pineapple, apricot, or other fruit flavors. Other useful flavorants include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodenal (citrus mandarin); and mixtures thereof.

Sweeteners that can be used in the taste-masking coating include glucose (corn syrup), dextrose, invert sugar, fructose, and mixtures thereof (when not used as a carrier); saccharin and its various salts, such as sodium salt; dipeptide sweeteners such as aspartame; dihydrochalcone compounds, glycyrrhizin; Steva Rebaudiana (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-1-2,2-dioxide, particularly the potassium salt (acesulfame-K), and sodium and calcium salts thereof. The sweeteners can be used alone or in any combination thereof.

The microparticle taste masking coat can also include one or more pharmaceutically acceptable excipients such as lubricants, emulsifiers, anti-foaming agents, plasticizers, solvents and the like.

Lubricants can be included to help reduce friction of coated microparticles during manufacturing. The lubricants that can be used in the taste masking coat of the present invention include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (i.e. COMPRITOL™), STEAR-O-WET™, MYVATEX™ TL and mixtures thereof. In at least one embodiment, the lubricant is selected from magnesium stearate, talc and a mixture thereof. Combinations of these lubricants are operable. The lubricant can each be present in an amount of from about 1% to about 100% by weight of the polymer dry weight in the taste masking coat including all values and ranges therebetween. For example, in certain embodiments wherein the taste masking polymer is EUDRAGIT® NE30D or EUDRAGIT® NE40D together with a hydrophilic pore former, the lubricant is present in an amount of from about 1% to about 30% by weight of the polymer dry weight; in other embodiments from about 2% to about 20%; and in still other embodiments at about 10% by weight of the microparticle taste masking coat dry weight. In another embodiment where the taste masking polymer is ethylcellulose (ETHOCEL™ PR100, PR45, PR20, PR10 or PR7 polymer, or a mixture thereof), the lubricant can be present in an amount of from about 10% to about 100% by weight of the microparticle taste masking coat dry weight; in another embodiment from about 20% to about 80%; and in still another embodiments at about 50% by weight of the microparticle taste masking coat dry weight. In other embodiments, the taste masking coat does not include a pore former.

Emulsifying agent(s) (also called emulsifiers or emulgents) can be included in the microparticle taste masking coat to facilitate actual emulsification during manufacture of the coat, and also to ensure emulsion stability during the shelf-life of the product. Emulsifying agents useful for the microparticle taste masking coat composition of certain embodiments include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. In at least one embodiment, the emulsifying agent is TWEEN™ 80. The emulsifying agent(s) can be present in an amount of from about 0.01% to about 5% by weight of the microparticle taste masking polymer dry weight including all values and ranges therebetween. For example, in certain embodiments the emulsifying agent is present in an amount of from about 0.05% to about 3%; in other embodiments from about 0.08% to about 1.5%, and in still other embodiments at about 0.1% by weight of the microparticle taste masking polymer dry weight.

Anti-foaming agent(s) can be included in the microparticle taste masking coat to reduce frothing or foaming during manufacture of the coat. Anti-foaming agents useful for the coat composition include, but are not limited to simethicone, polyglycol, silicon oil, and mixtures thereof. In at least one embodiment the anti-foaming agent is Simethicone C. The anti-foaming agent can be present in an amount of from about 0.1% to about 10% of the microparticle taste masking coat weight including all values and ranges therebetween. For example, in certain embodiments the anti-foaming agent is present in an amount of from about 0.2% to about 5%; in other embodiments from about 0.3% to about 1%, and in still other embodiments at about 0.6% by weight of the microparticle taste masking polymer dry weight.

Plasticizer(s) can be included in the microparticle taste masking coat to provide increased flexibility and durability during manufacturing. Plasticizers that can be used in the microparticle taste masking coat of certain embodiments include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropionin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. The plasticizer can be present in an amount of from about 1% to about 80% of the taste masking polymer dry weight including all values and ranges therebetween. For example, in certain embodiments the plasticizer is present in an amount of from about 5% to about 50%, in other embodiments from about 10% to about 40%, and in still other embodiments at about 20% of the taste masking polymer dry weight.

The taste-masking coating can be present in an amount of from about 1% to about 90% by weight of the microparticle including all values and ranges therebetween, depending upon the choice of polymer, the ratio of polymer:pore former, and the total surface area of the microparticle formulation. Since a certain thickness of taste masking coating has to be achieved in order to achieve effective taste masking, the amount of taste masking polymer coating used during manufacture is related to the total surface area of the batch of uncoated microparticles that requires a coating. The taste masking polymer surface area coverage can range from about 0.5 mg/cm$^2$ to about 20 mg/cm$^2$ including all values and ranges therebetween. For example, in certain embodiments the surface area coverage of the taste masking polymer is from about 0.6 mg/cm$^2$ to about 10 mg/cm$^2$, and in other embodiments is from about 1 mg/cm$^2$ to about 5 mg/cm$^2$. In at least one embodiment of the invention, EUDRAGIT® E is employed as the taste masking polymer at a surface area coverage of about 4 mg/cm$^2$. One approach in estimating the total surface area of a multiparticulate batch is the permeability method according to Blaine (ASTM Des. C 205-55), which is based upon the mathematical model of laminar flow through capillaries arranged in parallel.

In the absence of an accurate determination of total surface area of a microparticle, the amount of taste masking polymer to be applied can be expressed as a percentage of the uncoated microparticle. For example, in certain embodiments the taste-masking coating is present in an amount of from about 5% to about 60% including all values and ranges therebetween; in other embodiments from about 10% to about 40%; and in still other embodiments from about 15% to about 35% by weight of the microparticle. In at least one embodiment the taste-masking coating is present in an amount of about 30% by weight of the microparticle.

In certain embodiments, the diameter of the microparticles (with or without the taste-masking coating) range from about 50 μm to about 800 μm including all values and ranges therebetween. For example, in certain embodiments the diameter of the microparticles range from about 100 μm to about 600 μm, and in other embodiments from about 150 μm to about 450 μm.

Microparticle Controlled Release Coat

The microparticles of the present invention can each be coated with at least one controlled release coat. As used herein, the term "microparticle controlled release coat" refers to the controlled release coat that substantially surrounds each microparticle. The microparticle controlled release coat is designed to achieve a controlled release of the bupropion hydrobromide salt from the microparticle. For example, the microparticle controlled release coat can be an enteric coat with low solubility at a gastric pH to reduce or minimize the drug release in the lumen of the stomach, whilst possessing pH dependent solubility to facilitate drug release in the duodenum. In another embodiment, the controlled release coat can be a delayed release coating that provides a delayed release of the bupropion hydrobromide salt with a predetermined lagtime that is independent of, or alternatively dependent on, the pH of the dissolution medium. For example, by increasing the thickness of the microparticle controlled release coat using a pH independent diffusion polymer, lagtimes of about 1 hour, about 2 hours, about 3 hours, about 4 hours, about 5 hours, about 6 hours, about 7 hours, about 8 hours, about 9 hours, about 10 hours, about 11 hours, or about 12 hours can be achieved. Alternatively, controlled release polymers can be selected that become soluble above a certain pH. Drug release from such a system is reduced or minimized until the certain pH for the polymer of choice is exceeded. With either approach, following the predetermined lag, drug is released, for example within about 1 hour for an immediate release pulse, or alternatively over a prolonged period of time, for example from about 3 to about 24 hours. In other embodiments, the microparticle controlled release coat can provide a diffusion barrier that is independent of pH, thus facilitating a sustained release profile, with substantially full release of the bupropion hydrobromide salt occurring in from about 3 to about 24 hours following administration. In at least one embodiment, the microparticle controlled release coat provides a delayed and sustained release of the bupropion hydrobromide salt from the microparticle with substantially full release in about 24 hours following administration.

In certain embodiments, the microparticle controlled release coat can provide substantially full release of the bupropion hydrobromide salt from the microparticle without requiring the use of any pore formers. Unnecessary pore formers that are not required in the microparticle controlled release coat include hydrophilic polymers such as hydroxypropyl methylcellulose.

The microparticle controlled release coat includes at least one polymer in an amount sufficient to achieve a controlled release of the bupropion hydrobromide salt. In at least one embodiment of the invention the controlled release polymer is an acrylic polymer. Suitable acrylic polymers include but are not limited to acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid, methacrylic acid alkylamine copolymer, poly(methyl methacrylate), poly(methacrylic acid) (anhydride), glycidyl methacrylate copolymers, and mixtures thereof.

In at least one embodiment the controlled release coat comprises polymerizable quaternary ammonium compounds, of which non-limiting examples include quaternized aminoalkyl esters and aminoalkyl amides of acrylic acid and methacrylic acid, for example β-methacryl-oxyethyl-trimethyl-ammonium methosulfate, β-acryloxy-propyl-trimethyl-ammonium chloride, trimethylaminomethyl-methacrylamide methosulfate and mixtures thereof. The quaternary ammonium atom can also be part of a heterocycle, as in methacryloxyethylmethyl-morpholiniom chloride or the corresponding piperidinium salt, or it can be joined to an acrylic acid group or a methacrylic acid group by way of a group containing hetero atoms, such as a polyglycol ether group. Further suitable polymerizable quaternary ammonium compounds include quaternized vinyl-substituted nitrogen heterocycles such as methyl-vinyl pyridinium salts, vinyl esters of quaternized amino carboxylic acids, and styryltrialkyl ammonium salts. Other polymerizable quaternary ammonium compounds useful in the present invention include acryl- and methacryl-oxyethyltrimethyl-ammonium chloride and methosulfate, benzyldimethylammoniumethyl-methacrylate chloride, diethylmethylammoniumethyl-acrylate and -methacrylate methosulfate, N-trimethylammoniumpropylmethacrylamide chloride, N-trimethylammonium-2, 2-dimethylpropyl-1-methacrylate chloride and mixtures thereof.

In at least one embodiment, the polymer of the controlled release coat is an acrylic polymer comprised of one or more ammonio methacrylate copolymers. Ammonio methacrylate copolymers (e.g. EUDRAGIT® RS and RL) are described in NF XVII as fully polymerized copolymers of acrylic and methacrylic acid esters with a low content of quaternary ammonium groups. In order to obtain a desirable dissolution profile for a given therapeutically active agent such as bupropion hydrobromide, it may be helpful in some embodiments to incorporate two or more ammonio methacrylate copolymers having differing physical properties. For example, it is known that by changing the molar ratio of the quaternary ammonium groups to the neutral (meth)acrylic esters, the permeability properties of the resultant controlled release coat can be modified.

In other embodiments of the present invention, the acrylic polymer coating further includes a polymer whose permeability is pH dependent, such as anionic polymers synthesized from methacrylic acid and methacrylic acid methyl ester (e.g. EUDRAGIT® L and EUDRAGIT® S). EUDRAGIT® L is insoluble in acids and pure water, but becomes increasingly permeable above pH 5.0. EUDRAGIT® S is similar, except that it becomes increasingly permeable above pH 7. The hydrophobic acrylic polymer coatings can also include a polymer which is cationic in character based on dimethylaminoethyl methacrylate and neutral methacrylic acid esters (e.g. EUDRAGIT® E). The hydrophobic acrylic polymer coatings of certain embodiments can further include a neutral copolymer based on poly(meth)acrylates, such as EUDRAGIT® NE In other embodiments of the invention the controlled release polymer is a dispersion of poly (ethylacrylate, methyl methacrylate) 2:1 (e.g. KOLLICOAT® EMM 30 D). In other embodiments the controlled release polymer can be a polyvinyl acetate stabilized with polyvinylpyrrolidone and sodium lauryl sulfate such as KOLLICOAT® SR30D. The dissolution profile can be altered by changing the relative amounts of different acrylic resin lacquers included in the coating. Also, by changing the molar ratio of polymerizable permeability-enhancing agent (e.g., the quaternary ammonium compounds) in certain embodiments to the neutral (meth)acrylic esters, the permeability properties (and thus the dissolution profile) of the resultant coating can be modified.

In at least one embodiment the controlled release polymer is ethylcellulose, which can be used as a dry polymer (e.g. ETHOCEL®) solubilised in organic solvent prior to use, or as an aqueous dispersion. One commercially available aqueous dispersion of ethylcellulose is AQUACOAT®. AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, the AQUACOAT® is intimately mixed with a suitable plasticizer prior to use. Another aqueous dispersion of ethylcellulose is SURELEASE®. This product can be prepared by incorporating a plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

Other examples of polymers that can be used in the microparticle controlled release coat include cellulose acetate phthalate, cellulose acetate trimaletate, hydroxy propyl methylcellulose phthalate, polyvinyl acetate phthalate, polyvinyl alcohol phthalate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, ethyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, pullulan, collagen, casein, agar, gum arabic, sodium carboxymethyl cellulose, (swellable hydrophilic polymers) poly(hydroxyalkyl methacrylate) (molecular weight from about 5 k to about 5000 k), polyvinylpyrrolidone (molecular weight from about 10 k to about 360 k), anionic and cationic hydrogels, zein, polyamides, polyvinyl alcohol having a low acetate residual, a swellable mixture of agar and carboxymethyl cellulose, copolymers of maleic anhydride and styrene, ethylene, propylene or isobutylene, pectin (molecular weight from about 30 k to about 300 k), polysaccharides such as agar, acacia, karaya, tragacanth, algins and guar, polyacrylamides, POLYOX® polyethylene oxides (molecular weight from about 100 k to about 5000 k), AQUAKEEP® acrylate polymers, diesters of polyglucan, crosslinked polyvinyl alcohol and poly N-vinyl-2-pyrrolidone, hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, methyl ethyl cellulose, ethylhydroxy ethylcellulose, cellulose acetate, cellulose butyrate, cellulose propionate, gelatin, starch, maltodextrin, pullulan, polyvinyl pyrrolidone, polyvinyl alcohol, polyvinyl acetate, glycerol fatty acid esters, polyacrylamide, polyacrylic acid, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof.

In at least one embodiment the controlled release coat of the microparticles comprises polymers that can facilitate mucoadhesion within the gastrointestinal tract. Non-limiting examples of polymers that can be used for mucoadhesion include carboxymethylcellulose, polyacrylic acid, CARBOPOL™, POLYCARBOPHIL™, gelatin and other natural or synthetic polymers.

In at least one embodiment the microparticles are coated with a controlled release coat comprised of: at least one film-forming polymer which is insoluble in the liquids of the digestive tract, present in an amount of from about 50% to about 90% including all values and ranges therebetween (e.g. from about 50% to about 80%) by weight of dry matter of the controlled release coat composition, and including at least one non-hydrosoluble cellulose derivate, (e.g. ethylcellulose, cellulose acetate, or mixtures thereof); at least one nitrogen-containing polymer, present in an amount of from about 2% to about 25% including all values and ranges therebetween (e.g. from about 5% to about 15%) by weight of dry matter of the controlled release coat composition, and including at least one polyacrylamide, poly-N-vinylaride, poly-N-vinyl-lactame, polyvinylpyrrolidone, or mixtures thereof; optionally a plasticizer present in an amount of from about 2% to about 20% including all values and ranges therebetween (e.g. from about 4% to about 15%) by weight of dry matter of the controlled release coat composition, and including at least one of the following compounds: glycerol esters, phthalates, citrates, sebacates, cetylalcohol esters, castor oil, cutin, or mixtures thereof; at least one surface-active and/or lubricating agent, present in an amount of from about 2% to about 20% including all values and ranges therebetween (e.g. from about 4% to about 15%) by weight of dry matter of the controlled release coat composition, and chosen from anionic surfactants such as the alkali metal and alkaline-earth metal salts of fatty acids, (e.g. stearic acid, oleic acid, and mixtures thereof), and/or from nonionic surfactants such as polyoxyethylenated esters of sorbitan, polyoxyethylenated esters of sorbitan, polyoxyethylenated derivatives of castor oil, and/or from lubricants such as stearates (e.g. calcium, magnesium, aluminium, zinc stearate and mixtures thereof), stearylfumarates (e.g. sodium stearylfumarate, glyceryl behenate and mixtures thereof); and mixtures thereof; wherein the coated microparticles are designed so as to be able to remain in the small intestine for a period of at least about 5 hours; in certain embodiments at least about 7 hours; and in certain other embodiments for a period of from about 8 hours to about 24 hours; so as to allow absorption of the bupropion hydrobromide during at least part of its time in the small intestine.

In a prophetic example of this embodiment of the invention, the microparticles are coated in a fluidized bead coater with the following coating solution:

| | |
|---|---|
| Ethylcellulose | about 44.7 g |
| PVP | about 4.8 g |
| Castor oil | about 4.8 g |
| Magnesium Stearate | about 6.1 g |
| Acetone | about 479 g |
| Isopranol | about 53 g |

In other embodiments of the present invention, the release of the bupropion hydrobromide from a controlled release formulation can be further influenced, i.e., adjusted to a desired rate, by the addition of one or more pore-formers to the controlled release coat, where the pore-formers can be inorganic or organic, and can include materials that can be dissolved, extracted or leached from the controlled release coat in the environment of use. Upon exposure to fluids in the environment of use, the pore-formers are, for example, dissolved, and channels and pores are formed that fill with the environmental fluid. For example, the pore-formers can include one or more water-soluble hydrophilic polymers in order to modify the release characteristics of the formulation. Non-limiting examples of suitable hydrophilic polymers include hydroxypropylmethylcellulose, cellulose ethers and protein-derived materials of these polymers, the cellulose ethers, (e.g. hydroxyalkylcelluloses and carboxyalkylcelluloses), and mixtures thereof. Also, synthetic water-soluble polymers can be used, such as polyvinylpyrrolidone, cross-linked polyvinyl-pyrrolidone, polyethylene oxide, water-soluble polydextrose, saccharides and polysaccharides, such as pullulan, dextran, sucrose, glucose, fructose, mannitol, lactose, mannose, galactose, sorbitol, and mixtures thereof. In at least one embodiment the hydrophilic polymer(s) include hydroxypropyl-methylcellulose. Other examples of pore-formers include alkali metal salts such as lithium carbonate, sodium chloride, sodium bromide, potassium chloride, potassium sulfate, potassium phosphate, sodium acetate, sodium citrate, and mixtures thereof. The pore-forming solids can also be polymers which are soluble in the environment of use, such as CARBOWAX®, CARBOPOL®, and the like. The possible pore-formers embrace diols, polyols, polyhydric alcohols, polyalkylene glycols, polyglycols, poly(a-w) alkylenediols, and mixtures thereof. Other pore-formers which can be useful in the formulations of the present invention include starch, modified starch, and starch derivatives, gums, including but not limited to xanthan gum, alginic acid, other alginates, benitonite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambda-carrageenan, gum karaya, biosynthetic gum, and mixtures thereof. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone), and mixtures thereof.

In other embodiments a surfactant or an effervescent base can be included in the controlled release coat, which can reduce and in certain embodiments overcome surface tension effects. In addition, the controlled release coat of certain embodiments can include one or more osmagents (i.e., which can osmotically deliver the active agent from the device by providing an osmotic pressure gradient against the external fluid), swelling agents (i.e., which can include, but are not limited to hydrophilic pharmaceutically acceptable compounds with various swelling rates in water), or other pharmaceutically acceptable agents (i.e., provided in an amount sufficient to facilitate the entry of the environmental fluid without causing the disruption of the impermeable coating). The surfactants that can be used in the controlled release coat of certain embodiments can be anionic, cationic, nonionic, or amphoteric. Non-limiting examples of such surfactants include sodium lauryl sulfate, sodium dodecyl sulfate, sorbitan esters, polysorbates, pluronics, potassium laurate, and mixtures thereof. Non-limiting examples of effervescent bases that can be used in the controlled release coat of certain embodiments include sodium glycine carbonate, sodium carbonate, potassium carbonate, sodium bicarbonate, potassium bicarbonate, calcium bicarbonate, and mixtures thereof. Non-limiting examples of osmagents that can be used in the controlled release coat of certain embodiments include sodium chloride, calcium chloride, calcium lactate, sodium sulfate, lactose, glucose, sucrose, mannitol, urea, other organic and inorganic compounds known in the art, and mixtures thereof. The swelling agent can include, but is not limited to at least one pharmaceutically acceptable hydrophilic compound, having a swelling rate or swelling amount in water at about 25° C. that is: greater than or equal to at least about 10% by weight (wt/wt), greater than or equal to at least about 15% by weight (wt/wt), or greater than or equal to at least about 20% by weight (wt/wt). Non-limiting examples of swelling agents that can be used in the controlled release coat of certain embodiments of the present invention include crosslinked polyvinylpyrrolidones (e.g. polyplasdone, crospovidone and mixtures thereof), crosslinked carboxyalkylcelluloses, crosslinked carboxymethylcellulose (e.g. crosslinked sodium croscarmellose), hydrophilic polymers of high molar mass (i.e., which can be, but are not limited to being greater than or equal to 100,000 Daltons) which can include, but are not limited to: polyvinylpyrrolidone(s), polyalkylene oxides (e.g. polyethylene oxide, polypropylene oxide, and mixtures thereof), hydroxyalkylcelluloses (e.g. hydroxypropylcellulose, hydroxypropylmethylcellulose and mixtures thereof), carboxyalkylcellulose (e.g. carboxymethylcellulose), modified starch (e.g. sodium glycolate), starch or natural starch (e.g. corn, wheat, rice, potato and mixtures thereof), cellulose (i.e. which can be, but is not limited to being in powder form or microcrystalline form), sodium alginate, potassium polacriline, and corresponding blends or mixtures thereof. In other embodiments, non-limiting examples of the swelling agent include the following sub-set of compounds: crosslinked polyvinylpyrrolidone (e.g. polyplasdone, crospovidone or mixtures thereof), crosslinked carboxyalkylcelluloses (e.g. crosslinked carboxymethylcelluloses such as crosslinked sodium croscarmellose), and mixtures thereof. In other embodiments, the swelling agent can be a nitrogen containing polymer, non-limiting examples of which can include polyvinylpyrrolidone, crosslinked polyvinylpyrrolidone and mixtures thereof. The concentration of the swelling agent in the controlled release coat of certain embodiments of the present invention can be from about 3% to about 40% by weight of the microparticle including all values and ranges therebetween. For example, in certain embodiments the concentration of the swelling agent in the controlled release coat is from about 4% to about 30%, and in other embodiments from about 5% to about 25% by weight of the microparticle.

In certain embodiments one or more pharmaceutically acceptable excipients consistent with the objects of the present invention can be used in the controlled release coat, such as a lubricant, an emulsifying agent, an anti-foaming agent, and/or a plasticizer.

Lubricants can be included in the controlled release coat to help reduce friction of coated microparticles during manufacturing. The lubricants that can be used in the controlled release coat of certain embodiments of the present invention include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (e.g. COMPRITOL™), STEAR-O-WET™ and MYVATEX™ TL. In at least one embodiment, the lubricant is selected from magnesium stearate, talc and mixtures thereof. Combinations of these lubricants are operable. The lubricant can each be present in an amount of from about 1% to about 100% by weight of the controlled release coat dry weight including all values and ranges therebetween. For example, in certain embodiments wherein the controlled release polymer is EUDRAGIT® NE30D or EUDRAGIT® NE40D together with a hydrophilic pore former, the lubricant is present in an amount of from about 1% to about 30% by weight of the controlled release coat dry weight; in other embodiments from about 2% to about 20%; and in still other embodiments at about 10% by weight of the microparticle controlled release coat dry weight. In another embodiments where the controlled release polymer is ethylcellulose (ETHOCEL™ PR100, PR45, PR20, PR10 or PR7 polymer, or a mixture thereof), the lubricant can be present in an amount of from about 10% to about 100% by weight of the microparticle control-releasing coat dry weight; in another embodiment from about 20% to about 80%; and in still another embodiments at about 50% by weight of the microparticle control-releasing coat dry weight.

Emulsifying agent(s) (also called emulsifiers or emulgents) can be included in the microparticle controlled release coat to facilitate actual emulsification during manufacture of the coat, and also to ensure emulsion stability during the shelf-life of the product. Emulsifying agents useful for the microparticle control-releasing coat composition include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. In at least one embodiment, the emulsifying agent is TWEEN™ 80. The emulsifying agent(s) can be present in an amount of from about 0.01% to about 5% by weight of the microparticle controlled release coat dry weight including all values and ranges therebetween. For example, in certain embodiments the emulsifying agent is present in an amount of from about 0.05% to about 3%; in other embodiments from about 0.08% to about 1.5%, and in still other embodiments at about 0.1% by weight of the microparticle controlled release coat dry weight.

Anti-foaming agent(s) can be included in the microparticle controlled release coat to reduce frothing or foaming during manufacture of the coat. Anti-foaming agents useful for the coat composition include, but are not limited to simethicone, polyglycol and silicon oil. In at least one embodiment the anti-foaming agent is Simethicone C. The anti-foaming agent can be present in an amount of from about 0.1% to about 10% of the microparticle controlled release coat weight including all values and ranges therebetween. For example, in certain embodiments the anti-foaming agent is present in an amount of from about 0.2% to about 5%; in other embodiments from about 0.3% to about 1%, and in still other embodiments at about 0.6% by weight of the microparticle controlled release coat dry weight.

Plasticizer(s) can be included in the microparticle controlled release coat to modify the properties and characteristics of the polymers used in the coat for convenient processing during manufacturing (e.g. provide increased flexibility and durability during manufacturing). As used herein, the term "plasticizer" includes any compounds capable of plasticizing or softening a polymer or binder used in the present invention. Once the coat has been manufactured, certain plasticizers can function to increase the hydrophilicity of the coat in the environment of use. During manufacture of the coat, the plasticizer can lower the melting temperature or glass transition temperature (softening point temperature) of the polymer or binder. The addition of a plasticizer, such as low molecular weight PEG, generally broadens the average molecular weight of a polymer in which they are included thereby lowering its glass transition temperature or softening point. Plasticizers can also generally reduce the viscosity of a polymer. Non-limiting examples of plasticisers that can be used in the microparticle controlled release coat include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropionin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. The plasticizer can be present in an amount of from about 1% to about 80% of the controlled release coat dry weight including all values and ranges therebetween. For example, in certain embodiments the plasticizer is present in an amount of from about 5% to about 50%, in other embodiments from about 10% to about 40%, and in still other embodiments at about 20% of the controlled release coat dry weight.

The controlled release coat can be present in an amount of from about 1% to about 100% by weight of the microparticle including all values and ranges therebetween, depending upon the choice of polymer, the ratio of polymer:pore former, and the total surface area of the microparticle formulation. Since a certain thickness of controlled release coating has to be achieved in order to achieve the desired dissolution profile, the amount of polymer coating required during manufacture is related to the total surface area of the batch of uncoated microparticles that requires a coating. The controlled release polymer surface area coverage can range from about 0.5 $mg/cm^2$ to about 30 $mg/cm^2$ including all values and ranges therebetween. For example in certain embodiments the surface area coverage of the controlled release polymer is from about 0.6 $mg/cm^2$ to about 20 $mg/cm^2$, and in other embodiments from about 1 $mg/cm^2$ to about 5 $mg/cm^2$. In at least one embodiment of the invention, EUDRAGIT® NE30D is used as the controlled release polymer at a surface area coverage of about 10 $mg/cm^2$. One approach to estimate the total surface area of a multiparticulate batch is the permeability method according to Blaine (ASTM Des. C 205-55), which is based upon the mathematical model of laminar flow through capillaries arranged in parallel. In the absence of an accurate determination of total surface area of a microparticle, the amount of controlled release polymer to be applied can be expressed as a percentage of the uncoated microparticle.

The controlled release polymer can be present in an amount of from about 1% to about 99% by weight of the coated microparticle including all values and ranges therebetween, depending on the controlled release profile desired. For example, in certain embodiments the polymer is present in an amount of from about 5% to about 80%, and in other embodiments from about 10% to about 50% by weight of the coated microparticle. In at least one embodiment wherein the controlled release polymer is EUDRAGIT® NE30D, EUDRAGIT® NE40D, KOLLICOAT® SR 30D, or a mixture thereof, the polymer is present in an amount of from about 1% to about 50%; in other embodiments from about 5% to about 30%; and in still other embodiments is about 15% by weight of the coated microparticle. In at least one embodiment wherein the controlled release polymer is ethylcellulose, the polymer is present in an amount of from about 1% to about 99% by weight of the coated microparticle; in other embodiments from about 5% to about 50%; and in still other embodiments at about 20% by weight of the coated microparticle. In at least one embodiment wherein the controlled release polymer is ETHOCEL™, an ethyl cellulose grade PR100, PR45, PR20, PR10, PR7 polymer, or a mixture thereof, the polymer is present in an amount of from about 5% to about 30% by weight of the coated microparticle; in other embodiments from about 10% to about 25%; and in still other embodiments at about 20% by weight of the coated microparticle.

In certain embodiments, the diameter of the microparticles (with or without the controlled release coat) can range from about 50 µm to about 800 µm including all values and ranges therebetween. For example, in certain embodiments the diameter of the microparticles range from about 100 µm to about 600 µm, and in other embodiments from about 150 µm to about 450 µm.

It is contemplated that in alternative embodiments, other excipients consistent with the objects of the present invention can also be used in the microparticle controlled release coat.

In at least one embodiment, the microparticle controlled release coat includes about 96% EUDRAGIT® NE30D, about 1.9% Magnesium stearate, about 1.9% Talc, about 0.04% TWEEN® 80, and about 0.19% Simethicone C, when expressed as percentage by weight of the dry controlled release coat composition. In another embodiment, the microparticle controlled release coat includes about 68% ethylcellulose, about 17% glyceryl monostearate and about 15% acetyl tributylcitrate when expressed as percentage by weight of the dry controlled release coat composition.

In certain embodiments the microparticle controlled release coat can be made according to any one of the methods described herein.

The manufacturing process for the microparticle controlled release coat can be as follows. Water is split into two portions of about 15% and about 85%. The anti-foaming agent and the emulsifying agent are then added to the 15% water portion, and mixed at about 300 rpm to form portion A. In at least one embodiment, the anti-foaming agent is Simethicone C, and the emulsifying agent is TWEEN™ 80. A first lubricant is then added to the 85% water portion and mixed at about 9500 rpm to form portion B. In at least one embodiment, the first lubricant is talc. Then portion A is mixed with portion B, a second lubricant is slowly added, and mixed at about 700 rpm overnight. In at least one embodiment, the second lubricant is magnesium stearate. Finally, an aqueous dispersion of a neutral ester copolymer is added and mixed for about 30 minutes at about 500 rpm. In at least one embodiment, the aqueous dispersion of a neutral ester copolymer is EUDRAGIT® NE30D. The resultant controlled release coat solution can then be used to coat the microparticles to about a 35% weight gain with the following parameters: An inlet temperature of from about 10° C. to about 60° C. including all values and ranges therebetween, in certain embodiments from about 20° C. to about 40° C., and in at least one embodiment from about 25° C. to about 35° C.; an outlet temperature of from about 10° C. to about 60° C. including all values and ranges therebetween, in certain embodiments from about 20° C. to about 40° C., and in at least one embodiment from about 25° C. to about 35° C.; a product temperature of from about 10° C. to about 60° C. including all values and ranges therebetween, in certain embodiments from about 15° C. to about 35° C., and in at least one embodiment from about 22° C. to about 27° C.; an air flow of from about 10 cm/h to about 180 c·m/h including all values and ranges therebetween, in certain embodiments from about 40 c·m/h to about 120 c·m/h, and in at least one embodiment from about 60 c·m/h to about 80 c·m/h; and an atomizing pressure of from about 0.5 bar to about 4.5 bar including all values and ranges therebetween, in certain embodiments from about 1 bar to about 3 bar, and in at least one embodiment at about 2 bar. The resultant controlled release coated microparticles can then be discharged from the coating chamber and oven cured with the following parameters: A curing temperature of from about 20° C. to about 65° C. including all values and ranges therebetween, in certain embodiments from about 30° C. to about 55° C., and in at least one embodiment at about 40° C.; and a curing time of from about 2 hours to about 120 hours including all values and ranges therebetween, in certain embodiments from about 10 hours to about 40 hours, and in at least one embodiment at about 24 hours. Any other technology resulting in the formulation of the microparticle controlled release coat consistent with the objects of the invention can also be used.

Microparticle Dosage Forms

Highly useful dosage forms result when microparticles made from compositions containing a bupropion hydrobromide salt, spheronization aids, and other excipient(s) are coated with controlled release polymer(s). The controlled release coated microparticles can then be combined with an excipient mass and/or other pharmaceutical excipients, and compressed into tablets. Conventional tablets can be manufactured by compressing the coated microparticles with suitable excipients using known compression techniques. The dissolution profile of the controlled release coated multiparticles is not substantially affected by the compression of the microparticles into a tablet. The resultant dosage forms enjoy the processing ease associated with the use of excipient masses and the release properties associated with controlled release coated microparticles. Alternatively, the coated microparticles can be filled into capsules.

The forms of administration according to the invention are suitable for oral administration. In certain embodiments the forms of administration are tablets and capsules. However, the composition of the invention can also take the form of pellets, beads or microtablets, which can then be packaged into capsules or compressed into a unitary solid dosage form. Other solid oral dosage forms as disclosed herein can be prepared by the skilled artisan, despite the fact that such other solid oral dosage forms may be more difficult to commercially manufacture.

The present invention also contemplates combinations of differently coated microparticles into a dosage form to provide a variety of different release profiles. For example, in certain embodiments, microparticles with a delayed release profile can be combined with other microparticles having a sustained release profile to provide a multiple component controlled release bupropion formulation. In addition, other embodiments can include one or more further components of immediate release bupropion. The immediate release bupropion component can take the form of uncoated bupropion microparticles or powders; bupropion microparticles coated with a highly soluble immediate release coating, such as an OPADRY® type coating, as are known to those skilled in the art, or a combination of any of the foregoing. The multiple components can then be blended together in the desired ratio and placed in a capsule, or formed into a tablet. Examples of multiple component controlled release bupropion formulations are described in U.S. Pat. No. 6,905,708.

Dose Sipping Technology

The present invention also contemplates an oral delivery system for delivering microparticles containing bupropion hydrobromide in admixture with a fluid. For example, an oral delivery system is provided which comprises a hollow drug formulation chamber. In at least one embodiment, the chamber has a first end and a second end and contains a formulation in the form of microparticles. The drug formulation comprises bupropion hydrobromide. The system further comprises a fluid passing drug formulation retainer in the first end of the chamber. The retainer prevents release of the microparticles from the first end while permitting fluid entry into the chamber. In other embodiments, the microparticles contained within the chamber comprise bupropion hydrobromide and at least one other drug.

Certain embodiments of the present invention further provide a method for orally delivering microparticles containing bupropion hydrobromide formulation in admixture with a fluid. The method involves inserting microparticles of bupropion hydrobromide formulation into a hollow drug delivery chamber of a drug delivery device. The chamber has a first end and a second end. The first end of the chamber has a fluid passing drug formulation retainer. The drug delivery device has a first and second end. The first end of the drug delivering device is inserted into a fluid and the second end is inserted into the mouth of a patient. The patient then applies suction to the second end of the device to cause delivery of the fluid and microparticles of bupropion hydrobromide formulation into the patient's mouth.

The term "drug formulation retainer" as used herein, refers to a valve, plug or restriction, or the like that prevents passage of the drug formulation from the device. By "fluid passing drug formulation retainer" is intended a valve, plug or restriction or the like that allows for passage of fluids but does not allow for passage of other ingredients such as the drug formulation that is contained in the delivery device.

The dispensing device of this embodiment of the invention finds use where it is inconvenient or unsafe to use solid oral dosage forms such as capsules or tablets. The devices can be particularly useful in geriatric or pediatric patient populations but they can also be useful for those who have difficulty swallowing capsules or tablets. A single delivery device or several devices can be administered to a patient during a therapeutic program.

Generally the device is in prepared form prior to placement in a fluid. In at least one embodiment the dispensing device comprises a hollow drug formulation chamber with a first end and a second end. Contained within the chamber are drug formulation and fluid passing drug formulation retainers. The fluid passing drug formulation retainer comprises a restriction and a one-way plug. The diameter of the opening is smaller than the plug. In at least one embodiment the restriction is made by crimping an end of the chamber. The second end of the chamber has a drug formulation retainer for preventing release of the plug. In at least one embodiment the retainer is prepared by crimping the end of the chamber. Microparticles of bupropion hydrobromide are then placed in the chamber. An end-cap is placed over the second end of the chamber prior to use to prevent release of the drug formulation. In prepared form, the plug substantially seals the first end of the chamber, thereby preventing loss of the drug formulation from the first end.

The device can be formed from any suitable material that is physically and/or chemically compatible with both the active drug and the liquid diluent to be mixed therein. In certain embodiments, representative materials for forming devices including the drug formulation chamber, the elongated tubular member, the end caps and tabs, include, without limitation, paper, plastic such as propylene/styrene copolymers, polyproylene, high density polyethylene, low density polyethylene and the like. The devices can have an inner diameter of from about 3 mm to about 8 mm including all values and ranges therebetween, and a wall thickness of from about 0.1 mm to about 0.4 mm including all values and ranges therebetween. The devices can be from about 10 cm to about 30 cm in length including all values and ranges therebetween.

The fluid passing drug formulation retainer permits the free flow of liquid medium but prohibits passage of the drug formulation from the device prior to delivery. Where the retainer comprises a one-way plug or valve, the plug or valve will seal the straw at atmospheric pressure. When suction is applied, fluid will be drawn around the plug and into the drug formulation chamber. Further, the plug has a density of less than one so that it will ascend to the top as the drug formulation is delivered into the oral cavity. When suction is no longer applied, the plug will remain in the highest position it reached during sipping. The plug can be prepared from closed cell polyethylene foam such as ETHAFOAM®. Other forms of one way plugs can be a balloon of elastomeric material, a one-way mechanical ball valve and the like.

Examples of fluid that can be used for suspending the drug formulation by sipping through the drug formulation chamber include any palatable liquid such as water, juice, milk, soda, coffee, tea etc. Care must be taken to ensure compatibility of the fluid with the drug formulation.

In at least one embodiment, a dose sipping delivery device according to the present invention can be prepared as follows. Jumbo size straws with an inside diameter of about 0.21 inches and a length of about 8 inches are heat sealed at one end. The seal is partially cut off so that the "one-way" plug cannot escape. The partially sealed end is enclosed by half of a size 1 hard gelatin capsule. Microparticles are then placed inside the open end of the straw. A "one-way" plug made of closed cell polyethylene foam (e.g. MICROFOAM®) is trimmed to snugly fit inside the straw. The plug is then placed inside the straw, on top of the microparticles. During operation, the plug end of the straw is placed into a glass of water and the protective gelatin capsule on the top of the straw is removed. By slowly applying suction through the partially sealed end of the straw, the microparticles are sucked into the mouth and easily swallowed.

Osmotic Dosage Forms

Osmotic dosage forms, osmotic delivery devices, modified release osmotic dosage forms, or osmosis-controlled extended-release systems are terms used interchangeably herein and are defined to mean dosage forms which forcibly dispense the bupropion hydrobromide salt by pressure created by osmosis or by osmosis and diffusion of fluid into a material which expands and forces the bupropion hydrobromide salt to be dispensed from the osmotic dosage form.

Osmosis can be defined as the flow of solvent from a compartment with a low concentration of solute to a compartment with a high concentration of solute. The two compartments are separated by a membrane, wall, or coat, which allows flow of solvent (a liquid, aqueous media, or biological fluids) but not the solute. Non-limiting examples of such membranes include a semipermeable membrane, microporous, asymmetric membrane, which asymmetric membrane can be permeable, semipermeable, perforated, or unperforated. Such membrane can deliver the bupropion hydrobromide salt by osmotic pumping, diffusion or the combined mechanisms of diffusion and osmotic pumping. Thus, in principle, osmosis controlled release of the bupropion hydrobromide salt involves osmotic transport of an aqueous media into the osmotic dosage form followed by dissolution of the bupropion hydrobromide salt and the subsequent transport of the saturated solution of the bupropion hydrobromide salt by osmotic pumping of the solution through at least one passageway in the semipermeable membrane or by a combination of osmosis and diffusion through the semipermeable membrane.

It is well known to one of ordinary skill in the art that the desired in-vitro release rate and the in-vivo pharmacokinetic parameters can be influenced by several factors, such as for example, the amount of the bupropion hydrobromide salt used to form the core, the amount of pharmaceutically acceptable excipient used to form the core, the type of pharmaceutically acceptable excipient used to form the core, the amount or type of any other materials used to form the core such as, for example, osmagents (the term osmagent, osmotically effective solutes, osmotically effective compound and osmotic agents are used interchangeably herein) osmopolymers, and any combination thereof. The release profile can also be influenced by the material used to form the semipermeable membrane covering the core or by the material used to form any coating, such as a controlled release coating. With these factors in mind, an osmotic device can therefore be designed to exhibit an in-vitro release rate such that in certain embodiments, after about 2 hours from about 0 to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released, when measured for example by using a USP Type 1 apparatus (Rotating Basket Method) in 900 ml water, 0.1N HCl, 0.1NHCl+0.1% Cetrimide, USP Buffer pH 1.5, Acetate Buffer pH 4.5, Phosphate Buffer, pH 6.5 or Phosphate Buffer pH 7.4 at 75 rpm at 37° C.±0.5° C. Alternatively dissolution may be effected in USP-3 media such as SGF pH 1.2, Acetate Buffer at pH 4.5 or phosphate buffer at pH 6.8.

Osmotic devices also may be designed to achieve an in-vitro release of no more than about 40% after about 2 hours, from about 40% to about 75% release after about 4 hours, at least about 75% after about 8 hours, and at least about 85% after about 16 hours when assayed using a dissolution medium such as identified above or known in the art.

In certain embodiments of the present invention, an osmotic dosage form is provided having a core comprising the bupropion hydrobromide salt and one or more excipients. In at least one embodiment the osmotic dosage form comprises an osmagent. The osmotic delivery system for example, can be in the form of a tablet or capsule containing microparticles.

In certain embodiments, the core of the osmotic dosage form comprises a water swellable polymer, non-limiting examples of which include hydroxypropyl cellulose, alkylcellulose, hydroxyalkylcellulose, polyalkylene oxide, polyethylene oxide, and mixtures thereof. A binder can be included in the core of certain embodiments of the osmotic dosage form to increase the core's mechanical strength. Non-limiting examples of binders include polyvinyl pyrollidine, carboxyvinyl polymer, methylcellulose, hydroxyethylcellulose, hydroxypropylcellulose, hydroxypropylmethylcellulose, a low molecular weight polyethylene oxide polymer, hydroxypropylmethylcellulose, dextrin, maltodextrin, gelatin, polyvinyl alcohol, xanthan gum, carbomers, caragheen, starch derivatives, and mixtures thereof. Lubricants can be included in certain embodiments of the osmotic dosage form to provide decreased friction between the solid and die wall during tablet manufacturing. Non-limiting examples of lubricants include stearic acid, magnesium stearate, glyceryl behenate, talc, mineral oil, sodium stearyl fumarate, hydrogenated vegetable oil, sodium benzoate, calcium stearate, and mixtures thereof. In other embodiments, additional inert excipients consistent with the objects of the invention can also be included in the core of the osmotic dosage form to facilitate the preparation and/or improve patient acceptability of the final osmotic dosage form as described herein. Suitable inert excipients are well known to the skilled artisan and can be found in the relevant literature, for example in the Handbook of Pharmaceutical Excipients (Rowe et. al., 4th Ed., Pharmaceutical Press, 2003).

In at least one embodiment, a modified release osmotic dosage form comprises bupropion hydrobromide in a therapeutically effective amount, which releases the bupropion hydrobromide by forcibly dispensing the bupropion hydrobromide from a core via a semipermeable membrane by diffusion and/or at least one passageway in the membrane by osmotic pumping (i) all or in part by pressure created in the core by osmosis i.e., positive hydrostatic pressure of a liquid, solvent, biological fluid or aqueous media and/or all or in part by the expansion of a swellable material which forces the bupropion hydrobromide to be dispensed from the core of the dosage form, and (ii) is formulated such that the dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released.

In at least one embodiment, the modified release dosage form comprises an osmotic delivery device comprising a homogenous solid core comprising substantially the bupropion hydrobromide salt present in a therapeutically effective amount with at least one pharmaceutically acceptable excipient, said core surrounded by a semipermeable membrane which permits entry of an aqueous liquid into the core and delivery of the bupropion hydrobromide salt from the core to the exterior of the dosage form through at least one passageway or by a combination of osmosis and diffusion such that the dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release rate of the bupropion hydrobromide salt is such that after about 2 hours no more than about 40% is released, after about 4 hours from about 40% to about 75% is released, after about 8 hours at least about 75% is released, and after about 16 hours at least about 85% is released.

In at least one embodiment, the modified release dosage form comprises a multiparticulate dosage form, each microparticle comprising an osmotic delivery device, each microparticle comprising a homogenous solid core comprising substantially the bupropion hydrobromide salt with at least one pharmaceutically acceptable excipient, said core of each microparticle surrounded by a semipermeable membrane which permits entry of an aqueous liquid into the core and delivery of the bupropion hydrobromide salt from the core to the exterior of the dosage form through a plurality of pores formed in the semipermeable membrane by inclusion of a pore forming agent in the membrane or by a combination of osmosis and diffusion so as to allow communication of the core with the outside of the device for delivery of the bupropion hydrobromide salt and is formulated such that the dosage form comprises a therapeutically effective amount of the bupropion hydrobromide salt and exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release rate of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the modified release dosage form comprises a multiparticulate dosage form, each microparticle comprising an osmotic delivery device, each microparticle comprising a homogenous solid core comprising substantially the bupropion hydrobromide salt in admixture with at least one pharmaceutically acceptable excipient, an osmagent and/or an osmopolymer, said core of each microparticle surrounded by a semipermeable membrane which permits entry of an aqueous liquid into the core and delivery of the bupropion hydrobromide salt from the core to the exterior of the dosage form through a plurality of pores formed in the semipermeable membrane by inclusion of a pore forming agent in the membrane or by a combination of osmosis and by diffusion so as to allow communication of the core with the outside of the device for delivery of the bupropion hydrobromide salt and is formulated such that the dosage form comprises a therapeutically effective amount of the bupropion hydrobromide salt and exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release rate of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the modified release dosage form comprises a multiparticulate dosage form, each microparticle comprising a homogenous solid core comprising substantially the bupropion hydrobromide salt with at least one pharmaceutically acceptable excipient in admixture with an osmagent, and/or an osmopolymer, and/or an absorption enhancer, said microparticles compressed into a tablet together with at least one pharmaceutically acceptable excipient, said tablet surrounded by a semipermeable membrane which permits entry of an aqueous liquid into the core and delivery of the bupropion hydrobromide salt from the tablet interior to the exterior of the dosage form through at least one passageway in the semipermeable membrane and/or by diffusion through the semipermeable membrane so as to allow communication of the tablet interior with the exterior of the tablet for delivery of the bupropion hydrobromide salt and is formulated such that the dosage form comprises a therapeutically effective amount of the bupropion hydrobromide salt and exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released, and after about 16 hours at least about 85% is released.

In at least one embodiment, the modified release dosage form comprises a multiparticulate dosage form, each microparticle comprising a sugar sphere or nonpareil bead coated with at least one layer comprising substantially the bupropion hydrobromide salt with at least one pharmaceutically acceptable excipient, said at least one layer surrounded by a semipermeable membrane which permits entry of an aqueous liquid into the layer and delivery of the bupropion hydrobromide salt from the layer to the exterior of the dosage form through a plurality of pores formed in the semipermeable membrane by inclusion of a pore forming agent in the membrane and/or by diffusion so as to allow communication of the core with the outside of the device for delivery of the bupropion hydrobromide salt and is formulated such that the dosage form comprises a therapeutically effective amount of the bupropion hydrobromide salt and exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the modified release dosage form comprises a multiparticulate dosage form, each microparticle comprising a sugar sphere or nonpareil bead coated with at least one layer comprising substantially the bupropion hydrobromide salt in admixture with at least one pharmaceutically acceptable excipient, an osmagent and/or an osmopolymer, said at least one layer surrounded by a semipermeable membrane which permits entry of an aqueous liquid into the layer and delivery of the bupropion hydrobromide salt from the layer to the exterior of the dosage form through a plurality of pores formed in the semipermeable membrane by inclusion of a pore forming agent in the membrane and/or by diffusion so as to allow communication of the core with the outside of the device for delivery of the bupropion hydrobromide salt and is formulated such that the dosage form comprises a therapeutically effective amount of the bupropion hydrobromide salt and exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the modified release dosage form comprises a modified release osmotic dosage form comprising a homogenous core comprising a therapeutically effective amount of the bupropion hydrobromide salt in admixture with an osmagent, and/or an osmopolymer, and/or and absorption enhancer, said core surrounded by a nontoxic wall, membrane or coat, such as for example a semipermeable membrane which permits entry of an aqueous liquid into the core and delivery of the bupropion hydrobromide salt from the core to the exterior of the dosage form through at least one passageway in the semipermeable membrane and/or by diffusion through the membrane so as to allow communication of the core with the outside of the dosage form for delivery of the bupropion hydrobromide salt and is formulated such that the dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment the modified release dosage form comprises an osmotic delivery device comprising the bupropion hydrobromide salt present in a therapeutically effective amount in a layered, contacting arrangement with a swellable material composition to yield a solid core with two or more layers, which core is surrounded by a nontoxic wall, membrane or coat, such as for example a semipermeable membrane which permits entry of an aqueous liquid into the core and delivery of the bupropion hydrobromide salt from the core to the exterior of the dosage form through at least one passageway in the semipermeable membrane or by osmosis and diffusion through the membrane so as to allow communication of the core with the outside of the dosage form for delivery of the bupropion hydrobromide salt and is formulated such that the dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours about 40% to about 75% is released, after about 8 hours at least about 75% is released and after about 16 hours at least about 85% is released.

In at least one embodiment, the modified release dosage form comprises an osmotic delivery device comprising a core and a membrane surrounding said core, said core comprising a therapeutically effective amount of the bupropion hydrobromide salt, and optionally at least one means for forcibly dispensing the bupropion hydrobromide salt from the device, said membrane comprising at least one means for the exit of the bupropion hydrobromide salt from the device, said device formulated such that when the device is in an aqueous medium, the bupropion hydrobromide salt, and optionally the at least one means for forcibly dispensing the bupropion hydrobromide salt from the device and the at least one means for the exit of the bupropion hydrobromide salt from the device cooperatively function to exhibit an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the modified release dosage form comprises an osmotic delivery device comprising a core and a membrane surrounding said core, said core comprising a therapeutically effective amount of the bupropion hydrobromide salt, at least one means for increasing the hydrostatic pressure inside the membrane and optionally at least one means for forcibly dispensing the bupropion hydrobromide salt from the device, said membrane comprising at least one means for the exit of the bupropion hydrobromide salt from the device, said device formulated such that when the device is in an aqueous medium, the at least one means for increasing the hydrostatic pressure inside the membrane, and optionally the at least one means for forcibly dispensing the bupropion hydrobromide salt from the device and the at least one means for the exit of the bupropion hydrobromide salt cooperatively function to exhibit an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

Certain embodiments of the invention are directed to once-a-day bupropion hydrobromide sustained release formulations that are bioequivalent according to FDA guidelines to WELLBUTRIN™ ER or ZYBAN™/WELLBUTRIN™ SR when administered once-daily to a subject in need thereof and wherein the bupropion hydrobromide salt contained is more stable than an equivalent molar amount of the bupropion hydrochloride salt contained in WELLBUTRIN™ ER or ZYBAN™ when exposed to like conditions, for example when stored for 10 days, 13 days, 14 days, 20 days, 24 days, 1 month, 2 months, 3 months, 4 months, 5 months, 6 months, or more under accelerated storage conditions (e.g. 40 degrees C., 75% relative humidity). In at least one embodiment the invention encompasses 174 mg, 348 mg and 522 mg bupropion hydrobromide formulations that are bioequivalent to bupropion hydrochloride formulations.

At least one embodiment is directed to topical formulations containing bupropion hydrobromide that can be administered topically, e.g., transmucosally or transdermally. Particularly, the at least one embodiment embraces topically administrable gels and patch type delivery devices which can comprise another active agent such as nicotine.

At least one embodiment is directed to inhalable pulmonary deliverable compositions containing bupropion hydrobromide that can be administered via pulmonary delivery to a subject in need thereof. These compositions can be produced according to the aerosol technology as known in the art.

At least one embodiment is directed to injectable compositions comprising an effective amount of bupropion hydrobromide and a pharmaceutically acceptable carrier or excipient.

At least one embodiment is directed to a method of treating a condition comprising administering any one of the above described osmotic dosage forms to a patient in need of such administration once-daily.

At least one embodiment is directed to a method for administering a bupropion hydrobromide salt to the gastrointestinal tract of a human for the treatment or management of a condition, wherein the method comprises: (a) admitting orally into the human a modified release dosage form comprising a bupropion hydrobromide salt, the modified release dosage form comprising an osmotic dosage form; and (b) administering the bupropion hydrobromide salt from the osmotic dosage form in a therapeutically responsive dose to produce the treatment or management of the condition such that the osmotic dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

At least one embodiment is directed to a method for administering a bupropion hydrobromide salt to the gastrointestinal tract of a human for the treatment or management of a condition, wherein the method comprises: (a) admitting orally into the human a modified release dosage form comprising a core and a membrane surrounding said core, said core comprising the bupropion hydrobromide salt and optionally a means for forcibly dispensing the bupropion hydrobromide salt from the device, said membrane comprising at least one means for the exit of the bupropion hydrobromide salt from the dosage form, and (b) administering the bupropion hydrobromide salt from the dosage form which is formulated such that when the dosage form is in an aqueous medium, the bupropion hydrobromide salt and optionally the means for forcibly dispensing the bupropion hydrobromide salt and the at least one means for the exit of the bupropion hydrobromide salt cooperatively function to exhibit an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

At least one embodiment is directed to a method for administering a bupropion hydrobromide salt to the gastrointestinal tract of a human for the treatment or management of a condition, wherein the method comprises: (a) admitting orally into the human a modified release dosage form comprising a core and a membrane surrounding said core, said core comprising the bupropion hydrobromide salt, a means for increasing the hydrostatic pressure within the core and optionally a means for forcibly dispensing the bupropion hydrobromide salt from the device, said membrane comprising at least one means for the exit of the bupropion hydrobromide salt from the dosage form, and (b) administering the bupropion hydrobromide salt from the dosage form which is formulated such that when the dosage form is in an aqueous medium, the bupropion hydrobromide salt, the means for increasing the hydrostatic pressure within the core and optionally the means for forcibly dispensing the bupropion hydrobromide salt and the at least one means for the exit of the bupropion hydrobromide salt cooperatively function to exhibit an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one other embodiment, the osmotic dosage form further comprises an immediate release coat for the immediate release of the bupropion hydrobromide salt from the immediate release coat. In embodiments comprising the immediate release coat, the osmotic dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one other embodiment, the osmotic dosage forms further comprise an inert water-soluble coat covering the semipermeable membrane or coat. This inert water-soluble coat can be impermeable in a first external fluid, while being soluble in a second external fluid. In embodiments comprising the inert water-soluble coat, the osmotic dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one other embodiment, the osmotic dosage forms further comprise an osmotic subcoat. In certain embodiments comprising the osmotic subcoat, the osmotic dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one other embodiment, the osmotic dosage forms further comprise a controlled release coat. The controlled release coat of the osmotic dosage form can, for example, control, extend, and/or delay the release of the bupropion hydrobromide salt. In certain embodiments comprising the controlled release coat, the osmotic dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the controlled release coat of the osmotic dosage form comprises a material that is soluble or erodible in intestinal juices, substantially pH neutral or basic fluids of fluids having a pH higher than gastric fluid, but for the most part insoluble in gastric juices or acidic fluids.

In at least one embodiment, the controlled release coat of the osmotic dosage form comprises at least one water-insoluble water-permeable film-forming polymer and at least one water-soluble polymer.

In at least one embodiment, the controlled release coat of the osmotic dosage form comprises at least one water-insoluble water-permeable film-forming polymer and at least one water-soluble polymer and optionally at least one plasticizer.

In at least one embodiment, the controlled release coat of the osmotic dosage form comprises at least one water-insoluble water-permeable film-forming polymer, at least one water-soluble polymer and at least one means for the exit of the bupropion hydrobromide salt from the core of the osmotic dosage form.

In at least one embodiment, the controlled release coat of the osmotic dosage form comprises at least one water-insoluble water-permeable film-forming polymer, at least one water-soluble polymer and at least one passageway.

In at least one embodiment, the controlled release coat of the osmotic dosage form comprises at least one water-insoluble water-permeable film-forming polymer, at least one water-soluble polymer and at least one plasticizer.

In at least one embodiment, the controlled release coat of the osmotic dosage form comprises at least one water-insoluble water-permeable film-forming polymer, at least one water-soluble polymer, optionally at least one plasticizer, and at least one means for the exit of the bupropion hydrobromide salt from the core of the osmotic dosage form.

In at least one embodiment, the controlled release coat of the osmotic dosage form comprises at least one water-insoluble water-permeable film-forming polymer, at least one water-soluble polymer, optionally at least one plasticizer, and at least one passageway.

In at least one embodiment, the controlled release coat of the osmotic dosage form comprises an aqueous dispersion of a neutral ester copolymer without any functional groups; a poly glycol having a melting point greater than about 55° C., one or more pharmaceutically acceptable excipients, and optionally at least one means for the exit of the bupropion hydrobromide salt form the core of the osmotic dosage form. This controlled release coat is cured at a temperature at least equal to or greater than the melting point of the polyglycol.

In at least one other embodiment, the controlled release coat of the osmotic dosage form comprises at least one enteric polymer.

In certain embodiments the membrane or wall is permeable to the passage of aqueous media but not to the passage of the bupropion hydrobromide salt present in the core. The membrane can be, for example, a semipermeable membrane or an asymmetric membrane, which can be permeable, semipermeable, perforated, or unperforated and can deliver the bupropion hydrobromide salt by osmotic pumping, or the combined mechanisms of diffusion and osmotic pumping. The structural integrity of such membranes preferably remain substantially intact during the period of delivery of the bupropion hydrobromide salt. By "substantially intact" it is meant that the semipermeable property of the membrane is not compromised during the period of delivery of the bupropion hydrobromide salt.

The semipermeable membrane of the osmotic dosage form of certain embodiments comprises at least one pharmaceutically acceptable excipient, at least one polymer, wax, or combination thereof, although appropriately treated inorganic materials such as ceramics, metals or glasses can be used. When the semipermeable membrane comprises at least one polymer, the molecular weight of the at least one polymer or combination of polymers are preferably such that the polymer or combination of polymers is solid at the temperature of use i.e., both in-vitro and in-vivo.

In certain embodiments, the at least one polymer included in the semipermeable membrane of the osmotic dosage form can be a cellulose ester, such as for example, cellulose acetate, cellulose acetate acetoacetate, cellulose acetate benzoate, cellulose acetate butylsulfonate, cellulose acetate butyrate, cellulose acetate butyrate sulfate, cellulose acetate butyrate valerate. cellulose acetate caprate, cellulose acetate caproate, cellulose acetate caprylate, cellulose acetate carboxymethoxypropionate, cellulose acetate chloroacetate, cellulose acetate dimethaminoacetate, cellulose acetate dimethylaminoacetate, cellulose acetate dimethylsulfamate, cellulose acetate dipalmitate, cellulose acetate dipropylsulfamate, cellulose acetate ethoxyacetate, cellulose acetate ethyl carbamate, cellulose acetate ethyl carbonate, cellulose acetate ethyl oxalate. cellulose acetate furoate, cellulose acetate heptanoate, cellulose acetate heptylate, cellulose acetate isobutyrate, cellulose acetate laurate, cellulose acetate methacrylate, cellulose acetate methoxyacetate, cellulose acetate methylcarbamate, cellulose acetate methylsulfonate, cellulose acetate myristate, cellulose acetate octanoate, cellulose acetate palmitate, cellulose acetate phthalate, cellulose acetate propionate, cellulose acetate propionate sulfate, cellulose acetate propionate valerate, cellulose acetate p-toluene sulfonate, cellulose acetate succinate, cellulose acetate sulfate, cellulose acetate trimellitate, cellulose acetate tripropionate, cellulose acetate valerate, cellulose benzoate, cellulose butyrate napthylate, cellulose butyrate, cellulose chlorobenzoate, cellulose cyanoacetates, cellulose dicaprylate, cellulose dioctanoate, cellulose dipentanate, cellulose dipentanlate, cellulose formate, cellulose methacrylates, cellulose methoxybenzoate, cellulose nitrate, cellulose nitrobenzoate, cellulose phosphate (sodium salt), cellulose phosphinates, cellulose phosphites, cellulose phosphonates, cellulose propionate, cellulose propionate crotonate, cellulose propionate isobutyrate, cellulose propionate succinate, cellulose stearate, cellulose sulfate (sodium salt), cellulose triacetate, cellulose tricaprylate, cellulose triformate, cellulose triheptanoate, cellulose triheptylate, cellulose trilaurate, cellulose trimyristate, cellulose trinitrate, cellulose trioctanoate, cellulose tripalmitate, cellulose tripropionate, cellulose trisuccinate, cellulose trivalerate, cellulose valerate palmitate; a cellulose ether, such as for example, 2-cyanoethyl cellulose, 2-hydroxybutyl methyl cellulose, 2-hydroxyethyl cellulose, 2-hydroxyethyl ethyl cellulose, 2-hydroxyethyl methyl cellulose, 2-hydroxypropyl cellulose, 2-hydroxypropyl methyl cellulose, dimethoxyethyl cellulose acetate, ethyl 2-hydroxylethyl cellulose, ethyl cellulose, ethyl cellulose sulfate, ethylcellulose dimethylsulfamate, methyl cellulose, methyl cellulose acetate, methylcyanoethyl cellulose, sodium carboxymethyl 2-hydroxyethyl cellulose, sodium carboxymethyl cellulose; a polysulfone, such as for example, polyethersulfones; a polycarbonate; a polyurethane; a polyvinyl acetate; a polyvinyl alcohol; a polyester; a polyalkene such as polyethylene, ethylene vinyl alcohol copolymer, polypropylene, poly(1,2-dimethyl-1-butenylene), poly(1-bromo-1-butenylene), poly(1, butene), poly(1-chloro-1-butenylene), poly(1-decyl-1-butenylene), poly(1-hexane), poly(1-isopropyl-1-butenylene), poly(1-pentene), poly(3-vinylpyrene), poly(4-methoxyl 1-butenylene), poly(ethylene-co-methyl styrene), poly vinyl-chloride, poly(ethylene-co-tetrafluoroethylene), poly(ethylene-terephthalate), poly(dodecafluorobutoxylethylene), poly(hexafluoroprolylene), poly(hexyloxyethylene), poly(isobutene), poly(isobutene-co-isoprene), poly(isoprene), poly-butadiene, poly[(pentafluoroethyl)ethylene], poly[2-ethylhexyloxy)ethylene], poly(butylethylene), poly(tertbutylethylene), poly(cylclohexylethylene), poly[(cyclohexylmethyl)ethylene], poly(cyclopentylethylene), poly(decylethylene), poly-(dodecy-lethylene), poly(neopentylethylene), poly(propylethylene); a polystyrene, such as for example, poly(2,4-dimethyl styrene), poly(3-methyl styrene), poly(4-methoxystyrene), poly(4-methoxystyrene-stat-styrene), poly(4-methyl styrene), poly(isopentyl styrene), poly(isopropyl styrene), polyvinyl esters or polyvinyl ethers, such as form example, poly(benzoylethylene), poly(butoxyethylene), poly(chloroprene), poly(cyclohexloxyethylene), poly(decyloxyethylene), poly(dichloroethylene), poly(difluoroethylene), poly(vinyl acetate), poly(vinyltrimethyilstyrene); a polysiloxane, such as for example, poly(dimethylsiloxane); a polyacrylic acid derivative, such as for example, polyacrylates, polymethyl methacrylate, poly(acrylic acid) higher alkyl esters, poly(ethylmethacrylate), poly(hexadecyl methacrylate-co-methylmethacrylate), poly-(methylacrylate-co-styrene), poly(n-butyl methacrylate), poly(n-butyl-acrylate), poly (cyclododecyl acrylate), poly(benzyl acrylate), poly(butylacrylate), poly(secbutylacrylate), poly(hexyl acrylate), poly(octyl acrylate), poly(decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate), poly(octyl methacrylate), acrylic resins; a polyamide, such as for example, poly(iminoadipoyliminododecamethylene), poly(iminoadipoyliminohexamethylene), polyethers, such as for example, poly(octyloxyethylene), poly(oxyphenylethylene), poly(oxypropylene), poly(pentyloxyethylene), poly(phenoxy styrene), poly(secbutroxylethylene), poly(tertbutoxyethylene); and combinations thereof.

In at least one embodiment, the at least one wax included in the semipermeable membrane of the osmotic dosage form can be, for example, insect and animal waxes, such as for example, chinese insect wax, beeswax, spermaceti, fats and wool wax; vegetable waxes, such as for example, bamboo leaf wax, candelilla wax, carnauba wax, Japan wax, ouricury wax, Jojoba wax, bayberry wax, Douglas-Fir wax, cotton wax, cranberry wax, cape berry wax, rice-bran wax, castor wax, indian corn wax, hydrogenated vegetable oils (e.g., castor, palm, cottonseed, soybean), sorghum grain wax, Spanish moss wax, sugarcane wax, caranda wax, bleached wax, Esparto wax, flax wax, Madagascar wax, orange peel wax, shellac wax, sisal hemp wax and rice wax; mineral waxes, such as for example, Montan wax, peat waxes, petroleum wax, petroleum ceresin, ozokerite wax, microcrystalline wax and paraffins; synthetic waxes, such as for example, polyethylene wax, Fischer-Tropsch wax, chemically modified hydrocarbon waxes, cetyl esters wax; and combinations thereof.

In at least one embodiment, the semipermeable membrane of the osmotic dosage form can comprise a combination of at least one polymer, wax, or combinations thereof and optionally at least one excipient.

In embodiments where the bupropion hydrobromide salt is released through the membrane or wall in a controlled manner by the combined mechanisms of diffusion and osmotic pumping, the membrane or wall can comprise at least one of the above described polymers and/or waxes or a combination of polymers, such as for example, cellulose esters, copolymers of methacrylate salts and optionally a plasticizer.

The poly(methacrylate) copolymer salts used in the manufacturing of the membrane for the osmotic dosage form can be, for example, insoluble in water and in digestive fluids, but are permeable to different degrees. Examples of such copolymers are poly(ammonium methacrylate) copolymer RL (EUDRAGIT®RL), poly(ammonium methacrylate) copolymer (type A-USP/NF), poly(aminoalkyl methacrylate) copolymer RL-JSP I), and (ethyl acrylate)-(methyl methacrylate)-[(trimethylammonium)-ethylmethacrylate] (1:2:0.2) copolymer, MW 150,000. Other examples of such copolymers include EUDRAGIT®RS 100:solid polymer, EUDRAGIT®RL 12.5:12.5% solution in solvent, EUDRAGIT®RL 30 D: 30% aqueous dispersion, and other equivalent products. The following poly(ammonium methacrylate) copolymers can also be used: ammonium methacrylate copolymer RS (EUDRAGIT®RS), poly(ammonium methacrylate) copolymer (type B-USP/NF), poly(aminoalkyl methacrylate) copolymer (RSL-JSP I), (ethyl acrylate)-(Methyl methacrylate)-[(trimethylammonium)-ethyl methacrylate] (1:2:0.1) copolymer, PM 150,000. Specific polymers include: EUDRAGIT®RS 100:solid polymer, EUDRAGIT®RS 12.5:12.5% solution in solvent, EUDRAGIT®RS 30 D: 30% aqueous dispersion and other equivalent products. RL is readily water permeable while EUDRAGIT®RS is hardly water permeable. By employing mixtures of both EUDRAGIT®RL and EUDRAGIT®RS, membranes having the desired degree of permeability to achieve the in-vitro dissolution rates and in-vivo pharmacokinetic parameters can be prepared.

The use of plasticizers is optional but can be included in the osmotic dosage forms of certain embodiments to modify the properties and characteristics of the polymers used in the coats or core of the osmotic dosage forms for convenient processing during manufacture of the coats and/or the core of the osmotic dosage forms if necessary. As used herein, the term "plasticizer" includes any compounds capable of plasticizing or softening a polymer or binder used in invention. Once the coat or membrane has been manufactured, certain plasticizers can function to increase the hydrophilicity of the coat(s) and/or the core of the osmotic dosage form in the environment of use. During manufacture of the coat, the plasticizer lowers the melting temperature or glass transition temperature (softening point temperature) of the polymer or binder. Plasticizers, such as low molecular weight PEG, can be included with a polymer and lower its glass transition temperature or softening point. Plasticizers also can reduce the viscosity of a polymer. The plasticizer can impart some particularly advantageous physical properties to the osmotic device of the invention.

Plasticizers useful in the osmotic dosage form of certain embodiments of the invention can include, for example, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol, glycerin, ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate, allyl glycolate and mixtures thereof. It is also contemplated and within the scope of the invention, that a combination of plasticizers can be used in the present formulation. The PEG based plasticizers are available commercially or can be made by a variety of methods, such as disclosed in Poly(ethylene glycol) Chemistry: Biotechnical and Biomedical Applications (J. M. Harris, Ed.; Plenum Press, NY). Once the osmotic dosage form is manufactured, certain plasticizers can function to increase the hydrophilicity of the coat(s) and/or the core of the osmotic dosage form in the environment of use may it be in-vitro or in-vivo. Accordingly, certain plasticizers can function as flux enhancers.

The ratio of cellulose esters:copolymers of methacrylate salts:plasticizer of the osmotic dosage forms can be, for example, about 1% to about 99% of the cellulose ester by weight: about 0.5% to about 84% of the copolymers of methacrylate salt by weight: about 0.5% to about 15% of the plasticizer by weight including all values and ranges therebetween. The total weight percent of all components comprising the wall is 100%.

Aside from the semipermeable membranes of the osmotic dosage form described above, asymmetric membranes can also be used to surround the core of an osmotic dosage form for the controlled release of the bupropion hydrobromide salt to provide the in-vitro release rates described above and the therapeutically beneficial in-vivo pharmacokinetic parameters for the treatment or management of a condition. Such asymmetric membranes can be permeable, semipermeable, perforated, or unperforated and can deliver the bupropion hydrobromide salt by osmotic pumping, diffusion or the combined mechanisms of diffusion and osmotic pumping. The manufacture and use thereof of asymmetric membranes for the controlled-release of an active drug through one or more asymmetric membranes by osmosis or by a combination of diffusion osmotic pumping is known.

In certain embodiments of the osmotic dosage form, the semipermeable membrane can further comprise a flux enhancing, or channeling agent. "Flux enhancing agents" or "channeling agents" are any materials which function to increase the volume of fluid imbibed into the core to enable the osmotic dosage form to dispense substantially all of the bupropion hydrobromide salt through at least one passageway in the semipermeable membrane by osmosis or by osmosis and by diffusion through the semipermeable membrane. The flux enhancing agent dissolves to form paths in the semipermeable membrane for the fluid to enter the core and dissolve the bupropion hydrobromide salt in the core together with the osmagent, if one is present, but does not allow exit of the bupropion hydrobromide salt. The flux enhancing agent can be any water soluble material or an enteric material which allows an increase in the volume of liquid imbibed into the core but does not allow for the exit of the bupropion hydrobromide salt. Such materials can be, for example, sodium chloride, potassium chloride, sucrose, sorbitol, mannitol, polyethylene glycol, propylene glycol, hydroxypropyl cellulose, hydroxypropyl methylcellulose, hydroxypropyl methylcellulose phthalate, cellulose acetate phthalate, polyvinyl alcohols, methacrylic copolymers, and combinations thereof. Some plasticizers can also function as flux enhancers by increasing the hydrophilicity of the semipermeable membrane and/or the core of the osmotic dosage form. Flux enhancers or channeling agents can also function as a means for the exit of the bupropion hydrobromide salt from the core if the flux enhancing or channeling agent is used in a sufficient amount.

The expression "passageway" as used herein comprises means and methods suitable for the metered release of the bupropion hydrobromide salt from the core of the osmotic dosage form. The means for the exit of the bupropion hydrobromide salt comprises at least one passageway, including orifice, bore, aperture, pore, porous element, hollow fiber, capillary tube, porous overlay, or porous element that provides for the osmotic controlled release of the bupropion hydrobromide salt. The means for the exit can be linear or tortuous. The means for the exit includes a weakened area of the semipermeable membrane or a material that erodes or is leached from the wall in a fluid environment of use to produce at least one dimensioned passageway. The means for the exit of the bupropion hydrobromide salt can comprise any leachable material, which when leaches out of the semipermeable membrane forms a passageway suitable for the exit of the bupropion hydrobromide salt from the core of the osmotic dosage form. Such leachable materials can comprise, for example, a leachable poly(glycolic) acid or poly(lactic) acid polymer in the semipermeable membrane, a gelatinous filament, poly(vinyl alcohol), leachable polysaccharides, salts, oxides, sorbitol, sucrose or mixtures thereof. The means for exit can also comprise a flux enhancer or channeling agent if present in a sufficient amount. The means for the exit possesses controlled-release dimensions, such as round, triangular, square and elliptical, for the metered release of the bupropion hydrobromide salt from the dosage form. The dimensions of the means of the exit for the bupropion hydrobromide salt is sized such so as to allow the bupropion hydrobromide salt to pass through the means for the exit. The dosage form can be constructed with one or more means for the exit in spaced apart relationship on a single surface or on more than one surface of the wall.

The expression "fluid environment" denotes an aqueous or biological fluid as in a human patient, including the gastrointestinal tract. The means for the exit can be preformed for example by mechanical means after the semipermeable membrane is applied to the core of the osmotic dosage form, such as for example by mechanical perforation, laser perforation, or by using a properly sized projection on the interior of a tablet punch to form the means for the exit of the bupropion hydrobromide salt, such as for example a cylindrical or frustoconical pin which is integral with the inside surface of the upper punch of a punch used to form the osmotic dosage form. Alternatively, the means for the exit of the bupropion hydrobromide salt can be formed by incorporating a leachable material or pore forming agent into the semipermeable composition before the semipermeable membrane is applied to the core of the osmotic dosage form. The means for the exit of the bupropion hydrobromide salt can comprise a combination of the different exit means described above. The osmotic dosage form can comprise more than one means for the exit of the bupropion hydrobromide salt including two, three, four, five, six seven, eight, nine ten or more exit means and can be formed in any place of the osmotic dosage form. The various positions of the means for the exit are disclosed. The type, number, and dimension(s) of the means for the exit of the bupropion hydrobromide salt is such that the dosage form exhibits the desired in-vitro release rates described herein and can be determined by routine experimentation by those skilled in the pharmaceutical delivery arts. The means for the exit and equipment for forming the means for the exit are known.

The osmotic device can further comprise a controlled release coat surrounding the semipermeable membrane comprising an enteric or delayed release coat that is soluble or erodible in intestinal juices, substantially pH neutral or basic fluids of fluids having a pH higher than gastric fluid, but for the most part insoluble in gastric juices or acidic fluids. A wide variety of other polymeric materials are known to possess these various solubility properties. Such other polymeric materials include, for example, cellulose acetate phthalate (CAP), cellulose acetate trimelletate (CAT), poly(vinyl acetate) phthalate (PVAP), hydroxypropyl methyl cellulose phthalate (HP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, EUDRAGIT® L-30-D (MA-EA, 1:1), EUDRAGIT® L-100-55 (MA-EA, 1:1), hyciroxypropyl methylcellulose acetate succinate (HPMCAS), COATERIC® (PVAP), AQUATERIC® (CAP), AQUACOAT® (HPMCAS) and combinations thereof. The enteric coat can also comprise dissolution aids, stability modifiers, and bioabsorption enhancers.

In at least one embodiment the controlled release coat of certain osmotic dosage forms include materials such as hydroxypropylcellulose, microcrystalline cellulose (e.g. MCC, AVICEL™), poly(ethylene-vinyl acetate) (60:40) copolymer (EVAC), 2-hydroxyethylmethacrylate (HEMA), MMA, terpolymers of HEMA: MMA:MA synthesized in the presence of N,N'-bis(methacryloyloxyethyloxycarbonylamino)-azobenzene, azopolymers, enteric coated timed release system (TIME CLOCK®), calcium pectinate, and mixtures thereof.

Polymers that can be used in the controlled release coat of osmotic dosage forms of certain embodiments can be, for example, enteric materials that resist the action of gastric fluid avoiding permeation through the semipermeable wall while one or more of the materials in the core of the dosage form are solubilized in the intestinal tract thereby allowing delivery of the bupropion hydrobromide salt in the core by osmotic pumping in the osmotic dosage form to begin. A material that adapts to this kind of requirement can be, for example, a poly(vinylpyrrolidone)-vinyl acetate copolymer (e.g. KOLLIDON® VA64), mixed with magnesium stearate and other similar excipients. The coat can also comprise povidone (e.g. KOLLIDON® K 30), and hydroxypropyl methylcellulose (e.g. METHOCEL® E-15). The materials can be prepared in solutions having different concentrations of polymer according to the desired solution viscosity. For example, a 10% P/V aqueous solution of KOLLIDON® K 30 has a viscosity of about 5.5 to about 8.5 cps at 20° C., and a 2% P/V aqueous solution of METHOCEL® E-15 has a viscosity of about 13 to about 18 cps at 20° C.

The controlled release coat of osmotic dosage forms of certain embodiments can comprise one or more materials that do not dissolve, disintegrate, or change their structural integrity in the stomach and during the period of time that the tablet resides in the stomach, such as for example a member chosen from the group (a) keratin, keratin saridarac-tolu, salol (phenyl salicylate), salol beta-naphthylbenzoate and acetotannin, salol with balsam of Peru, salol with tolu, salol with gum mastic, salol and stearic acid, and salol and shellac; (b) a member chosen from the group of formalized protein, formalized gelatin, and formalized cross-linked gelatin and exchange resins; (c) a member chosen from the group of myristic acid-hydrogenated castor oil-cholesterol, stearic acid-mutton tallow, stearic acid-balsam of tolu, and stearic acid-castor oil; (d) a member chosen from the group of shellac, ammoniated shellac, ammoniated shellac-salol, shellac-wool fat, shellac-acetyl alcohol, shellac-stearic acid-balsam of tolu, and shellac n-butyl stearate; (e) a member chosen from the group of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethyl-methacrylate-butylmethacrylate-methylmethacrylate copolymer of about 150,000 molecular weight, methacrylic acid-methylmethacrylate 50:50 copolymer of about 135,000 molecular weight, methacrylic acid-methylmethacrylate-30: 70-copolymer of about 135,000 mol. wt., methacrylic acid-dimethylaminoethyl-methacrylate-ethylacrylate of about 750,000 mol. wt., methacrylic acid-methylmethacrylate-ethylacrylate of about 1,000,000 mol. wt., and ethylacrylate-methylmethacrylate-ethylacrylate of about 550,000 mol. wt; and, (g) an enteric composition chosen from the group of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from about 1 to about 7 straight and branched alkyl groups, aryl phthalates, and other materials known to one or ordinary skill in the art. Combinations thereof are operable.

Accordingly, in at least one other embodiment, the controlled release coat of osmotic dosage forms of certain embodiments comprises a water-insoluble water-permeable film-forming polymer, water-soluble polymer, and optionally a plasticizer and/or a pore-forming agent. The water-insoluble, water-permeable film-forming polymers useful for the manufacture of the controlled release coat can be cellulose ethers, such as for example, ethyl celluloses chosen from the group of ethyl cellulose grade PR100, ethyl cellulose grade PR20, cellulose esters, polyvinyl alcohol, and any combination thereof. The water-soluble polymers useful for the controlled release coat can be, for example, polyvinylpyrrolidone, hydroxypropyl methylcellulose, hydroxypropyl cellulose, and any combination thereof.

The skilled artisan will appreciate that that the desired in-vitro release rates described herein for the bupropion hydrobromide salt can be achieved by controlling the permeability and/or the amount of coating applied to the core of the osmotic dosage form. The permeability of the controlled release coat, can be altered by varying the ratio of the water-insoluble, water-permeable film-forming polymer:water-soluble polymer:optionally the plasticizer and/or the quantity of coating applied to the core of the osmotic dosage form. A more extended release is generally obtained with a higher amount of water-insoluble, water-permeable film forming polymer. The addition of other excipients to the core of the osmotic dosage form can also alter the permeability of the controlled release coat. For example, if the core of the osmotic dosage form comprises a swellable polymer, the amount of plasticizer in the controlled release coat can be increased to make the coat more pliable as the pressure exerted on a less pliable coat by the swellable polymer could rupture the coat. Further, the proportion of the water-insoluble water-permeable film forming polymer and water-soluble polymer can also be altered depending on whether a faster or slower in-vitro dissolution is desired.

In at least one other embodiment, the controlled release coat of the osmotic dosage form comprises an aqueous dispersion of a neutral ester copolymer without any functional groups; a poly glycol having a melting point greater than about 55° C., and one or more pharmaceutically acceptable excipients and cured at a temperature at least equal to or greater than the melting point of the poly glycol. The manufacture and use of such coating formulations are known. In brief, examples of neutral ester copolymers without any functional groups comprising the coat can be EUDRAGIT® NE30D, EUDRAGIT® NE40D, or mixtures thereof. This coat can comprise hydrophilic agents to promote wetting of the coat when in contact with gastrointestinal fluids. Such hydrophilic agents include, for example, hydrophilic water-soluble polymers such as hydroxypropyl methylcellulose (HPMC), hydroxypropyl cellulose (HPC) and combinations thereof. The poly glycol can be, for example, chosen from the group of polyethylene glycol 6000, polyethylene glycol 8000, polyethylene glycol 10000, polyethylene glycol 20000, Poloxamer 188, Poloxamer 338, Poloxamer 407, Polyethylene Oxides, Polyoxyethylene Alkyl Ethers, and Polyoxyethylene Stearates, and combinations thereof. This controlled release coat of the osmotic dosage form can further comprise a pore-forming agent. In at least one embodiment the pore former is sufficiently insoluble in the aqueous dispersion, and is sufficiently soluble in the environment of use. Methods for producing such coats are known.

The controlled release coat of certain embodiments of the osmotic dosage form of certain embodiments of the present invention includes at least one polymer in an amount sufficient to achieve a controlled release of the bupropion hydrobromide salt. Examples of polymers that can be used in the controlled release coat of these embodiments include cellulose acetate phthalate, cellulose acetate trimaletate, hydroxy propyl methylcellulose phthalate, polyvinyl acetate phthalate, ammonio methacrylate copolymers such as EUDRAGIT® RS and RL, poly acrylic acid and poly acrylate and methacrylate copolymers such as EUDRAGIT® S and L, polyvinyl acetaldiethylamino acetate, hydroxypropyl methylcellulose acetate succinate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, aminoacryl-methacrylate copolymer (e.g. EUDRAGIT® RS-PM), pullulan, collagen, casein, agar, gum arabic, sodium carboxymethyl cellulose, (swellable hydrophilic polymers) poly(hydroxyalkyl methacrylate) (molecular weight from about 5K to about 5000K), polyvinylpyrrolidone (molecular weight from about 10K to about 360K), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (molecular weight from about 30K to about 300K), polysaccharides such as agar, acacia, karaya, tragacanth, algins and guar, polyacrylamides, POLYOX® polyethylene oxides (molecular weight from about 100K to about 5000K), AQUA-KEEP® acrylate polymers, diesters of polyglucan, crosslinked polyvinyl alcohol and poly N-vinyl-2-pyrrolidone, sodium starch glycolate (e.g. EXPLOTAB®); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. POLYOX), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. EUDRAGIT®), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof. In at least one embodiment of the osmotic dosage form of the present invention, the polymer is an acrylate dispersion such as EUDRAGIT® NE30D, EUDRAGIT® NE40D, KOLLICOAT® SR 30D, SURELEASE®, or a mixture thereof. The polymer can be present in an amount of from about 20% to about 90% by weight of the controlled release coat including all values and ranges therebetween, depending on the controlled release profile desired. For example, in certain embodiments of the osmotic dosage form, the polymer is present in an amount of from about 50% to about 95%, in other embodiments from about 60% to about 90%, and in still other embodiments about 75% of the controlled release coat weight.

The controlled release coat of certain embodiments of the osmotic dosage form of the present invention can also include one or more pharmaceutically acceptable excipients such as lubricants, emulsifiers, anti-foaming agents, plasticisers, solvents and the like.

Lubricants can be included in the controlled release coat of certain embodiments of the osmotic dosage form of the present invention to help reduce friction of coated microparticles during manufacturing. The lubricants that can be used in the controlled release coat include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (i.e. COMPRITOL™), STEAR-O-WET™ and MYVATEX™ TL. Combinations of these lubricants are operable. In at least one embodiment, the lubricant is selected from magnesium stearate, talc and a mixture thereof. The lubricant(s) can each be present in an amount of from about 0.1% to about 80% of the controlled release coat weight including all values and ranges therebetween. For example, in certain embodiments the lubricant is present in an amount of from about 0.5% to about 20%, in other embodiments from about 0.8% to about 10%, and in still other embodiments about 1.5% of the controlled release coat weight.

Emulsifying agent(s) (also called emulsifiers or emulgents) can be included in the controlled release coat of the osmotic dosage forms of certain embodiments of the present invention to facilitate actual emulsification during manufacture of the coat, and also to increase or ensure emulsion stability during the shelf-life of the product. Emulsifying agents useful for the controlled release coat composition of the osmotic dosage form include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. The emulsifying agent(s) can be present in an amount of from about 0.01% to about 0.25% of the controlled release coat weight including all values and ranges therebetween. For example, in certain embodiments the emulsifying agent is present in an amount of from about 0.01% to about 0.15%, in other embodiments from about 0.01% to about 0.07%, and in still other embodiments about 0.03% of the controlled release coat weight.

Anti-foaming agent(s) can be included in the controlled release coat of the osmotic dosage form of certain embodiments of the present invention to reduce frothing or foaming during manufacture of the coat. Anti-foaming agents useful for the controlled release coat composition of the osmotic dosage form include, but are not limited to simethicone, polyglycol, silicon oil and mixtures thereof. In at least one embodiment the anti-foaming agent is Simethicone C. The anti-foaming agent can be present in an amount of from about 0.01% to about 10% of the controlled release coat weight including all values and ranges therebetween. For example, in certain embodiments the anti-foaming agent is present in an amount of from about 0.05% to about 1%, in other embodiments from about 0.1% to about 0.3%, and in still other embodiments about 0.15% of the controlled release coat weight.

It is contemplated that in certain embodiments, other excipients consistent with the objects of the present invention can also be used in the controlled release coat of the osmotic dosage form.

In at least one embodiment, the controlled release coat of the osmotic dosage form includes about 75% EUDRAGIT® NE30D, about 1.5% Magnesium stearate, about 1.5% Talc, about 0.03% TWEEN™ 80, about 0.15% Simethicone C, and about 21.82% water, by weight of the controlled release coat composition.

The osmotic dosage form of certain embodiments can be made according to any one of the methods described herein. In a prophetic example of certain embodiments of osmotic dosage forms of the present invention, the manufacturing process for the controlled release coat of the osmotic dosage form can hypothetically be as follows: Water is split into two portions of about 15% and about 85%. The anti-foaming agent and the emulsifying agent are then added to the 15% water portion, and mixed at about 300 rpm to form portion A. In at least one embodiment, the anti-foaming agent is Simethicone C, and the emulsifying agent is TWEEN™ 80. A first lubricant is then added to the 85% water portion and mixed at about 9500 rpm to form portion B. In at least one embodiment, the first lubricant is talc. Then portion A is mixed with portion B, a second lubricant is slowly added, and mixed at about 700 rpm overnight. In at least one embodiment, the second lubricant is magnesium stearate. Finally, an aqueous dispersion of a neutral ester copolymer is added and mixed for about 30 minutes at about 500 rpm. In at least one embodiment, the aqueous dispersion of a neutral ester copolymer is EUDRAGIT® NE30D. The resultant coat solution can then be used to coat the osmotic subcoated microparticles to about a 35% weight gain with the following parameters: An inlet temperature of from about 10° C. to about 60° C. including all values and ranges therebetween, in certain embodiments from about 20° C. to about 40° C., and in at least one embodiment from about 25° C. to about 35° C.; an outlet temperature of from about 10° C. to about 60° C. including all values and ranges therebetween, in certain embodiments from about 20° C. to about 40° C., and in at least one embodiment from about 25° C. to about 35° C.; a product temperature of from about 10° C. to about 60° C. including all values and ranges therebetween, in certain embodiments from about 15° C. to about 35° C., and in at least one embodiment from about 22° C. to about 27° C.; an air flow of from about 10 cm/h to about 180 cm/h including all values and ranges therebetween, in certain embodiments from about 40 cm/h to about 120 cm/h, and in at least one embodiment from about 60 cm/h to about 80 cm/h; and an atomizing pressure of from about 0.5 bar to about 4.5 bar including all values and ranges therebetween, in certain embodiments from about 1 bar to about 3 bar, and in at least one embodiment at about 2 bar. The resultant coated microparticles can then be discharged from the coating chamber and overcured with the following parameters: A curing temperature of from about 20° C. to about 65° C. including all values and ranges therebetween, in certain embodiments from about 30° C. to about 55° C., and in at least one embodiment at about 40° C.; and a curing time of from about 2 hours to about 120 hours including all values and ranges therebetween, in certain embodiments from about 10 hours to about 40 hours, and in at least one embodiment at about 24 hours. Any other technology resulting in the coating formulation of the controlled release coat of the osmotic dosage form that is consistent with the objects of the invention can also be used.

In at least one other embodiment, the osmotic dosage forms comprise a water-soluble or rapidly dissolving coat between the semipermeable membrane and the controlled release coat. The rapidly dissolving coat can be soluble in the buccal cavity and/or upper GI tract, such as the stomach, duodenum, jejunum or upper small intestines. Materials suitable for the manufacture of the water-soluble coat are known. In certain embodiments, the rapidly dissolving coat can be soluble in saliva, gastric juices, or acidic fluids. Materials which are suitable for making the water soluble coat or layer can comprise, for example, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as, for example, hydroxymethylcellulose, hydroxyethylcellulose, and hydroxypropylcellulose; synthetic water-soluble cellulose-based lamina formers such as, for example, methyl cellulose and its hydroxyalkyl methylcellulose cellulose derivatives such as a member chosen from the group of hydroxyethyl methylcellulose, hydroxypropyl methylcellulose, and hydroxybutyl methylcellulose; croscarmellose sodium; other cellulose polymers such as sodium carboxymethylcellulose; and mixtures thereof. Other lamina forming materials that can be used for this purpose include, for example, poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer and mixtures thereof. The water soluble coating can comprise other pharmaceutical excipients that in certain embodiments can alter the way in which the water soluble coating behaves. The artisan of ordinary skill will recognize that the above-noted materials include film-forming polymers. The inert water-soluble coat covering the semipermeable wall and blocking the passageway of osmotic dosage forms of the present invention, is made of synthetic or natural material which, through selective dissolution or erosion can allow the passageway to be unblocked thus allowing the process of osmotic delivery to start. This water-soluble coat can be impermeable to a first external fluid, while being soluble in a second external fluid. This property can help to achieve a controlled and selective release of the bupropion hydrobromide salt from the osmotic dosage form so as to achieve the desired in-vitro release rates.

In embodiments where the core of the osmotic dosage form does not comprise an osmagent, the osmotic dosage forms can comprise an osmotic subcoat, which can surround the core of the osmotic dosage form. The osmotic subcoat comprises at least one osmotic agent and at least one hydrophilic polymer. The osmotic subcoat of these embodiments provides for the substantial separation of the bupropion hydrobromide salt from the osmotic agent into substantially separate compartments/layers. This separation can potentially increase the stability of the bupropion hydrobromide salt by reducing possible unfavorable interactions between the bupropion hydrobromide salt and the osmagent, and/or between the bupropion hydrobromide salt and the components of the controlled release coat. For example, the osmagent can be hygroscopic in nature, and can attract water that can lead to the degradation of the bupropion hydrobromide salt. Since the osmotic agent of these embodiments can be substantially separated from the bupropion hydrobromide salt, the bupropion hydrobromide salt can be less prone to degradation from the water drawn in by the osmagent. The controlled release coat comprises at least one controlled release polymer and optionally a plasticizer. The coated cores of the osmotic dosage form can be filled into capsules, or alternatively can be compressed into tablets using suitable excipients. In these embodiments the osmotic dosage form can utilize both diffusion and osmosis to control drug release, and can be incorporated into sustained release and/or delayed release dosage forms. In addition, in certain embodiments the osmotic pressure gradient and rate of release of the bupropion hydrobromide salt can be controlled by varying the level of the osmotic agent and/or the level of the hydrophilic polymer in the osmotic subcoat, without the need for a seal coat around the osmotic subcoat.

The hydrophilic polymer used in an osmotic subcoat of certain embodiments of the present invention functions as a carrier for the osmotic agent. In certain embodiments the hydrophilic polymer in the osmotic subcoat does not substantially affect the drug release. In at least one embodiment, the hydrophilic polymer used in the osmotic subcoat does not act as a diffusion barrier to the release of the bupropion hydrobromide salt. In at least one embodiment the release profile of the osmotic agent is substantially the same as the release profile of the bupropion hydrobromide salt. Such hydrophilic polymers useful in an osmotic subcoat of certain embodiments of the present invention include by way of example, polyvinyl pyrrolidone, hydroxyethyl cellulose, hydroxypropyl cellulose, low molecular weight hydroxypropyl methylcellulose (HPMC), polymethacrylate, ethyl cellulose, and mixtures thereof. In at least one embodiment, the hydrophilic polymer of the osmotic subcoat is a low molecular weight and a low viscosity hydrophilic polymer. A wide variety of low molecular weight and low viscosity hydrophilic polymers can be used in the osmotic subcoat. Examples of HPMC polymers that can be used in the osmotic subcoat include PHARMACOAT® 606, PHARMACOAT® 606G, PHARMACOAT® 603, METHOCEL® E3, METHOCEL® E5, METHOCEL® E6, and mixtures thereof. The hydrophilic polymer of the osmotic subcoat can be present in an amount of from about 1% to about 30% by weight of the osmotic subcoat composition including all values and ranges therebetween. For example, in certain embodiments the hydrophilic polymer is present in an amount of from about 1% to about 20%, in other embodiments from about 3% to about 10%, and in still other embodiments about 7% by weight of the osmotic subcoat composition.

In at least one embodiment, the osmotic subcoat comprises about 7% PHARMACOAT® 606, about 1% sodium chloride, and about 92% water, by weight of the osmotic subcoat composition.

One method for producing the osmotic subcoat can be as follows. The at least one osmotic agent, for example sodium chloride, is dissolved in water. The solution of osmotic agent and water is then heated to about 60° C. The hydrophilic polymer is then added gradually to the solution. A magnetic stirrer can be used to aid in the mixing of the hydrophilic polymer to the solution of osmotic agent and water. The resultant osmotic subcoating solution can then be used to coat the core of the osmotic dosage form in a fluidized bed granulator, such as a granulator manufactured by Glatt (Germany) or Aeromatic (Switzerland) to the desired weight gain. An inlet temperature of from about 10° C. to about 70° C. including all values and ranges therebetween, in certain embodiments from about 30° C. to about 55° C., and in at least one embodiment from about 40° C. to about 45° C.; an outlet temperature of from about 10° C. to about 70° C. including all values and ranges therebetween, in certain embodiments from about 20° C. to about 45° C., and in at least one embodiment from about 30° C. to about 35° C.; a product temperature of from about 10° C. to about 70° C. including all values and ranges therebetween, in certain embodiments from about 20° C. to about 45° C., and in at least one embodiment from about 30° C. to about 35° C.; an air flow of from about 10 cm/h to about 180 cm/h including all values and ranges therebetween; in certain embodiments from about 40 cm/h to about 120 cm/h; and in at least one embodiment from about 60 cm/h to about 80 cm/h; an atomizing pressure of from about 0.5 bar to about 4.5 bar including all values and ranges therebetween, in certain embodiments from about 1 bar to about 3 bar, and in at least one embodiment at about 2 bar; a curing temperature of from about 10° C. to about 70° C. including all values and ranges therebetween, in certain embodiments from about 20° C. to about 50° C., and in at least one embodiment from about 30° C. to about 40° C.; and a curing time of from about 5 minutes to about 720 minutes including all values and ranges therebetween; in certain embodiments from about 10 minutes to about 120 minutes, and in at least one embodiment at about 30 minutes. Any other technology resulting in the coating formulation of the osmotic subcoat consistent with the objects of the invention can also be used.

The ratio of the components in the core, semipermeable membrane and/or water-soluble membrane and/or at least one controlled release coat and/or osmotic subcoat as well as the amount of the various membranes or coats applied can be varied to control delivery of the bupropion hydrobromide salt either predominantly by diffusion across the surface of the semipermeable membrane to predominantly by osmotic pumping through the at least one passageway in the semipermeable membrane, and combinations thereof such that the dosage form can exhibit a modified-release, controlled-release, sustained-release, extended-release, prolonged-release, bi-phasic release, delayed-release profile or a combination of release profiles whereby the in-vitro release rates of the bupropion hydrobromide salt is such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In embodiments where the mode of exit of the bupropion hydrobromide salt comprises a plurality of pores, the amount of pore forming agent employed to achieve the desired in-vitro dissolution rates can be readily determined by those skilled in the drug delivery art.

In at least one embodiment of the osmotic dosage form, the core comprises bupropion hydrobromide in an amount of from about 40% to about 99% of the core dry weight including all values and ranges therebetween. For example in certain embodiments the core comprises bupropion hydrobromide in an amount of about 40%, about 45%, about 50%, about 55%, about 60%, about 65%, about 70%, about 75%, about 80%, about 85%, about 90%, about 95% or about 99% of the core dry weight.

In certain embodiments, the core of the osmotic dosage form comprises at least one means for increasing the hydrostatic pressure inside the membrane or coat. The membrane or coat can be a semipermeable membrane, a controlled release coat, a water-soluble coat, an osmotic subcoat, or any combination thereof. The core of the osmotic dosage form has an effective osmotic pressure greater than that of the surrounding fluid in the environment of use so that there is a net driving force for water to enter the core. The at least one means for increasing the hydrostatic pressure inside the membrane or coat can be any material that increases the osmotic pressure of the core of the osmotic dosage form. The at least one means for increasing the hydrostatic pressure inside the membrane or coat can be, for example, the bupropion hydrobromide salt, an osmagent, any material which can interact with water and/or an aqueous biological fluid, swell and retain water within their structure, such as for example an osmopolymer, and any combination thereof. The osmagent can be soluble or swellable. Examples of osmotically effective solutes are inorganic and organic salts and sugars. The bupropion hydrobromide salt can itself be an osmagent or can be combined with one or more other osmagents, such as for example, magnesium sulfate, magnesium chloride, sodium chloride, lithium chloride, potassium sulfate, sodium carbonate, sodium sulfite, lithium sulfate, potassium chloride, calcium carbonate, sodium sulfate, calcium sulfate, potassium acid phosphate, calcium lactate, d-mannitol, urea, inositol, magnesium succinate, tartaric acid, water soluble acids, alcohols, surfactants, and carbohydrates such as raffinose, sucrose, glucose, lactose, fructose, algin, sodium alginate, potassium alginate, carrageenan, fucoridan, furcellaran, laminaran, hypnea, gum arabic, gum ghatti, gum karaya, locust bean gum, pectin, starch and mixtures thereof. In certain embodiments the core comprises osmagent in an amount of about 15%, about 20%, about 25%, about 30%, about 35%, about 40%, about 45%, about 50%, about 55%, about 60%, about 65%, about 70%, about 75%, about 80%, about 85%, about 90%, or about 95% of the core dry weight.

The osmagent useful in certain embodiments of the present invention can be any agent that can generate an osmotic pressure gradient for the transport of water from the external environment of use into the osmotic dosage form. Osmagents are also known as osmotically effective compounds, osmotic solutes, and osmotic fluid imbibing agents. Osmagents useful in certain embodiments of the present invention are soluble in aqueous and biological fluids, such as ionizing compounds, inherently polar compounds, inorganic acids, organic acids, bases and salts. In at least one embodiment the osmagent is a solid and dissolves to form a solution with fluids imbibed into the osmotic dosage form. A wide variety of osagents can be used to provide the osmotic pressure gradient used to drive the bupropion hydrobromide salt from the core of the osmotic dosage form. Examples of inorganic salts useful as osmagents include lithium chloride, lithium sulfate, lithium phosphate, magnesium chloride, magnesium sulfate, potassium chloride, potassium sulfate, potassium phosphate, potassium acid phosphate, sodium chloride, sodium sulfate, sodium phosphate, sodium sulfite, sodium nitrate, sodium nitrite, and mixtures thereof. Examples of salts of organic acids useful as osagents include sodium citrate, potassium acid tartrate, potassium bitartrate, sodium bitartrate, and mixtures thereof. Examples of ionizable solid acids useful as osmagents include tartaric, citric, maleic, malic, fumaric, tartronic, itaconic, adipic, succinic, mesaconic acid, and mixtures thereof. Examples of other compounds useful as osmagents include potassium carbonate, sodium carbonate, ammonium carbonate, calcium lactate, mannitol, urea, inositol, magnesium succinate, sorbitol, and carbohydrates such as raffinose, sucrose, glucose, lactose, lactose monohydrate, a blend of fructose glucose and mixtures thereof. In at least one embodiment the osmagent is selected from sodium chloride, sodium bromide, sodium bisulfate, potassium acid tartrate, citric acid, mannitol, sucrose and mixtures thereof. Combinations of these osmagents is permissible. The osmagent can be present in an amount of from about 0.1% to about 50% of the dosage form weight including all values and ranges therebetween. For example, in certain embodiments the osmagent is present in an amount of from about 1% to about 40%, and in other embodiments from about 1% to about 20% of the dosage form weight.

In certain embodiments, the at least one means for increasing the hydrostatic pressure can comprise, in addition to an osmagent, any material which can interact with water and/or an aqueous biological fluid, swell and retain water within their structure. In certain embodiments where the at least one means for increasing the hydrostatic pressure is an osmopolymer, which can be slightly cross-linked or uncross-linked. The uncross-linked polymers to be used as osmopolymers, when in contact with water and/or aqueous biological fluid, preferably do not dissolve in water, hence maintaining their physical integrity. Such polymers can be, for example, chosen from the group of polyacrylic acid derivatives (e.g., polyacrylates, poly-methyl methacrylate, poly(acrylic acid) higher alkyl esters, poly(ethylmethacrylate), poly(hexadecyl methacrylate-co-methylmethacrylate), poly(methylacrylate-co-styrene), poly(n-butyl methacrylate), poly(n-butyl-acrylate), poly(cyclododecyl acrylate), poly(benzyl acrylate), poly(butylacrylate), poly(secbutylacrylate), poly(hexyl acrylate), poly(octyl acrylate), poly(decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate), poly(octyl methacrylate), acrylic resins), polyacrylamides, poly(hydroxy ethyl methacrylate), poly(vinyl alcohol), poly(ethylene oxide), poly N-vinyl-2-pyrrolidone, naturally occurring resins such as polysaccharides (e.g., dextrans, water-soluble gums, starches, chemically modified starches), cellulose derivatives (e.g., cellulose esters, cellulose ethers, chemically modified cellulose, microcrystalline cellulose, sodium carboxymethylcellulose and methylcellulose), starches, CARBOPOL™, acidic carboxy polymer, CYANAMER™, polyacrylamides, cross-linked water-swellable indene-maleic anhydride polymers, GOOD-RITE™, polyacrylic acid, polyethyleneoxide, starch graft copolymers, AQUA-KEEPS™, acrylate polymer, diester cross-linked polyglucan, and any combination thereof.

In certain embodiments, the core of the osmotic dosage form further comprises a means for forcibly dispensing the bupropion hydrobromide salt from the core to the exterior of the dosage form. The at least one means for forcibly dispensing the bupropion hydrobromide salt can be any material which can swell in water and/or aqueous biological fluid and retain a significant fraction of water within its structure, and will not dissolve in water and/or aqueous biological fluid, a means for generating a gas, an osmotically effective solute or any combination thereof which can optionally be surrounded by a membrane or coat depending on the particular means used. The membrane or coat can be, for example, a membrane or coat that is essentially impermeable to the passage of the bupropion hydrobromide salt, gas and compounds, and is permeable to the passage of water and/or aqueous biological fluids. Such a coat or membrane comprises, for example, a semipermeable membrane, microporous membrane, asymmetric membrane, which asymmetric membrane can be permeable, semipermeable, perforated, or unperforated. In at least one embodiment, the at least one means for forcibly dispensing the bupropion hydrobromide salt from the core of the osmotic dosage form comprises a means for generating gas, which means for generating gas is surrounded by, for example, a semipermeable membrane. In operation, when the gas generating means imbibes water and/or aqueous biological fluids, the means for generating gas reacts and generates gas, thereby enlarging and expanding the at least one means for forcibly dispensing the bupropion hydrobromide salt unidirectionally or multidirectionally. The means for generating a gas comprises any compound or compounds, which can produce effervescence, such as for example, at least one solid acid compound and at least one solid basic compound, which in the presence of a fluid can react to form a gas, such as for example, carbon dioxide. Examples of acid compounds include, organic acids such as malic, fumaric, tartaric, itaconic, maleic, citric, adipic, succinic and mesaconic, and inorganic acids such as sulfamic or phosphoric, also acid salts such as monosodium citrate, potassium acid tartrate and potassium bitartrate. The basic compounds include, for example, metal carbonates and bicarbonates salts, such as alkali metal carbonates and bicarbonates. The acid and base materials can be used in any convenient proportion from about 1 to about 200 parts of the at least one acid compound to the at least one basic compound or from about 1 to about 200 parts of the at least one basic compound to the at least one acid compound. The means for generating gas is known.

In at least one embodiment, the at least one means for forcibly dispensing the bupropion hydrobromide salt form the core of the osmotic dosage form comprises any material which can swell in water and/or aqueous biological fluid and retain a significant fraction of water within its structure, and will not dissolve in water and/or aqueous biological fluid, such as for example, a hydrogel. Hydrogels include, for example, lightly cross-linked hydrophilic polymers, which swell in the presence of fluid to a high degree without dissolution, usually exhibiting a 5-fold to a 50-fold volume increase. Non-limiting examples of hydrogels include poly (hydroxyalkyl methacrylates), poly(acrylamide), poly(methacrylamide), poly(N-vinyl-2-pyrrolidone), anionic and cationic hydrogels, polyelectrolyte complexes, a water-insoluble, water-swellable copolymer produced by forming a dispersion of finely divided copolymers of maleic anhydride with styrene, ethylene, propylene butylene or isobutylene cross-linked with from about 0.001 to about 0.5 moles of a polyunsaturated cross-linking agent per mole of maleic anhydride in a copolymer, water-swellable polymers or N-vinyl lactams, semi-solid cross-linked poly(vinyl pyrrolidone), diester cross-linked polyglucan hydrogels, anionic hydrogels of heterocyclic N-vinyl monomers, ionogenic hydrophilic gels, and mixtures thereof. Some of the osmopolymers and hydrogels are interchangeable. Such means can optionally be covered by a membrane or coat impermeable to the passage of the bupropion hydrobromide salt, and compounds, and is permeable to the passage of water and/or aqueous biological fluids. Such a coat or membrane comprises, for example, a semipermeable membrane, microporous membrane, asymmetric membrane, which asymmetric membrane can be permeable, semipermeable, perforated, or unperforated.

In at least one other embodiment, the at least one means for forcibly dispensing the bupropion hydrobromide salt from the core of the osmotic dosage form comprises at least one osmotically effective solute surrounded by a membrane or coat impermeable to the passage of the bupropion hydrobromide salt, and compounds, and is permeable to the passage of water and/or aqueous biological fluids such that the osmotically effective solute exhibits an osmotic pressure gradient across a membrane or coat. Such coat or membrane comprises, for example, a semipermeable membrane, microporous membrane, asymmetric membrane, which asymmetric membrane can be permeable, semipermeable, perforated, or unperforated. The osmotically effective solutes include, for example, the osmagents described above.

In embodiments of the osmotic dosage form where the means for forcibly dispensing the bupropion hydrobromide salt is surrounded by a membrane or coat, at least one plasticizer can be added to the membrane composition to impart flexibility and stretchability to the membrane or coat. In embodiments where the means for forcibly dispensing the bupropion hydrobromide salt comprises a means for generating a gas, the membrane or coat preferably is stretchable so as to prevent rupturing of the membrane or coat during the period of delivery of the bupropion hydrobromide salt. Methods of manufacturing such a membrane or coat is known. Plasticizers, which can be used in these embodiments include, for example, cyclic and acyclic plasticizers, phthalates, phosphates, citrates, adipates, tartrates, sebacates, succinates, glycolates, glycerolates, benzoates, myristates, sulfonamides halogenated phenyls, poly(alkylene glycols), poly(alkylenediols), polyesters of alkylene glycols, dialkyl phthalates, dicycloalkyl phthalates, diaryl phthalates and mixed alkyl-aryl phthalates, such as for example, dimethyl phthalate, dipropyl phthalate, di(2-ethylhexyl)phthalate, diisopropyl phthalate, diamyl phthalate and dicapryl phthalate; alkyl and aryl phosphates, such as for example, tributyl phosphate, trioctyl phosphate, tricresyl phosphate, trioctyl phosphate, tricresyl phosphate and triphenyl phosphate; alkyl citrate and citrates esters such as tributyl citrate, triethyl citrate, and acetyl triethyl citrate; alkyl adipates, such as for example, dioctyl adipate, diethyl adipate and di(2-methoxyethyl)adipate; dialkyl tartrates, such as for example, diethyl tartrates and dibutyl tartrate; alkyl sebacates, such as for example, diethyl sebacate, dipropyl sebacate and dinonyl sebacate; alkyl succinates, such as for example, diethyl succinate and dibutyl succinate; alkyl glycolates, alkyl glycerolates, glycol esters and glycerol esters, such as for example, glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate, triethylene glycol dipropionate and mixtures thereof. Other plasticizers include camphor, N-ethyl (o- and p-toulene) sulfonamide, chlorinated biphenyl, benzophenone, N-cyclohexyl-p-toluene sulfonamide, substituted epoxides and mixtures thereof.

The at least one means for forcibly dispensing the bupropion hydrobromide salt from the core of certain embodiments of the osmotic dosage form can be located such that it is approximately centrally located within the core of the osmotic dosage form and is surrounded by a layer comprising the bupropion hydrobromide salt. Alternatively, the core of the osmotic dosage form comprises at least two layers in which the first layer comprises the bupropion salt, osmagent and/or osmopolymer and optionally at least one pharmaceutically acceptable excipient adjacent to a second layer comprising the means for forcibly dispensing the bupropion hydrobromide salt. Alternatively, the core of the osmotic dosage form comprises a multilayered structure in which the layer comprising the bupropion hydrobromide salt is sandwiched between two layers of the means for forcibly dispensing the bupropion hydrobromide salt from the osmotic dosage form.

Combinations

The present invention also contemplates combinations of the bupropion hydrobromide salt with at least one other drug. For example, a composition is provided which comprises a first component of bupropion hydrobromide, and a second component of at least one other drug, wherein the two components are each present in an amount effective in the treatment of a condition. The present invention further provides a method for treating a condition, comprising administering to a patient an effective amount of a first component of bupropion hydrobromide in combination with an effective amount of at least one other drug. The skilled artisan will know or can determine by known methods which drug combinations are acceptable. Types of drugs that can be selected as the second drug include by way of example other depressants, anti-anxiety agents, steroidal and non-steroidal inflammatories, SSRIs, serotonin receptor agonists, anti-migraine agents, anti-pain agents, anti-emetics, drugs for treating abuse such as nicotine, appetite modulators, anti-virals, vasodilators, and anti-pain agents. For example, the other drug can be an antidepressant selected from: monoamine oxidase (MAO) inhibitor, tricyclic antidepressant, serotonin reuptake inhibitor, selective norepinephrine reuptake inhibitors (SNRIs), aminoketones, serotonin antagonists, dopamine reuptake inhibitors, dual reuptake inhibitors, norepinephrine enhancers, serotonin activity enhancers, dopamine activity enhancers, and combinations thereof. Examples of other drugs that can be combined with bupropion hydrobromide include citalopram, escitalopram, venlafaxine, clozapine, melperone, amperozide, iloperidone, risperidone, quetiapene, olanzapine, ziprasidone, aripiprazole, reboxetine, VIAGRA®, sertraline, paroxetine, fluoxetine, gabapentin, valproic acid, amitriptyline, lofepramine, fluvoxamine, imipramine, mirtazapine, nefazodone, nortriptyline, SAM-E, buspirone, and combinations thereof. In at least one embodiment, a combination of bupropion hydrobromide and citalopram is provided. In at least one other embodiment, a combination of bupropion hydrobromide and escitalopram is provided. In at least one other embodiment a combination of bupropion hydrobromide and venlafaxine is provided. In at least one other embodiment a combination of bupropion hydrobromide and quetiapene is provided.

In certain embodiments combination products can be made by providing an overcoat that contains at least one other drug. For example, certain embodiments can include a core that comprises bupropion hydrobromide, wherein the core is substantially surrounded by a controlled release coat, which in turn is substantially surrounded by an overcoat that contains at least one other drug. In certain embodiments the overcoat provides an immediate release of the other drug. In addition to the other drug, the overcoat can include at least one low viscosity hydrophilic polymer. The low-viscosity polymer provides for the immediate release of the other drug from the overcoat. In at least one embodiment, the low-viscosity polymer used in the overcoat is hydroxypropyl methylcellulose (HPMC). The overcoat can also include a lubricant such as talc. For example, such embodiments can provide an immediate release of at least one other drug from the overcoat in a first phase of drug release, and then a subsequent controlled release of the bupropion hydrobromide from the controlled release coated core in a second phase of drug release.

In addition, combinations of microparticles of the invention each with a different functional coating can be combined together in a dosage form. For example, by combining a first group of uncoated, taste-masked or enteric coated microparticles with a second group of delayed or sustained release coated microparticles, a pulsatile drug release profile or chronotherapeutic profile can be achieved. (e.g. see U.S. Pat. No. 5,260,068, U.S. Pat. No. 6,270,805, U.S. Pat. No. 6,926,909, US2002/0098232, US2004/0197405, U.S. Pat. No. 6,635,284, or U.S. Pat. No. 6,228,398).

In other embodiments, the combination can comprise at least 2 different microparticles. For example, the combination can include one group of microparticles that provide for a controlled release of bupropion hydrobromide, and a second group of microparticles that provide for an immediate release of the other drug. The microparticles can be combined in a capsule formulation.

While only specific combinations of the various features and components of the present invention have been discussed herein, it will be apparent to those of skill in the art that desired subsets of the disclosed features and components and/or alternative combinations of these features and components can be utilized as desired.

As will be seen from the non-limiting examples described below, the coatings of the invention are quite versatile. For example, the length and time for the lagtime can be controlled by the rate of hydration and the thickness of the controlled release coat. It is possible to regulate the rate of hydration and permeability of the controlled release coat so that the desired controlled release profile can be achieved. There is no general preferred controlled release coat thickness, as this will depend on the controlled release profile desired. Other parameters in combination with the thickness of the controlled release coat include varying the concentrations of one or more of the ingredients of the controlled release coat composition, varying the curing temperature and length of time for curing the coated tablet microparticles, and in certain embodiments, varying the level of osmotic agent. The skilled artisan will know which parameters or combination of parameters to change for a desired controlled release profile.

Stability Studies

The enhanced stability of the bupropion hydrobromide salt and compositions containing the bupropion hydrobromide salt, in particular when compared to the bupropion hydrochloride salt and compositions containing the bupropion hydrochloride salt respectively, is evident from degradation studies performed on the active pharmaceutical ingredient (API), alone, in the presence of excipients and in the form of tablets (e.g. extended release tablets). The results are described in greater detail in the examples below and for example in U.S. Pat. No. 7,241,805, the contents of which are incorporated herein by reference.

A comparison of the stability of several bupropion salts, including the hydrobromide, hydrochloride, maleate, tosylate, fumarate, succinate, tartrate and citrate salts, was performed by placing these salts in both open and closed vials in a stability chamber kept at about 40 degrees C. and about 75% relative humidity for various periods of time (e.g. 10 days, 13 days, 14 days, 20 days, 24 days, or 32 days). The stability of the salts was evaluated based on the formation of the main degradation products as determined by HPLC analysis and the % potency (or assay) of the API, after specific time periods in the stability chamber. The effect of the addition of solvents, such as water, ethanol and isopropyl alcohol, was also studied.

The results unexpectedly show that after various periods of time the hydrobromide salt of bupropion, on average, showed the least amount of degradation products, particularly when compared to the hydrochloride salt. Accordingly the bupropion hydrobromide salt showed greater stability than the hydrochloride salt.

Further stability tests were performed by directly comparing bupropion hydrobromide and bupropion hydrochloride salts in forced degradation studies. These studies were performed in closed bottles in a stability chamber kept at about 40 degrees C. and about 75% relative humidity. At specified times, the material in the bottles was analyzed for the presence of degradation products and % potency (% assay). It was unexpectedly found that the amount of impurities was generally lower and the % potency was generally higher for the bupropion hydrobromide salt when compared to the bupropion hydrochloride salt.

Forced degradation studies were also performed on bupropion hydrobromide and bupropion hydrochloride API's in the presence of standard excipients used in pharmaceutical formulations. The amount of the main degradation products was observed at about 24 and about 48 hours after treatment at about 55° C., at about 55° C. and 100% relative humidity, and at about 105° C. Once again, it was unexpectedly found that the bupropion hydrobromide salt showed the lowest amount of degradation (as determined by the formation of bupropion degradation impurities) under these conditions.

The stability of the tablet formulations of bupropion hydrobromide and bupropion hydrochloride salts was also compared. With both salts, a single coated tablet having a controlled release coat (e.g. ETHOCEL® or "EC" coat), as well as a double-coated tablet (with a controlled release coat and a moisture barrier coat) were evaluated. The tablets were placed individually on an open dish, and exposed to the accelerated conditions of about 40° C. and about 75% relative humidity in a stability chamber. After 13 days and 20 days, the samples were assayed and impurity analysis was performed. For the single coated bupropion hydrochloride tablets, the main degradation impurities 3-CBZ and 852U77 were about 0.12% and about 0.38% respectively, whereas, for the bupropion hydrobromide tablets, these values were about 0.07% and about 0.49% respectively. The other degradation impurities and the total unknowns were very similar for both products; however, the assay value for the hydrobromide product was higher than the hydrochloride. The difference in the assay and the impurity levels were more significant in the double coated tablets products. For the same period of the study the assay of the bupropion hydrochloride was lower (about 95.5% compared to about 98.6% for bupropion hydrobromide) and the level of the degradation and total unknowns were higher (3-CBZ: about 0.28%; 852U77: about 1.23%; 827U76: about 0.10%; and total about 1.73%) than the bupropion hydrobromide (3-CBZ: about 0.12%, 852U77: about 0.41%, 827U76: about 0.05%; and total about 0.75%).

The stability studies performed herein have demonstrated the unexpected enhanced stability of bupropion hydrobromide, in particular when compared to bupropion hydrochloride. This enhanced stability is seen with the API form alone, the API form plus excipients, and the extended release and enhanced absorption tablets. The enhanced stability of pharmaceutical formulations comprising bupropion hydrobromide will provide enhanced shelf life and an ability to withstand storage at higher temperatures and humidity levels when compared with bupropion hydrochloride formulations.

Additional Embodiments

Further embodiments of the invention described herein and enabled by the present description include the following:

Certain embodiments include bupropion hydrobromide and 3'-chloro-2-bromo-propiophenone. 3'-chloro-2-bromo-propiophenone is an impurity associated with the preparation of bupropion hydrobromide. In certain embodiments, 3'-chloro-2-bromo-propiophenone is present in an amount that is non-genotoxic; or in an amount that would result in a daily exposure of not more than ("NMT") about 1.5 µg/day in the drug product. Certain embodiments contain less than about 1.5 µg of 3'-chloro-2-bromo-propiophenone. For example in certain embodiments the 3'-chloro-2-bromo-propiophenone impurity is present in an amount of less than about 1.5 µg, 1.4 µg, 1.3 µg, 1.2 µg, 1.1 µg, 1.0 µg, 0.9 µg, 0.8 µg, 0.7 µg, 0.6 µg, 0.5 µg, 0.4 µg, 0.3 µg, 0.2 µg, 0.1 µg, 0.09 µg, 0.08 µg, 0.07 µg, 0.06 µg, 0.05 µg, 0.04 µg, 0.03 µg, 0.02 µg, or 0.01 µg, including all values and subranges therebetween. In at least one embodiment the 3'-chloro-2-bromo-propiophenone impurity is present in undetectable amounts wherein the limit of detection is 1.0 µg, or 1 ppm.

In certain embodiments the 3-chlorobenzoic acid degradation product is limited in the drug product to about 0.7% or less. In at least one embodiment the 3-chlorobenzoic acid degradation product is limited in the composition to about 0.5% or less. In at least one further embodiment the 3-chlorobenzoic acid degradation product is limited in the composition to about 0.3% or less.

In certain embodiments the moisture content in the drug product is limited to not more than about 2.0%. In certain embodiments the moisture content is limited to not more than about 2.0% after a storage time of about 1 minute when stored in a closed container using a Karl Fischer apparatus and UPS Method 1. For example in certain embodiments the moisture content after a storage time of about 1 minute when stored in a closed container using a Karl Fischer apparatus, and USP Method 1, is less than about 2.0%, 1.9%, 1.8%, 1.7%, 1.6%, 1.5% 1.4%, 1.3%, 1.2%, 1.1%, 1.0%, 0.9%, 0.8%, 0.7%, 0.6%, 0.5%, 0.4%, 0.3%, 0.2%, or 0.1%, including all values and subranges therebetween.

In another embodiment there is a tablet comprising (i) a core and (ii) a controlled release coat, said core comprising:
(a) bupropion HBr;
(b) binder (e.g. polyvinyl alcohol); and
(c) lubricant (e.g. glyceryl behenate—Compritol® 888); said controlled release coat (e.g., "SMARTCOAT") comprising:
(d) water-insoluble water-permeable film-forming polymer (e.g. ethyl cellulose grade PR 100);
(e) plasticizer (e.g. polyethylene glycol 4000, dibutyl sebacate, or a mixture thereof);
(f) water-soluble polymer (e.g. polyvinylpyrrolidone—Povidone® USP);
wherein in the controlled release coat the ratio of (d):(e):(f)= from about 3:1:4 to about 5:1:2; or from about 7:2:6 to about 19:5:18; or about 13:4:12; or about 13:6:16;
the tablet optionally further comprising a moisture barrier coat;
said optional moisture barrier coat comprising:
(g) enteric polymer (e.g. an acrylic polymer such as methacrylic acid copolymer type C—Eudragit® L30 D-55);
(h) permeation enhancer (e.g. silicon dioxide—Syloid® 244FP); and
(i) plasticizer (optional)—(e.g. mixture of triethyl citrate and polyethylene glycol 4000—Carbowax® 4000).

In another embodiment there is a once-daily modified release pharmaceutical composition comprising 522 mg of bupropion hydrobromide, said composition providing an in-vivo plasma profile selected from:
Mean Tmax of from about 2 hours to about 7 hours;
Mean Cmax of from about 113 ng/ml to about 239 ng/ml;
Mean Cmin of from about 18 ng/ml to about 44 ng/ml; and
Mean AUC0-t of from about 1236 ng-hr/ml to about 2224 ng-hr/ml.

In another embodiment there is a once-daily modified release pharmaceutical composition comprising 348 mg of bupropion hydrobromide, said composition providing an in-vivo plasma profile selected from:
Mean Tmax of from about 2 hours to about 7 hours;
Mean Cmax of from about 96 ng/ml to about 172 ng/ml;
Mean Cmin of from about 17 ng/ml to about 36 ng/ml; and
Mean AUC0-t of from about 1063 ng-hr/ml to about 1755 ng-hr/ml.

In another embodiment there is a once-daily modified release pharmaceutical composition comprising bupropion hydrobromide, said composition providing a mean Tmax of from about 2 hours to about 7 hours.

In another embodiment there is a once-daily modified release pharmaceutical composition comprising bupropion hydrobromide, said composition providing a mean Tmax that is substantially equivalent to that of a once-daily modified release pharmaceutical composition comprising bupropion hydrochloride.

In another embodiment there is a once-daily modified release pharmaceutical composition comprising bupropion hydrobromide, said composition providing a mean Tmax that is from about 80% to about 125% of that of a once-daily modified release pharmaceutical composition comprising bupropion hydrochloride.

In another embodiment there is a once-daily modified release pharmaceutical composition comprising bupropion hydrobromide, said composition providing a mean Cmax that is substantially equivalent to that of a once-daily modified release pharmaceutical composition comprising bupropion hydrochloride.

In another embodiment there is a once-daily modified release pharmaceutical composition comprising bupropion hydrobromide, said composition providing a mean Cmax that is from about 80% to about 125% of that of a once-daily modified release pharmaceutical composition comprising bupropion hydrochloride.

In another embodiment there is a once-daily modified release pharmaceutical composition comprising bupropion hydrobromide, said composition providing a mean Cmin that is substantially equivalent to that of a once-daily modified release pharmaceutical composition comprising bupropion hydrochloride.

In another embodiment there is a once-daily modified release pharmaceutical composition comprising bupropion hydrobromide, said composition providing a mean Cmin that is from about 80% to about 125% of that of a once-daily modified release pharmaceutical composition comprising bupropion hydrochloride.

In another embodiment there is a once-daily modified release pharmaceutical composition comprising bupropion hydrobromide, said composition providing a mean AUC0-t that is substantially equivalent to that of a once-daily modified release pharmaceutical composition comprising bupropion hydrochloride.

In another embodiment there is a once-daily modified release pharmaceutical composition comprising bupropion hydrobromide, said composition providing a mean AUC0-t that is from about 80% to about 125% of that of a once-daily modified release pharmaceutical composition comprising bupropion hydrochloride.

In another embodiment there is a modified release pharmaceutical composition comprising:
a core comprising a therapeutically effective amount of bupropion hydrobromide; and
a controlled release polymeric coat comprising a water-insoluble polymer and a water-soluble polymer;
wherein said coat surrounds at least a part of said core; and
wherein the amount of bupropion hydrobromide released at a time point from about 0 hours to about 16 hours, in the presence of at least 5% ethanol, using USP Apparatus I at 75 rpm and 37±0.5° C., is less than the amount of bupropion hydrobromide released at the same time point in 0.1 N HCl using USP Apparatus I at 75 rpm and 37±0.5° C.

In another embodiment there is a modified release pharmaceutical composition comprising:
a core comprising a therapeutically effective amount of bupropion hydrobromide; and
a controlled release polymeric coat comprising a water-insoluble polymer and a water-soluble polymer;
wherein said coat surrounds at least a part of said core; and
wherein the amount of bupropion hydrobromide released at a time point from about 0 hours to about 16 hours, in the presence of at least 5% ethanol, using USP Apparatus I at 75 rpm and 37±0.5° C., is less than about 125% of the amount of bupropion hydrobromide released at the same time point in 0.1 N HCl using USP Apparatus I at 75 rpm and 37±0.5° C.

In another embodiment there is a modified release pharmaceutical composition comprising:
a core comprising a therapeutically effective amount of bupropion hydrobromide; and
a controlled release polymeric coat comprising a water-insoluble polymer and a water-soluble polymer;
wherein said coat at least partially surrounds said core; and
wherein dose dumping does not occur in the presence of 0.1 N HCl with 40% EtOH.

In another embodiment there is a method of reducing dose dumping comprising administering to a subject a modified release pharmaceutical composition comprising:
a core comprising a therapeutically effective amount of bupropion hydrobromide; and
a controlled release polymeric coat comprising a water-insoluble polymer and a water-soluble polymer;
wherein said coat at least partially surrounds said core.

In another embodiment there is a pharmaceutical composition comprising 522 mg of bupropion hydrobromide, said composition providing an in-vivo plasma profile selected from:
Mean Tmax of from about 2 hours to about 7 hours;
Mean Cmax of from about 115 ng/ml to about 235 ng/ml;
Mean Cmin of from about 20 ng/ml to about 40 ng/ml; and
Mean AUC0-24 hr of from about 1240 ng-hr/ml to about 2220 ng-hr/ml.

In another embodiment there is a pharmaceutical composition comprising 522 mg of bupropion hydrobromide, said composition providing an in-vivo plasma profile selected from:
Mean Tmax of about 4 hours;
Mean Cmax of less than about 200 ng/ml; and
Mean AUC0-24 hr of more than about 2000 ng-hr/ml.

In another embodiment there is a once-daily modified release pharmaceutical composition comprising bupropion hydrobromide, said composition providing a mean Tmax that is substantially equivalent to that of the same once-daily modified release pharmaceutical composition comprising bupropion hydrochloride instead of bupropion hydrobromide.

In another embodiment there is a once-daily modified release pharmaceutical composition comprising bupropion hydrobromide, said composition providing a mean Tmax that is from about 80% to about 125% of that of the same once-daily modified release pharmaceutical composition comprising bupropion hydrochloride instead of bupropion hydrobromide.

In another embodiment there is a modified release tablet comprising
(i) a core comprising
(a) a therapeutically effective amount of bupropion hydrobromide;
(b) a binder; and
(c) a lubricant; and
(ii) a control-releasing polymeric coat at least partially surrounding said core;
wherein said modified release tablet provides for the controlled release of said bupropion hydrobromide from said modified release tablet over a period of about 24 hours; and
wherein said modified release tablet has improved stability when compared to an otherwise similar or identical modified release tablet comprising an equivalent molar amount of bupropion hydrochloride instead of bupropion hydrobromide, when each are stored for at least about 12 months at about 25° C. and at about 60% relative humidity.

In another embodiment there is a modified release bupropion hydrobromide tablet suitable for oral administration comprising
(i) a core comprising
(a) a therapeutically effective amount of bupropion hydrobromide;
(b) a binder; and
(c) a lubricant;
(ii) a controlled release polymeric coat which at least partially surrounds said core; and
(iii) a degradation product chosen from 3-chlorobenzoic acid, 827U76, 20U78, 852U77, and mixtures thereof;
wherein said modified release bupropion hydrobromide tablet contains less of said degradation product as compared to an otherwise similar or identical modified release tablet containing an equivalent molar amount of bupropion hydrochloride instead of bupropion hydrobromide;
when the modified release bupropion hydrobromide tablet and the otherwise similar or identical modified release tablet containing bupropion hydrochloride are each are stored for at least about 12 months at 25° C. and 60% relative humidity after tablet formulation.

In another embodiment there is a modified release tablet comprising:
a therapeutically effective amount of bupropion hydrobromide;
wherein at about 12 months after formulation of said modified release tablet, at about 37±0.5° C., from about 0% to 40% of said bupropion hydrobromide is released after 2 hours; from about 40% to about 75% of said bupropion hydrobromide is released after 4 hours; not less than about 75% of said bupropion hydrobromide is released after 8 hours; and not less than about 85% of said bupropion hydrobromide is released after 16 hours, in 900 ml of 0.1 N HCl using USP Type 1 apparatus with a rotational speed of 75 rpm.

In another embodiment there is a modified release pharmaceutical composition comprising:
(i) a core comprising a therapeutically effective amount of bupropion hydrobromide; and
(ii) a controlled release polymeric coat comprising a water-insoluble polymer and a water-soluble polymer;

wherein said coat at least partially surrounds said core; and wherein said composition is resistant to alcohol-induced dose dumping.

In another embodiment there is a modified release pharmaceutical composition comprising:
(i) a core comprising a therapeutically effective amount of bupropion hydrobromide; and
(ii) a controlled release polymeric coat comprising a water-insoluble polymer and a water-soluble polymer;
wherein said coat at least partially surrounds said core; and
wherein the rate of release of bupropion hydrobromide in dissolution media containing alcohol is slower than the rate of release of bupropion hydrobromide in dissolution media not containing alcohol.

In another embodiment there is a modified release pharmaceutical composition comprising:
(i) a core comprising a therapeutically effective amount of bupropion hydrobromide; and
(ii) a controlled release polymeric coat comprising a water-insoluble polymer and a water-soluble polymer;
wherein said coat at least partially surrounds said core; and
wherein the amount of bupropion hydrobromide released at a time point from about 0 hours to about 16 hours, in dissolution media comprising about 40% EtOH and 60% 0.1N HCl, using USP Apparatus Type 1 at 75 rpm, is not more than the amount of bupropion hydrobromide released at the same time point in dissolution media comprising about 100% 0.1N HCl using USP Apparatus Type 1 at 75 rpm.

In another embodiment there is a modified release pharmaceutical composition comprising:
(i) a core comprising a therapeutically effective amount of bupropion hydrobromide; and
(ii) a controlled release polymeric coat comprising a water-insoluble polymer and a water-soluble polymer;
wherein said coat at least partially surrounds said core; and
wherein the amount of bupropion hydrobromide released at a time point from about 0 minutes to about 120 minutes, in dissolution media comprising about 40% EtOH and 60% 0.1N HCl, using USP Apparatus Type 1 at 75 rpm, is not more than the amount of bupropion hydrobromide released at the same time point in dissolution media comprising about 100% 0.1N HCl using USP Apparatus Type 1 at 75 rpm.

In another embodiment there is a method of resisting alcohol-induced dose dumping of bupropion hydrobromide comprising administering to a subject a modified release pharmaceutical composition, said composition comprising:
(i) a core comprising a therapeutically effective amount of bupropion hydrobromide; and
(ii) a controlled release polymeric coat comprising a water-insoluble polymer and a water-soluble polymer;
wherein said coat at least partially surrounds said core.

In another embodiment there is a method of treating a subject at risk of alcohol-induced dose dumping of bupropion hydrobromide and in need of bupropion treatment, the method comprising administering to a subject a modified release pharmaceutical composition, said composition comprising:
(i) a core comprising a therapeutically effective amount of bupropion hydrobromide; and
(ii) a controlled release polymeric coat comprising a water-insoluble polymer and a water-soluble polymer;
wherein said coat at least partially surrounds said core.

In another embodiment there is a composition comprising bupropion hydrobromide and 3'-chloro-2-bromo-propiophenone.

In another embodiment there is a composition comprising bupropion hydrobromide and less than about 1.5 µg of 3'-chloro-2-bromo-propiophenone.

In another embodiment there is a composition comprising bupropion hydrobromide and less than about 1.0 µg of 3'-chloro-2-bromo-propiophenone.

In another embodiment there is a modified release composition comprising bupropion hydrobromide wherein the moisture content is not more than about 2.0% in said composition after a storage time of about 1 minute, when stored in a closed container using a Karl Fischer apparatus, USP Method 1.

In another embodiment there is a composition comprising bupropion hydrobromide and at least one pharmaceutically acceptable excipient, wherein the amount of bupropion hydrobromide is chosen from 174 mg, 348 mg and 522 mg.

In another embodiment there is a modified release tablet comprising bupropion hydrobromide and at least one pharmaceutically acceptable excipient, wherein the amount of bupropion hydrobromide is chosen from 174 mg, 348 mg and 522 mg.

In another embodiment there is a modified release tablet comprising bupropion hydrobromide and at least one pharmaceutically acceptable excipient, wherein the amount of bupropion hydrobromide is chosen from 174 mg, 348 mg and 522 mg; and wherein the bupropion hydrobromide is contained within a core of the tablet further comprising a controlled release coating over the core.

In another embodiment there is a composition comprising at least bupropion hydrobromide in the concentration specified in one of A, B, and C in the following Table admixed with one or more additional components listed in A, B and C in the following Table:

|  | Component | | |
|---|---|---|---|
|  | A | B | C |
| Bupropion Hydrobromide | 174 mg | 348 mg | 522 mg |
| Polyvinyl Alcohol | 5.8 mg | 11.6 mg | 22.5 mg |
| Glyceryl Behenate | 5.8 mg | 11.6 mg | 22.5 mg |
| Target Core Tablet Weight (mg) | 185.6 mg | 371.2 mg | 567 mg |
| Ethylcellulose 100, NF | 15.4 mg | 16.4 mg | 18.13 mg |
| Povidone (K-90) | 9.5 mg | 10.2 mg | 21.87 mg |
| Polyethylene Glycol, 4000 | 3.4 mg | 3.7 mg | 5.33 mg |
| Dibutyl Sebacate (DBS) | 1.7 mg | 1.8 mg | 2.67 mg |
| Target Coating Weight Gain (mg) | +30 mg | +32 mg | +48 mg |
| Carnauba Wax | Trace Amount | Trace Amount | N/A |
| Denatured Ethyl Alcohol, 200 proof | Evaporated Off | Evaporated Off | Evaporated Off |
| Ethyl Alcohol, 190 proof | Evaporated Off | Evaporated Off | Evaporated Off |
| Purified Water | Evaporated Off | Evaporated Off | Evaporated Off |
| Opacode R Black Ink | Trace Amount | Trace Amount | Trace Amount |
| Isopropyl Alcohol, 99% | None | None | None |
| Final Printed Tablet Weight (mg) | 216 mg | 403 mg | 615 mg |

In another embodiment there is a composition comprising at least about 522 mg of bupropion hydrobromide and at least one pharmaceutically acceptable excipient. In other aspects of this embodiment the composition is in tablet form. In other aspects of this embodiment the composition is a modified release formulation. In other aspects of this embodiment the composition is in tablet form and the bupropion hydrobromide is contained within a core of the tablet further comprising a coating over the core. In other aspects of this embodiment the coating is a controlled release coating.

In at least one embodiment the bupropion hydrobromide 174 mg tablet composition releases bupropion hydrobromide in a first dissolution medium consisting of ethanol (5%-40%) and 0.1N HCl, at a rate that is less than or equal to about 1.1 times the rate of release of bupropion hydrobromide from the identical bupropion hydrobromide 174 mg tablet composition in a second dissolution medium consisting of 0.1N HCl (100%), measured over a time period of at least from 0 to 2 hours, measured using a USP Apparatus I at 75 rpm and at 37° C. See for example U.S. patent application Ser. No. 11/930,644 (Pub. No. 2008-0274181), the contents of which are incorporated herein by reference. In at least one embodiment the bupropion hydrobromide 174 mg tablet composition releases bupropion hydrobromide in a first dissolution medium consisting of ethanol (40%) and 0.1N HCl, at a rate that is less than the rate of release of bupropion hydrobromide from the identical bupropion hydrobromide 174 mg tablet composition in a second dissolution medium consisting of 0.1N HCl (100%), measured over a time period of at least from 0 to 24 hours, measured using a USP Apparatus I at 75 rpm and at 37° C.

In at least one embodiment the bupropion hydrobromide 174 mg tablet composition releases bupropion hydrobromide in a first dissolution medium consisting of ethanol (5%-40%) and 0.1N HCl at a rate that is less than or equal to about 1.1 times the rate of release of bupropion hydrobromide from the identical bupropion hydrobromide 174 mg tablet composition in a second dissolution medium consisting of 0.1N HCl (100%), measured over a time period of at least from 0 to 2 hours, measured using a USP Apparatus I at 75 rpm and at 37° C.

In at least one embodiment the bupropion hydrobromide 348 mg tablet composition releases bupropion hydrobromide in a first dissolution medium consisting of ethanol (5%-40%) and 0.1N HCl at a rate that is less than or equal to about 1.1 times the rate of release of bupropion hydrobromide from the identical bupropion hydrobromide 348 mg tablet composition in a second dissolution medium consisting of 0.1N HCl (100%), measured over a time period of at least from 0 to 2 hours, measured using a USP Apparatus I at 75 rpm and at 37° C.

In at least one embodiment the bupropion hydrobromide 522 mg tablet composition releases bupropion hydrobromide in a first dissolution medium consisting of ethanol (40%) and 0.1N HCl (60%) at a rate that is less than the rate of release of bupropion hydrobromide from the identical bupropion hydrobromide 522 mg tablet composition in a second dissolution medium consisting of 0.1N HCl (100%), measured over a time period of at least from 0 to 16 hours, measured using a USP Apparatus I at 75 rpm and at 37° C.

In at least one embodiment the bupropion hydrobromide 522 mg tablet composition releases bupropion hydrobromide in a first dissolution medium consisting of ethanol (5%-40%) and 0.1N HCl, at a rate that is less than or equal to the rate of release of bupropion hydrobromide from the identical bupropion hydrobromide 522 mg tablet composition in a second dissolution medium consisting of 0.1N HCl (100%), measured over a time period of at least from 0 to 2 hours, measured using a USP Apparatus I at 75 rpm and at 37° C.

In at least one embodiment a bupropion hydrobromide 174 mg tablet composition releases bupropion hydrobromide in a first dissolution medium consisting of ethanol (40%) and 0.1N HCl (60%), at a rate that is less than the rate of release of bupropion hydrobromide from the identical bupropion hydrobromide 174 mg tablet composition in a second dissolution medium consisting of 0.1N HCl (100%), measured over a time period of at least from 0 to 24 hours, measured using a USP Apparatus I at 75 rpm and at 37° C. In at least one embodiment a bupropion hydrobromide 174 mg tablet releases bupropion hydrobromide in a dissolution medium consisting of ethanol (40%) and 0.1N HCl (60%), at a rate that is less than the rate of release of bupropion hydrochloride from a bupropion hydrochlroide 150 mg tablet having the identical polymeric controlled release coat composition used in the bupropion hydrobromide 174 mg tablet, in the identical dissolution medium consisting of ethanol (40%) and 0.1N HCl (60%), measured over a time period of at least from 0 to 16 hours, measured using a USP Apparatus I at 75 rpm and at 37° C.

In at least one embodiment a bupropion hydrobromide 174 mg tablet composition releases bupropion hydrobromide in a first dissolution medium consisting of ethanol (40%) and 0.1N HCl (60%), at a rate that is less than the rate of release of bupropion hydrobromide from the identical bupropion hydrobromide 174 mg tablet composition in a second dissolution medium consisting of 0.1N HCl (100%), measured over a time period of at least from 0 to 2 hours, measured using a USP Apparatus I at 75 rpm and at 37° C. In at least one embodiment a bupropion hydrobromide 174 mg tablet releases bupropion hydrobromide in a dissolution medium consisting of ethanol (40%) and 0.1N HCl (60%), at a rate that is less than the rate of release of bupropion hydrochloride from a bupropion hydrochlroide 150 mg tablet having the identical polymeric controlled release coat composition used in the bupropion hydrobromide 174 mg tablet, in the identical dissolution medium consisting of ethanol (40%) and 0.1N HCl (60%), measured over a time period of at least from 0 to 2 hours, measured using a USP Apparatus I at 75 rpm and at 37° C.

The examples below are non-limiting and are representative of various aspects of certain embodiments of the present invention.

EXAMPLES

Example 1

Preparation of Bupropion HBr Salt

Bupropion HBr salt was prepared according to the method shown in Scheme 1:

Scheme 1
Bromination Reaction

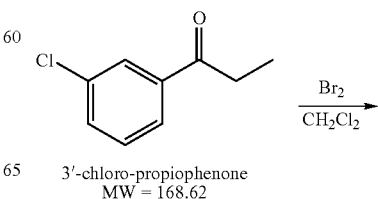

3'-chloro-propiophenone
MW = 168.62

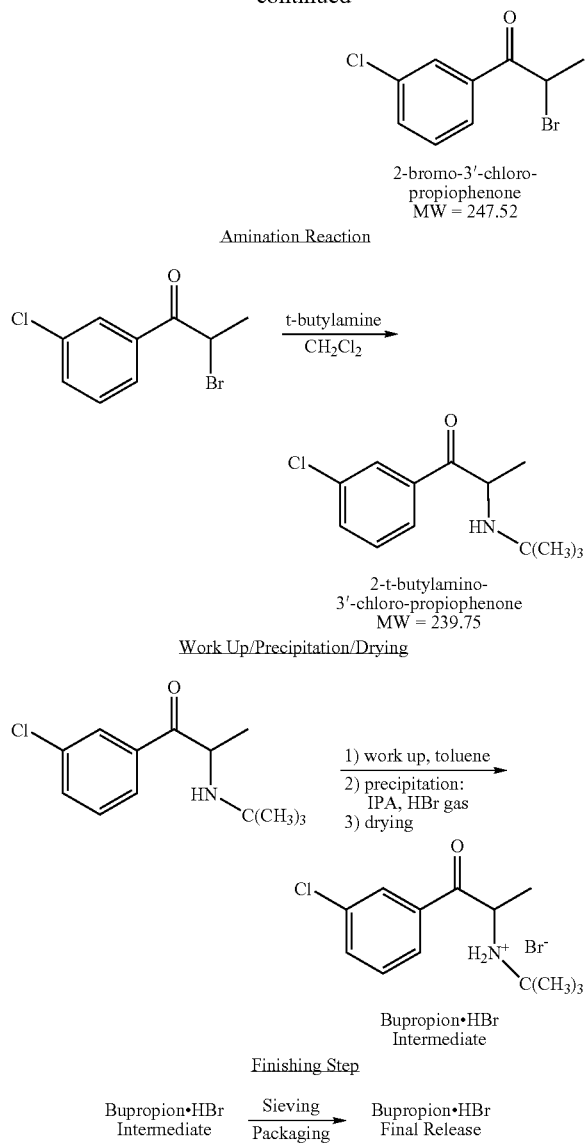

(a) Bromination and Condensation Reactions

3-Chloro-propiophenone starting material was brominated in methylene chloride by dropping bromine under controlled conditions. On reaction completion the mother liquor was worked up and then the second reaction was executed by transferring the bromoderivative solution onto the tert-butylamine. The second substitution reaction (the tert-butylamine amino-group substitutes the bromine atom) forms the final bupropion molecule. After work up of the mother liquor, a bupropion toluene solution was obtained. The solvent was evaporated and bupropion was dissolved in isopropanol. From the isopropanol solution, the hydrobromide was precipitated with hydrogen bromide gas. On precipitation completion, the product was centrifuged, washed with isopropanol and dried under vacuum. On dryer discharge approval it was discharged in Kraft drums within double polyethylene bags.

In the last finishing step, the above intermediate was sieved to obtain the Final Release which was packed in Kraft drums within double polyethylene bags.

Elemental analysis of the bupropion HBr was carried out using a Fisons Elemental Analyser EA 1108. The results were consistent with the molecular formula of bupropion HBr.

Example 2

Bupropion HBr Extended Release (XL) Tablets

The aim of this example was to describe the development of bupropion HBr XL (174 and 348 mg). Granulation, tabletting and coating procedures are all described thoroughly in this example. In-vitro testing was conducted on the cores, the ethylcellulose coated cores and the final coated tablets in order to determine which formulation gave the desired results.

From their structural formulae, it is observable that the difference between bupropion HCl and bupropion HBr is the salt. This, of course, results in a different molecular weight. However, these differences were taken into account in the present study, and modifications were made in order to obtain in-vitro correlation results to the bupropion HCl using dissolution studies.

It was previously observed that when 150 mg of bupropion HCl was tested for its release of bupropion, the base value that was released was 130 mg. However, when 150 mg of bupropion HBr was tested, the base value released was only 112 mg. Thus, the amount of bupropion HBr had to be increased in order to increase the base value from 112 mg to 130 mg, which was the target. Studies showed that 174 mg of bupropion HBr gave a base value release of 130 mg and is therefore why 174 mg was used as opposed to 150 mg bupropion HBr.

Bupropion HBr XL—Granulation Process

A summary of the manufacturing process used for the preparation of bupropion HBr XL tablets is shown in FIG. 1.

The following materials were used in the granulation of the immediate release core of the bupropion HBr EA tablets: bupropion HBr, polyvinyl alcohol (PVA) and purified water. Once granulated, lubricant (COMPRITOL® 888) was added to complete the formulation. Each Trial was divided into 5 parts. The percentage of API in each formulation was 93.75%; the percentage of PVA in each formulation was 3.125%. A summary of the breakdown of each trial per part is described in Table 1.

The PVA was dissolved into the purified water using a magnetic stirrer and a clear colourless solution was made.

Figure 2:
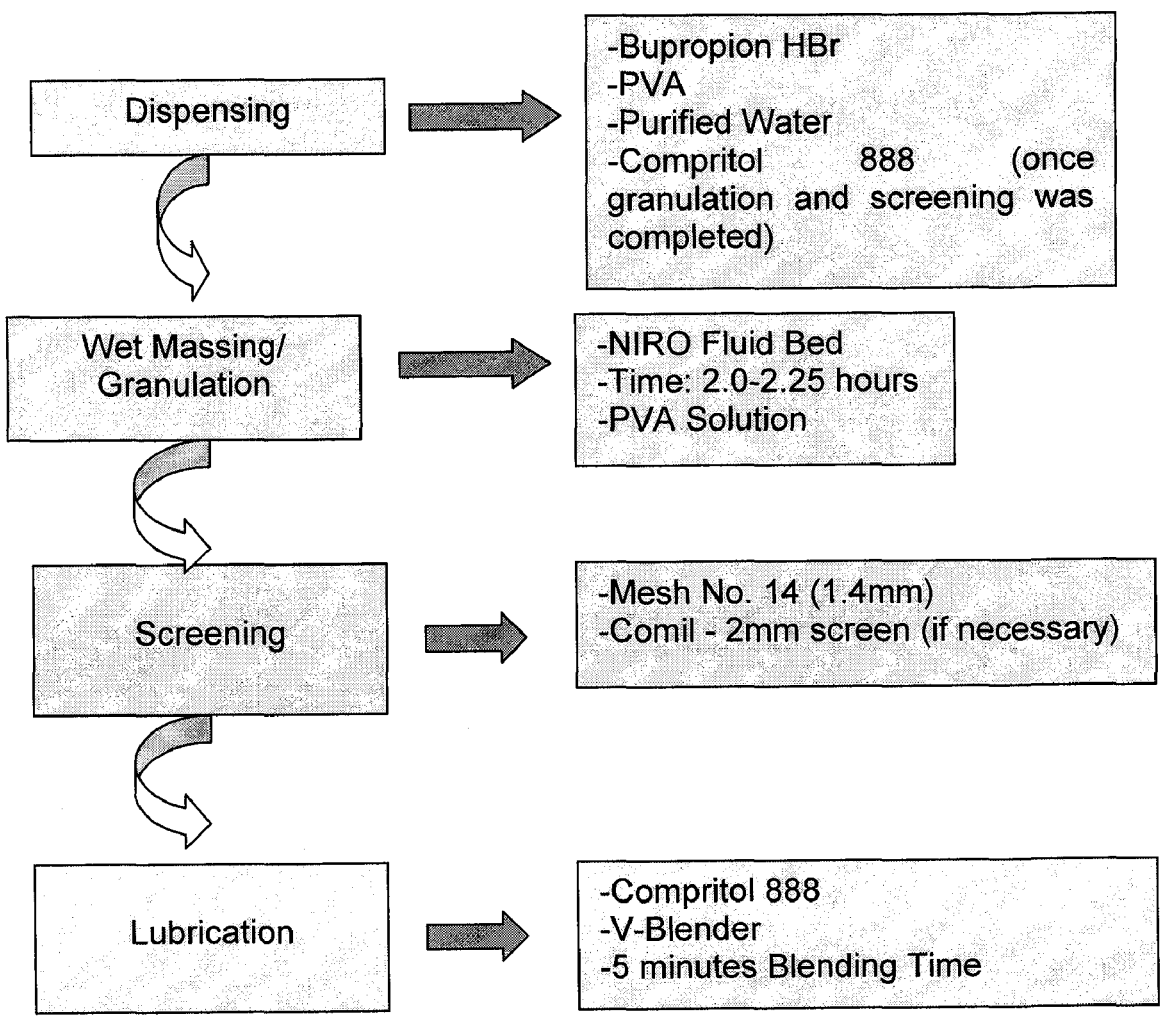
FIG. 2 is a flow chart demonstrating the granulation process of the bupropion HBr XL and EA tablets.

The NIRO Fluid Bed was used to granulate the bupropion HBr Granules with the PVA solution in a process known as wet massing. FIG. 2 shows a summary of the granulation procedure.

The Bupropion HBr was loaded into the fluid bed and granulation was initiated. The specifications that were used as guidelines are listed in Table 2.

Loss on Drying was determined after each granulation using the Moisture Analyzer. A 1 g sample was taken and loaded into the moisture analyzer. The sample ran for 5 minutes at a temperature of 105° C.

Upon completion of each batch part's granulation, the five parts were combined together. They were hand screened using Mesh No. 14 (1.4 mm) and any oversized granulation was passed through the Comil fitted with a 2 mm screen.

COMPRITOL® 888 was used as a lubricant in the formulation. The screened bupropion HBr granules and the COMPRITOL® 888 were loaded into the V-blender and were blended for 5 minutes. The COMPRITOL® 888 made up 3.125% of the formulation. The final granule batch size is described in Table 3.

Bupropion HBr XL—Tabletting Process

The Beta Press was used to compress the Bupropion HBr tablets. Depending on the dose of the tablet, 174 mg or 348 mg, different tooling sets were used. The 7 mm punches were used to compress the 174 mg tablets and 9 mm and 10 mm punches were used to compress the 348 mg tablets. Tooling was polished prior to each run.

The tablet weights were determined as being 185.6 mg for the 174 mg dose tablets and 371.2 mg for the 348 mg dose tablets. These adjustments to tablet weight were made in order to compensate for the fact that bupropion HBr was being used in place of bupropion HCl.

The individual tablet weights had a control limit of ±5%, and the average tablet weight had a control limit of ±3% (using ten tablets).

A hardness tester was used to determine the load required to diametrically break the tablets (crushing strength) into two equal halves. A predetermined range set the specifications for hardness, which was 6.0-12.0 SC for both the 174 mg and 348 mg tablets.

Friability was determined using tablets that equaled a weight of 6.5 g in a friability tester for 4 minutes at 25 rpm. Tablets were de-dusted before and after testing. A weight loss of less than 0.8% was used as the criteria in order to accept or reject a batch.

Table 4 summarizes the specifications of the tablet press set-up. All the specifications were kept within the range and at the setting that was assigned, throughout all of the batches. Table 5 summarizes the specifications that were kept constant throughout the compression of all the batches.

Figure 3:
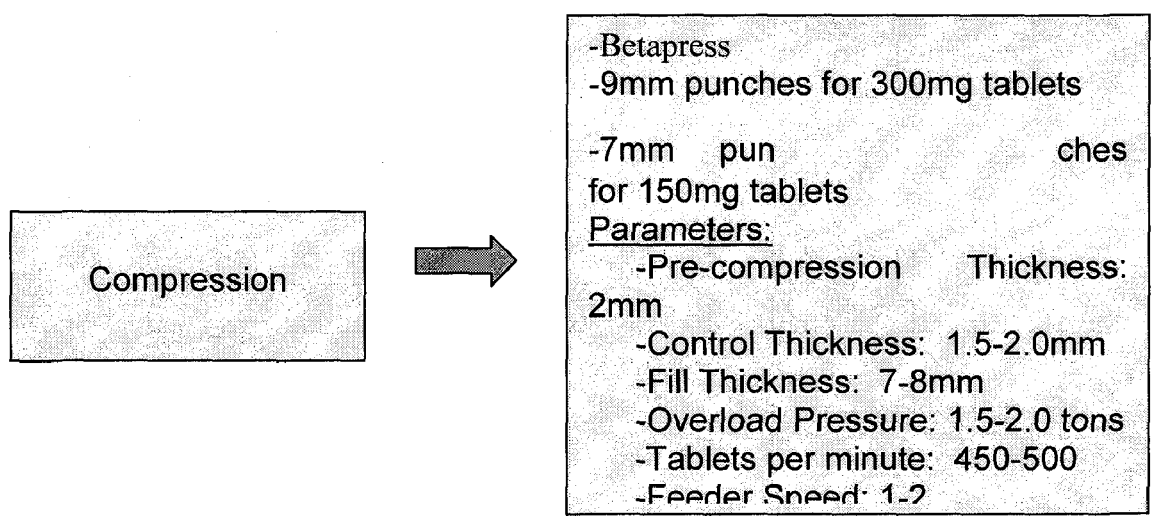
FIG. 3 is a flow chart showing the overall tabletting process of bupropion HBr XL.

The flow chart shown in FIG. 2 describes the steps that led up to and including the tabletting process. FIG. 3 shows a summary of the tabletting procedure.

Bupropion HBr XL—Coating Process

Figure 4:
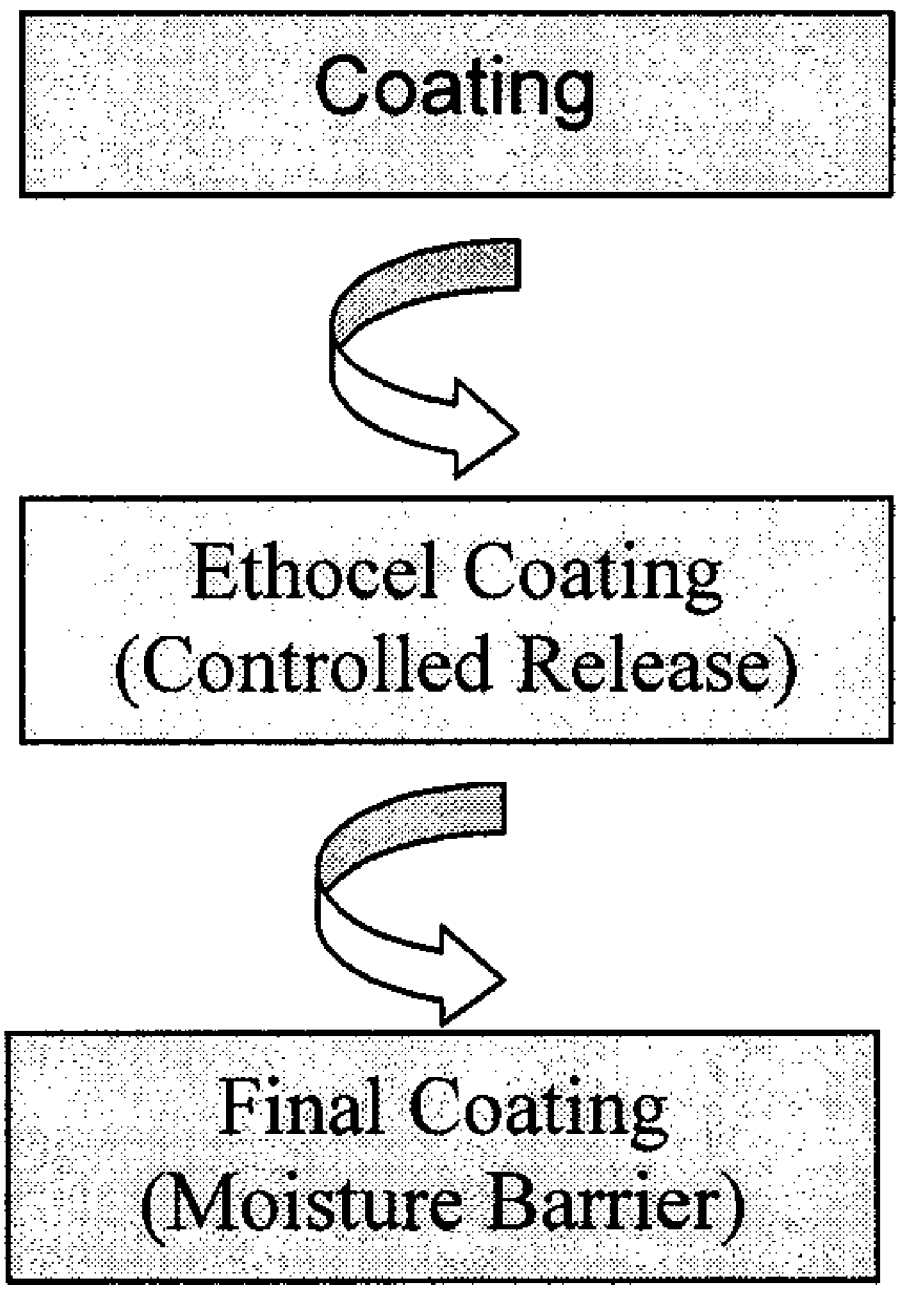
FIG. 4 is a flow chart showing the overall coating process of bupropion HBr XL.

A summary of the coating process used for the coating of the Bupropion HBr XL tablets is shown in FIG. 4. The first coat is an ethylcellulose (e.g. ETHOCEL®) coat that controls the release, which is followed by a final coat that acts as a moisture barrier.

For the ethylcellulose coating and final coating of the Bupropion HBr XL tablets, the 15 inches O'Hara Labcoat II System was used. An attached spraying nozzle and a propeller mixer were also used.

Several ethylcellulose coating solutions were developed and used to coat the Bupropion HBr tablets. The ethylcellulose coating layer was placed on the tablets containing one of the formulations listed in Table 6.

In formulation 1, ethyl Alcohol 95% and IPA 99% were combined together in a stainless steel container. While stirring, PEG 4000 was added and allowed to dissolve. Once dissolved, ethylcellulose (e.g. ETHOCEL®) was added and left to stir for 30 minutes. Then, Povidone was added to the solution and was mixed for an overnight period (15-20 hours).

In formulation 2, PEG4000 was placed into a beaker with the Dibutyl Sebacate and was stirred until it dissolved. Ethyl Alcohol 95% was added accordingly in order to allow the PEG 4000 to completely dissolve. In a separate stainless steel container, the remaining Ethyl Alcohol 95% was placed and, while being stirred, ethylcellulose was added and stirred for 30 minutes. Following that, Povidone was added and allowed to stir for an overnight period (15-20 hours).

In formulation 3, Ethyl Alcohol 95% was placed in a stainless steel container. While stirring, PEG 4000 was added and allowed to dissolve. Once dissolved, ethylcellulose was added and left to stir for 30 minutes. Then, Povidone was added to the solution and was mixed for an overnight period (15-20 hours).

Two Final coating solutions were developed and used to coat the Bupropion HBr tablets after they had been first coated with the ethylcellulose coat.

One of the following formulations shown in Table 7 was used to coat the tablets with a final coat.

In Formulation A, the purified water was placed in a glass beaker and Chroma-Tone DEB 5156-CLE was added and allowed to mix for 15 minutes. The EUDRAGIT® was passed through a Mesh screen (no. 60) prior to use. Following this, the EUDRAGIT® was added to the beaker and was stirred for 15 more minutes.

In Formulation B, part 1 of the Purified Water was placed into a glass beaker and PEG 4000 was added to it and allowed to mix until it was completely dissolved (5 minutes). The Triethyl Citrate was then added and left to mix for another 5 minutes. Once dissolved, the solution was then added to the EUDRAGIT® Suspension and left to stir for 45 minutes. The EUDRAGIT® was passed through a Mesh screen (no. 60) prior to use. In a separate beaker, part 2 of the purified water was added to the SYLOID® 244FP and mixed until it was completely dissolved (10 minutes). Finally the SYLOID® Suspension was added to the EUDRAGIT® Suspension and left to stir for another 10 minutes.

Table 8 summarizes the specifications that were monitored in the ethylcellulose coating process and their ranges.

Table 9 summarizes the specifications that were monitored in the final coating process and their ranges.

In-Vitro Studies on the Bupropion HBr Cores

Dissolution was performed on the Bupropion HBr cores, on the different weight gains of ethylcellulose coated cores and on the different weight gains of final coated tablets. USP-1 method was used to conduct these studies. The dissolution test was performed using 900 mL of 0.1N HCl and at a speed of 75 rpm. Samples were taken at every hour for 16 hours. The dissolution profiles were obtained by plotting the cumulative percent of API dissolved against sampling time points. Sink conditions were maintained throughout all the experiments.

On several trials, USP-3 method was used to conduct the dissolution studies. These dissolution tests were performed for 16 hours total with the following breakdown: 2 hours using 900 mL of Simulated Gastric Fluid (SGF) at pH 1.2 with 0.5% of Sodium Lauryl Sulfate (SLS), followed by 2 hours in 900 mL of Acetate Buffer at a pH of 4.5, followed by 12 hours in 900 mL of Phosphate Buffer Simulated Intestinal Fluid (SIF) at a pH of 6.8. These results were plotted with the in-vivo data and the Bupropion HCl data in order for a comparison to be made.

Study on Batch BUP-HBr-XL-009-5

Figure 5:
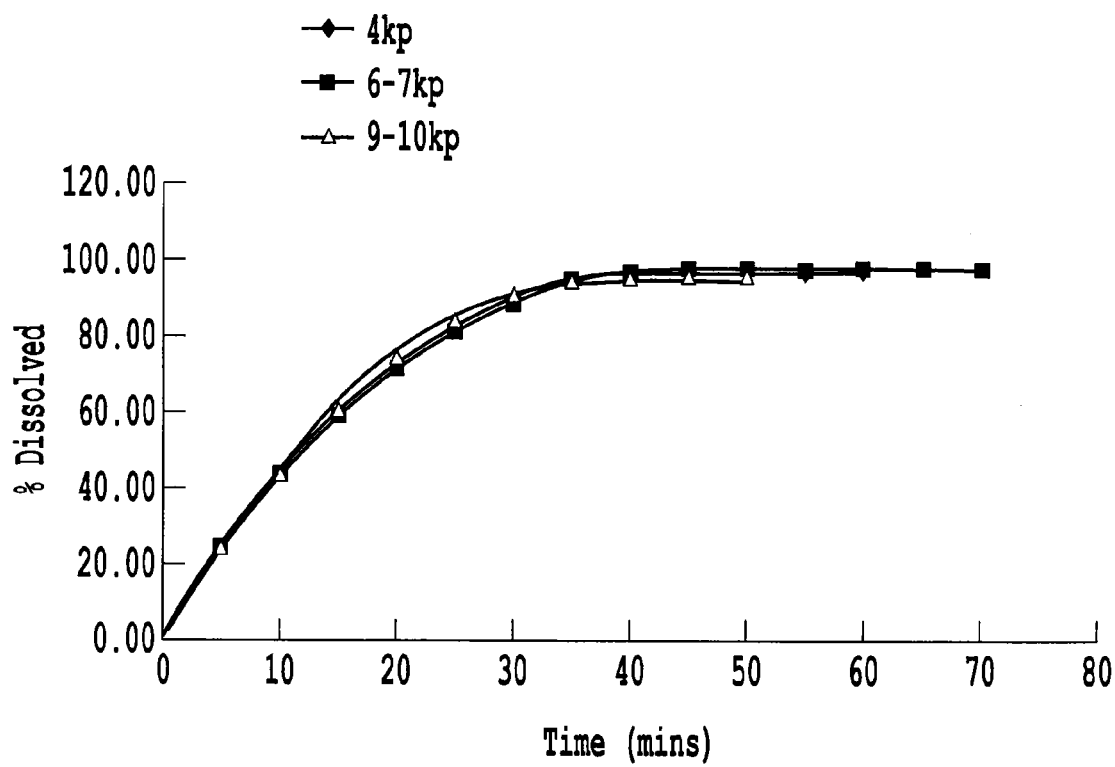
FIG. 5 is a dissolution profile of the 4 kp, 6-7 kp and 9-10 kp tablets, comparing the effects of hardness on dissolution in the study on Batch BUP-HBr-XL-009-5.
Figure 6:
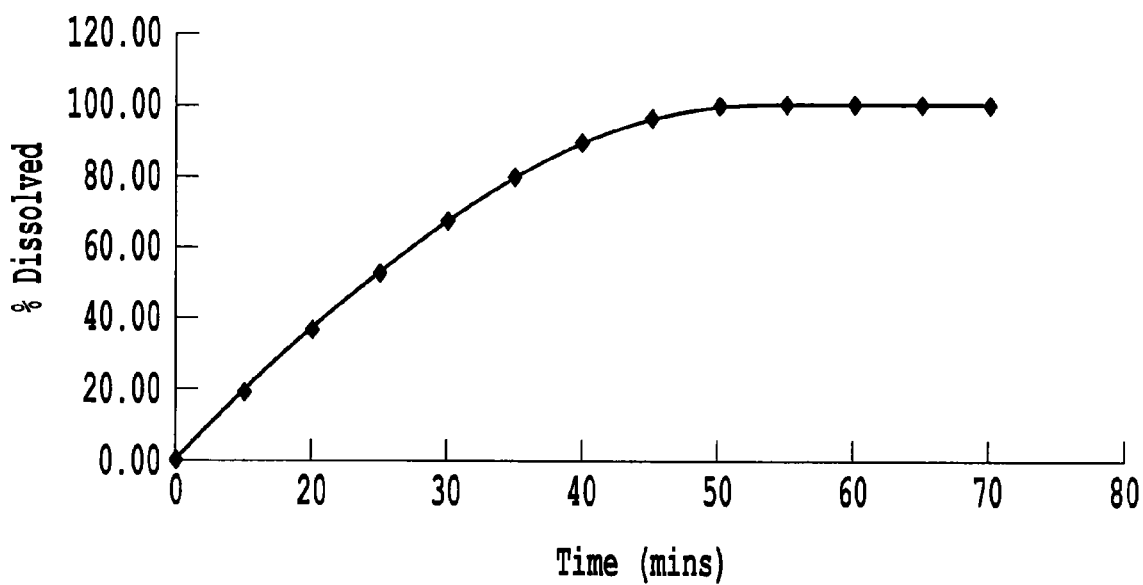
FIG. 6 is a dissolution profile of the 348 mg Bupropion HBr cores which have been compressed using 9 mm tooling in the study on Batch BUP-HBr-XL-009-5.

The formulation was granulated using NIRO Fluid Bed. After granulation was completed, the batch was screened and then prior to compression the lubricant (COMPRITOL® 888) was added. The final blend was compressed into 348 mg tablets using the Beta press with 9 mm and 10 mm standard, round, concave tooling. Table 10 describes the amounts of each material in the granulation of the 348 mg tablets. A first compression run was done to produce tablets with different hardness values so as to determine the effects of hardness, if any, on the dissolution (FIG. 5). Dissolution was conducted on the 348 mg cores in order to determine their release (FIG. 6).

The granulation results show that the average granulation time is 2.0 hours and the average LOD % is 0.345%. Tables 11 and 12 summarize the theoretical and actual values of the parameters that were monitored in the compression process using the 9 mm and 10 mm tooling, respectively.

In order to determine the tablet hardness for this study, tablets of different hardness values were compressed and dissolution was conducted on them to see the difference.

Tablets with a hardness of 4 kp, 6-7 kp and 9-10 kp were compressed and the dissolution profiles of each were shown in FIG. 5. It was observed that there was no significant difference between the three different hardness ranges.

The dissolution profiles of the 348 mg (FIG. 6) and 174 mg cores (FIG. 7) showed that the cores were releasing approximately 100 percent of API in an hour.

Figure 7:
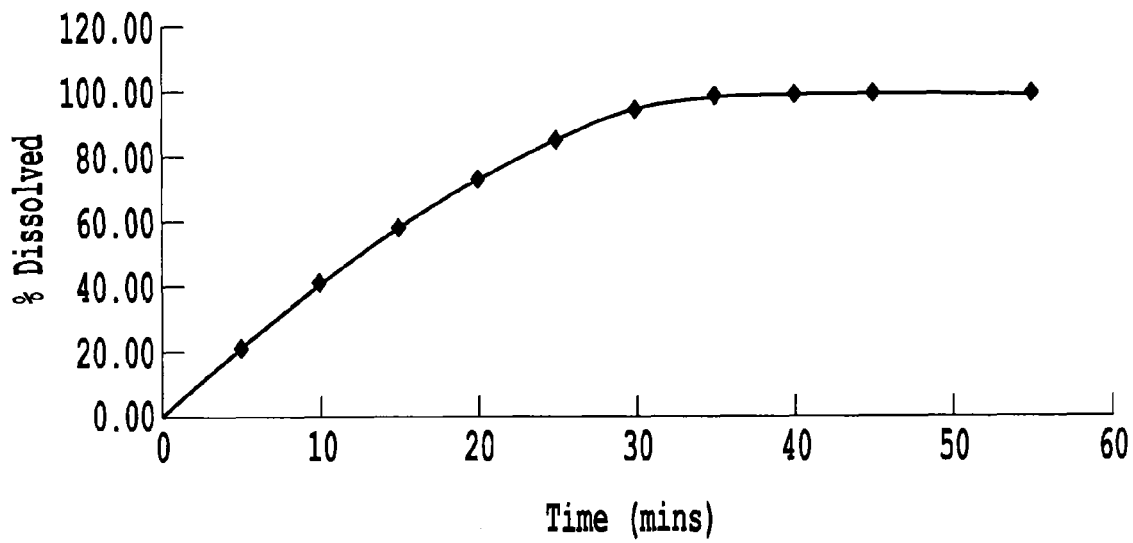
FIG. 7 is a dissolution profile of the 348 mg Bupropion HBr cores which have been compressed using 10 mm tooling in the study on Batch BUP-HBr-XL-009-5.

Dissolution of the 10 mm, 348 mg cores was done also in order to see if these tablets released faster when compared to the 9 mm cores due to their larger surface area (FIG. 7).

Figure 8:
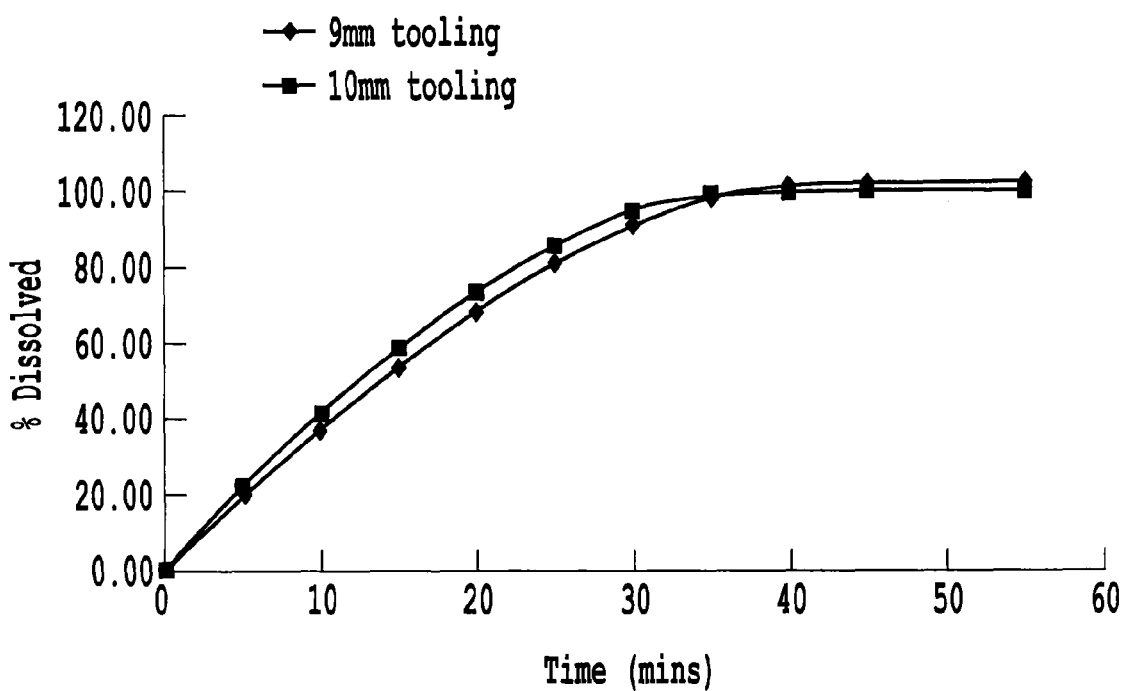
FIG. 8 is a dissolution profile comparison of the 9 mm and 10 mm diameter 348 mg Bupropion HBr cores in the study on Batch BUP-HBr-XL-009-5.

When the dissolution results of the 9 mm and 10 mm cores were compared (FIG. 8), the 10 mm cores showed no difference from the 9 mm cores. Thus, the 10 mm cores were no longer manufactured or used in this study.

Study on Batch BUP-HBr-XL-021-5

Figure 9:
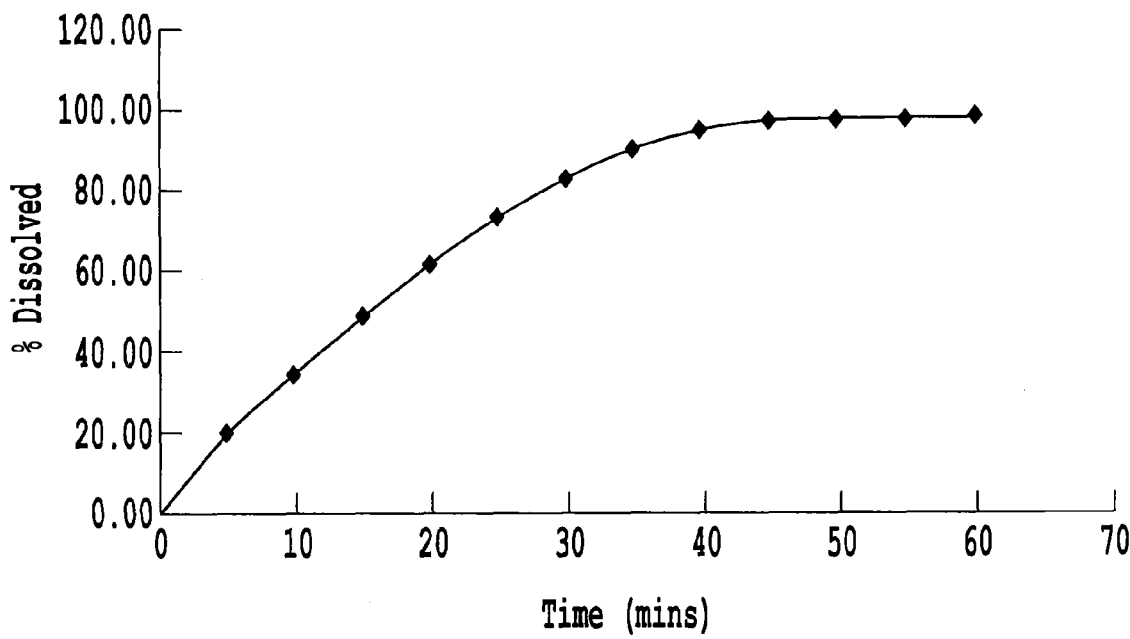
FIG. 9 is a dissolution profile of the 174 mg in the study on Batch BUP-HBr-XL-021-5.

The Formulation was granulated using NIRO Fluid Bed. The final blend was compressed into 174 mg tablets using the Beta press with 7 mm standard, round, concave, stainless steel tooling. Table 13 describes the amounts of each material in the granulation of the 174 mg tablets. It was noted that the 348 and the 174 mg tablets had the same composition and amounts of each material; the only variation was the tablet weight, which was adjusted at the compression stage. Dissolution was conducted on the 174 mg cores in order to see their release (FIG. 9).

The granulation results show that the granulation time is 2 hours 6 minutes and the average LOD % is 0.26%. Table 14 summarizes the theoretical and actual values of the parameters that were monitored in the compression process using the 7 mm tooling.

The dissolution profile of the 174 mg (FIG. 9) showed that the cores were releasing approximately 100 percent of API in an hour.

Study on Batch BUP-HBr-XL-348 mg-013-5

Using 348 mg tablets, an ethylcellulose (e.g. ETHOCEL® or "EC") coating followed by a Final coating, were sprayed onto the tablets using the O'Hara Labcoat II Coating Equipment. The materials used in the ethylcellulose coating, their percent contribution to the total solution, the amounts of each in the batch and the percentage of the solids in the solution were all listed in Table 15.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 25 minutes to coat the tablets with a weight gain of 32 mg. Tablet weights were taken and recorded in Table 16 at 28 mg, 30 mg, 32 mg, and 34 mg weight gains.

Figure 10:
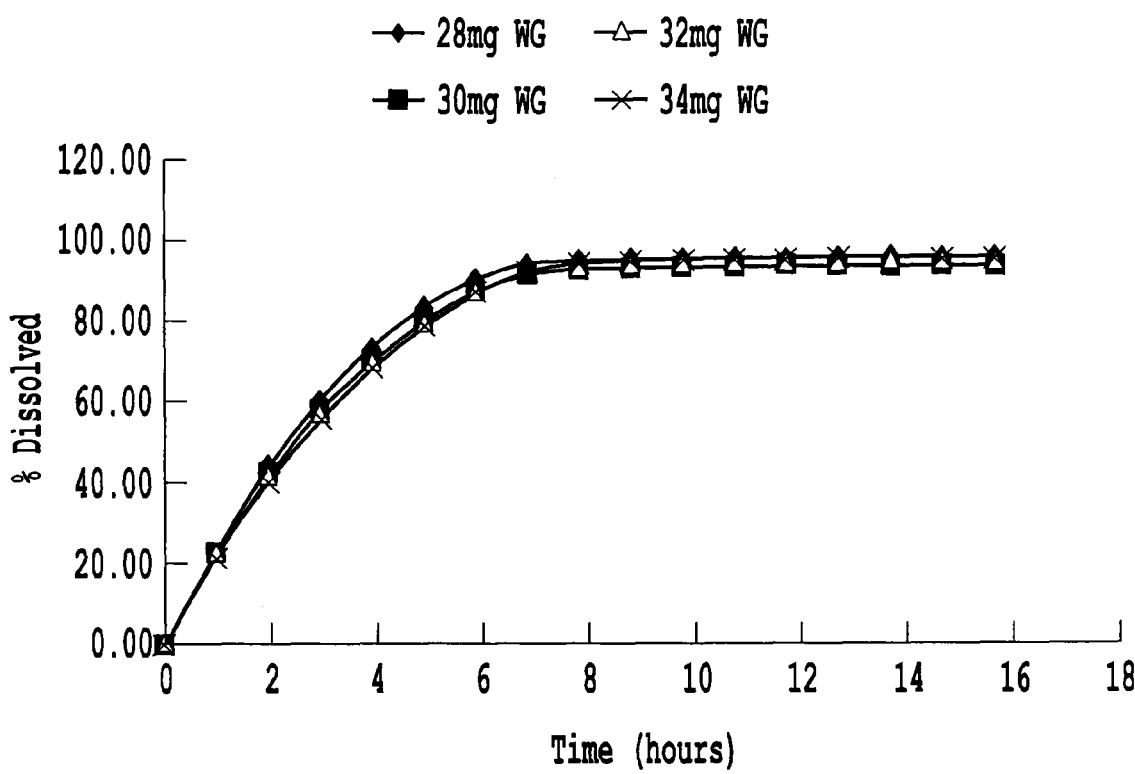
FIG. 10 is a dissolution profile of BUP-HBr-XL-348 mg-013-5 (28 mg, 30 mg, 32 mg and 34 mg weight gains).

The dissolution profile (FIG. 10) shows that the tablets with the 34 mg weight gain of ethylcellulose coating released Bupropion HBr the slowest when compared to the others and that the tablets with the 28 mg weight gain released Bupropion HBr the fastest when compared to the other weight gains.

The materials used in the final coating, their percent contribution to the total solution, the amounts of each in the batch, the amount of solid contribution in grams and the percentage of the solids in the solution were all listed in Table 17.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

After this trial run, Chroma-Tone was no longer used due to the formulation problems it caused. First, it limited the composition of the formulation due to its inflexibility, as SYLOID®, PEG and Triethyl Citrate ratios could not be varied. Second, the solution foamed and coagulated, which in turn caused the process for making the coating solution to be changed from the original so that it did not re-coagulate. Chroma-Tone can, however, still be considered an option for the formulation but different grades and mixtures would need to be used and made in order to accommodate the Bupropion HBr XL tablets.

It took 31 minutes to add a 7 mg weight gain of the final coating solution to the tablets. Tablet weights were taken and recorded in Table 18 at 4 mg, 5 mg, 6 mg and 7 mg weight gains.

Figure 11:
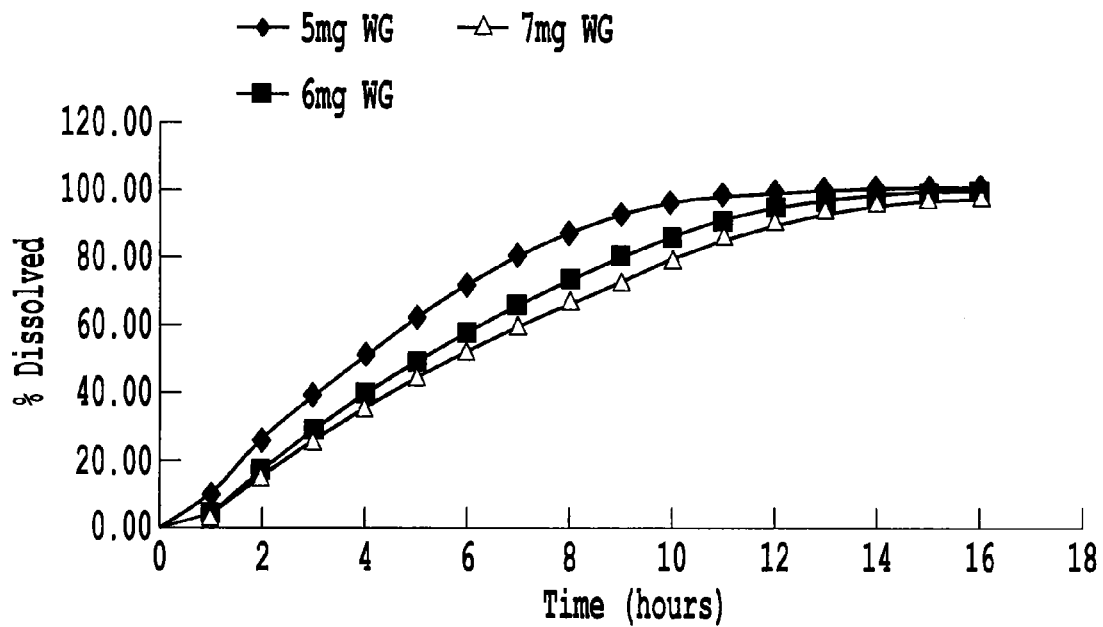
FIG. 11 is a dissolution profile of BUP-HBr-XL-348 mg-013-5 (5 mg, 6 mg, and 7 mg weight gains).

The dissolution profile (FIG. 11) shows that the tablets with the 7 mg weight gain of Final coating released the slowest when compared to the other two weight gains (5 mg and 6 mg weight gains).

Study on Batch BUP-HBr-XL-348 mg-018-5

Using 348 mg tablets, an ethylcellulose coating followed by a final coating, were sprayed onto the tablets using the O'Hara Labcoat II Coating Equipment.

The materials used in the ethylcellulose (e.g. ETHOCEL®) coating, their percent contribution to the total solution, the amounts of each in the batch and the percentage of the solids in the solution were all listed in Table 19.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

The coating process of this trial took 2 hours and 13 minutes to obtain a 32 mg weight gain. Tablet weights were taken and recorded in Table 20 at 26 mg, 28 mg, 30 mg, and 32 mg weight gains.

Figure 12:
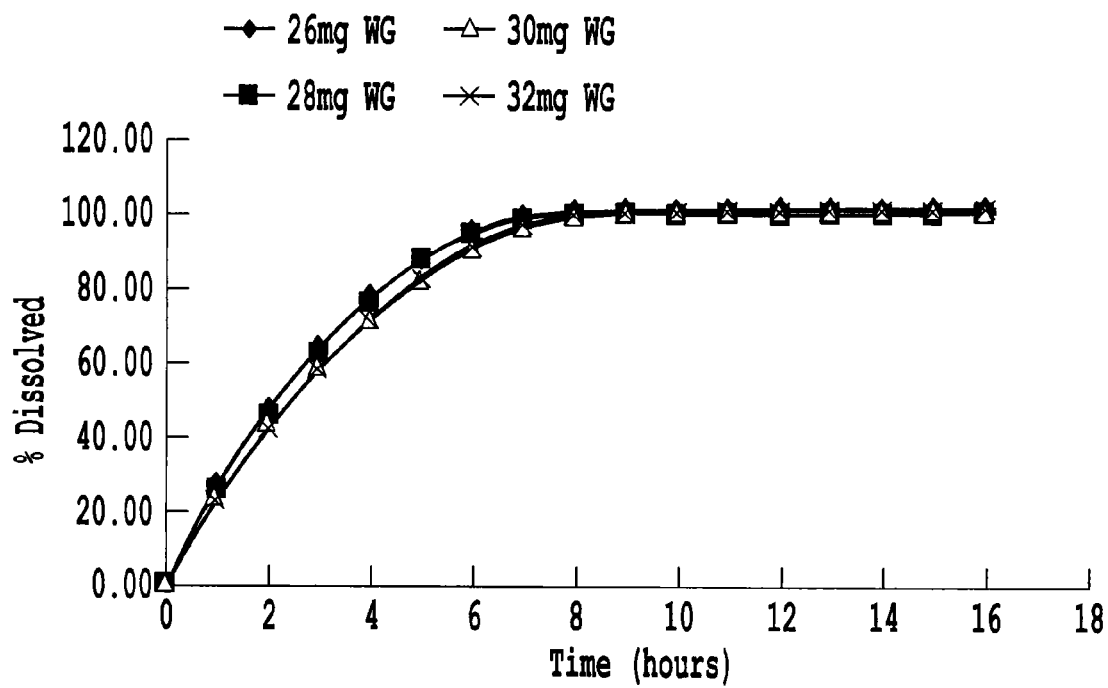
FIG. 12 is a dissolution profile of BUP-HBr-XL-348 mg-018-5 (26 mg, 28 mg, 30 mg and 32 mg weight gains).

FIG. 12 shows that the tablets with the 30 mg and 32 mg weight gain of ethylcellulose coating solution released at almost the same rate. The tablets with the 32 mg weight gain released slower than the tablets with the 30 mg weight gain in the first 5 hours of dissolution. After 6 hours, the tablets with the 32 mg weight gain released slightly faster than those with a 30 mg weight gain. The f2 similarity factor confirmed that the release rate of both weight gains was similar (91.32%).

The materials used in the final coating, their percent contribution to the total solution, the amounts of each in the batch, the amount of solid contribution in grams and the percentage of the solids in the solution were all listed in Table 21.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

It took 41 minutes to add a 7 mg weight gain of the final coating solution to the tablets. Tablet weights were taken and recorded in Table 22 at 4 mg, 5 mg, 6 mg, and 7 mg weight gains.

Figure 13:
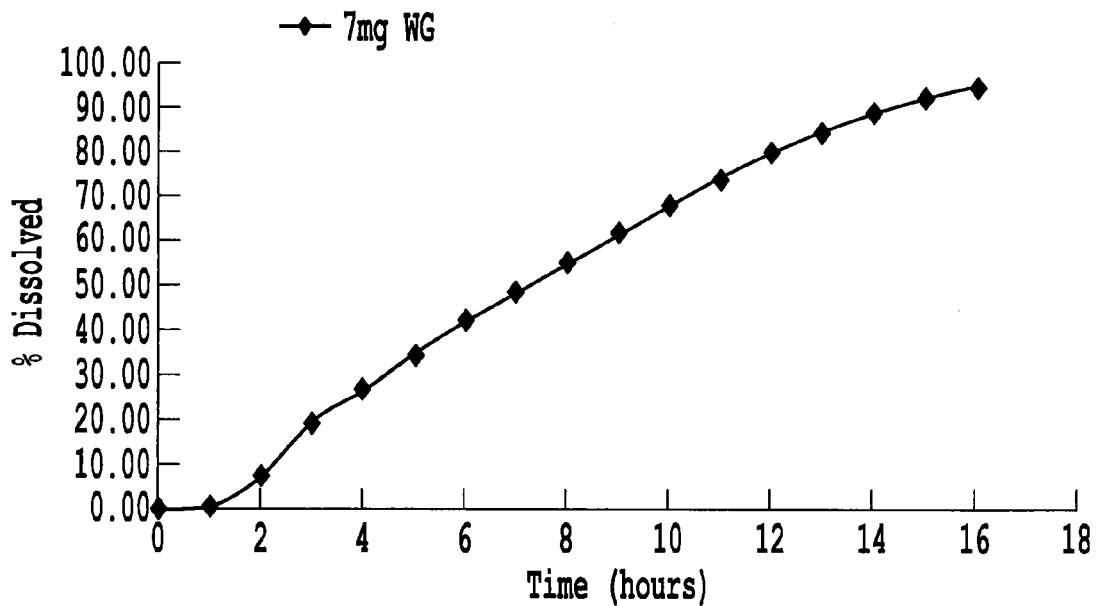
FIG. 13 is a dissolution profile of BUP-HBr-XL-348 mg-018-5 (7 mg weight gain).

FIG. 13 shows the release profile of the tablets with the 7 mg weight gain of Final coating.

Study on Batch BUP-HBr-XL-174 mg-022-5

Using 174 mg tablets, an ethylcellulose coating followed by a final coating, were sprayed onto the tablets using the O'Hara Labcoat II Coating Equipment.

The materials used in the ethylcellulose (e.g. ETHOCEL®) coating, their percent contribution to the total solution, the amounts of each in the batch and the percentage of the solids in the solution were all listed in Table 23.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 4 hours and 30 minutes to add a 30 mg weight gain of the ethylcellulose coating solution to the tablets. Tablet weights were taken at 20 mg, 22 mg, 24 mg, 26 mg, 28 mg, 29 mg, and 30 mg weight gains and were recorded in Table 24.

Figure 14:
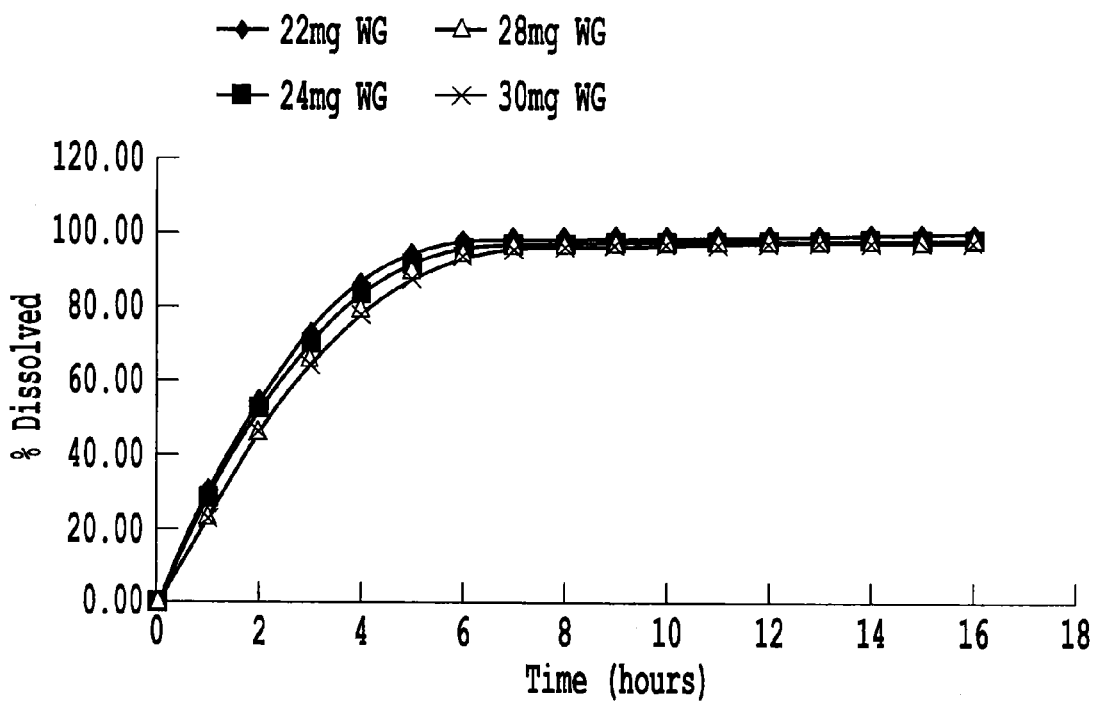
FIG. 14 is a dissolution profile of BUP-HBr-XL-174 mg-022-5 (22 mg, 24 mg, 28 mg and 30 mg weight gains).

FIG. 14 shows the % dissolved of each of the samples with different weight gains of ethylcellulose coating (22 mg, 24 mg, 28 mg and 30 mg weight gains). From the graph, it was evident that the tablets with the 30 mg weight gain of ethylcellulose coating released slower than the other weight gains. When the release rates of the tablets with the 30 mg and the 28 mg weight gains were compared, there was only a slight difference noticed in the release. The f2 similarity factor confirmed the similarity of the two releases (92.34%).

The materials used in the final coating, their percent contribution to the total solution, the amounts of each in the batch, the amount of solid contribution in grams and the percentage of the solids in the solution were all listed in Table 25.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

It took 1 hour and 26 minutes to add a 7 mg weight gain of the final coating solution to the tablets. Tablet weights were taken and recorded in Table 26 at 4 mg, 5 mg, 6 mg, and 7 mg weight gains.

Figure 15:
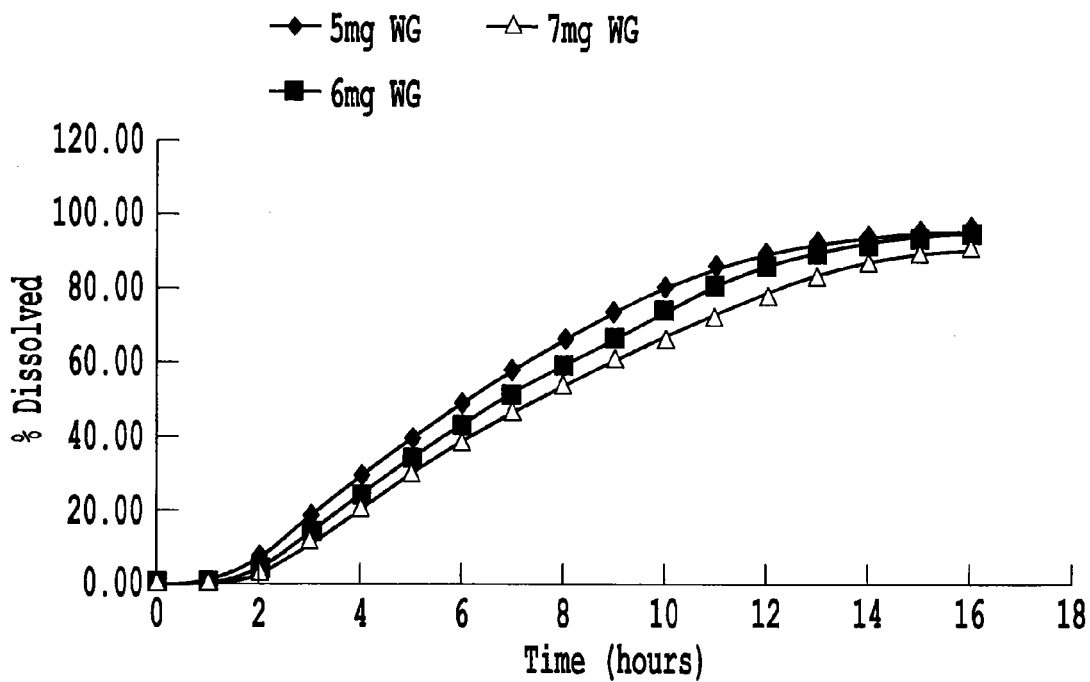
FIG. 15 is a dissolution profile of BUP-HBr-XL-174 mg-022-5 (5 mg, 6 mg, and 7 mg weight gains).

The dissolution profile (FIG. 15) shows that the tablets with the 7 mg weight gain of final coating released the slowest, in comparison to the 5 mg and the 6 mg weight gains.

Study on Batch BUP-HBr-XL-348 mg-023-5

Using 348 mg tablets, an ethylcellulose coating was sprayed onto the tablets using the O'Hara Labcoat II Coating Equipment.

The materials used in the ethylcellulose (e.g. ETHOCEL®) coating, their percent contribution to the total solution, the amounts of each in the batch and the percentage of the solids in the solution were all listed in Table 27.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 16 minutes to add a 32 mg weight gain of the ethylcellulose coating solution to the tablets. Tablet weights were taken at 26 mg, 28 mg, 30 mg, and 32 mg weight gains and were recorded in Table 28.

Figure 16:
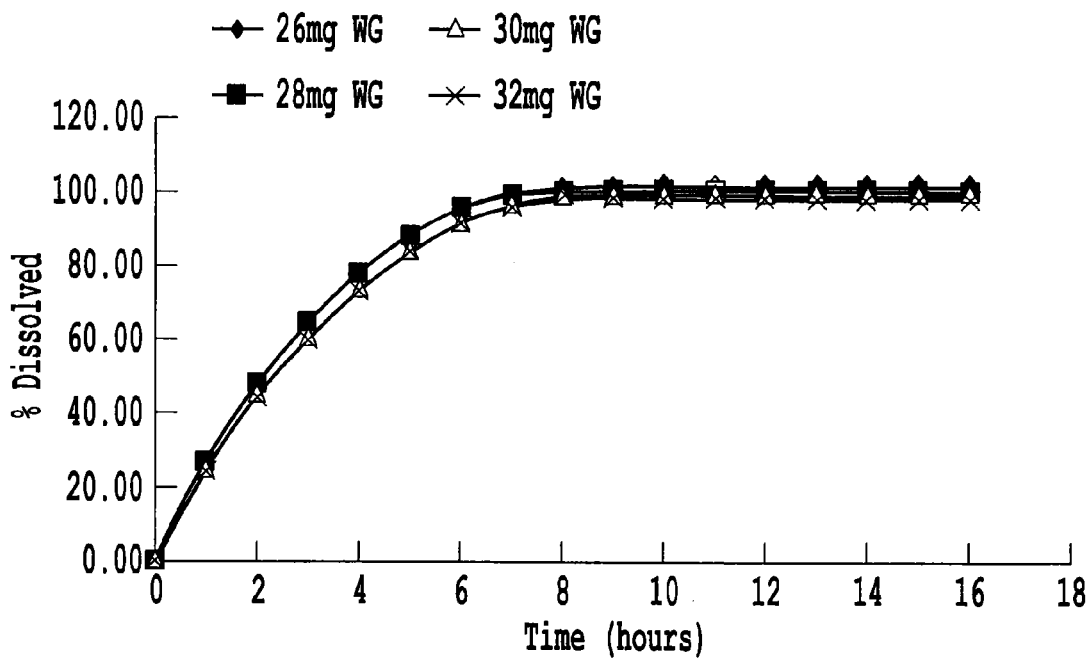
FIG. 16 is a dissolution profile of BUP-HBr-XL-348 mg-023-5 (26 mg, 28 mg, 30 mg and 32 mg weight gains).

The dissolution profile (FIG. 16) shows that the tablets with the 32 mg weight gain of ethylcellulose coating, when compared to the tablets with the 26 mg, 28 mg and the 30 mg weight gain of ethylcellulose coating, released at the slowest rate.

Study on Batch BUP-HBr-XL-348 mg-025-5

Using 348 mg tablets, an ethylcellulose coating followed by a final coating, were sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 29.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 13 minutes to add a 32 mg weight gain of the ethylcellulose coating solution to the tablets. Tablet weights were taken at 26 mg, 28 mg, 30 mg, and 32 mg weight gains and were recorded in Table 30.

Figure 17:
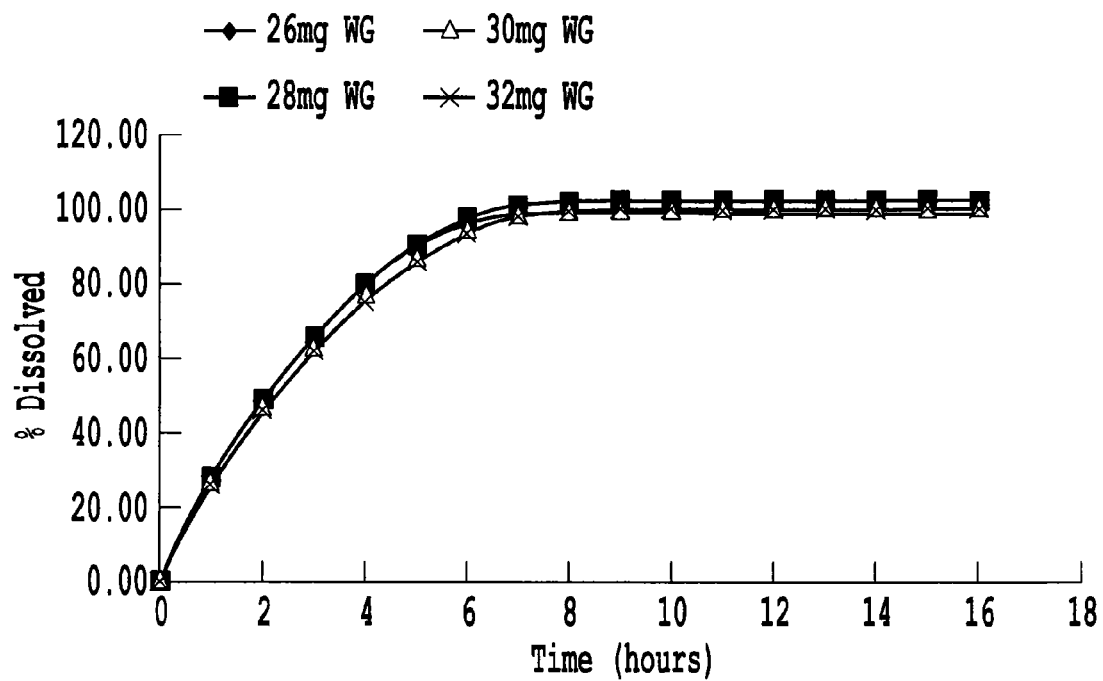
FIG. 17 is a dissolution profile of BUP-HBr-XL-348 mg-025-5 (26 mg, 28 mg, 30 mg, and 32 mg weight gains).

The dissolution profile (FIG. 17) shows that the tablets with the 32 mg weight gain of ethylcellulose coating when compared to those with 26 mg weight gain released slower in the beginning and then faster after 7 hours. When comparing the tablets with 32 mg weight gain of ethylcellulose coating to those with 30 mg weight gain of ethylcellulose coating, the tablets with the 32 mg weight gain released slower up until 10 hours. The f2 similarity factor showed that the release of the tablets with the 30 mg and 32 mg weight gains were in fact similar (93.72%).

The materials used in the final coating, their percent contribution to the total solution, the amounts of each in the batch, the amount of solid contribution in grams and the percentage of the solids in the solution were all listed in Table 31.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

The coating solution was altered for this batch by changing the percentage of solid from each of the solid components in the solution. The percentage of EUDRAGIT® solid contribution was decreased from 65% to 56.5%. The percentage of SYLOID®, CARBOWAX® and Triethyl Citrate were increased from 25%, 6.65% and 3.39% to 30%, 9% and 4.5%, respectively.

Figure 18:
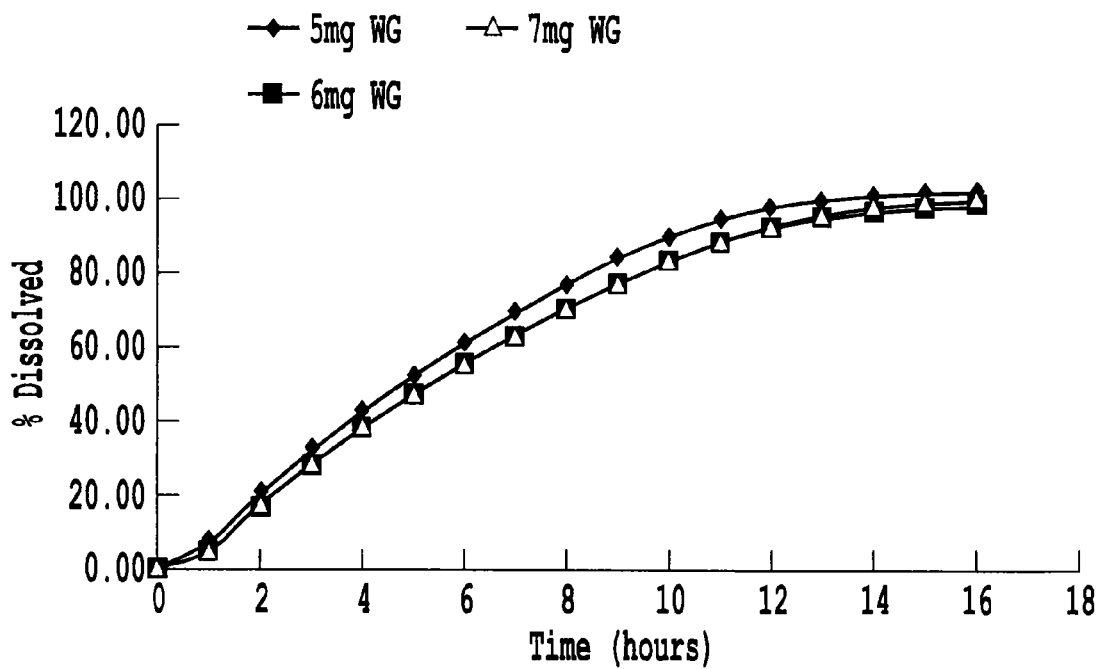
FIG. 18 is a dissolution profile of BUP-HBr-XL-348 mg-025-5 (5 mg, 6 mg, and 7 mg weight gains).

It took 40 minutes to add a 7 mg weight gain of the final coating solution to the tablets. Tablet weights were taken and recorded (Table 32) at 4 mg, 5 mg, 6 mg, and 7 mg weight gains. The dissolution profile (FIG. 18) shows that the tablets with the 7 mg weight gains released the slowest of the three samples tested. However, f2 calculation showed that the tablets with the 6 mg weight gain released similarly to those with the 7 mg weight gain of Final coating (93.33%).

Study on Batch BUP-HBr-XL-348 mg-026-5

Using 348 mg tablets, an ethylcellulose coating was sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 33.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 11 minutes to add a 32 mg weight gain of the ethylcellulose coating solution to the tablets. Tablet weights were taken at 26 mg, 28 mg, 30 mg, and 32 mg weight gains and were recorded in Table 34.

Figure 19:
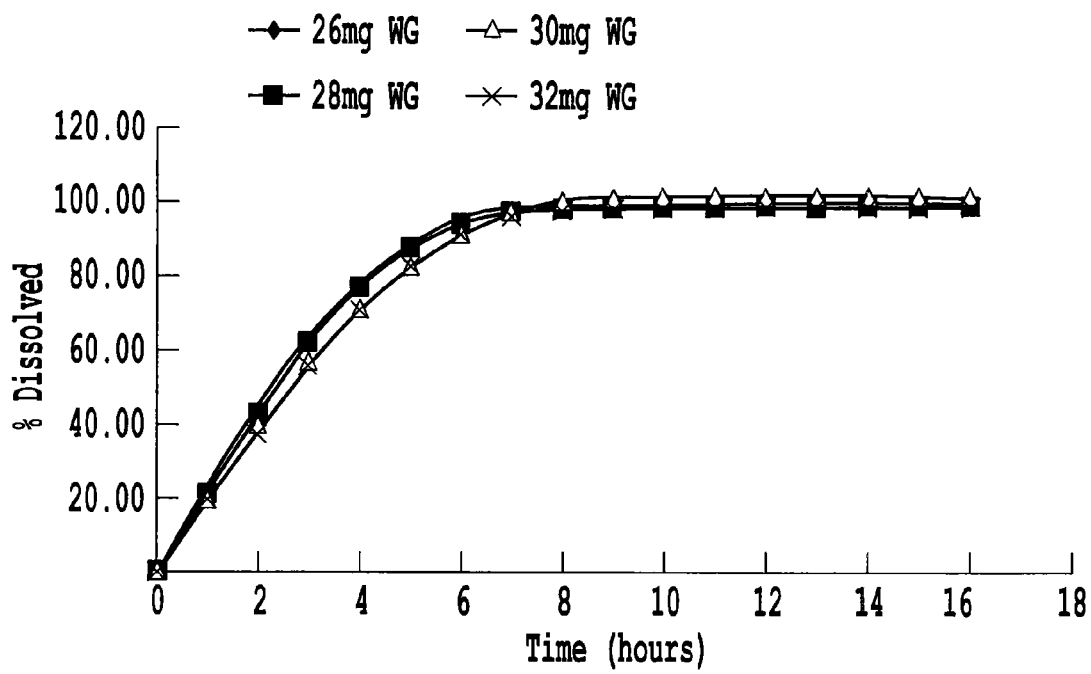
FIG. 19 is a dissolution profile of BUP-HBr-XL-348 mg-026-5 (26 mg, 28 mg, 30 mg, and 32 mg weight gains).

The dissolution profile (FIG. 19) shows that the tablets with the 32 mg weight gain of ethylcellulose coating released the slowest when compared to the other three samples with lower weight gains of ethylcellulose coating (26 mg, 28 mg and 30 mg).

Study on Batch BUP-HBr-XL-174 mg-027-5

Using 174 mg tablets, an ethylcellulose coating followed by a final coating, were sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 35.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 3 hours and 29 minutes to add a 32 mg weight gain of the ethylcellulose coating solution to the tablets. Tablet weights were taken at 22 mg, 24 mg, and 26 mg weight gains and were recorded in Table 36.

Figure 20:
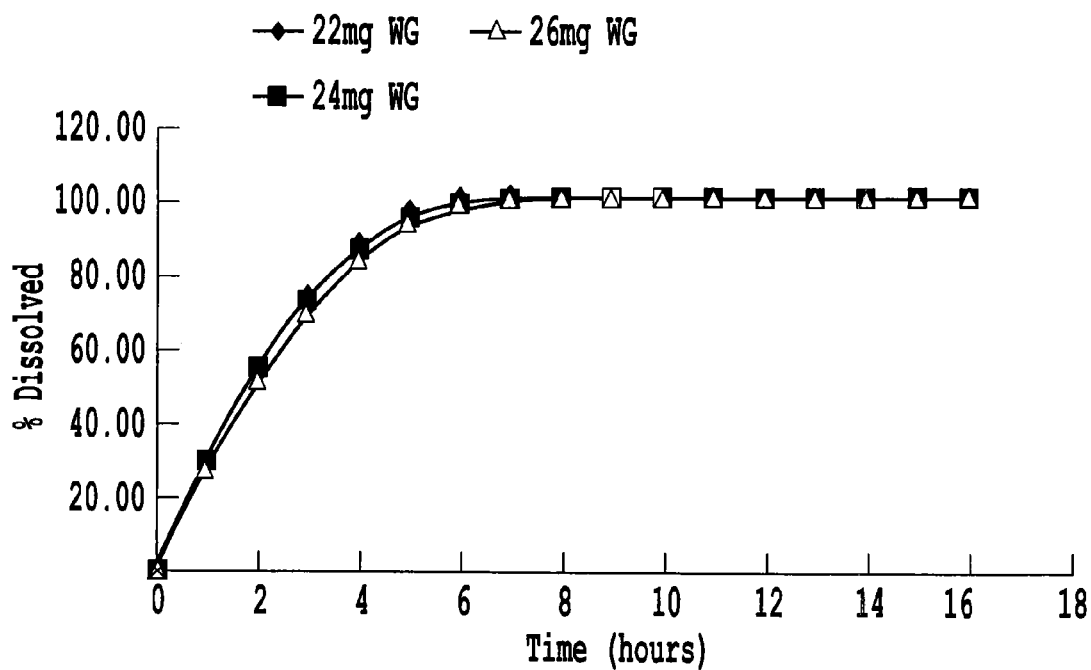
FIG. 20 is a dissolution profile of BUP-HBr-XL-174 mg-027-5 (22 mg, 24 mg, and 26 mg weight gains).

The dissolution profile (FIG. 20) shows that the tablets with the 26 mg weight gain of ethylcellulose coating released the slowest of the three samples tested.

The materials used in the final coating, their percent contribution to the total solution, the amounts in each in the batch, the amount of solid contribution in grams and the percentage of the solids in the solution were all listed in Table 37.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

It took 1 hour and 17 minutes to add a 7 mg weight gain of the final coating solution to the tablets. Tablet weights were taken and recorded in Table 38 at 4 mg, 5 mg, 6 mg, and 7 mg weight gains.

Figure 21:
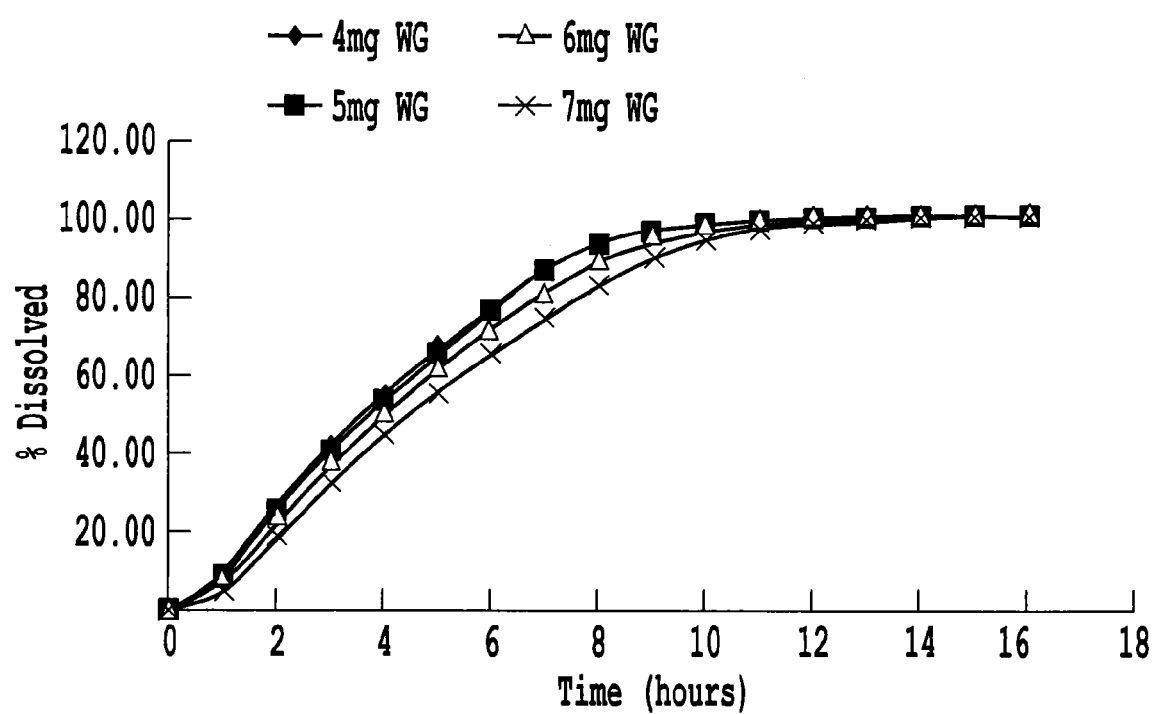
FIG. 21 is a dissolution profile of BUP-HBr-XL-174 mg-027-5 (4 mg, 5 mg, 6 mg, and 7 mg weight gains).

The dissolution profile (FIG. 21) shows that the tablets with the 7 mg weight gain of final coating initially released slower that the tablets with 4 mg, 5 mg and 6 mg weight gains. However, at approximately 12 hours, all 4 samples were releasing similarly.

Example 3

Preparation and Stability Study of Bupropion Hbr Polymorphs I, II and III Bupropion Hydrobromide Polymorphic Forms I, II and III were Prepared in the Following Manner and Their Stability was Studied Under the Conditions Described Below Form I:

A 250 ml flask equipped with overhead stirrer and gas inlet was charged with 34 g of bupropion base and 138 ml of isopropanol. The solution was maintained under stirring while 13 g of gaseous HBr was introduced through the gas inlet in a time of 20' while the internal temperature of the mixture raises from 25° C. to 40° C. During the gas addition a heavy white precipitate formed. At the end of the gas addition the temperature of the mixture was raised to reflux (80° C.), to get complete solution of the suspended solid. The temperature was then lowered to 25° C. in 1 hour and further lowered to 0-5° C. in 1 additional hour. The precipitate obtained was filtered and washed with 20 ml of cold isopropanol. The discharged wet solid was dried under vacuum (30 mmHg) in a static drier at 50° C. for 16 hours. 34 g of bupropion hydrobromide form I were obtained.

Samples of bupropion hydrobromide form I were subjected to the conditions for the accelerated stability study and the shelf life stability study as described for example in U.S. Pat. No. 7,241,805 (eg. see examples 10 and 11), the contents of which are incorporated herein by reference. PXRD studies carried out after 3 months and 6 months for each sample gave the same results. The PXRD profile of one of the samples of form I after 6 months in the accelerated stability condition is provided in FIG. 24.

Form II:

10 g of bupropion hydrobromide form I were dissolved in a mixture of 170 ml of acetone and 7 ml of water. The mixture was brought to reflux with dissolution of the solid. The solution was then cooled to room temperature. After one night the precipitate formed was filtered and dried at 40° C. under vacuum (30 mmHg) for 12 hours. 2.4 g of bupropion hydrobromide form II were obtained. A sample of the product was prepared for an accelerated stability test, in ICH (International Conference on Harmonisation of Technical Requirements for Registration of Pharmaceuticals for Human Use) conditions (40° C./75% R.H.), by sealing the product in polyethylene bags, which in turn were placed in aluminium bags containing silica and sealed and placed in the stability chamber in ICH conditions (40° C./75% R.H.). The crystalline form was checked after maintaining the product under these conditions for 1 month. The PXRD profile shown in FIG. 27 shows that the compound is still in form II. This demonstrates the stability of crystal form II under these conditions.

Form III:

20 g of bupropion hydrobromide form 1 and 96 ml of absolute ethanol were placed in a 250 ml flask. The mixture was brought to reflux obtaining complete dissolution of the solid. The solution was then cooled to room temperature without stirring and left in these conditions for 18 hours. The resulting crystalline solid was then filtered and dried under vacuum (30 mmHg) at 50° C. for 4 hours. 11.2 g of bupropion hydrobromide form III were obtained. A sample of the product was prepared for stability testing by sealing the product in polyethylene bags, which in turn were placed in aluminium bags containing silica and sealed, and placed in the stability chamber in ICH conditions (40° C./75% R.H.). The crystalline form was checked after maintaining the product in these conditions for 1 month. The PXRD profile shown in FIG. 30 demonstrates that the product is not stable in this form under these conditions, as the majority of the product changed to form II.

Example 4

Preparation of Bupropion Hbr Polymorphs Iv, V, VI and VII, and Amorphous Bupropion HBr Bupropion hydrobromide polymorphic forms IV, V, VI and VII and amorphous form were prepared in the following manner:

Form IV:

50 mg of bupropion hydrobromide form I is dissolved in 4 ml of chloroform, with stirring, and filtered on a Whatman filter (0.45 micron). The solution obtained is left to evaporate at room temperature until the solvent has evaporated completely. In this way we obtain a wet solid crystalline residue comprising bupropion hydrobromide in form IV. The PXRD, DSC, TGA and IR profiles of this crystalline form are shown respectively in FIGS. 31, 32, 33 and 34. The sample is then dried to constant weight and the PXRD, DSC, TGA and IR analyses are repeated, obtaining profiles identical to those obtained on the sample prior to drying.

Form V:

100 mg of bupropion hydrobromide form I is suspended in 2 ml of 1,4-dioxan and stirred at room temperature for seven days. The suspension obtained is then filtered on Whatman filter paper and discharged wet from the filter. In this way we obtain a wet crystalline solid residue comprising bupropion hydrobromide in form V. The PXRD, DSC, TGA and IR profiles of this crystalline form are shown respectively in FIGS. 35, 36, 37 and 38. The sample is then dried to constant weight and the PXRD, DSC, TGA and IR analyses are repeated, obtaining profiles identical to those obtained on the sample prior to drying.

In another preparation of form V, a mixture of 50 mg of bupropion hydrobromide form 1 and 50 mg of bupropion hydrobromide form II is suspended in 2 ml of 1,4-dioxan and stirred at room temperature for seven days. The suspension obtained is then filtered on Whatman filter paper and discharged wet from the filter. In this way we obtain a wet crystalline solid residue comprising bupropion hydrobromide in form V. The PXRD, DSC, TGA and IR profiles of the wet product and product after drying are identical to those shown respectively in FIGS. 35, 36, 37 and 38.

Form VI:

2 g of bupropion hydrobromide form I is suspended in 15 ml of 1-propanol and refluxed, observing dissolution of the solid. The solution obtained is then cooled at a rate of 0.45° C./min to a temperature of 20° C. The solid obtained is then filtered, obtaining bupropion hydrobromide form VI. The PXRD, DSC, TGA and IR profiles of this crystalline form are shown respectively in FIGS. 39, 40, 41 and 42. The sample is then dried to constant weight and the PXRD, DSC, TGA and IR analyses are repeated, obtaining profiles identical to those obtained on the sample prior to drying.
Form VII:

50 mg of bupropion hydrobromide form I is dissolved in 4 ml of dimethylformamide (DMF), with stirring, and is filtered on a Whatman filter (0.45 micron). The solution obtained is left to evaporate at 60° C. until the solvent has evaporated completely. As a result, we obtain a wet solid crystalline residue comprising bupropion hydrobromide in form VII. The PXRD, DSC, TGA and IR profiles of this crystalline form are shown in FIGS. 43, 44, 45 and 46 respectively. The sample is then dried to constant weight and the PXRD, DSC, TGA and IR analyses are repeated, obtaining profiles identical to those obtained on the sample before drying.
Amorphous Form:

5 g of bupropion hydrobromide form I is dissolved at room temperature in 195 ml of deionized water. The solution is loaded in a 1-liter flask and frozen by immersion of the flask in rotation in a rotary evaporator, on a bath of isopropanol and dry ice maintained at a temperature of −50° C. The freezing process is continued for two hours, then the flask is mounted in lyophilization apparatus and submitted to lyophilization in the following conditions:

Apparatus: CHRIST Alpha 1-4 LSC
Coil conditioning temperature: −30° C.
Pump conditioning pressure: atmospheric.
Condenser temperature during drying: −50° C.
Residual pressure during drying: 0.02 mbar
Drying time: 18 hours.

At the end of the process, a solid is discharged from the flask and is analyzed by X-ray diffraction. The profile obtained is shown in FIG. 47; it is the typical PXRD profile of an amorphous solid.

In another preparation of bupropion hydrobromide in amorphous form, a sample of bupropion hydrobromide form I is dissolved in 4 ml of p-xylene, with stirring. After about one hour in these conditions, the solution is filtered on Whatman paper (0.45 micron) and the solution obtained is left to evaporate until the solvent has been removed. The resultant solid is analyzed by PXRD, giving the profile shown in FIG. 48. It can be seen from the PXRD profile that the product is obtained in amorphous form.

Example 5

Polymorph Screening

Solvent Screening:
We analyzed the powder sample obtained by recrystallization from different solvents chosen on the basis of the following parameters: (i) dielectric constants; (ii) boiling point (BP); (iii) melting point (MP); and (iv) solubility of sample. See Table 40 for solvents used during the experiments.
Qualitative Solubility Screening:
Bupropion hydrobromide (50 mg) was introduced in 4 mL of solvent under stirring for about 1 hour at room temperature. See Table 41 for the qualitative solubility data.
Room Temperature Recrystallization:
Bupropion hydrobromide (50 mg) was dissolved in 4 mL of solvent under stirring, after about 1 hour the solution was filtered with a Whatman filter (0.45 µm) and left to evaporate at room temperature (RT). The solutions were evaporated at RT for 3 days, in some cases for 1 week. Four different crystal forms were identified: Form I, Form IV, Form VII and an amorphous phase. See Table 42 for the recrystallization results (experiments of evaporation of Bupropion Hydrobromide at room temperature).
Low Temperature Recrystallization:
Bupropion hydrobromide (50 mg) was dissolved in 4 mL of solvent under stirring, after about 1 hour the solution was filtered with a Whatman filter (0.45 µm) and left to evaporate at 4° C. for 1-2 weeks. See Table 43 for the recrystallization results (experiments of evaporation of bupropion hydrobromide at low temperature).
High Temperature Recrystallization:
Bupropion hydrobromide (50 mg) was dissolved in 4 mL of solvent under stirring, after about 1 hour the solution was filtered with a Whatman filter (0.45 µm) and left to evaporate at 60° C. for 2-3 days. See Table 44 for the recrystallization results (experiments of evaporation of bupropion hydrobromide at high temperature).
Low Pressure Recrystallization:
Bupropion hydrobromide (50 mg) was dissolved in 4 mL of solvent under stirring, after about 1 hour the solution was filtered with a Whatman filter (0.45 µm) and left to evaporate at low pressure for 1-2 days. See Table 45 for the recrystallization results (experiments of evaporation of bupropion hydrobromide at low pressure).

Example 6

Slurries

Slurries of Form I-7 Days
Slurry experiments of Form I were performed at room temperature to verify if Form I is the thermodynamic crystal form. 0.050 g of Form I was suspended in 2 ml of solvent and stirred for 1 week. The sample was filtered and analyzed by X-ray diffraction. In the large majority of the experiments, Form I converts into Form II. As such, Form II is the thermodynamic stable form of bupropion hydrobromide. By 1,4-Dioxane, a new crystal form was obtained named Form V. See Table 46 for the Form I slurries results (7 days).

Further slurry experiments of Form I were performed at room temperature using 0.5 g of powder in 10 mL of solvent to confirm the results obtained even in large scale. With both Ethyl Acetate and p-Xylene as solvents, Form I was found to convert into Form II.
Slurries of Form I-30 Days
0.050 g of Form I were suspended in 2 ml of solvent and stirred at room temperature for 4 weeks (30 days). The sample was filtered and analyzed by X-ray diffraction. By 1,4-Dioxane, Form V was obtained. By tetrahydrofuran, Form II and Form VII were obtained. In all other experiments, Form I converts to Form II; showing that Form II is the thermodynamic stable form of bupropion hydrobromide. See Table 47 for the Form I slurries results (30 days).
Slurries of Form I Mixed with Form II-7 Days
Slurry experiments of mixtures of Form I and Form II were performed at room temperature to verify their thermodynamic stability. 0.040 g of Form I+0.040 g of Form II were suspended in 4 ml of solvent and stirred for 1 week (7 days). The samples were filtered and analyzed by X-ray diffraction. By 1,4-Dioxane, Form V was obtained. In all other experiments, Form I converts to Form II; showing that Form II is the thermodynamic stable form of bupropion hydrobromide. See Table 48 for the Form I+Form II slurries results (7 days).
Slurries of Form II Mixed with Form III-7 Days
Slurry experiments of mixtures of Form II and Form III were performed at room temperature to verify their thermodynamic stability. 0.040 g of Form II+0.040 g of Form III were suspended in 4 ml of solvent and stirred for 1 week (7 days). The samples were filtered and analyzed by X-ray diffraction. By 1,4-Dioxane, Form V was obtained. In all other experiments, Form III converts to Form II; showing that Form II is the thermodynamic stable form of bupropion hydrobromide. See Table 49 for the Form II+Form III slurries results (7 days).

Slurries of Form II Mixed with Form IV-7 Days

Slurry experiments of mixtures of Form II and Form IV were performed at room temperature to verify their thermodynamic stability. 0.040 g of Form II+0.040 g of Form IV were suspended in 4 ml of solvent and stirred for 1 week (7 days). The samples were filtered and analyzed by X-ray diffraction. By 1,4-Dioxane, Form V was obtained. In all other experiments, Form IV converts to Form II; showing that Form II is the thermodynamic stable form of bupropion hydrobromide. See Table 50 for the Form II+Form IV slurries results (7 days).

Slurries of Form II Mixed with Form V-7 Days

Slurry experiments of mixtures of Form II and Form V were performed at room temperature to verify their thermodynamic stability. 0.040 g of Form II+0.040 g of Form V were suspended in 4 ml of solvent and stirred for 1 week (7 days). The samples were filtered and analyzed by X-ray diffraction. By 1,4-Dioxane, Form V was obtained. In all other experiments, Form V converts to Form II; showing that Form II is the thermodynamic stable form of bupropion hydrobromide. See Table 51 for the Form II+Form V slurries results (7 days).

Slurries of Form H Mixed with Form VI-7 Days

Slurry experiments of mixtures of Form II and Form VI were performed at room temperature to verify their thermodynamic stability. 0.040 g of Form II+0.040 g of Form VI were suspended in 4 ml of solvent and stirred for 1 week (7 days). The samples were filtered and analyzed by X-ray diffraction. By 1,4-Dioxane, Form V was obtained. In all other experiments, Form VI converts to Form II; showing that Form II is the thermodynamic stable form of bupropion hydrobromide. See Table 52 for the Form II+Form VI slurries results (7 days).

Slurries of Form II Mixed with Form VII-7 Days

Slurry experiments of mixtures of Form II and Form VII were performed at room temperature to verify their thermodynamic stability. 0.040 g of Form II+0.040 g of Form VII were suspended in 4 ml of solvent and stirred for 1 week (7 days). The samples were filtered and analyzed by X-ray diffraction. By 1,4-Dioxane, Form V was obtained. In all other experiments, Form VII converts to Form II; showing that Form II is the thermodynamic stable form of bupropion hydrobromide. See Table 53 for the Form II+Form VII slurries results (7 days).

Example 7

Slurries in 2-Propanol

Slurries of Form I at Room Temperature.

0.050 g of Form I were suspended in 4 ml of solvent and stirred at room temperature. for 1 week (7 days). The sample was filtered and analyzed by X-ray diffraction. By 2-propanol, Form I converted to Form II at room temperature.

Slurries of Mixture Form I and Form II at Room Temperature.

0.040 g of Form I+0.040 g of Form II were suspended in 4 ml of solvent and stirred at room temperature for 1 week (7 days). The sample was filtered and analyzed by X-ray diffraction experiments. By 2-propanol, Form I converted to Form II at room temperature. The final result was that Form II was obtained.

Slurries of Form II at Room Temperature.

0.050 g of Form II were suspended in 4 ml of solvent and stirred at room temperature for 1 week (7 days). The sample was filtered and analyzed by X-ray diffraction experiments. The final result was that by 2-propanol, Form II was obtained.

Slurries of Form I at 50° C.

0.050 g of Form I were suspended in 4 ml of solvent and stirred at 50° C. for 1 Week (7 days). The sample was filtered and analyzed by X-ray diffraction experiments. By 2-propanol, Form I converted to Form II at 50° C.

Slurries of Mixture Form I and Form II at 50° C.

0.040 g of Form I+0.040 g of Form II were suspended in 4 ml of solvent and stirred at 50° C. for 1 week (7 days). The sample was filtered and analyzed by X-ray diffraction experiments. By 2-propanol, Form I converted to Form II at 50° C. The final result was that Form II was obtained.

Slurries of Mixture Form I and Form II at 80° C.

Form I+Form II were suspended in solvent and stirred at 80° C. for 14 hours. The sample was filtered and analyzed by X-ray diffraction experiments. By 2-propanol, Form I remained as Form I, whereas Form II converted to Form I after this assay at 80° C. Slurry in 2-propanol at 80° C. is an atypical experiment because if we consider the boiling point of the solvent, it could be defined as a combination between a slurry and precipitation experiment. Form I was obtained during the precipitation from supersaturated solution by 2-propanol. However the high temperature and the reflux produce the energetic conditions needed by the stable crystal form (Form II) to convert to the metastable crystal form (Form I).

Example 8

Precipitation

Precipitation by Anti-Solvent Addition

Bupropion hydrobromide was dissolved at room temperature in the solvent in which the sample showed high solubility, ethyl acetate was chosen as antisolvent. The samples were filtered and analyzed by X-ray diffraction. Form I converts into Form II using chloroform, and also with benzyl alcohol. The other experiments yield only Form I. See Table 54 for Form I precipitation results by anti-solvent addition.

Precipitation from Oversaturated Solution

Bupropion hydrobromide Form I was dissolved at 100° C. in solvent to obtain the oversaturated solution. The cooling rate applied was 0.45° C./min. The samples were filtered and analyzed by X-ray diffraction. Form I converts into Form VI using 1-Propanol, and into Form V using 1,4-Dioxane. The other experiments yield only Form I. See Table 55 for Form I precipitation results by oversaturated solution.

Precipitation from 2-Propanol

Bupropion hydrobromide Form I was dissolved in 2-propanol at 100° C. to obtain oversaturated solution. The cooling rate applied was 0.45° C./min. The experiment was repeated to verify the reproducibility of the crystal form obtained. The samples were filtered and analyzed by X-ray diffraction. The precipitation experiments yielded only Form I.

Example 9

Stability Tests on Bupropion Hydrobromide Polymorphs

Stability tests were performed on bupropion hydrobromide Form I, Form II, Form III, Form IV, Form V and Form VI. The powders were stored in a controlled atmosphere (85% R.H.)

at 40° C. Form I and Form II were stored for 7 and 30 days respectively, while the other forms were stored only for 30 days. The sample was positioned on the sample-holder which was introduced, without any cover, into the humidity chamber at 40° C. The layer of the sample on the sample-holder was about 0.5 cm. The experiments after 7 and 30 days evidenced that Form I and II did not show modification in their XRD pattern, and remained as Form I and Form II respectively. Form III, Form IV and Form V converted into Form I after 30 days, while Form VI converted into a mixture of Form I+Form II after 30 days.

In addition, stability tests were performed on bupropion hydrobromide Form VII. Form VII was stored for 28 days at 25° C., 75% R.H. The XRD pattern did not show modification, and as such, Form VII was evidenced to be stable after 28 days.

Example 10

Characterization

PXRD, DSC, TGA and IR analyses were obtained for Bupropion Hydrobromide Polymorph Form I, Form II, Form III, Form IV, Form V, Form VI, and Form VII. PXRD analyses were obtained for the amorphous form. With respect to the PXRD analyses, the Peak List is shown for Form I, Form II, Form III, Form IV, Form V, Form VI, Form VII and the amorphous form in Table 56, Table 57, Table 58, Table 59, Table 60, Table 61, Table 62 and Table 63 respectively. Table 64 shows the TGA and DSC summary for Form I, Form II, Form III, Form IV, Form V, Form VI, and Form VII.

TABLE 1

Each trial's contents and amounts of each material per part

| Materials | Amount (g) | | | | |
|---|---|---|---|---|---|
| | Part 1 | Part 2 | Part 3 | Part 4 | Part 5 |
| Bupropion HBr | 2062.5 | 2062.5 | 2062.5 | 2062.5 | 2062.5 |
| PVA | 68.75 | 68.75 | 68.75 | 68.75 | 68.75 |
| Purified Water | 1452.5 | 1452.5 | 1452.5 | 1452.5 | 1452.5 |

TABLE 2

Summary of specifications for granulation procedure.

| Specification | Range | Target |
|---|---|---|
| Fan Speed | Slow | Slow |
| Air Volume (CMH) | 60-65 | 65 |
| Exhaust Temperature (° C.) | 35-45 | 40 |
| Supply Temperature (° C.) | 60-65 | 65 |
| Product Temperature (° C.) | 35-55 | 45 |
| Atomizing Air Pressure (Bar/psi) | 35 | 35 |
| Pump Speed (rpm) | 18 | 18 |
| Liquid Flow Rate (g/min) | 13 | 13 |
| Bed Dew Point (MMWC) | 0 | 0 |
| Filter Dew Point (MMWC | 100-300 | 200 |

TABLE 3

The amount of lubricant in the final formulation was 343.75 g, which was 3.125% of the total.

| Materials | Amount (g) |
|---|---|
| Part 1 | 2131.25 |
| Part 2 | 2131.25 |
| Part 3 | 2131.25 |
| Part 4 | 2131.25 |
| Part 5 | 2131.25 |
| COMPRITOL ® 888 | 343.75 |
| Total | 11000.0 |

TABLE 4

Summary of Specifications for Tablet Press Set-up.

| Parameters | Settings/Ranges |
|---|---|
| Pre-Compression Thickness (mm) | 2 |
| Control Thickness (mm) | 1.5 |
| Fill Thickness (mm) | 7-8 |
| Overload Pressure (Tons) | 1.5-2.0 |
| Tablets per minute | 450-500 |
| Feeder Speed | 1-2 |
| Feeder Control | Auto |

TABLE 5

Summary of specifications for compression

| Parameters | Specification for 174 mg Tablet | Specification for 348 mg Tablet |
|---|---|---|
| Individual Tablet Weight (mg) | 185.6 ± 5% (176.3 mg-194.9 mg) | 371.2 ± 5% (352.6 mg-389.8 mg) |
| Average Tablet Weight (mg) | 185.6 ± 3% (180.0 mg-191.2 mg) | 371.2 ± 3% (360.1 mg-382.3 mg) |
| Tablet Hardness (SC) | 6.0-12.0 | 6.0-12.0 |
| Tablet Thickness (mm) | 5.0-6.0 | 4.5-5.0 |
| Friability (%) | <0.8 | <0.8 |

TABLE 6

Formulations used as the ethylcellulose (e.g. ETHOCEL ® or EC) coating on the 174 mg and 348 mg Bupropion HBr cores.

| FORMULATION 1 | FORMULATION 2 | FORMULATION 3 |
|---|---|---|
| ETHOCEL ® (Ethyl Cellulose) Standard 100 Premium | ETHOCEL ® (Ethyl Cellulose) Standard 100 Premium | ETHOCEL ® (Ethyl Cellulose) Standard 100 Premium |
| Povidone USP (KOLLIDON ® 90F) | Povidone USP (KOLLIDON ® 90F) | Povidone USP (KOLLIDON ® 90F) |
| Polyethylene Glycol 4000 | Polyethylene Glycol 4000 | Polyethylene Glycol 4000 |
| Ethyl Alcohol 95% USP | Dibutyl Sebacate | Ethyl Alcohol 95% USP |
| Isopropyl Alcohol (IPA) | Ethyl Alcohol 95% USP | |

TABLE 7

Formulations used as the Final Coats on the 174 mg and 348 mg Bupropion HBr tablets.

| FORMULATION A | FORMULATION B |
|---|---|
| EUDRAGIT ® L30D-55 | EUDRAGIT ® L30D-55 |
| Chroma-Tone DEB 5156-CLE | SYLOID ® 244FP |
| Purified Water | Polyethylene Glycol 4000 |
| | Triethyl Citrate |
| | Purified Water |

TABLE 8

Summary of Specifications that were kept constant in the ethylcellulose coating Process.

| Process Parameters | Operational Ranges | Target |
|---|---|---|
| Inlet Temperature for coating (° C.) | SV: 40 ± 5<br>PV: 40 ± 5 | 40 |
| Inlet Temperature for Drying (° C.) | 30-35 | 35 |
| Exhaust Temperature | 30 ± 10 | 30 |
| Product Temperature | 25-35 | 28 |
| ΔP Differential Pressure (W.C) | (−0.1)-(−0.12) | −0.10 |
| Supply Air Flow (CFM) | 200 ± 50 | 200 |
| Pan Speed (rpm) | 2.5-12 | 5.0 |
| Atomizing Air (psi) | 35-40 | 35 |
| Pattern Air (psi) | 20-30 | 25 |
| Spray Rate (g/min) | 5-15 | 6.0 |

TABLE 9

Summary of Specifications that were kept constant in the Final coating Process.

| Process Parameters | Operational Ranges | Target |
|---|---|---|
| Inlet Temperature for coating (° C.) | SV: 50 ± 5<br>PV: 50 ± 5 | 50 |
| Inlet Temperature for Drying (° C.) | 40 ± 5 | 40 |
| Exhaust Temperature | 35 ± 5 | 38 |
| Product Temperature | 35 ± 2 | 35 |
| ΔP Differential Pressure (W.C) | (−0.1)-(−0.12) | −0.10 |
| Supply Air Flow (CFM) | 200 ± 50 | 200 |
| Pan Speed (rpm) | 2.5-15 | 12.0 |
| Atomizing Air (psi) | 25-35 | 35 |
| Pattern Air (psi) | 20-30 | 25 |
| Spray Rate (g/min) | 5-15 | 13.0 |

TABLE 10

Materials used in one part of the batch, the percentage of each constituent, the amount per tablet and the amount per batch, for BUP-HBr-XL-009-5

| Materials | % | mg/tablet | Batch Quantity (g) |
|---|---|---|---|
| Bupropion HBr | 93.75 | 348.00 | 1993.75 |
| PVA | 3.125 | 11.60 | 68.75 |
| COMPRITOL ® 888 | 3.125 | 11.60 | 68.75 |
| Total | 100.00 | 371.2 mg | 2131.25 |

TABLE 11

Results obtained using 9 mm tooling for batch BUP-HBr-XL-009-5.

| Parameters | Theoretical | Actual |
|---|---|---|
| Average Individual Tablet Weight | 371.2 mg | 371.5 mg |
| Average Hardness | 6.0-12.0 SC | 10.77 SC |
| Average Thickness | 5.0-6.0 mm | 5.60 mm |
| Friability | <0.8% | 0% |

TABLE 12

Results obtained using 10 mm tooling for batch BUP-HBr-XL-009-5.

| Parameters | Theoretical | Actual |
|---|---|---|
| Average Individual Tablet Weight | 371.2 mg | 366.5 mg |
| Average Hardness | 6.0-12.0 SC | 7.50 SC |
| Average Thickness | 5.0-6.0 mm | 4.97 mm |
| Friability | <0.8% | 0% |

TABLE 13

Materials used in one part of the batch, the percentage of each constituent, the amount per tablet and the amount per batch for batch BUP-HBr-XL-021-5.

| Materials | % | mg/tablet | Batch Quantity (g) |
|---|---|---|---|
| Bupropion HBr | 93.75 | 174.00 | 1993.75 |
| PVA | 3.125 | 5.80 | 68.75 |
| COMPRITOL ® 888 | 3.125 | 5.80 | 68.75 |
| Total | 100.00 | 185.60 | 2131.25 |

TABLE 14

Results obtained using 7 mm tooling for batch BUP-HBr-XL-021-5.

| Parameters | Theoretical | Actual |
|---|---|---|
| Average Individual Tablet Weight | 185.6 mg | 186.8 mg |
| Average Hardness | 6.0-12.0 SC | 9.23 SC |
| Average Thickness | 4.5-5.0 mm | 4.70 mm |
| Friability | <0.8% | 0% |

TABLE 15

Materials used in the ethylcellulose coating and their quantities for batch BUP-HBr-XL-348-013-5.

| Materials | % Contribution to Total Solution | Batch Quantity (g) | % of Solids in Solution |
|---|---|---|---|
| ETHOCEL ® (Ethyl Cellulose) Standard 100 Premium | 3.60 | 77.44* | 38.74 |
| Povidone USP (KOLLIDON ® 90F) | 4.600 | 99.22* | 49.64 |
| PEG 4000 | 1.07 | 23.23* | 11.62 |
| Ethyl Alcohol 95% USP | 86.44 | 1859.50 | N/A |
| Isopropyl Alcohol 99% USP | 4.54 | 97.87 | N/A |
| Total | 100.00 | 2151.00 | 100.00 |

*Total solid component of the formulation included 77.44 g of ethylcellulose (e.g. ETHOCEL ®), 99.22 g of Povidone and 23.23 g of PEG 4000, which gave a total solid amount of 199.89 g. The solid component of the formulation made up 9% of the total solution and the remaining 91% was made up of liquid.

TABLE 16

Theoretical and Actual Tablet weights at 28 mg, 30 mg, 32 mg and 34 mg weight gains for batch BUP-HBr-XL-348-013-5.

| Weight Gain (mg) | Theoretical Weight (mg) | Actual Weight (mg) |
|---|---|---|
| 28.0 | 400.0 | 401.3 |
| 30.0 | 402.0 | 402.6 |
| 32.0 | 404.0 | 404.5 |
| 34.0 | 406.0 | 406.8 |

TABLE 17

Materials used in the Final coating and their quantities for batch BUP-HBr-XL-348-013-5.

| Materials | % Contribution to Total Solution | Batch Quantity (g) | Amount of Solid (g) | % of Solids in Solution |
|---|---|---|---|---|
| EUDRAGIT ® L30 D-55 | 22.73 | 104.8 | 31.44 | 65.00* |
| Chroma-Tone DEB 5156-CLE | 3.66 | 16.90 | 16.90 | 35.00** |
| Purified Water (1) | 21.78 | 100.40 | N/A | N/A |
| Purified Water (2) | 51.89 | 239.20 | N/A | N/A |
| Total | 100.00 | 460.95 | 48.34*** | 100.00 |

*The percentage of EUDRAGIT ®, solid, that contributed to the total amount of solid was 65%.
**The percentage of Chroma-Tone, solid, that contributed to the total amount of solid was 35%.
***The Total amount of solid (48.34 g) was 10.5% of the total solution.

TABLE 18

Theoretical and Actual Tablet weights at 4 mg, 5 mg, 6 mg and 7 mg weight gains.

| Weight Gain (mg) | Theoretical Weight (mg) | Actual Weight (mg) |
|---|---|---|
| 4.0 | 410.0 | 410.5 |
| 5.0 | 411.0 | 410.8 |
| 6.0 | 412.0 | 412.4 |
| 7.0 | 413.0 | 413.9 |

TABLE 19

Materials used in the ethylcellulose coating and their quantities for batch BUP-HBr-XL-348 mg-018-5.

| Materials | % Contribution to Total Solution | Batch Quantity (g) | % of Solids in Solution* |
|---|---|---|---|
| ETHOCEL ® (ethylcellulose) Standard 100 Premium | 3.42 | 73.57 | 38.00 |
| Povidone USP (KOLLIDON ® 90F) | 4.41 | 94.86 | 49.00 |
| PEG 4000 | 1.17 | 25.17 | 13.00 |
| Ethyl Alcohol 95% USP | 86.45 | 1859.53 | N/A |
| Isopropyl Alcohol 99% USP | 4.55 | 97.87 | N/A |
| Total | 100.00 | 2151.00 | 100.00 |

*Total solid included 73.57 g of ethylcellulose 94.86 g of Povidone and 25.17 g of PEG 4000. This gave a total of 193.6 g total solid amount.

TABLE 20

Theoretical and Actual Tablet weights at 26 mg, 28 mg, 30 mg, and 32 mg weight gains for batch BUP-HBr-XL-348 mg-018-5.

| Weight Gain (mg) | Theoretical Weight (mg) | Actual Weight (mg) |
|---|---|---|
| 26.0 | 398.0 | 397.7 |
| 28.0 | 400.0 | 399.5 |
| 30.0 | 402.0 | 401.5 |
| 32.0 | 404.0 | 404.0 |

TABLE 21

Materials used in the Final coating and their quantities for batch BUP-HBr-XL-348 mg-018-5.

| Materials | % Contribution to Total Solution | Batch Quantity (g) | Amount of Solid (g) | % of Solids in Solution |
|---|---|---|---|---|
| EUDRAGIT ® L30D D-55 | 22.75 | 104.86 | 31.46 | 65.00* |
| SYLOID ® 244FP | 2.62 | 12.08 | 12.08 | 25.00** |
| CARBOWAX ® 4000 | 0.70 | 3.22 | 3.22 | 6.65** |
| Triethyl Citrate | 0.36 | 1.64 | 1.64 | 3.39** |
| Purified Water (1) | 33.84 | 156.00 | N/A | N/A |
| Purified Water (2) | 39.73 | 183.15 | N/A | N/A |
| Total | 100.00 | 460.95 | 48.40*** | 100.00 |

*The percentage of EUDRAGIT ®, solid, that contributed to the total amount of solid was 65%.
**The percentage of SYLOID ®, CARBOWAX ® 4000 and Triethyl Citrate that contributed to the total amount of solid was 25%, 6.65% and 3.39%, respectively. This gave a total of 35%.
***The total amount of solid (48.4 g) was 10.5% of the total solution.

TABLE 22

Theoretical and Actual Tablet weights at 4 mg, 5 mg, 6 mg, and 7 mg weight gains for batch BUP-HBr-XL-348 mg-018-5.

| Weight Gain (mg) | Theoretical Weight (mg) | Actual Weight (mg) |
|---|---|---|
| 4.0 | 408.0 | 408.5 |
| 5.0 | 409.0 | 409.3 |
| 6.0 | 410.0 | 410.7 |
| 7.0 | 411.0 | 411.1 |

TABLE 23

Materials used in the ethylcellulose coating and their quantities for batch BUP-HBr-XL-174 mg-022-5.

| Materials | % Contribution to Total Solution | Batch Quantity (g) | % of Solids in Solution* |
|---|---|---|---|
| ETHOCEL ® (ethylcellulose) Standard 100 Premium | 3.60 | 116.12 | 40.00 |
| Povidone USP (KOLLIDON ® 90F) | 4.32 | 139.34 | 48.00 |
| PEG 4000 | 1.08 | 34.84 | 12.00 |
| Ethyl Alcohol 95% USP | 86.45 | 2788.54 | N/A |
| Isopropyl Alcohol 99% USP | 4.55 | 146.76 | N/A |
| Total | 100.00 | 3225.60 | 100.00 |

*Total Solid included 116.12 g of ETHOCEL ®, 139.34 g of Povidone and 34.84 g of PEG 4000. This gave a total solid amount of 290.3 g.

TABLE 24

Theoretical and Actual Tablet weights at 20 mg, 22 mg, 24 mg, 26 mg, 28 mg, 29 mg, and 30 mg weight gains for batch BUP-HBr-XL-174 mg-022-5.

| Weight Gain (mg) | Theoretical Weight (mg) | Actual Weight (mg) |
|---|---|---|
| 20.0 | 206.0 | 206.1 |
| 22.0 | 208.0 | 207.8 |
| 24.0 | 210.0 | 210.2 |
| 26.0 | 212.0 | 211.5 |
| 28.0 | 214.0 | 213.7 |
| 29.0 | 215.0 | 214.9 |
| 30.0 | 216.0 | 216.5 |

TABLE 25

Materials used in the Final coating and their quantities for batch BUP-HBr-XL-174 mg-022-5.

| Materials | % Contribution to Total Solution | Batch Quantity (g) | Amount of Solid (g) | % of Solids in Solution |
|---|---|---|---|---|
| EUDRAGIT ® L30D D-55 | 22.75 | 104.86 | 31.46 | 65.0* |
| SYLOID ® 244FP | 2.62 | 12.08 | 12.08 | 25.0** |
| CARBOWAX ® 4000 | 0.70 | 3.22 | 3.22 | 6.65** |
| Triethyl Citrate | 0.36 | 1.64 | 1.64 | 3.39** |
| Purified Water (1) | 33.84 | 156.00 | N/A | N/A |
| Purified Water (2) | 39.73 | 183.15 | N/A | N/A |
| Total | 100.00 | 460.95 | 48.40*** | 100.00 |

*The percentage of EUDRAGIT ®, solid, that contributed to the total amount of solid was 65%.
**The percentage of SYLOID ®, CARBOWAX ® 4000 and Triethyl Citrate that contributed to the total amount of solid was 25%, 6.65% and 3.39%, respectively. This gave a total of 35%.
***The Total amount of solid (48.4 g) was 10.5% of the total solution.

TABLE 26

Theoretical and Actual Tablet weights at 4 mg, 5 mg, 6 mg, and 7 mg weight gains for batch BUP-HBr-XL-174 mg-022-5.

| Weight Gain (mg) | Theoretical Weight (mg) | Actual Weight (mg) |
|---|---|---|
| 4.0 | 219.0 | 219.4 |
| 5.0 | 220.0 | 220.2 |
| 6.0 | 221.0 | 221.2 |
| 7.0 | 222.0 | 223.0 |

TABLE 27

Materials used in the ethylcellulose coating and their quantities for batch BUP-HBr-XL-348 mg-023-5.

| Materials | % Contribution to Total Solution | Batch Quantity (g) | % of Solids in Solution* |
|---|---|---|---|
| ETHOCEL ® (ethylcellulose) Standard 100 Premium | 3.69 | 79.37 | 42.71 |
| Povidone USP (KOLLIDON ® 90F) | 3.69 | 79.37 | 42.71 |
| PEG 4000 | 1.26 | 27.11 | 14.58 |
| Dibutyl Sebacate, NF | 0.36 | 7.75 | N/A |
| Ethyl Alcohol 95% USP | 91.00 | 1957.4 | N/A |
| Total | 100.00 | 2151.00 | 100.00 |

*Total Solid includes 79.37 g of ETHOCEL ®, 79.37 g of Povidone, 27.11 g of PEG 4000 and 7.75 g of Dibutyl Sebacate. This gave a total solid amount of 193.6 g.

TABLE 28

Theoretical and Actual Tablet weights at 26 mg, 28 mg, 30 mg, and 32 mg weight gains for batch BUP-HBr-XL-348 mg-023-5.

| Weight Gain (mg) | Theoretical Weight (mg) | Actual Weight (mg) |
|---|---|---|
| 26.0 | 398.0 | 399.3 |
| 28.0 | 400.0 | 401.0 |
| 30.0 | 402.0 | 401.7 |
| 32.0 | 404.0 | 402.7 |

TABLE 29

Materials used in the ethylcellulose coating and their quantities for batch BUP-HBr-XL-348 mg-025-5.

| Materials | % Contribution to Total Solution | Batch Quantity (g) | % of Solids in Solution* |
|---|---|---|---|
| ETHOCEL ® (ethylcellulose) Standard 100 Premium | 3.69 | 79.40 | 41.00 |
| Povidone USP (KOLLIDON ® 90F) | 3.78 | 81.30 | 42.00 |
| PEG 4000 | 1.53 | 32.90 | 17.00 |
| Ethyl Alcohol 95% USP | 91.00 | 1957.40 | N/A |
| Total | 100.00 | 2151.00 | 100.00 |

*Total Solid included 79.40 g of ETHOCEL ®, 81.30 g of Povidone and 32.90 g of PEG 4000. This gave a total solid amount of 193.6 g.

TABLE 30

Theoretical and Actual Tablet weights at 26 mg, 28 mg, 30 mg, and 32 mg weight gains for batch BUP-HBr-XL-348 mg-025-5.

| Weight Gain (mg) | Theoretical Weight (mg) | Actual Weight (mg) |
|---|---|---|
| 26.0 | 398.0 | 397.8 |
| 28.0 | 400.0 | 400.6 |
| 30.0 | 402.0 | 401.4 |
| 32.0 | 404.0 | 402.2 |

TABLE 31

Materials used in the Final coating and their quantities for batch BUP-HBr-XL-348 mg-025-5.

| Materials | % Contribution to Total Solution | Batch Quantity (g) | Amount of Solid (g) | % of Solids in Solution |
|---|---|---|---|---|
| EUDRAGIT ® L30D D-55 | 19.77 | 91.13 | 27.34 | 56.50* |
| SYLOID ® 244FP | 3.15 | 14.52 | 14.52 | 30.00** |
| CARBOWAX ® 4000 | 0.95 | 4.36 | 4.36 | 9.00** |
| Triethyl Citrate | 0.47 | 2.17 | 2.17 | 4.50** |
| Purified Water (1) | 21.70 | 100.00 | N/A | N/A |
| Purified Water (2) | 53.96 | 248.77 | N/A | N/A |
| Total | 100.00 | 460.95 | 48.39*** | 100.00 |

*The percentage of EUDRAGIT ®, solid, that contributed to the total amount of solid was 65%.
**The percentage of SYLOID ®, CARBOWAX ® 4000 and Triethyl Citrate that contributed to the total amount of solid was 30%, 9% and 4.5%, respectively. This gave a total of 43.5%.
***The Total amount of solid (48.39 g) was 10.5% of the total solution.

TABLE 32

Theoretical and Actual Tablet weights at 4 mg, 5 mg, 6 mg, and 7 mg weight gains for batch BUP-HBr-XL-348 mg-025-5.

| Weight Gain (mg) | Theoretical Weight (mg) | Actual Weight (mg) |
|---|---|---|
| 4.0 | 408.0 | 408.3 |
| 5.0 | 409.0 | 408.8 |
| 6.0 | 410.0 | 409.5 |
| 7.0 | 411.0 | 411.1 |

TABLE 33

Materials used in the ethylcellulose coating and their quantities for batch BUP-HBr-XL-348 mg-026-5.

| Materials | % Contribution to Total Solution | Batch Quantity (g) | % of Solids Solution* |
|---|---|---|---|
| ETHOCEL ® (ethylcellulose) Standard 100 Premium | 3.69 | 79.37 | 41.00 |
| Povidone USP (KOLLIDON ® 90F) | 3.69 | 79.37 | 41.00 |
| PEG 4000 | 0.36 | 7.75 | 4.00 |
| Dibutyl Sebacate, NF | 1.26 | 27.11 | 14.00 |
| Ethyl Alcohol 95% USP | 91.00 | 1957.4 | N/A |
| Total | 100.00 | 2151.00 | 100.00 |

*Total Solid included 79.37 g of ETHOCEL ®, 79.37 g of Povidone, 7.75 g of PEG 4000 and 27.11 g of Dibutyl Sebacate. This gave a total solid amount of 193.6 g.

TABLE 34

Theoretical and Actual Tablet weights at 26 mg, 28 mg, 30 mg, and 32 mg weight gains for batch BUP-HBr-XL-348 mg-026-5.

| Weight Gain (mg) | Theoretical Weight (mg) | Actual Weight (mg) |
|---|---|---|
| 26.0 | 398.0 | 398.8 |
| 28.0 | 400.0 | 400.5 |
| 30.0 | 402.0 | 402.5 |
| 32.0 | 404.0 | 403.6 |

TABLE 35

Materials used in the ethylcellulose coating and their quantities for batch BUP-HBr-XL-174 mg-027-5.

| Materials | % Contribution to Total Solution | Batch Quantity (g) | % of Solid in Solution* |
|---|---|---|---|
| ETHOCEL ® (ethylcellulose) Standard 100 Premium | 3.69 | 138.87 | 41.00 |
| Povidone USP (KOLLIDON ® 90 F.) | 3.78 | 142.25 | 42.00 |
| PEG 4000 | 1.53 | 57.58 | 17.00 |
| Ethyl Alcohol 95% USP | 91.00 | 3424.63 | N/A |
| Total | 100.00 | 3763.33 | 100.00 |

*Total Solid included 138.87 g of ETHOCEL ®, 142.25 g of Povidone and 57.58 g of PEG 4000. This gave a total solid amount of 338.7 g.

TABLE 36

Theoretical and Actual Tablet weights at 22 mg, 24 mg, and 26 mg weight gains for batch BUP-HBr-XL-174 mg-027-5.

| Weight Gain (mg) | Theoretical Weight (mg) | Actual Weight (mg) |
|---|---|---|
| 22.0 | 208.0 | 207.7 |
| 24.0 | 210.0 | 210.8 |
| 26.0 | 212.0 | 212.4 |

TABLE 37

Materials used in the Final coating and their quantities for batch BUP-HBr-XL-174 mg-027-5.

| Materials | % Contribution to Total Solution | Batch Quantity (g) | Amount of Solid (g) | % of Solid in Solution |
|---|---|---|---|---|
| EUDRAGIT ® L30D D-55 | 19.77 | 182.27 | 54.68 | 56.5* |
| SYLOID ® 244FP | 3.15 | 29.03 | 29.03 | 30.0** |
| CARBOWAX ® 4000 | 0.95 | 8.71 | 8.71 | 9.0** |
| Triethyl Citrate | 0.47 | 4.35 | 4.35 | 4.5** |
| Purified Water (1) | 21.70 | 200.00 | N/A | N/A |
| Purified Water (2) | 53.98 | 497.26 | N/A | N/A |
| Total | 100.00 | 921.62 | 96.77*** | 100.00 |

*The percentage of EUDRAGIT ®, solid, that contributed to the total amount of solid was 56.5%.
**The percentage of SYLOID ®, CARBOWAX ® 4000 and Triethyl Citrate that contributed to the total amount of solid was 30.0%, 9.0% and 4.5%, respectively. This gave a total of 43.5%.
***The Total amount of solid (9.77 g) was 10.5% of the total solution.

TABLE 38

Theoretical and Actual Tablet weights at 4 mg, 5 mg, 6 mg, and 7 mg weight gains for batch BUP-HBr-XL-174 mg-027-5.

| Weight Gain (mg) | Theoretical Weight (mg) | Actual Weight (mg) |
|---|---|---|
| 4.0 | 216.0 | 216.6 |
| 5.0 | 217.0 | 217.6 |
| 6.0 | 218.0 | 217.8 |
| 7.0 | 219.0 | 219.8 |

TABLE 39

Bupropion Hydrobromide Polymorphs

| Trial | Solvent (voll.) | Cosolvent (voll.) | Yield (%) | Form | K. F. (%) | Notes |
|---|---|---|---|---|---|---|
| 085 | IPA + HBr gas | | | I | 0.07 | Standard procedure |
| 097 | Water 2 | / | 72 | I | 0.06 | |
| 098A | Methanol 2.4 | / | | II | 0.13 | |
| 098B | Acetone 17 | water 0.7 | 24 | II | 0.16 | |
| 099 | Ethanol abs. 4.8 | / | 56 | III | 0.12 | |
| 100 | IPA 15.1 | / | 77 | I | 0.11 | |
| 102 | AcOi-Pr 20 | MeOH 3.6 | 26 | I | 0.25 | |
| 108 | Acetonitrile 20 | / | 70 | I | 0.14 | |
| 109 | Dichloromethane 30 | / | 25 | II | 0.21 | |
| 110 | Water 2 | HBr 48% 1 | 83 | I | 0.12 | |
| 111 | IPA 6 | HBr 48% 1 | 69 | I | 0.32 | |
| 112 | MTBE 10 | MeOH 3 | 67 | I | 0.18 | |
| 113 | Toluene 10 | MeOH 1.25 | 40 | II | 0.39 | |
| 114 | DMC 10 | MeOH 1.75 | 67 | II | 0.17 | |
| 115 | t-BuOH 20 | Water 0.55 | 74 | I | 0.15 | |
| 116 | Form I in rotavapor 100° C. 24 h | | | I | 0.45 | |
| 117 | IPA 10 | Water 0.125 | 88 | I | 0.32 | |
| 118 | Toluene 10 | MeOH 1.15 | 99 | I | 0.16 | |
| 119 | IPA 8 | MeOH 1.32 | 83 | I | 0.47 | |
| 120 | Sec-BuOH 25 | / | 89 | I | 0.13 | |
| 122 | Water 8 | / | | I | 1.3 | Spray dried |

TABLE 40

Solvents used during the polymorph screening experiments

| Solvent | ID | MP ° C. | BP ° C. | Polarity (ε) |
|---|---|---|---|---|
| Diethyl Ether | DEE | −116 | 35 | 4.34 |
| Dichloromethane | DCM | −97 | 40 | 9.08 |
| Acetone | ACT | −94 | 56 | 20.7 |
| Chloroform | CHF | −63 | 61 | 4.81 |
| Methanol | MET | −98 | 65 | 33 |
| n-Hexane | NHX | −95 | 69 | 2.02 |
| Ethyl Acetate | ETA | −84 | 75 | 6.02 |
| Ethanol | ETH | −114 | 78 | 24.3 |
| 1,2-Dimethoxy Ethane | DMX | −58 | 82 | 7.2 |
| Water | H20 | 0 | 100 | 78.54 |
| Nitromethane | NMT | −29 | 101 | 35.9 |
| 1,4-Dioxane | DIX | 11 | 101 | 2.21 |
| Acetonitrile | ACN | −48 | 82 | 36.6 |
| p-Xylene | PXY | 13 | 138 | 2.27 |
| 2-Methoxy Ethanol | 2MX | −85 | 124 | — |
| 1-Butanol | 1BT | −90 | 116 | 17.8 |
| DMSO | DMS | 17 | 189 | 47.2 |
| DMF | DMF | −61 | 153 | 38.3 |
| 1-Propanol | 1PR | −127 | 97 | 20.1 |
| Ethyl Formate | EFM | −80 | 54 | 7.1 |
| t-Butyl Methyl Ether | BME | −109 | 55 | — |
| Methyl Acetate | MAC | −98 | 56.9 | 6.7 |
| Tetrahydrofuran | THF | −108 | 65 | 7.52 |
| Iso-Propyl Ether | IPE | −85 | 68 | 3.9 |
| Methyl Ethyl Ketone | MEK | −87 | 80 | 18.5 |
| Cyclohexane | CHX | 5 | 81 | 2.02 |
| 2-Propanol | 2PR | −90 | 82 | 18.3 |
| Tert-Butanol | TBT | 24 | 83 | 12.5 |
| Isopropyl Acetate | IPA | −73 | 89 | — |
| Propyl Acetate | PAC | −95 | 97 | 6.3 |
| (±) 2-Butanol | 2BT | −115 | 98 | 18.7 |
| 3-Pentanone | 3PN | −39 | 100 | 17.3 |
| 2-Methyl-1-Propanol | MPR | −108 | 108 | — |
| Toluene | TOL | −93 | 110 | 2.38 |
| Diethyl Carbonate | DEC | −43 | 126 | — |
| Mesitylene | MST | −45 | 164 | 3.4 |
| Benzonitrile | BNT | −13 | 188 | 26 |
| Benzyl Alcohol | ABZ | −13 | 203 | 13 |
| Ethyl Benzoate | EBZ | −34 | 212 | 6 |

TABLE 41

Qualitative Solubility

| Solvent | Solubility at Room Temp (RT) | Solubility at High Temp (HT) |
|---|---|---|
| 1,2-Dimethoxy Ethane | Low | Low |
| 1-Butanol | High | — |
| 1-Propanol | High | — |
| 2-Methoxy Ethanol | High | — |
| Acetone | Low | Low |
| Acetonitrile | High | — |
| Chloroform | High | — |
| Dichloromethane | High | — |
| Diethyl Ether | Low | Low |
| Dioxane | Low | High |
| Dimethil sulfoxyde | High | — |
| Ethanol | High | — |
| Ethyl Acetate | Low | Low |
| Methanol | High | — |
| n-Hexane | Low | Low |
| Nitromethane | High | — |
| p-Xylene | Low | Low |
| Water | High | — |
| (±) 2-Butanol | Low | High |
| 1-Methyl-2-Pyrrolidone | High | — |
| 1-Octanol | Low | Low |
| 2-Methyl-1-Propanol | High | — |
| 2-Propanol | High | — |
| 3-Pentanone | Low | Low |
| 4-Methyl-2-Pentanone | Low | Low |
| Benzonitrile | Low | Low |
| Benzyl Alcohol | High | — |
| Cyclohexane | Low | Low |
| Diethyl Carbonate | Low | Low |
| Dimethyl Formamide | High | — |
| Ethyl Benzoate | Low | Low |
| Ethyl Formate | Low | Low |
| Isopropyl Acetate | Low | Low |
| Iso-Propyl-Ether | Low | Low |
| Mesitylene | Low | Low |
| Methyl Benzoate | Low | Low |
| Methyl Ethyl Ketone | Low | Low |
| Methyl-Cyclohexan | Low | Low |
| n-Hexan | Low | Low |
| Nitrobenezene | Low | Low |
| Propyl Acetate | Low | Low |
| t-Butyl Methyl Ether | Low | Low |
| Tert-Butanol | Low | Low |
| Tetrahydrofuran | Low | Low |
| Toluene | Low | Low |

Low: a large amount of solid remains in suspension.
Med: solid is not totally solved.
High: clear solution without solid suspended.

TABLE 42

Recrystallization Results
Evaporation of Bupropion Hydrobromide at Room Temperature

| Solvent | Recrystallization Result (Form) |
|---|---|
| Acetonitrile | Form I |
| Acetone | Form I |
| Chloroform | Form IV |
| Dichloromethane | Form I |
| 1,4-Dioxane | Form I |
| Ethyl Acetate | Form I |
| Ethanol | Form I |
| Water | Form I |
| Methanol | Form I |
| Nitromethane | Form I |
| p-Xylene | Amorphous |
| (±)2-Butanol | Form II |
| 2-Methyl-1-Propanol | Form I |
| 2-Propanol | Form I |
| 3-Pentanone | Form II |
| 4-Methyl-2-Pentanone | Form I |
| Benzonitrile | Form VII |
| Diethyl Carbonate | Form I |
| Dimethyl Formamide | Form I |
| Ethyl Formate | Form I |
| Isopropyl Acetate | Form I |
| Mesitylene | Amorphous |
| Methyl Benzoate | Form VII |
| Methyl Ethyl Ketone | Form I |
| Propyl Acetate | Form I |
| Tert-Butanol | Form I |
| Tetrahydrofuran | Form I |

TABLE 43

Recrystallization Results
Evaporation of Bupropion Hydrobromide at Low Temperature (4° C.)

| Solvent | Recrystallization Result (Form) |
|---|---|
| Acetonitrile | Form I |
| Acetone | Form I |
| Chloroform | Form I |

TABLE 43-continued

Recrystallization Results
Evaporation of Bupropion Hydrobromide at Low Temperature (4° C.)

| Solvent | Recrystallization Result (Form) |
|---|---|
| Dichloromethane | Form I |
| 1,4-Dioxane | Form I |
| Ethyl Acetate | Form I |
| Ethanol | Form I |
| Water | Form I |
| Methanol | Form I |
| Nitromethane | Form I |
| p-Xylene | Amorphous |
| 2-Propanol | Form I |
| 3-Pentanone | Form II |
| Ethyl Formate | Form I |
| Isopropyl Acetate | Form I |
| Methyl Ethyl Ketone | Form I |
| Propyl Acetate | Form I |
| Tetrahydrofuran | Form I |

TABLE 44

Recrystallization Results
Evaporation of Bupropion Hydrobromide at High Temperature (60° C.)

| Solvent | Recrystallization Result (Form) |
|---|---|
| 1-Butanol | Form I |
| 1-Propanol | Form I |
| 2-Methoxy Ethanol | Form I |
| Acetonitrile | Form I |
| 1,4-Dioxane | Form I |
| DMSO | Form I |
| 1,2-Dimethoxy Ethane | Form I |
| Water | Form I |
| Nitromethane | Form I |
| p-Xylene | Amorphous |
| Methyl Ethyl Ketone | Form I |
| 2-Propanol | Form I |
| Tert-Butanol | Form I |
| Isopropyl Acetate | Form I |
| Propyl Acetate | Form I |
| (±)2-Butanol | Form I |
| 3-Pentanone | Form I |
| 2-Methyl-1-Propanol | Form I |
| Diethyl Carbonate | Form I |
| Dimethyl Formamide | Form VII |
| Benzonitrile | Form VII |
| Nitrobenzene | Form I + VII |
| Ethyl Benzoate | Form VII |

TABLE 45

Recrystallization Results
Evaporation of Bupropion Hydrobromide at Low Pressure

| Solvent | Recrystallization Result (Form) |
|---|---|
| Dichloromethane | Form I |
| Ethyl Formate | Form I |
| 2-Methoxy Ethanol | Form I |
| Methyl Acetate | Form I |
| Chloroform | Form I |
| Methanol | Form I |
| Ethanol | Form I |
| Methyl Ethyl Ketone | Form I |
| 2-Propanol | Form I |
| Acetonitrile | Form I |
| Isopropyl Acetate | Form I |
| 1-Propanol | Form I |
| Water | Form I |
| Ethyl Acetate | Form I + VI |
| 1,2-Dimetoxy Ethane | Form I |
| Tert-Butanol | Form I |

TABLE 45-continued

Recrystallization Results
Evaporation of Bupropion Hydrobromide at Low Pressure

| Solvent | Recrystallization Result (Form) |
|---|---|
| Propyl Acetate | Form I |
| (±)2-Butanol | Form I |

TABLE 46

Form I Slurries Results - 7 days
At Room Temperature

| Solvent | Slurry Result |
|---|---|
| Ethyl acetate | Form II |
| n-Hexan | Form II |
| p-Xylene | Form II |
| 1,2-Dimethoxy Ethane | Form II |
| Acetone | Form II |
| Diethyl ether | Form II |
| 1,4-Dioxane | Form V |
| 1-Octanol | Form II |
| 3-Pentanone | Form II |
| 4-Methyl-2-Pentanone | Form II |
| Benzonitrile | Form II + VII |
| Cyclohexane | Form I |
| Diethyl Carbonate | Form II |
| Ethyl Benzoate | Form II |
| Ethyl Formate | Form II |
| Isopropyl Acetate | Form II |
| Iso-Propyl Ether | Form II |
| Mesitylene | Form II |
| Methyl Benzoate | Form II |
| Methyl Ethyl Ketone | Form II |
| Methyl-Cyclohexane | Form I |
| Nitrobenzene | Form II |
| Propyl Acetate | Form II |
| t-Butyl Methyl Ether | Form II |
| Tert-Butanol | Form II |
| Tetrahydrofuran | Form II |
| Toluene | Form II |

TABLE 47

Form I Slurries Results - 30 days
At Room Temperature

| Solvent | Slurry Result |
|---|---|
| Ethyl acetate | Form II |
| n-Hexan | Form II |
| p-Xylene | Form II |
| 1-Octanol | Form II |
| Acetone | Form II |
| t-Butyl Methyl Ether | Form II |
| Toluene | Form II |
| 4-Methyl-2-Pentanone | Form II |
| Methyl-Cyclohexane | Form II |
| Methyl Ethyl Ketone | Form II |
| Methyl Benzoate | Form II |
| Cyclohexane | Form II |
| Ethyl Formate | Form II |
| Isopropyl Acetate | Form II |
| Ethyl Acetate | Form II |
| Iso-Propyl Ether | Form II |
| Diethyl Carbonate | Form II |
| Diethyl Ether | Form II |
| 1,2-Dimethoxy Ethane | Form II |
| 1,4-Dioxane | Form V |
| Tetrahydrofuran | Form II + VII |

TABLE 48

Form I + Form II Slurries Results - 7 days At Room Temperature

| Solvent | Slurry Result |
|---|---|
| Ethyl acetate | Form II |
| n-Hexan | Form II |
| p-Xylene | Form II |
| 1,2-Dimethoxy Ethane | Form II |
| Acetone | Form II |
| Diethyl Ether | Form II |
| 1,4-Dioxane | Form V |

TABLE 49

Form II + Form III Slurries Results - 7 days At Room Temperature

| Solvent | Slurry Result |
|---|---|
| Ethyl acetate | Form II |
| n-Hexan | Form II |
| p-Xylene | Form II |
| 1,2-Dimethoxy Ethane | Form II |
| Acetone | Form II |
| Diethyl Ether | Form II |
| 1,4-Dioxane | Form V |

TABLE 50

Form II + Form IV Slurries Results - 7 days At Room Temperature

| Solvent | Slurry Result |
|---|---|
| Ethyl acetate | Form II |
| n-Hexan | Form II |
| p-Xylene | Form II |
| 1,2-Dimethoxy Ethane | Form II |
| Acetone | Form II |
| Diethyl Ether | Form II |
| 1,4-Dioxane | Form V |

TABLE 51

Form II + Form V Slurries Results - 7 days At Room Temperature

| Solvent | Slurry Result |
|---|---|
| Ethyl acetate | Form II |
| n-Hexan | Form II |
| p-Xylene | Form II |
| 1,2-Dimethoxy Ethane | Form II |
| Acetone | Form II |
| Diethyl Ether | Form II |
| 1,4-Dioxane | Form V |

TABLE 52

Form II + Form VI Slurries Results - 7 days At Room Temperature

| Solvent | Slurry Result |
|---|---|
| Ethyl acetate | Form II |
| n-Hexan | Form II |
| p-Xylene | Form II |
| 1,2-Dimethoxy Ethane | Form II |
| Acetone | Form II |
| Diethyl Ether | Form II |
| 1,4-Dioxane | Form V |

TABLE 53

Form II + Form VII Slurries Results - 7 days At Room Temperature

| Solvent | Slurry Result |
|---|---|
| Ethyl acetate | Form II |
| n-Hexan | Form II |
| p-Xylene | Form II |
| 1,2-Dimethoxy Ethane | Form II |
| Acetone | Form II |
| Diethyl Ether | Form II |
| 1,4-Dioxane | Form V |

TABLE 54

Form I Precipitation Results By Anti-Solvent (Ethyl Acetate) addition at Room Temperature

| Solvent | Precipitation Result |
|---|---|
| Dichloromethane | Form I |
| 1-Butanol | Form I |
| 1-Propanol | Form I |
| 2-Methoxy Ethanol | Form I |
| Dimethylformamide | Form I |
| Chloroform | Form II |
| Ethanol | Form I |
| Methanol | Form I |
| 1-Methyl-2-Pyrrolidone | Form I |
| 2-Methyl-1-Propanol | Form I |
| 2-Propanol | Form I |
| Benzyl Alcohol | Form II |

TABLE 55

Form I Precipitation Results By Oversaturated Solution at 100° C.

| Solvent | Precipitation Result |
|---|---|
| Water | Form I |
| Nitromethane | Form I |
| p-Xylene | Form I |
| 1-Butanol | Form I |
| 1-Propanol | Form VI |
| 2-Methoxy Ethanol | Form I |
| Dimethyl sulfoxyde | Form I |
| Dimethyl formamide | Form I |
| 1,4-Dioxane | Form V |
| 2-Methyl-1-Propanol | Form I |
| 1-Methyl-2-Pyrrolidone | Form I |
| (±)2-Butanol | Form I |

TABLE 56

Form I Characterization Peak List:

| Pos. [°2Th.] | Height [cts] | FWHM [°2Th.] | d-spacing [Å] | Rel. Int. [%] |
|---|---|---|---|---|
| 6.6956 | 441.99 | 0.1171 | 13.20171 | 6.25 |
| 12.5142 | 1078.18 | 0.0669 | 7.07347 | 15.24 |
| 13.8338 | 495.49 | 0.0836 | 6.40157 | 7.01 |
| 14.1418 | 494.24 | 0.0836 | 6.26283 | 6.99 |
| 14.7981 | 708.72 | 0.1004 | 5.98651 | 10.02 |
| 18.7980 | 129.44 | 0.1338 | 4.72073 | 1.83 |
| 19.6003 | 959.53 | 0.0836 | 4.52928 | 13.57 |
| 21.2026 | 258.33 | 0.0669 | 4.19048 | 3.65 |
| 22.9330 | 604.92 | 0.1004 | 3.87806 | 8.55 |
| 23.6006 | 223.99 | 0.1171 | 3.76985 | 3.17 |
| 23.9869 | 597.98 | 0.1338 | 3.71000 | 8.45 |
| 24.3037 | 347.66 | 0.1004 | 3.66236 | 4.92 |
| 24.7629 | 271.46 | 0.2676 | 3.59547 | 3.84 |

TABLE 56-continued

Form I Characterization
Peak List:

| Pos. [°2Th.] | Height [cts] | FWHM [°2Th.] | d-spacing [Å] | Rel. Int. [%] |
|---|---|---|---|---|
| 25.5127 | 530.63 | 0.0669 | 3.49147 | 7.50 |
| 26.1117 | 7073.02 | 0.1338 | 3.41273 | 100.00 |
| 26.8429 | 162.01 | 0.0502 | 3.32140 | 2.29 |
| 27.2174 | 261.03 | 0.0669 | 3.27654 | 3.69 |
| 27.5656 | 85.43 | 0.1004 | 3.23594 | 1.21 |
| 28.4838 | 255.21 | 0.1171 | 3.13368 | 3.61 |
| 28.9551 | 94.43 | 0.1338 | 3.08374 | 1.34 |
| 29.4381 | 462.52 | 0.0836 | 3.03423 | 6.54 |
| 30.6366 | 159.60 | 0.1338 | 2.91821 | 2.26 |
| 31.5518 | 511.29 | 0.0669 | 2.83562 | 7.23 |
| 32.3505 | 143.17 | 0.1004 | 2.76741 | 2.02 |
| 32.7014 | 2460.48 | 0.1020 | 2.73625 | 34.79 |
| 32.7926 | 1562.72 | 0.0612 | 2.73564 | 22.09 |
| 33.8601 | 103.38 | 0.1224 | 2.64522 | 1.46 |
| 34.5527 | 153.32 | 0.1632 | 2.59377 | 2.17 |
| 35.5727 | 437.91 | 0.0612 | 2.52170 | 6.19 |
| 37.0456 | 106.77 | 0.2448 | 2.42475 | 1.51 |
| 37.8227 | 51.80 | 0.2856 | 2.37669 | 0.73 |
| 38.7631 | 92.78 | 0.1632 | 2.32117 | 1.31 |

TABLE 57

Form II Characterization
Peak List:

| Pos. [°2Th.] | Height [cts] | FWHM [°2Th.] | d-spacing [Å] | Rel. Int. [%] |
|---|---|---|---|---|
| 6.5301 | 1078.87 | 0.1171 | 13.53592 | 54.01 |
| 12.1839 | 56.28 | 0.2007 | 7.26445 | 2.82 |
| 13.0302 | 341.23 | 0.3011 | 6.79449 | 17.08 |
| 14.1804 | 144.73 | 0.1338 | 6.24587 | 7.24 |
| 15.9162 | 237.30 | 0.1171 | 5.56838 | 11.88 |
| 16.5218 | 194.05 | 0.2007 | 5.36561 | 9.71 |
| 18.0133 | 104.98 | 0.2007 | 4.92457 | 5.26 |
| 18.8275 | 105.92 | 0.2007 | 4.71341 | 5.30 |
| 19.2806 | 106.21 | 0.2342 | 4.60365 | 5.32 |
| 20.6685 | 123.77 | 0.1004 | 4.29754 | 6.20 |
| 21.6359 | 140.14 | 0.1004 | 4.10752 | 7.01 |
| 21.9490 | 600.59 | 0.1171 | 4.04962 | 30.06 |
| 23.1059 | 1727.56 | 0.1506 | 3.84943 | 86.48 |
| 24.1802 | 175.85 | 0.1338 | 3.68077 | 8.80 |
| 25.7472 | 1691.24 | 0.0612 | 3.45734 | 84.66 |
| 25.8320 | 1997.69 | 0.0502 | 3.44904 | 100.00 |
| 26.8343 | 428.10 | 0.1004 | 3.32245 | 21.43 |
| 27.1433 | 175.53 | 0.1338 | 3.28532 | 8.79 |
| 27.8691 | 210.21 | 0.1506 | 3.20139 | 10.52 |
| 28.8111 | 507.17 | 0.1171 | 3.09883 | 25.39 |
| 29.6743 | 86.27 | 0.1338 | 3.01062 | 4.32 |
| 30.0692 | 343.86 | 0.0836 | 2.97197 | 17.21 |
| 31.8185 | 276.39 | 0.1673 | 2.81246 | 13.84 |
| 32.4172 | 421.65 | 0.0669 | 2.76188 | 21.11 |
| 33.2620 | 194.88 | 0.1673 | 2.69364 | 9.76 |
| 34.0877 | 90.26 | 0.2007 | 2.63025 | 4.52 |
| 34.8735 | 115.88 | 0.1338 | 2.57277 | 5.80 |
| 38.0294 | 133.57 | 0.1673 | 2.36621 | 6.69 |
| 38.7493 | 332.79 | 0.0669 | 2.32389 | 16.66 |
| 39.1289 | 148.12 | 0.1338 | 2.30222 | 7.41 |

TABLE 58

Form III Characterization
Peak List:

| Pos. [°2Th.] | Height [cts] | FWHM [°2Th.] | d-spacing [Å] | Rel. Int. [%] |
|---|---|---|---|---|
| 8.0596 | 279.60 | 0.0669 | 10.97017 | 14.71 |
| 12.2853 | 367.57 | 0.1004 | 7.20473 | 19.34 |

TABLE 58-continued

Form III Characterization
Peak List:

| Pos. [°2Th.] | Height [cts] | FWHM [°2Th.] | d-spacing [Å] | Rel. Int. [%] |
|---|---|---|---|---|
| 12.8315 | 58.26 | 0.2007 | 6.89923 | 3.07 |
| 13.2434 | 71.14 | 0.1338 | 6.68559 | 3.74 |
| 15.2149 | 203.50 | 0.1171 | 5.82344 | 10.71 |
| 15.6269 | 312.41 | 0.1004 | 5.67081 | 16.44 |
| 16.0036 | 698.13 | 0.1004 | 5.53819 | 36.73 |
| 18.0692 | 1900.51 | 0.0836 | 4.90946 | 100.00 |
| 19.6718 | 224.36 | 0.0836 | 4.51297 | 11.81 |
| 20.6861 | 27.67 | 0.4015 | 4.29392 | 1.46 |
| 21.3980 | 87.79 | 0.2007 | 4.15264 | 4.62 |
| 22.7526 | 276.24 | 0.0502 | 3.90839 | 14.54 |
| 23.4234 | 433.75 | 0.3346 | 3.79796 | 22.82 |
| 24.2420 | 612.88 | 0.0669 | 3.67154 | 32.25 |
| 25.1221 | 1338.52 | 0.0836 | 3.54487 | 70.43 |
| 25.4298 | 765.07 | 0.0502 | 3.50267 | 40.26 |
| 26.5814 | 122.23 | 0.1673 | 3.35348 | 6.43 |
| 28.0071 | 89.35 | 0.2676 | 3.18593 | 4.70 |
| 28.9857 | 194.62 | 0.3011 | 3.08056 | 10.24 |
| 29.6568 | 289.74 | 0.1673 | 3.01236 | 15.25 |
| 30.6470 | 164.56 | 0.1338 | 2.91724 | 8.66 |
| 31.5990 | 64.65 | 0.2676 | 2.83150 | 3.40 |
| 32.3908 | 215.03 | 0.1338 | 2.76407 | 11.31 |
| 33.1938 | 318.21 | 0.0669 | 2.69901 | 16.74 |
| 34.0570 | 126.02 | 0.2676 | 2.63255 | 6.63 |
| 34.8593 | 60.37 | 0.2007 | 2.57379 | 3.18 |
| 36.3049 | 160.14 | 0.1338 | 2.47455 | 8.43 |
| 37.2156 | 100.45 | 0.2676 | 2.41606 | 5.29 |

TABLE 59

Form IV Characterization
Peak List:

| Pos. [°2Th.] | Height [cts] | FWHM [°2Th.] | d-spacing [Å] | Rel. Int. [%] |
|---|---|---|---|---|
| 4.2724 | 62.71 | 0.8029 | 20.68230 | 10.43 |
| 10.7161 | 108.51 | 0.1673 | 8.25595 | 18.04 |
| 12.0264 | 176.45 | 0.2007 | 7.35926 | 29.34 |
| 12.4816 | 210.22 | 0.1673 | 7.09184 | 34.95 |
| 14.1738 | 202.54 | 0.1673 | 6.24875 | 33.68 |
| 14.8827 | 252.70 | 0.1338 | 5.95267 | 42.01 |
| 16.2511 | 79.85 | 0.2676 | 5.45440 | 13.28 |
| 16.8644 | 150.41 | 0.2007 | 5.25738 | 25.01 |
| 17.1048 | 104.89 | 0.1004 | 5.18404 | 17.44 |
| 17.8687 | 303.47 | 0.1673 | 4.96408 | 50.46 |
| 18.7619 | 119.28 | 0.2342 | 4.72973 | 19.83 |
| 19.2392 | 97.51 | 0.2342 | 4.61345 | 16.21 |
| 20.0869 | 283.86 | 0.2342 | 4.42063 | 47.19 |
| 21.7601 | 248.87 | 0.1673 | 4.08436 | 41.38 |
| 22.8957 | 601.46 | 0.1004 | 3.88428 | 100.00 |
| 23.8771 | 324.04 | 0.1338 | 3.72681 | 53.88 |
| 24.4544 | 410.44 | 0.2342 | 3.64013 | 68.24 |
| 25.5250 | 477.75 | 0.2007 | 3.48982 | 79.43 |
| 25.9015 | 275.99 | 0.1004 | 3.43995 | 45.89 |
| 29.1312 | 52.91 | 0.4015 | 3.06550 | 8.80 |
| 30.5089 | 258.69 | 0.2007 | 2.93014 | 43.01 |
| 32.0377 | 76.71 | 0.4684 | 2.79372 | 12.75 |
| 32.5333 | 42.72 | 0.2676 | 2.75228 | 7.10 |
| 33.0116 | 63.93 | 0.2342 | 2.71349 | 10.63 |
| 34.3203 | 34.09 | 0.5353 | 2.61296 | 5.67 |
| 35.9170 | 107.99 | 0.2007 | 2.50038 | 17.95 |
| 37.7676 | 59.12 | 0.2676 | 2.38201 | 9.83 |
| 38.5403 | 42.22 | 0.4015 | 2.33601 | 7.02 |

TABLE 60

Form V Characterization
Peak List:

| Pos. [°2Th.] | Height [cts] | FWHM [°2Th.] | d-spacing [Å] | Rel. Int. [%] |
|---|---|---|---|---|
| 7.4871 | 204.47 | 0.1004 | 11.80774 | 28.74 |
| 11.8387 | 410.79 | 0.1338 | 7.47548 | 57.73 |
| 12.1526 | 209.30 | 0.1338 | 7.28311 | 29.42 |
| 14.9302 | 611.31 | 0.2007 | 5.93382 | 85.92 |
| 15.1873 | 422.88 | 0.1171 | 5.83395 | 59.43 |
| 17.3545 | 711.51 | 0.1171 | 5.10998 | 100.00 |
| 17.6294 | 576.40 | 0.1338 | 5.03095 | 81.01 |
| 19.5302 | 48.43 | 0.2007 | 4.54538 | 6.81 |
| 20.8970 | 102.38 | 0.6022 | 4.25107 | 14.39 |
| 22.4834 | 278.31 | 0.3346 | 3.95457 | 39.11 |
| 23.0890 | 609.75 | 0.1673 | 3.85220 | 85.70 |
| 23.3165 | 586.83 | 0.1338 | 3.81512 | 82.48 |
| 23.9911 | 280.63 | 0.2676 | 3.70936 | 39.44 |
| 24.9295 | 418.94 | 0.2676 | 3.57182 | 58.88 |
| 25.4770 | 303.12 | 0.2676 | 3.49628 | 42.60 |
| 27.1047 | 244.42 | 0.1673 | 3.28991 | 34.35 |
| 27.2757 | 253.41 | 0.1004 | 3.26968 | 35.62 |
| 28.8668 | 449.81 | 0.1171 | 3.09297 | 63.22 |
| 29.1165 | 459.78 | 0.1171 | 3.06701 | 64.62 |
| 30.2032 | 224.45 | 0.3346 | 2.95910 | 31.55 |
| 31.2523 | 110.46 | 0.4015 | 2.86211 | 15.52 |
| 32.1235 | 138.52 | 0.4015 | 2.78645 | 19.47 |
| 33.0720 | 178.41 | 0.3011 | 2.70868 | 25.07 |
| 35.2183 | 65.08 | 0.2676 | 2.54837 | 9.15 |
| 35.7909 | 62.54 | 0.2676 | 2.50890 | 8.79 |
| 36.5174 | 66.19 | 0.2007 | 2.46064 | 9.30 |
| 37.1599 | 52.08 | 0.5353 | 2.41956 | 7.32 |

TABLE 61

Form VI Characterization
Peak List:

| Pos. [°2Th.] | Height [cts] | FWHM [°2Th.] | d-spacing [Å] | Rel. Int. [%] |
|---|---|---|---|---|
| 7.8496 | 1580.05 | 0.0836 | 11.26324 | 67.30 |
| 11.8964 | 1854.21 | 0.0836 | 7.43939 | 78.98 |
| 12.6410 | 202.90 | 0.0836 | 7.00278 | 8.64 |
| 15.0380 | 777.82 | 0.0836 | 5.89152 | 33.13 |
| 15.2810 | 1173.32 | 0.0836 | 5.79841 | 49.98 |
| 15.5243 | 1225.24 | 0.0836 | 5.70807 | 52.19 |
| 16.1145 | 164.99 | 0.0669 | 5.50030 | 7.03 |
| 17.6095 | 2347.80 | 0.1004 | 5.03657 | 100.00 |
| 19.0798 | 169.45 | 0.1004 | 4.65165 | 7.22 |
| 19.3067 | 302.45 | 0.0836 | 4.59748 | 12.88 |
| 20.3324 | 103.42 | 0.1171 | 4.36782 | 4.40 |
| 21.1331 | 526.05 | 0.1004 | 4.20409 | 22.41 |
| 22.4375 | 700.44 | 0.1004 | 3.96257 | 29.83 |
| 22.9995 | 1347.34 | 0.1004 | 3.86699 | 57.39 |
| 23.3043 | 684.79 | 0.1004 | 3.81710 | 29.17 |
| 23.7841 | 1744.10 | 0.1171 | 3.74117 | 74.29 |
| 24.5054 | 230.40 | 0.1004 | 3.63266 | 9.81 |
| 24.7579 | 434.11 | 0.1004 | 3.59618 | 18.49 |
| 25.0253 | 1655.56 | 0.1171 | 3.55836 | 70.52 |
| 25.5033 | 344.02 | 0.1171 | 3.49274 | 14.65 |
| 26.0438 | 327.56 | 0.0669 | 3.42147 | 13.95 |
| 26.2753 | 170.54 | 0.1004 | 3.39185 | 7.26 |
| 26.6025 | 80.83 | 0.1338 | 3.35086 | 3.44 |
| 27.5096 | 292.81 | 0.1004 | 3.24241 | 12.47 |
| 28.1175 | 878.41 | 0.1171 | 3.17367 | 37.41 |
| 28.7048 | 251.20 | 0.0836 | 3.11006 | 10.70 |
| 29.0435 | 1318.15 | 0.1004 | 3.07456 | 56.14 |
| 29.4202 | 234.78 | 0.0836 | 3.03604 | 10.00 |
| 30.3099 | 340.86 | 0.0836 | 2.94892 | 14.52 |
| 30.9237 | 358.99 | 0.1338 | 2.89177 | 15.29 |
| 31.6783 | 193.78 | 0.1338 | 2.82459 | 8.25 |
| 32.0151 | 172.84 | 0.1338 | 2.79564 | 7.36 |
| 32.4820 | 165.13 | 0.1338 | 2.75651 | 7.03 |
| 32.8446 | 219.60 | 0.1673 | 2.72691 | 9.35 |
| 33.2526 | 169.79 | 0.1506 | 2.69437 | 7.23 |
| 33.7436 | 333.64 | 0.0669 | 2.65628 | 14.21 |
| 35.1498 | 145.85 | 0.1004 | 2.55317 | 6.21 |
| 35.4257 | 223.46 | 0.2342 | 2.53392 | 9.52 |
| 36.1195 | 160.13 | 0.1171 | 2.48682 | 6.82 |
| 36.6412 | 148.76 | 0.1004 | 2.45261 | 6.34 |
| 37.3742 | 134.83 | 0.1004 | 2.40617 | 5.74 |
| 38.9668 | 127.14 | 0.1004 | 2.31142 | 5.42 |

TABLE 62

Form VII Characterization
Peak List:

| Pos. [°2Th.] | Height [cts] | FWHM [°2Th.] | d-spacing [Å] | Rel. Int. [%] |
|---|---|---|---|---|
| 9.8602 | 13202.67 | 0.0787 | 8.97058 | 64.80 |
| 13.8310 | 1102.79 | 0.0590 | 6.40286 | 5.41 |
| 18.6304 | 430.48 | 0.0590 | 4.76283 | 2.11 |
| 19.4724 | 20373.14 | 0.0590 | 4.55874 | 100.00 |
| 19.5919 | 19333.60 | 0.0590 | 4.53120 | 94.90 |
| 19.9962 | 629.82 | 0.0787 | 4.44048 | 3.09 |
| 20.2520 | 337.93 | 0.0590 | 4.38498 | 1.66 |
| 21.8775 | 1392.67 | 0.0590 | 4.06271 | 6.84 |
| 23.3213 | 545.78 | 0.0787 | 3.81436 | 2.68 |
| 24.0376 | 1305.06 | 0.0787 | 3.70229 | 6.41 |
| 25.9551 | 143.45 | 0.0984 | 3.43296 | 0.70 |
| 27.6781 | 626.31 | 0.0787 | 3.22304 | 3.07 |
| 28.1796 | 573.45 | 0.0787 | 3.16682 | 2.81 |
| 29.3112 | 8508.46 | 0.0720 | 3.04456 | 41.76 |
| 29.4207 | 10351.49 | 0.0394 | 3.03599 | 50.81 |
| 31.0133 | 836.93 | 0.0984 | 2.88362 | 4.11 |
| 32.6067 | 111.06 | 0.0984 | 2.74626 | 0.55 |
| 35.5593 | 84.45 | 0.1968 | 2.52471 | 0.41 |
| 36.8168 | 190.51 | 0.1771 | 2.44131 | 0.94 |
| 39.5031 | 2222.25 | 0.0590 | 2.28127 | 10.91 |

TABLE 63

Amorphouse Form Characterization
Peak List:

| Pos. [°2Th.] | Height [cts] | FWHM [°2Th.] | d-spacing [Å] | Rel. Int. [%] |
|---|---|---|---|---|
| 14.2290 | 373.13 | 0.7673 | 6.21949 | 100.00 |
| 14.2645 | 186.57 | 0.7673 | 6.21949 | 50.00 |
| 17.1264 | 157.26 | 0.3914 | 5.17326 | 42.15 |
| 17.1692 | 78.63 | 0.3914 | 5.17326 | 21.07 |
| 18.7217 | 154.19 | 0.4789 | 4.73588 | 41.32 |
| 18.7686 | 77.09 | 0.4789 | 4.73588 | 20.66 |
| 21.8014 | 177.84 | 1.4698 | 4.07334 | 47.66 |
| 21.8563 | 88.92 | 1.4698 | 4.07334 | 23.83 |

TABLE 64

TGA - DSC Summary

| Polymorph | DSC (onset ° C.) | TGA (mass change) |
|---|---|---|
| Form I | 236.81 | −100.04% |
| Form II | 194.20 | — |
|  | 236.65 | −93.35% |
| Form III | 77.66 | −6.06% |
|  | 236.97 | −85.54% |
| Form IV | 149.89 | −9.41% |
|  | 233.14 | 83.89% |

TABLE 64-continued

TGA - DSC Summary

| Polymorph | DSC (onset ° C.) | TGA (mass change) |
|---|---|---|
| Form V | — | −4.58% |
|  | 237.85 | −90.5% |
| Form VI | 235 | −97.68% |
| Form VII | — | −6.58% |
|  | — | −17.52% |
|  | 268.7 | −71.65% |

The invention claimed is:

1. Bupropion hydrobromide in crystalline form, characterized by at least one of the following properties:
PXRD as in FIG. 31,
DSC as in FIG. 32,
TGA as in FIG. 33,
IR as in FIG. 34.

2. A composition comprising the bupropion hydrobromide according to claim 1 and a pharmaceutically acceptable carrier or excipient.

3. The composition according to claim 2, further comprising at least one other drug other than bupropion hydrobromide selected from the group consisting of anti-depressants, anti-anxiety agents, steroidal inflammatories, non-steroidal inflammatories, SSRIs, anti-migraine agents, anti-emetics, drugs for treating abuse, appetite modulators, anti-virals, vasodilators, anti-pain agents, and combinations thereof.

4. The composition according to claim 2 further comprising at least one other drug other than bupropion hydrobromide selected from the group consisting of a monoamine oxidase (MAO) inhibitor, a tricyclic antidepressant, a serotonin reuptake inhibitor, a selective norepinephrine reuptake inhibitor (SNRIs), aminoketones, serotonin antagonists, dopamine reuptake inhibitors, dual reuptake inhibitors, norepinephrine enhancers, serotonin activity enhancers, dopamine activity enhancers, and combinations thereof.

5. The composition of claim 2, in the form of a microparticle comprising a solid core, said core comprising the bupropion hydrobromide and the at least one pharmaceutically acceptable excipient, said core of said microparticle being at least partially surrounded by a controlled release coat which permits entry of an aqueous liquid into the core and delivery of the bupropion hydrobromide from the core to the exterior of the microparticle through the controlled release coat.

6. The composition of claim 2, in the form of a tablet comprising a core comprising the bupropion hydrobromide and a controlled release coating at least partially surrounding said core, the coating comprising at least one water-soluble polymer, at least one water-insoluble polymer, and optionally a plasticizer.

7. A composition comprising a crystalline form having the following properties PXRD as in FIG. 31, DSC as in FIG. 32, TGA as in FIG. 33, IR as in FIG. 34; and one or more of the following forms of bupropion hydrobromide:
(a) a crystalline form having the following properties PXRD as in FIG. 35, DSC as in FIG. 36, TGA as in FIG. 37, IR as in FIG. 38;
(b) a crystalline form having the following properties PXRD as in FIG. 39, DSC as in FIG. 40, TGA as in FIG. 41, IR as in FIG. 42;
(c) a crystalline form having the following properties PXRD as in FIG. 43, DSC as in FIG. 44, TGA as in FIG. 45, IR as in FIG. 46;
(d) an amorphous form having the following property PXRD as in FIG. 47; and
(e) an amorphous form having the following property PXRD as in FIG. 48.

* * * * *